US009580465B2

(12) United States Patent
Cerami et al.

(10) Patent No.: US 9,580,465 B2
(45) Date of Patent: Feb. 28, 2017

(54) TISSUE PROTECTIVE PEPTIDES AND PEPTIDE ANALOGS FOR PREVENTING AND TREATING DISEASES AND DISORDERS ASSOCIATED WITH TISSUE DAMAGE

(71) Applicant: ARAIM PHARMACEUTICALS, INC., Tarrytown, NY (US)

(72) Inventors: Anthony Cerami, La Jolla, CA (US); Michael Brines, Woodbridge, CT (US)

(73) Assignee: Araim Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/502,735

(22) Filed: Sep. 30, 2014

(65) Prior Publication Data

US 2015/0239932 A1    Aug. 27, 2015

Related U.S. Application Data

(62) Division of application No. 12/863,973, filed as application No. PCT/US2009/000424 on Jan. 22, 2009, now Pat. No. 8,853,358.

(60) Provisional application No. 61/062,012, filed on Jan. 22, 2008, provisional application No. 61/062,022, filed on Jan. 22, 2008, provisional application No. 61/062,045, filed on Jan. 22, 2008, provisional application No. 61/133,912, filed on Jul. 3, 2008, provisional application No. 61/203,890, filed on Dec. 30, 2008.

(51) Int. Cl.
*A61K 38/00* (2006.01)
*C07K 7/06* (2006.01)
*C07K 14/505* (2006.01)

(52) U.S. Cl.
CPC .............. *C07K 7/06* (2013.01); *C07K 14/505* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,700,909 A | 12/1997 | O'Brien | |
| 8,071,554 B2 | 12/2011 | Cerami et al. | |
| 8,653,028 B2 | 2/2014 | Yuan et al. | |
| 8,673,861 B2 | 3/2014 | Cerami et al. | |
| 8,716,245 B2 | 5/2014 | Cerami et al. | |
| 2007/0166794 A1 | 7/2007 | Novak et al. | |
| 2011/0190217 A1 | 8/2011 | Wang et al. | |
| 2011/0263504 A1 | 10/2011 | Cerami et al. | |
| 2014/0323401 A1 | 10/2014 | Cerami et al. | |

FOREIGN PATENT DOCUMENTS

| | | |
|---|---|---|
| EP | 0116446 A2 | 8/1984 |
| EP | 0410246 B1 | 7/1990 |
| EP | 0410246 A1 | 1/1991 |
| EP | 1736481 A1 | 12/2006 |
| JP | 2004-305006 A | 11/2004 |
| JP | 2007-509955 A | 4/2007 |
| JP | 2007-529530 A | 10/2007 |
| JP | 2007-534667 A | 11/2007 |
| WO | 95/21919 A2 | 8/1995 |
| WO | 00/61164 A1 | 10/2000 |
| WO | 01/83548 A1 | 11/2001 |
| WO | 02/053580 A2 | 7/2002 |
| WO | 2004/003176 A2 | 1/2004 |
| WO | 2004/004656 A2 | 1/2004 |
| WO | 2004/096148 A2 | 11/2004 |
| WO | 2005/025606 A1 | 3/2005 |
| WO | 2005/032467 A2 | 4/2005 |
| WO | 2005/039554 A2 | 5/2005 |
| WO | 2005/079854 A1 | 9/2005 |
| WO | 2005/089269 A2 | 9/2005 |
| WO | 2006/091727 A2 | 8/2006 |
| WO | 2006/119767 A2 | 11/2006 |
| WO | 2006/127910 A2 | 11/2006 |
| WO | 2007/010552 A2 | 1/2007 |
| WO | 2007/019545 A2 | 2/2007 |

OTHER PUBLICATIONS

Sales-Campos, "Classical and recent advances in the treatment of inflammatory bowel diseases", Brazilian Journal of Medical and Biological Research, 2016, p. 96-107.*
Muscaritoli et al., "Prevention and treatment of cancer cachexia: New insights into an old problem", European Journal of Cancer, 2006, p. 31-41.*
Dodson et al., "Muscle Wasting in Cancer Cachexia: Clinical Implications, Diagnosis, and Emerging Treatment Strategies", Annu. Rev. Med. 2011, pp. 265-279.*
Barlow, "Peptide Drug Design," Smith and William's Introduction to the Principles of Drug Design and Action, 4th Edition, Taylor & Francis Group, USA, 327-354 (2006).
Beffy et al., "An immunodominant epitope in a functional domain near the N-terminus of human granulocyte-macrophage colony-stimulating factor identified by cross-reaction of synthetic peptides with neutralizing anti-protein and anti-peptide antibodies," Hybridoma 13(6):457-468 (1994).
Brines et al., "Erythropoietin mediates tissue protection through an erythropoietin and common β-subunit heteroreceptor," Proc. Natl. Acad. Sci. U.S.A. 101(41):14907-14912 (2004).
Brines et al., "Nonerythropoietin, tissue-protective peptides derived from the tertiary structure of erythropoietin," Proc. Natl. Acad. Sci. U.S.A. 105(31):10925-10930 (2008).

(Continued)

*Primary Examiner* — Lianko Garyu
(74) *Attorney, Agent, or Firm* — Jones Day

(57) ABSTRACT

The present invention provides peptides and peptide analogs that have tissue protective activities while having little or no potentially undesirable hematopoetic effects. The peptides and peptide analogs are useful in preventing and treating a variety of diseases and disorders associated with tissue damage.

18 Claims, 22 Drawing Sheets

(56) References Cited

OTHER PUBLICATIONS

Congote et al., "The C-terminal peptide of thrombospondin-4 stimulates erythroid cell proliferation," Biochem. Biophys. Res. Commun. 324(2):673-678 (2004).
Elliott et al., "Fine-structure epitope mapping of antierythropoietin monoclonal antibodies reveals a model of recombinant human erythropoietin structure," Blood 87(7):2702-2713 (1996).
Elliott et al., "Mapping of the Active Site of Recombinant Human Erythropoietin," Blood 89(2):493-502 (1997).
Elliott et al., "Structural requirements for additional N-linked carbohydrate on recombinant human erythropoietin," J Biol. Chem. 279(16):16854-16862 (2004).
Ghezzi et al., "Erythropoietin as an antiapoptotic, tissue protective cytokine," Cell Death & Differentiation 11(S1):S37-S44 (2004).
IPEA/EP, PCT International Preliminary Report on Patentability dated May 18, 2010 for International Application No. PCT/US2009/00424.
ISA/EP PCT International Search Report and Written Opinion dated Oct. 27, 2009, for International Application No. PCT/US2009/00424.
ISA/US International Search Report dated Jul. 29, 2008, for International Application No. PCT/US2006/031061, filed Aug. 7, 2006.
European Search Report dated Jun. 22, 2009, for European Application No. 06801051.1, filed Aug. 7, 2006.
Kaiser et al., "Recombinant human erythropoietin prevents the death of mice during cerebral malaria," J. Infectious Diseases 193(7):987-995 (2006).
Konstantinopoulos et al., "Selective modulation of the erythropoietic and tissue-protective effects of erythropoietin: Time to reach the full therapeutic potential of erythropoietin," Biochimica et Biophysica Acta, 1776:1-9 (2007).
Leist et al., "Derivatives of Erythropoietin that are Tissue protective but not Erythropoietic," Science 305 (5681):239-242 (2004).
Noli et al., "Design, Synthesis and Conformational Analysis of hGM-CSF(13-31)-Gly-Pro-Gly-(103-116)," J. Pept. Sci. 3(5):323-335 (1997).
Park et al., "Identification of functionally important residues of human thrombopoietin," J. Biol. Chem. 273(1):256-261 (1998).
Peggion et al., "Design, synthesis, and conformational studies of the hGM-CSF derived peptide (13-27)-Gly-(75-87)," Biopolymers 50(5):545-554 (1999).
Skelton et al., "Amino acid determinants of beta-hairpin conformation in erythropoeitin receptor agonist peptides derived from a phage display library," J. Mol. Biol. 316(5):1111-1125 (2002).
Sun et al., "Redox Regulation of Cell Signaling by Selenocysteine in Mammalian Thioredoxin Reductases," J. Biol. Chem. 274(35):24522-24530 (1999).
Tahara et al., "Neutralization of biological activity and inhibition of receptor binding by antibodies against human thrombopoietin," Stem Cells 16(1):54-60 (1998).
Takashi et al., "Protein characteristics of thrombopoietin," Stem Cells 14(S1):139-147 (1996).
Von Feldt et al., "Development of GM-CSF antagonist peptides," Peptide Res. 8(1):20-27, 30-32 (1995).
Website: http://www.merckmanuals.com/professional/neurologic_disorders/peripheral_nervous_system_and_motor_unit_disorders/overview_of_peripheral_nervous_system_disorders.html, 8 pages, retrieved on Mar. 7, 2013.
Website: http://www.nlm.nih.gov/medlineplus/peripheralnervesdisorders.html, 4 pages, retrieved on Mar. 7, 2013.
Wen et al., "Erythropoietin structure-function relationships," J. Biol. Chem. 269(36):22839-22846 (1994).
Wolfert et al., "Chloroquine and Amphipathic Peptide Helices Show Synergistic Transfection In Vitro," Gene Ther. 5 (3):409-411 (1998).
Yu et al., "Investigation of n-terminal glutamate cyclization of recombinant monoclonal antibody in formulation development," J. Pharm. Biomed. Anal. 42(4): 455-463 (2006).
Coleman and Brines, "Science review: Recombinant human erythropoietin in critical illness: a role beyond anemia?" Critical Care 8:337-341 (2004) (Epub Jun. 16, 2004).
Savino and Ciliberto, "A paradigm shift for erythropoietin: no longer a specialized growth factor, but rather an all-purpose tissue-protective agent," Cell Death Differ. 11 Suppl 1:S2-S4 (2004).
Ueba et al., "Cardioprotection by a nonerythropoietic, tissue-protective peptide mimicking the 3D structure of erythropoietin," Proc. Natl. Acad. Sci U. S. A. 107(32):14357-14362 (2010) (Epub Jun. 26, 2010).
Campana et al., "Identification of a neurotrophic sequence in erythropoietin," Int. J. Mol. Med. 1(1):235-241 (1998).

\* cited by examiner

US 9,580,465 B2

SEQUENCE LISTING

```
<160> NUMBER OF SEQ ID NOS: 308

<210> SEQ ID NO 1
<211> LENGTH: 166
<212> TYPE: PRT
<213> ORGANISM: Artificial Sequence
<220> FEATURE:
<223> OTHER INFORMATION: Recombinant human erythropoietin (EPO)
      comprising mutations N24K, N38K, N83K
<220> FEATURE:
<221> NAME/KEY: misc_feature
<222> LOCATION: (166)..(166)
<223> OTHER INFORMATION: Xaa is any amino acid

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
                20                  25                  30

Cys Ser Leu Asn Glu Lys Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
```

```
                    100                 105                 110
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Xaa
                165

<210> SEQ ID NO 2
<211> LENGTH: 20
<212> TYPE: PRT
<213> ORGANISM: Artificial Sequence
<220> FEATURE:
<223> OTHER INFORMATION: EPO structures: (1) loop AB and N-terminal
      portion of helix B, Peptide A

<400> SEQUENCE: 2

Asn Ile Thr Val Pro Asp Thr Lys Val Asn Phe Tyr Ala Trp Lys Arg
1               5                   10                  15

Met Glu Val Gly
            20

<210> SEQ ID NO 3
<211> LENGTH: 25
<212> TYPE: PRT
<213> ORGANISM: Artificial Sequence
<220> FEATURE:
<223> OTHER INFORMATION: EPO structures: (2) C-terminal portion of helix
      B, Peptide B

<400> SEQUENCE: 3

Gln Gln Ala Val Glu Val Trp Gln Gly Leu Ala Leu Leu Ser Glu Ala
1               5                   10                  15

Val Leu Arg Gly Gln Ala Leu Leu Val
            20                  25

<210> SEQ ID NO 4
<211> LENGTH: 20
<212> TYPE: PRT
<213> ORGANISM: Artificial Sequence
<220> FEATURE:
<223> OTHER INFORMATION: EPO structures: (3) a portion of the A-B loop
      consisting of a small cysteine loop and a Beta-pleated sheet,
      Peptide C

<400> SEQUENCE: 4

Gly Cys Ala Glu His Cys Ser Leu Asn Glu Asn Ile Thr Val Pro Asp
1               5                   10                  15

Thr Lys Val Asn
            20

<210> SEQ ID NO 5
<211> LENGTH: 9
<212> TYPE: PRT
<213> ORGANISM: Artificial Sequence
<220> FEATURE:
<223> OTHER INFORMATION: Structural Motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
```

```
<222> LOCATION: (2)..(2)
<223> OTHER INFORMATION: Xaa is a negatively charged amino acid
<220> FEATURE:
<221> NAME/KEY: misc_feature
<222> LOCATION: (3)..(7)
<223> OTHER INFORMATION: Xaa is any amino acid or is absent
<220> FEATURE:
<221> NAME/KEY: misc_feature
<222> LOCATION: (8)..(8)
<223> OTHER INFORMATION: Xaa is a negatively charged amino acid
<220> FEATURE:
<221> NAME/KEY: misc_feature
<222> LOCATION: (9)..(9)
<223> OTHER INFORMATION: Xaa is a hydrophobic amino acid

<400> SEQUENCE: 5

Xaa Xaa Xaa Xaa Xaa Xaa Xaa Xaa Xaa
1               5

<210> SEQ ID NO 6
<211> LENGTH: 4
<212> TYPE: PRT
<213> ORGANISM: Artificial Sequence
<220> FEATURE:
<223> OTHER INFORMATION: Structural Motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(3)
<223> OTHER INFORMATION: Xaa is a negatively charged amino acid
<220> FEATURE:
<221> NAME/KEY: misc_feature
<222> LOCATION: (4)..(4)
<223> OTHER INFORMATION: Xaa is a hydrophobic amino acid

<400> SEQUENCE: 6

Xaa Xaa Xaa Xaa
1

<210> SEQ ID NO 7
<211> LENGTH: 5
<212> TYPE: PRT
<213> ORGANISM: Artificial Sequence
<220> FEATURE:
<223> OTHER INFORMATION: Structural Motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is a negatively charged amino acid
<220> FEATURE:
<221> NAME/KEY: misc_feature
<222> LOCATION: (5)..(5)
<223> OTHER INFORMATION: Xaa is a hydrophobic amino acid

<400> SEQUENCE: 7

Xaa Xaa Xaa Xaa Xaa
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Structural Motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(4)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is negatively charged amino acid
<220> FEATURE:
<221> NAME/KEY: misc_feature
<222> LOCATION: (6)..(6)
<223> OTHER INFORMATION: Xaa is a hydrophobic amino acid

<400> SEQUENCE: 8

Xaa Xaa Xaa Xaa Xaa Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Structural Motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(5)
<223> OTHER INFORMATION: Xaa is any amino acid
<220> FEATURE:
<221> NAME/KEY: misc_feature
<222> LOCATION: (6)..(6)
<223> OTHER INFORMATION: Xaa is a negatively charged amino acid
<220> FEATURE:
<221> NAME/KEY: misc_feature
<222> LOCATION: (7)..(7)
<223> OTHER INFORMATION: Xaa is a hydrophobic amino acid

<400> SEQUENCE: 9

Xaa Xaa Xaa Xaa Xaa Xaa Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Structural Motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
```

-continued

```
<223> OTHER INFORMATION: Xaa is a negatively charged amino acid
<220> FEATURE:
<221> NAME/KEY: misc_feature
<222> LOCATION: (3)..(6)
<223> OTHER INFORMATION: Xaa is any amino acid
<220> FEATURE:
<221> NAME/KEY: misc_feature
<222> LOCATION: (7)..(7)
<223> OTHER INFORMATION: Xaa is a negatively charged amino acid
<220> FEATURE:
<221> NAME/KEY: misc_feature
<222> LOCATION: (8)..(8)
<223> OTHER INFORMATION: Xaa is a hydrophobic amino acid

<400> SEQUENCE: 10

Xaa Xaa Xaa Xaa Xaa Xaa Xaa Xaa
1               5

<210> SEQ ID NO 11
<211> LENGTH: 9
<212> TYPE: PRT
<213> ORGANISM: Artificial Sequence
<220> FEATURE:
<223> OTHER INFORMATION: Structural Motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(7)
<223> OTHER INFORMATION: Xaa is any amino acid
<220> FEATURE:
<221> NAME/KEY: misc_feature
<222> LOCATION: (8)..(8)
<223> OTHER INFORMATION: Xaa is a negatively charged amino acid
<220> FEATURE:
<221> NAME/KEY: misc_feature
<222> LOCATION: (9)..(9)
<223> OTHER INFORMATION: Xaa is a hydrophobic amino acid

<400> SEQUENCE: 11

Xaa Xaa Xaa Xaa Xaa Xaa Xaa Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Variation of structural motif A
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(7)
<223> OTHER INFORMATION: Xaa is any amino acid or is absent
<220> FEATURE:
<221> NAME/KEY: misc_feature
<222> LOCATION: (8)..(8)
<223> OTHER INFORMATION: Xaa is a negatively charged amino acid
<220> FEATURE:
<221> NAME/KEY: misc_feature
<222> LOCATION: (9)..(9)
<223> OTHER INFORMATION: Xaa is a polar amino acid
```

-continued

```
<400> SEQUENCE: 12

Xaa Xaa Xaa Xaa Xaa Xaa Xaa Xaa Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Variation of structural motif
<220> FEATURE:
<221> NAME/KEY: misc_feature
<222> LOCATION: (1)..(1)
<223> OTHER INFORMATION: Xaa is a polar amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(7)
<223> OTHER INFORMATION: Xaa is any amino acid or is absent
<220> FEATURE:
<221> NAME/KEY: misc_feature
<222> LOCATION: (8)..(8)
<223> OTHER INFORMATION: Xaa is a negatively charged amino acid
<220> FEATURE:
<221> NAME/KEY: misc_feature
<222> LOCATION: (9)..(9)
<223> OTHER INFORMATION: Xaa is a hydrophobic amino acid

<400> SEQUENCE: 13

Xaa Xaa Xaa Xaa Xaa Xaa Xaa Xaa Xaa
1               5

<210> SEQ ID NO 14
<211> LENGTH: 23
<212> TYPE: PRT
<213> ORGANISM: Artificial Sequence
<220> FEATURE:
<223> OTHER INFORMATION: Structural motif A, Peptide D

<400> SEQUENCE: 14

Ala Pro Pro Arg Leu Ile Cys Asp Ser Arg Val Leu Glu Arg Tyr Leu
1               5                   10                  15

Leu Glu Ala Lys Glu Ala Glu
            20

<210> SEQ ID NO 15
<211> LENGTH: 29
<212> TYPE: PRT
<213> ORGANISM: Artificial Sequence
<220> FEATURE:
<223> OTHER INFORMATION: Formula I of structural motif A
<220> FEATURE:
<221> NAME/KEY: misc_feature
<222> LOCATION: (1)..(1)
<223> OTHER INFORMATION: Xaa is Cys (C) or Pro (P)
<220> FEATURE:
<221> NAME/KEY: misc_feature
<222> LOCATION: (2)..(2)
<223> OTHER INFORMATION: Xaa is Asp (D) or Pro (P)
<220> FEATURE:
<221> NAME/KEY: misc_feature
<222> LOCATION: (3)..(3)
<223> OTHER INFORMATION: Xaa is Ser (S) or Arg (R)
<220> FEATURE:
<221> NAME/KEY: misc_feature
<222> LOCATION: (4)..(4)
<223> OTHER INFORMATION: Xaa is Arg (R) or Leu (L)
<220> FEATURE:
```

```
<221> NAME/KEY: misc_feature
<222> LOCATION: (5)..(5)
<223> OTHER INFORMATION: Xaa is Val (V) or Ile (I)
<220> FEATURE:
<221> NAME/KEY: misc_feature
<222> LOCATION: (6)..(6)
<223> OTHER INFORMATION: Xaa is Leu (L) or Cys (C)
<220> FEATURE:
<221> NAME/KEY: misc_feature
<222> LOCATION: (7)..(7)
<223> OTHER INFORMATION: Xaa is Glu (E) or Asp (D)
<220> FEATURE:
<221> NAME/KEY: misc_feature
<222> LOCATION: (8)..(8)
<223> OTHER INFORMATION: Xaa is Arg (R) or Ser (S)
<220> FEATURE:
<221> NAME/KEY: misc_feature
<222> LOCATION: (9)..(9)
<223> OTHER INFORMATION: Xaa is Tyr (Y) or Arg (R)
<220> FEATURE:
<221> NAME/KEY: misc_feature
<222> LOCATION: (10)..(10)
<223> OTHER INFORMATION: Xaa is Leu (L) or Val (V)
<220> FEATURE:
<221> NAME/KEY: misc_feature
<222> LOCATION: (11)..(11)
<223> OTHER INFORMATION: Xaa is Leu (L) or Ala (A)
<220> FEATURE:
<221> NAME/KEY: misc_feature
<222> LOCATION: (12)..(12)
<223> OTHER INFORMATION: Xaa is a negatively charged amino acid
<220> FEATURE:
<221> NAME/KEY: misc_feature
<222> LOCATION: (13)..(13)
<223> OTHER INFORMATION: Xaa is any amino acid
<220> FEATURE:
<221> NAME/KEY: misc_feature
<222> LOCATION: (14)..(17)
<223> OTHER INFORMATION: Xaa is any amino acid or is absent
<220> FEATURE:
<221> NAME/KEY: misc_feature
<222> LOCATION: (18)..(18)
<223> OTHER INFORMATION: Xaa is a negatively charged amino acid
<220> FEATURE:
<221> NAME/KEY: misc_feature
<222> LOCATION: (19)..(19)
<223> OTHER INFORMATION: Xaa is Ala (A) or Leu (L)
<220> FEATURE:
<221> NAME/KEY: misc_feature
<222> LOCATION: (20)..(20)
<223> OTHER INFORMATION: Xaa is Glu (E) or Lys (K)
<220> FEATURE:
<221> NAME/KEY: misc_feature
<222> LOCATION: (21)..(21)
<223> OTHER INFORMATION: Xaa is Asn (N), Glu (E), or Lys (K)
<220> FEATURE:
<221> NAME/KEY: misc_feature
<222> LOCATION: (22)..(22)
<223> OTHER INFORMATION: Xaa is Ile (I) or Ala (A)
<220> FEATURE:
<221> NAME/KEY: misc_feature
<222> LOCATION: (23)..(23)
<223> OTHER INFORMATION: Xaa is Thr (T), Glu (E), or Gly (G)
<220> FEATURE:
<221> NAME/KEY: misc_feature
<222> LOCATION: (24)..(24)
<223> OTHER INFORMATION: Xaa is Thr (T), Asn (N), or Ala (A)
<220> FEATURE:
<221> NAME/KEY: misc_feature
<222> LOCATION: (25)..(25)
<223> OTHER INFORMATION: Xaa is Gly (G) or Ile (I)
<220> FEATURE:
<221> NAME/KEY: misc_feature
<222> LOCATION: (26)..(26)
<223> OTHER INFORMATION: Xaa is Cys (C) or Thr (T)
<220> FEATURE:
<221> NAME/KEY: misc_feature
<222> LOCATION: (27)..(27)
<223> OTHER INFORMATION: Xaa is Ala (A) or Thr (T)
```

```
<220> FEATURE:
<221> NAME/KEY: misc_feature
<222> LOCATION: (28)..(28)
<223> OTHER INFORMATION: Xaa is Glu (E) or Gly (G)
<220> FEATURE:
<221> NAME/KEY: misc_feature
<222> LOCATION: (29)..(29)
<223> OTHER INFORMATION: Xaa is His (H) or Cys (C)

<400> SEQUENCE: 15

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25

<210> SEQ ID NO 16
<211> LENGTH: 26
<212> TYPE: PRT
<213> ORGANISM: Artificial Sequence
<220> FEATURE:
<223> OTHER INFORMATION: Structural motif A, Peptide F

<400> SEQUENCE: 16

Cys Asp Ser Arg Val Leu Glu Arg Tyr Leu Leu Glu Ala Lys Glu Ala
1               5                   10                  15

Glu Asn Ile Thr Thr Gly Cys Ala Glu His
            20                  25

<210> SEQ ID NO 17
<211> LENGTH: 28
<212> TYPE: PRT
<213> ORGANISM: Artificial Sequence
<220> FEATURE:
<223> OTHER INFORMATION: Structural motif A, Peptide G

<400> SEQUENCE: 17

Pro Pro Arg Leu Ile Cys Asp Ser Arg Val Leu Glu Arg Tyr Leu Leu
1               5                   10                  15

Glu Ala Lys Glu Ala Glu Asn Ile Thr Thr Gly Cys
            20                  25

<210> SEQ ID NO 18
<211> LENGTH: 10
<212> TYPE: PRT
<213> ORGANISM: Artificial Sequence
<220> FEATURE:
<223> OTHER INFORMATION: Structural motif A, Peptide H

<400> SEQUENCE: 18

Ala Asp Arg Glu Leu Glu Lys Ile Gly Ala
1               5                   10

<210> SEQ ID NO 19
<211> LENGTH: 4
<212> TYPE: PRT
<213> ORGANISM: Artificial Sequence
<220> FEATURE:
<223> OTHER INFORMATION: Structural motif B
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
```

```
<222> LOCATION: (3)..(3)
<223> OTHER INFORMATION: Xaa is a positively charged amino acid
<220> FEATURE:
<221> NAME/KEY: misc_feature
<222> LOCATION: (4)..(4)
<223> OTHER INFORMATION: Xaa is a hydrophobic amino acid

<400> SEQUENCE: 19

Xaa Xaa Xaa Xaa
1

<210> SEQ ID NO 20
<211> LENGTH: 4
<212> TYPE: PRT
<213> ORGANISM: Artificial Sequence
<220> FEATURE:
<223> OTHER INFORMATION: Structural motif B
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a positively charged amino acid
<220> FEATURE:
<221> NAME/KEY: misc_feature
<222> LOCATION: (3)..(3)
<223> OTHER INFORMATION: Xaa is a negatively charged amino acid
<220> FEATURE:
<221> NAME/KEY: misc_feature
<222> LOCATION: (4)..(4)
<223> OTHER INFORMATION: Xaa is a hydrophobic amino acid

<400> SEQUENCE: 20

Xaa Xaa Xaa Xaa
1

<210> SEQ ID NO 21
<211> LENGTH: 5
<212> TYPE: PRT
<213> ORGANISM: Artificial Sequence
<220> FEATURE:
<223> OTHER INFORMATION: Variation of Structural motif B
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(3)
<223> OTHER INFORMATION: Xaa is a polar amino acid
<220> FEATURE:
<221> NAME/KEY: misc_feature
<222> LOCATION: (4)..(4)
<223> OTHER INFORMATION: Xaa is a positively charged amino acid
<220> FEATURE:
<221> NAME/KEY: misc_feature
<222> LOCATION: (5)..(5)
<223> OTHER INFORMATION: Xaa is a hydrophobic amino acid

<400> SEQUENCE: 21

Xaa Xaa Xaa Xaa Xaa
1               5

<210> SEQ ID NO 22
<211> LENGTH: 5
<212> TYPE: PRT
<213> ORGANISM: Artificial Sequence
```

```
<220> FEATURE:
<223> OTHER INFORMATION: Variation of Structural motif B
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a positively charged amino acid
<220> FEATURE:
<221> NAME/KEY: misc_feature
<222> LOCATION: (3)..(3)
<223> OTHER INFORMATION: Xaa is a polar amino acid
<220> FEATURE:
<221> NAME/KEY: misc_feature
<222> LOCATION: (4)..(4)
<223> OTHER INFORMATION: Xaa is a negatively charged amino acid
<220> FEATURE:
<221> NAME/KEY: misc_feature
<222> LOCATION: (5)..(5)
<223> OTHER INFORMATION: Xaa is a hydrophobic amino acid

<400> SEQUENCE: 22

Xaa Xaa Xaa Xaa Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: Structural motif B
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(3)
<223> OTHER INFORMATION: Xaa is a polar amino acid or is absent
<220> FEATURE:
<221> NAME/KEY: misc_feature
<222> LOCATION: (4)..(4)
<223> OTHER INFORMATION: Xaa is a positively charged amino acid
<220> FEATURE:
<221> NAME/KEY: misc_feature
<222> LOCATION: (5)..(5)
<223> OTHER INFORMATION: Xaa is a hydrophobic amino acid

<400> SEQUENCE: 23

Xaa Xaa Xaa Xaa Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: Structural Motif B
<220> FEATURE:
<221> NAME/KEY: misc_feature
<222> LOCATION: (1)..(1)
<223> OTHER INFORMATION: Xaa is a hydrophobic amino acid
<220> FEATURE:
<221> NAME/KEY: misc_feature
<222> LOCATION: (2)..(2)
<223> OTHER INFORMATION: Xaa is a positively charged amino acid
<220> FEATURE:
<221> NAME/KEY: misc_feature
<222> LOCATION: (3)..(3)
```

```
<223> OTHER INFORMATION: Xaa is a polar amino acid or is absent
<220> FEATURE:
<221> NAME/KEY: misc_feature
<222> LOCATION: (4)..(4)
<223> OTHER INFORMATION: Xaa is a negatively charged amino acid
<220> FEATURE:
<221> NAME/KEY: misc_feature
<222> LOCATION: (5)..(5)
<223> OTHER INFORMATION: Xaa is hydrophobic amino acid

<400> SEQUENCE: 24

Xaa Xaa Xaa Xaa Xaa
1               5

<210> SEQ ID NO 25
<211> LENGTH: 24
<212> TYPE: PRT
<213> ORGANISM: Artificial Sequence
<220> FEATURE:
<223> OTHER INFORMATION: FOrmula II of Structural Motif B
<220> FEATURE:
<221> NAME/KEY: misc_feature
<222> LOCATION: (1)..(1)
<223> OTHER INFORMATION: Xaa is Ser (S)
<220> FEATURE:
<221> NAME/KEY: misc_feature
<222> LOCATION: (2)..(2)
<223> OTHER INFORMATION: Xaa is Arg (R)
<220> FEATURE:
<221> NAME/KEY: misc_feature
<222> LOCATION: (3)..(3)
<223> OTHER INFORMATION: Xaa is Val (V)
<220> FEATURE:
<221> NAME/KEY: misc_feature
<222> LOCATION: (4)..(4)
<223> OTHER INFORMATION: Xaa is Leu (L)
<220> FEATURE:
<221> NAME/KEY: misc_feature
<222> LOCATION: (5)..(5)
<223> OTHER INFORMATION: Xaa is Glu (E)
<220> FEATURE:
<221> NAME/KEY: misc_feature
<222> LOCATION: (6)..(6)
<223> OTHER INFORMATION: Xaa is Arg (R)
<220> FEATURE:
<221> NAME/KEY: misc_feature
<222> LOCATION: (7)..(7)
<223> OTHER INFORMATION: Xaa is Tyr (Y)
<220> FEATURE:
<221> NAME/KEY: misc_feature
<222> LOCATION: (8)..(8)
<223> OTHER INFORMATION: Xaa is Leu (L)
<220> FEATURE:
<221> NAME/KEY: misc_feature
<222> LOCATION: (9)..(9)
<223> OTHER INFORMATION: Xaa is Leu (L)
<220> FEATURE:
<221> NAME/KEY: misc_feature
<222> LOCATION: (10)..(10)
<223> OTHER INFORMATION: Xaa is Glu (E)
<220> FEATURE:
<221> NAME/KEY: misc_feature
<222> LOCATION: (11)..(11)
<223> OTHER INFORMATION: Xaa is Ala (A)
<220> FEATURE:
<221> NAME/KEY: misc_feature
<222> LOCATION: (12)..(12)
<223> OTHER INFORMATION: Xaa is a positively charged amino acid
<220> FEATURE:
<221> NAME/KEY: misc_feature
<222> LOCATION: (13)..(13)
<223> OTHER INFORMATION: Xaa is a negatively charged amino acid
<220> FEATURE:
<221> NAME/KEY: misc_feature
<222> LOCATION: (14)..(14)
<223> OTHER INFORMATION: Xaa is Ala (A)
<220> FEATURE:
```

```
<221> NAME/KEY: misc_feature
<222> LOCATION: (15)..(15)
<223> OTHER INFORMATION: Xaa is Glu (E)
<220> FEATURE:
<221> NAME/KEY: misc_feature
<222> LOCATION: (16)..(16)
<223> OTHER INFORMATION: Xaa is Asn (N)
<220> FEATURE:
<221> NAME/KEY: misc_feature
<222> LOCATION: (17)..(17)
<223> OTHER INFORMATION: Xaa is Ile (I)
<220> FEATURE:
<221> NAME/KEY: misc_feature
<222> LOCATION: (18)..(18)
<223> OTHER INFORMATION: Xaa is Thr (T)
<220> FEATURE:
<221> NAME/KEY: misc_feature
<222> LOCATION: (19)..(19)
<223> OTHER INFORMATION: Xaa is Thr (T)
<220> FEATURE:
<221> NAME/KEY: misc_feature
<222> LOCATION: (20)..(20)
<223> OTHER INFORMATION: Xaa is Gly (G)
<220> FEATURE:
<221> NAME/KEY: misc_feature
<222> LOCATION: (21)..(21)
<223> OTHER INFORMATION: Xaa is Cys (C)
<220> FEATURE:
<221> NAME/KEY: misc_feature
<222> LOCATION: (22)..(22)
<223> OTHER INFORMATION: Xaa is Ala (A)
<220> FEATURE:
<221> NAME/KEY: misc_feature
<222> LOCATION: (23)..(23)
<223> OTHER INFORMATION: Xaa is Glu (E)
<220> FEATURE:
<221> NAME/KEY: misc_feature
<222> LOCATION: (24)..(24)
<223> OTHER INFORMATION: Xaa is His (H)

<400> SEQUENCE: 25

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 26
<211> LENGTH: 24
<212> TYPE: PRT
<213> ORGANISM: Artificial Sequence
<220> FEATURE:
<223> OTHER INFORMATION: Structural motif B, Peptide I

<400> SEQUENCE: 26

Ser Arg Val Leu Glu Arg Tyr Leu Leu Glu Ala Lys Glu Ala Glu Asn
1               5                   10                  15

Ile Thr Thr Gly Cys Ala Glu His
            20

<210> SEQ ID NO 27
<211> LENGTH: 23
<212> TYPE: PRT
<213> ORGANISM: Artificial Sequence
<220> FEATURE:
<223> OTHER INFORMATION: Formula III of structural motif B
<220> FEATURE:
<221> NAME/KEY: misc_feature
<222> LOCATION: (1)..(1)
<223> OTHER INFORMATION: Xaa is Pro (P), Lys (K), or Ser (S)
<220> FEATURE:
<221> NAME/KEY: misc_feature
<222> LOCATION: (2)..(2)
<223> OTHER INFORMATION: Xaa is Pro (P), Glu (E), or Gln (Q)
```

```
-continued

<220> FEATURE:
<221> NAME/KEY: misc_feature
<222> LOCATION: (3)..(3)
<223> OTHER INFORMATION: Xaa is Arg (R), Ala (A), or Pro (P)
<220> FEATURE:
<221> NAME/KEY: misc_feature
<222> LOCATION: (4)..(4)
<223> OTHER INFORMATION: Xaa is Leu (L), Glu (E), or Trp (W)
<220> FEATURE:
<221> NAME/KEY: misc_feature
<222> LOCATION: (5)..(5)
<223> OTHER INFORMATION: Xaa is Ile (I), Asn (N), or Glu (E)
<220> FEATURE:
<221> NAME/KEY: misc_feature
<222> LOCATION: (6)..(6)
<223> OTHER INFORMATION: Xaa is Cys (C), Ile (I), or Pro (P)
<220> FEATURE:
<221> NAME/KEY: misc_feature
<222> LOCATION: (7)..(7)
<223> OTHER INFORMATION: Xaa is Asp (D), Thr (T), Leu (L), or Ala (A)
<220> FEATURE:
<221> NAME/KEY: misc_feature
<222> LOCATION: (8)..(8)
<223> OTHER INFORMATION: Xaa is Ser (S), Thr (T), Gln (Q), or Asp (D)
<220> FEATURE:
<221> NAME/KEY: misc_feature
<222> LOCATION: (9)..(9)
<223> OTHER INFORMATION: Xaa is Arg (R), Gly (G), or Leu (L)
<220> FEATURE:
<221> NAME/KEY: misc_feature
<222> LOCATION: (10)..(10)
<223> OTHER INFORMATION: Xaa is Val (V), Cys (C), His (H), or Glu (E)
<220> FEATURE:
<221> NAME/KEY: misc_feature
<222> LOCATION: (11)..(11)
<223> OTHER INFORMATION: Xaa is Leu (L), Ala (A), Val (V)
<220> FEATURE:
<221> NAME/KEY: misc_feature
<222> LOCATION: (12)..(12)
<223> OTHER INFORMATION: Xaa is a negatively charged amino acid
<220> FEATURE:
<221> NAME/KEY: misc_feature
<222> LOCATION: (13)..(13)
<223> OTHER INFORMATION: Xaa is a positively charged amino acid
<220> FEATURE:
<221> NAME/KEY: misc_feature
<222> LOCATION: (14)..(14)
<223> OTHER INFORMATION: Xaa is Tyr (Y), Cys (C), Ala (A), or Ile (I)
<220> FEATURE:
<221> NAME/KEY: misc_feature
<222> LOCATION: (15)..(15)
<223> OTHER INFORMATION: Xaa is Leu (L), Ser (S), Val (V), or Gly (G)
<220> FEATURE:
<221> NAME/KEY: misc_feature
<222> LOCATION: (16)..(16)
<223> OTHER INFORMATION: Xaa is Leu (L), Ser (S), or Ala (A)
<220> FEATURE:
<221> NAME/KEY: misc_feature
<222> LOCATION: (17)..(17)
<223> OTHER INFORMATION: Xaa is Glu (E), Asn (N), or Gly (G)
<220> FEATURE:
<221> NAME/KEY: misc_feature
<222> LOCATION: (18)..(18)
<223> OTHER INFORMATION: Xaa is Ala (A), Glu (E), or Leu (L)
<220> FEATURE:
<221> NAME/KEY: misc_feature
<222> LOCATION: (19)..(19)
<223> OTHER INFORMATION: Xaa is Lys (K), Asn (N), or Arg (R)
<220> FEATURE:
<221> NAME/KEY: misc_feature
<222> LOCATION: (20)..(20)
<223> OTHER INFORMATION: Xaa is Glu (E), Ile (I), or Ser (S)
<220> FEATURE:
<221> NAME/KEY: misc_feature
<222> LOCATION: (21)..(21)
<223> OTHER INFORMATION: Xaa is Ala (A), Thr (T), or Leu (L)
<220> FEATURE:
<221> NAME/KEY: misc_feature
<222> LOCATION: (22)..(22)
```

```
<223> OTHER INFORMATION: Xaa is Glu (E), Val (V), or Thr (T)
<220> FEATURE:
<221> NAME/KEY: misc_feature
<222> LOCATION: (23)..(23)
<223> OTHER INFORMATION: Xaa is Asn (N), Pro (P), or Thr (T)
<220> FEATURE:
<221> NAME/KEY: misc_feature
<222> LOCATION: (24)..(24)
<223> OTHER INFORMATION: Xaa is Ile (I), Asp (D), or Leu (L)

<400> SEQUENCE: 27

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 28
<211> LENGTH: 24
<212> TYPE: PRT
<213> ORGANISM: Artificial Sequence
<220> FEATURE:
<223> OTHER INFORMATION: Structural motif B, Peptide J

<400> SEQUENCE: 28

Pro Pro Arg Leu Ile Cys Asp Ser Arg Val Leu Glu Arg Tyr Leu Leu
1               5                   10                  15

Glu Ala Lys Glu Ala Glu Asn Ile
            20

<210> SEQ ID NO 29
<211> LENGTH: 24
<212> TYPE: PRT
<213> ORGANISM: Artificial Sequence
<220> FEATURE:
<223> OTHER INFORMATION: Structural motif B, Peptide K

<400> SEQUENCE: 29

Lys Glu Ala Glu Asn Ile Thr Thr Gly Cys Ala Glu His Cys Ser Leu
1               5                   10                  15

Asn Glu Asn Ile Thr Val Pro Asp
            20

<210> SEQ ID NO 30
<211> LENGTH: 24
<212> TYPE: PRT
<213> ORGANISM: Artificial Sequence
<220> FEATURE:
<223> OTHER INFORMATION: Structural motif B, Peptide L

<400> SEQUENCE: 30

Ser Gln Pro Trp Glu Pro Leu Gln Leu His Val Asp Lys Ala Val Ser
1               5                   10                  15

Gly Leu Arg Ser Leu Thr Thr Leu
            20

<210> SEQ ID NO 31
<211> LENGTH: 25
<212> TYPE: PRT
<213> ORGANISM: Artificial Sequence
<220> FEATURE:
<223> OTHER INFORMATION: Formula IV of structural motif B
<220> FEATURE:
<221> NAME/KEY: misc_feature
<222> LOCATION: (1)..(1)
<223> OTHER INFORMATION: Xaa is His (H)
<220> FEATURE:
<221> NAME/KEY: misc_feature
```

-continued

```
<222> LOCATION: (2)..(2)
<223> OTHER INFORMATION: Xaa is Cys (C)
<220> FEATURE:
<221> NAME/KEY: misc_feature
<222> LOCATION: (3)..(3)
<223> OTHER INFORMATION: Xaa is Ser (S)
<220> FEATURE:
<221> NAME/KEY: misc_feature
<222> LOCATION: (4)..(4)
<223> OTHER INFORMATION: Xaa is Leu (L)
<220> FEATURE:
<221> NAME/KEY: misc_feature
<222> LOCATION: (5)..(5)
<223> OTHER INFORMATION: Xaa is Ala (A) or Asn (N)
<220> FEATURE:
<221> NAME/KEY: misc_feature
<222> LOCATION: (6)..(6)
<223> OTHER INFORMATION: Xaa is Pro (P) or Glu (E)
<220> FEATURE:
<221> NAME/KEY: misc_feature
<222> LOCATION: (7)..(7)
<223> OTHER INFORMATION: Xaa is Pro (P) or Asn (N)
<220> FEATURE:
<221> NAME/KEY: misc_feature
<222> LOCATION: (8)..(8)
<223> OTHER INFORMATION: Xaa is Arg (R) or Ile (I)
<220> FEATURE:
<221> NAME/KEY: misc_feature
<222> LOCATION: (9)..(9)
<223> OTHER INFORMATION: Xaa is Leu (L) or Thr (T)
<220> FEATURE:
<221> NAME/KEY: misc_feature
<222> LOCATION: (10)..(10)
<223> OTHER INFORMATION: Xaa is Ile (I) or Val (V)
<220> FEATURE:
<221> NAME/KEY: misc_feature
<222> LOCATION: (11)..(11)
<223> OTHER INFORMATION: Xaa is Cys (C) or Pro (P)
<220> FEATURE:
<221> NAME/KEY: misc_feature
<222> LOCATION: (12)..(12)
<223> OTHER INFORMATION: Xaa is a negatively charged amino acid
<220> FEATURE:
<221> NAME/KEY: misc_feature
<222> LOCATION: (13)..(13)
<223> OTHER INFORMATION: Xaa is a polar amino acid
<220> FEATURE:
<221> NAME/KEY: misc_feature
<222> LOCATION: (14)..(14)
<223> OTHER INFORMATION: Xaa is a positively charged amino acid
<220> FEATURE:
<221> NAME/KEY: misc_feature
<222> LOCATION: (15)..(15)
<223> OTHER INFORMATION: Xaa is Val (V)
<220> FEATURE:
<221> NAME/KEY: misc_feature
<222> LOCATION: (16)..(16)
<223> OTHER INFORMATION: Xaa is Leu (L) or Asn (N)
<220> FEATURE:
<221> NAME/KEY: misc_feature
<222> LOCATION: (17)..(17)
<223> OTHER INFORMATION: Xaa is Glu (E) or Phe (F)
<220> FEATURE:
<221> NAME/KEY: misc_feature
<222> LOCATION: (18)..(18)
<223> OTHER INFORMATION: Xaa is Arg (R) or Tyr (Y)
<220> FEATURE:
<221> NAME/KEY: misc_feature
<222> LOCATION: (19)..(19)
<223> OTHER INFORMATION: Xaa is Tyr (Y) or Ala (A)
<220> FEATURE:
<221> NAME/KEY: misc_feature
<222> LOCATION: (20)..(20)
<223> OTHER INFORMATION: Xaa is Leu (L) or Trp (W)
<220> FEATURE:
<221> NAME/KEY: misc_feature
<222> LOCATION: (21)..(21)
<223> OTHER INFORMATION: Xaa is Leu (L) or Lys (K)
<220> FEATURE:
```

```
<221> NAME/KEY: misc_feature
<222> LOCATION: (22)..(22)
<223> OTHER INFORMATION: Xaa is Glu (E) or Arg (R)
<220> FEATURE:
<221> NAME/KEY: misc_feature
<222> LOCATION: (23)..(23)
<223> OTHER INFORMATION: Xaa is Ala (A) or Met (M)
<220> FEATURE:
<221> NAME/KEY: misc_feature
<222> LOCATION: (24)..(24)
<223> OTHER INFORMATION: Xaa is Lys (K) or Glu (E)
<220> FEATURE:
<221> NAME/KEY: misc_feature
<222> LOCATION: (25)..(25)
<223> OTHER INFORMATION: Xaa is Glu (E) or Val (V)

<400> SEQUENCE: 31

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 32
<211> LENGTH: 21
<212> TYPE: PRT
<213> ORGANISM: Artificial Sequence
<220> FEATURE:
<223> OTHER INFORMATION: Structural motif B, Peptide M

<400> SEQUENCE: 32

Ala Pro Pro Arg Leu Ile Cys Asp Ser Arg Val Leu Glu Arg Tyr Leu
1               5                   10                  15

Leu Glu Ala Lys Glu
            20

<210> SEQ ID NO 33
<211> LENGTH: 25
<212> TYPE: PRT
<213> ORGANISM: Artificial Sequence
<220> FEATURE:
<223> OTHER INFORMATION: Structural motif B, Peptide N

<400> SEQUENCE: 33

His Cys Ser Leu Asn Glu Asn Ile Thr Val Pro Asp Thr Lys Val Asn
1               5                   10                  15

Phe Tyr Ala Trp Lys Arg Met Glu Val
            20                  25

<210> SEQ ID NO 34
<211> LENGTH: 6
<212> TYPE: PRT
<213> ORGANISM: Artificial Sequence
<220> FEATURE:
<223> OTHER INFORMATION: Structural motif C
<220> FEATURE:
<221> NAME/KEY: misc_feature
<222> LOCATION: (1)..(1)
<223> OTHER INFORMATION: Xaa is a charged amino acid residue
<220> FEATURE:
<221> NAME/KEY: misc_feature
<222> LOCATION: (2)..(5)
<223> OTHER INFORMATION: Xaa is any amino acid
<220> FEATURE:
<221> NAME/KEY: misc_feature
<222> LOCATION: (6)..(6)
<223> OTHER INFORMATION: Xaa is a hydrophobic amino acid residue or Ala

<400> SEQUENCE: 34

Xaa Xaa Xaa Xaa Xaa Xaa
```

```
<210> SEQ ID NO 35
<211> LENGTH: 6
<212> TYPE: PRT
<213> ORGANISM: Artificial Sequence
<220> FEATURE:
<223> OTHER INFORMATION: Structural motif C
<220> FEATURE:
<221> NAME/KEY: misc_feature
<222> LOCATION: (3)..(5)
<223> OTHER INFORMATION: Xaa is any amino acid

<400> SEQUENCE: 35

Arg Ser Xaa Xaa Xaa Leu
1               5

<210> SEQ ID NO 36
<211> LENGTH: 6
<212> TYPE: PRT
<213> ORGANISM: Artificial Sequence
<220> FEATURE:
<223> OTHER INFORMATION: Structural motif C
<220> FEATURE:
<221> NAME/KEY: misc_feature
<222> LOCATION: (3)..(5)
<223> OTHER INFORMATION: Xaa is any amino acid

<400> SEQUENCE: 36

Arg Val Xaa Xaa Xaa Ala
1               5

<210> SEQ ID NO 37
<211> LENGTH: 6
<212> TYPE: PRT
<213> ORGANISM: Artificial Sequence
<220> FEATURE:
<223> OTHER INFORMATION: Structural motif C
<220> FEATURE:
<221> NAME/KEY: misc_feature
<222> LOCATION: (4)..(5)
<223> OTHER INFORMATION: Xaa is any amino acid

<400> SEQUENCE: 37

Arg Val Leu Xaa Xaa Tyr
1               5

<210> SEQ ID NO 38
<211> LENGTH: 6
<212> TYPE: PRT
<213> ORGANISM: Artificial Sequence
<220> FEATURE:
<223> OTHER INFORMATION: Structural motif C
<220> FEATURE:
<221> NAME/KEY: misc_feature
<222> LOCATION: (4)..(5)
<223> OTHER INFORMATION: Xaa is any amino acid

<400> SEQUENCE: 38

Lys Ala Val Xaa Xaa Leu
1               5

<210> SEQ ID NO 39
<211> LENGTH: 6
<212> TYPE: PRT
<213> ORGANISM: Artificial Sequence
<220> FEATURE:
<223> OTHER INFORMATION: Structural motif C
<220> FEATURE:
<221> NAME/KEY: misc_feature
```

```
<222> LOCATION: (2)..(2)
<223> OTHER INFORMATION: Xaa is any amino acid
<220> FEATURE:
<221> NAME/KEY: misc_feature
<222> LOCATION: (4)..(5)
<223> OTHER INFORMATION: Xaa is any amino acid

<400> SEQUENCE: 39

Arg Xaa Leu Xaa Xaa Leu
1               5

<210> SEQ ID NO 40
<211> LENGTH: 6
<212> TYPE: PRT
<213> ORGANISM: Artificial Sequence
<220> FEATURE:
<223> OTHER INFORMATION: Structural motif C
<220> FEATURE:
<221> NAME/KEY: misc_feature
<222> LOCATION: (4)..(5)
<223> OTHER INFORMATION: Xaa is any amino acid

<400> SEQUENCE: 40

Arg Ser Leu Xaa Xaa Leu
1               5

<210> SEQ ID NO 41
<211> LENGTH: 14
<212> TYPE: PRT
<213> ORGANISM: Artificial Sequence
<220> FEATURE:
<223> OTHER INFORMATION: Structural motif C, Peptide O

<400> SEQUENCE: 41

Asp Ser Arg Val Leu Glu Arg Tyr Leu Leu Glu Ala Lys Glu
1               5                   10

<210> SEQ ID NO 42
<211> LENGTH: 18
<212> TYPE: PRT
<213> ORGANISM: Artificial Sequence
<220> FEATURE:
<223> OTHER INFORMATION: Structural motif C, Peptide P

<400> SEQUENCE: 42

Asn Glu Asn Ile Thr Val Pro Asp Thr Lys Val Asn Phe Tyr Ala Trp
1               5                   10                  15

Lys Arg

<210> SEQ ID NO 43
<211> LENGTH: 20
<212> TYPE: PRT
<213> ORGANISM: Artificial Sequence
<220> FEATURE:
<223> OTHER INFORMATION: Structural motif C, Peptide Q

<400> SEQUENCE: 43

Gln Leu His Val Asp Lys Ala Val Ser Gly Leu Arg Ser Leu Thr Thr
1               5                   10                  15

Leu Leu Arg Ala
            20

<210> SEQ ID NO 44
<211> LENGTH: 18
<212> TYPE: PRT
<213> ORGANISM: Artificial Sequence
<220> FEATURE:
```

<223> OTHER INFORMATION: Structural motif C, Peptide R

<400> SEQUENCE: 44

Arg Val Tyr Ser Asn Phe Leu Arg Gly Lys Leu Lys Leu Tyr Thr Gly
1               5                   10                  15

Glu Ala

<210> SEQ ID NO 45
<211> LENGTH: 22
<212> TYPE: PRT
<213> ORGANISM: Artificial Sequence
<220> FEATURE:
<223> OTHER INFORMATION: Peptide derived from saposin C, Peptide HR

<400> SEQUENCE: 45

Cys Glu Phe Leu Val Lys Glu Val Thr Lys Leu Ile Asp Asn Asn Lys
1               5                   10                  15

Thr Glu Lys Glu Ile Leu
            20

<210> SEQ ID NO 46
<211> LENGTH: 20
<212> TYPE: PRT
<213> ORGANISM: Artificial Sequence
<220> FEATURE:
<223> OTHER INFORMATION: hCNTF AB loop derived Peptide HS

<400> SEQUENCE: 46

Tyr Val Lys His Gln Gly Leu Asn Lys Asn Ile Asn Leu Asp Ser Val
1               5                   10                  15

Asp Gly Val Pro
            20

<210> SEQ ID NO 47
<211> LENGTH: 23
<212> TYPE: PRT
<213> ORGANISM: Artificial Sequence
<220> FEATURE:
<223> OTHER INFORMATION: Neurotrophic peptide consensus sequence of
      structural motif D
<220> FEATURE:
<221> NAME/KEY: misc_feature
<222> LOCATION: (1)..(1)
<223> OTHER INFORMATION: Xaa is Leu (L) or Ile (I)
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is any amino acid or is absent
<220> FEATURE:
<221> NAME/KEY: misc_feature
<222> LOCATION: (5)..(5)
<223> OTHER INFORMATION: Xaa is Asn (N)
<220> FEATURE:
<221> NAME/KEY: misc_feature
<222> LOCATION: (6)..(6)
<223> OTHER INFORMATION: Xaa is any amino acid or is absent
<220> FEATURE:
<221> NAME/KEY: misc_feature
<222> LOCATION: (7)..(7)
<223> OTHER INFORMATION: Xaa is Asn (N)
<220> FEATURE:
<221> NAME/KEY: misc_feature
<222> LOCATION: (8)..(8)
<223> OTHER INFORMATION: Xaa is any amino acid
<220> FEATURE:
<221> NAME/KEY: misc_feature

```
<222> LOCATION: (9)..(14)
<223> OTHER INFORMATION: Xaa is any amino acid or is absent
<220> FEATURE:
<221> NAME/KEY: misc_feature
<222> LOCATION: (15)..(15)
<223> OTHER INFORMATION: Xaa is Asp (D), Lys (K), Glu (E), or Arg (R)
<220> FEATURE:
<221> NAME/KEY: misc_feature
<222> LOCATION: (16)..(19)
<223> OTHER INFORMATION: Xaa is any amino acid
<220> FEATURE:
<221> NAME/KEY: misc_feature
<222> LOCATION: (20)..(22)
<223> OTHER INFORMATION: Xaa is any amino acid or is absent
<220> FEATURE:
<221> NAME/KEY: misc_feature
<222> LOCATION: (23)..(23)
<223> OTHER INFORMATION: Xaa is Ala (A), Leu (L), Ile (I), or Val (V)

<400> SEQUENCE: 47

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 48
<211> LENGTH: 17
<212> TYPE: PRT
<213> ORGANISM: Artificial Sequence
<220> FEATURE:
<223> OTHER INFORMATION: Structural motif D, Peptide U

<400> SEQUENCE: 48

Ala Glu His Cys Ser Leu Asn Glu Asn Ile Thr Val Pro Asp Thr Lys
1               5                   10                  15

Val

<210> SEQ ID NO 49
<211> LENGTH: 10
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (1)..(1)
<223> OTHER INFORMATION: Xaa is Cys (C), Glu (E), Ala (A), alpha-amino-
      gamma-bromobutyric acid, or homocysteine
<220> FEATURE:
<221> NAME/KEY: misc_feature
<222> LOCATION: (2)..(2)
<223> OTHER INFORMATION: Xaa is Arg (R), His (H), Tyr (Y), Leu (L), or
      Trp (W), or is absent
<220> FEATURE:
<221> NAME/KEY: misc_feature
<222> LOCATION: (3)..(3)
<223> OTHER INFORMATION: Xaa is Met (M), Phe (F), or Ile (I)
<220> FEATURE:
<221> NAME/KEY: misc_feature
<222> LOCATION: (6)..(6)
<223> OTHER INFORMATION: Xaa is any amino acid
<220> FEATURE:
<221> NAME/KEY: misc_feature
<222> LOCATION: (9)..(9)
<223> OTHER INFORMATION: Xaa is Asp (D), Glu (E), Ile (I), Leu (L), or
      Val (V)
<220> FEATURE:
<221> NAME/KEY: misc_feature
<222> LOCATION: (10)..(10)
<223> OTHER INFORMATION: Xaa is Cys (C), Lys (K), Ala (A), alpha-amino-
      gamma-bromobutyric acid, or homocysteine

<400> SEQUENCE: 49
```

```
Xaa Xaa Xaa Gly Pro Xaa Thr Trp Xaa Xaa
1               5                   10
```

<210> SEQ ID NO 50
<211> LENGTH: 12
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is Cys (C), Glu (E), Ala (A), alpha-amino-
      gamma-bromobutyric acid, or homocysteine
<220> FEATURE:
<221> NAME/KEY: misc_feature
<222> LOCATION: (4)..(4)
<223> OTHER INFORMATION: Xaa is Arg (R), His (H), Tyr (Y), Leu (L), or
      Trp (W), or is absent
<220> FEATURE:
<221> NAME/KEY: misc_feature
<222> LOCATION: (5)..(5)
<223> OTHER INFORMATION: Xaa is Met (M), Phe (F), or Ile (I)
<220> FEATURE:
<221> NAME/KEY: misc_feature
<222> LOCATION: (8)..(8)
<223> OTHER INFORMATION: Xaa is any amino acid
<220> FEATURE:
<221> NAME/KEY: misc_feature
<222> LOCATION: (11)..(11)
<223> OTHER INFORMATION: Xaa is Asp (D), Glu (E), Ile (I), Leu (L), or
      Val (V)
<220> FEATURE:
<221> NAME/KEY: misc_feature
<222> LOCATION: (12)..(12)
<223> OTHER INFORMATION: Xaa is Cys (C), Lys (K), Ala (A), alpha-amino-
      gamma-bromobutyric acid, or homocysteine

<400> SEQUENCE: 50

```
Tyr Xaa Xaa Xaa Xaa Gly Pro Xaa Thr Trp Xaa Xaa
1               5                   10
```

<210> SEQ ID NO 51
<211> LENGTH: 12
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is Cys (C)
<220> FEATURE:
<221> NAME/KEY: misc_feature
<222> LOCATION: (4)..(4)
<223> OTHER INFORMATION: Xaa is Arg (R), His (H), Tyr (Y), Leu (L), or
      Trp (W), or is absent
<220> FEATURE:
<221> NAME/KEY: misc_feature
<222> LOCATION: (5)..(5)
<223> OTHER INFORMATION: Xaa is Met (M), Phe (F), or Ile (I)
<220> FEATURE:
<221> NAME/KEY: misc_feature
<222> LOCATION: (8)..(8)
<223> OTHER INFORMATION: Xaa is any amino acid
<220> FEATURE:
<221> NAME/KEY: misc_feature

```
<222> LOCATION: (11)..(11)
<223> OTHER INFORMATION: Xaa is Asp (D), Glu (E), Ile (I), Leu (L), or
      Val (V)
<220> FEATURE:
<221> NAME/KEY: misc_feature
<222> LOCATION: (12)..(12)
<223> OTHER INFORMATION: Xaa is Cys (C)

<400> SEQUENCE: 51

Tyr Xaa Xaa Xaa Xaa Gly Pro Xaa Thr Trp Xaa Xaa
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (1)..(1)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is Cys (C), Glu (E), Ala (A)
<220> FEATURE:
<221> NAME/KEY: misc_feature
<222> LOCATION: (5)..(5)
<223> OTHER INFORMATION: Xaa is Arg (R), His (H), Tyr (Y), or is absent
<220> FEATURE:
<221> NAME/KEY: misc_feature
<222> LOCATION: (6)..(6)
<223> OTHER INFORMATION: Met (M), Phe (F), or Ile
<220> FEATURE:
<221> NAME/KEY: misc_feature
<222> LOCATION: (9)..(9)
<223> OTHER INFORMATION: Xaa is any amino acid
<220> FEATURE:
<221> NAME/KEY: misc_feature
<222> LOCATION: (12)..(12)
<223> OTHER INFORMATION: Xaa is Asp (D) or Val (V)
<220> FEATURE:
<221> NAME/KEY: misc_feature
<222> LOCATION: (13)..(13)
<223> OTHER INFORMATION: Xaa is Cys (C), Lys (K), or Ala (A)
<220> FEATURE:
<221> NAME/KEY: misc_feature
<222> LOCATION: (14)..(16)
<223> OTHER INFORMATION: Xaa is any amino acid

<400> SEQUENCE: 52

Xaa Tyr Xaa Xaa Xaa Xaa Gly Pro Xaa Thr Trp Xaa Xaa Xaa Xaa
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (1)..(1)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
```

```
<222> LOCATION: (5)..(5)
<223> OTHER INFORMATION: Xaa is Arg (R), His (H), Tyr (Y), or is absent
<220> FEATURE:
<221> NAME/KEY: misc_feature
<222> LOCATION: (6)..(6)
<223> OTHER INFORMATION: Xaa is Met (M), Phe (F), or Ile (I)
<220> FEATURE:
<221> NAME/KEY: misc_feature
<222> LOCATION: (9)..(9)
<223> OTHER INFORMATION: Xaa is any amino acid
<220> FEATURE:
<221> NAME/KEY: misc_feature
<222> LOCATION: (12)..(12)
<223> OTHER INFORMATION: Xaa is Asp (D) or Val (V)
<220> FEATURE:
<221> NAME/KEY: misc_feature
<222> LOCATION: (14)..(16)
<223> OTHER INFORMATION: Xaa is any amino acid

<400> SEQUENCE: 53

Xaa Tyr Xaa Cys Xaa Xaa Gly Pro Xaa Thr Trp Xaa Cys Xaa Xaa Xaa
 1               5                  10                  15

<210> SEQ ID NO 54
<211> LENGTH: 16
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (1)..(1)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is Arg (R) or His (H)
<220> FEATURE:
<221> NAME/KEY: misc_feature
<222> LOCATION: (6)..(6)
<223> OTHER INFORMATION: Xaa is Phe (F) or Met (M)
<220> FEATURE:
<221> NAME/KEY: misc_feature
<222> LOCATION: (9)..(9)
<223> OTHER INFORMATION: Xaa is Ile (I), Leu (L), Thr (T), Met (M), or
     Val (V)
<220> FEATURE:
<221> NAME/KEY: misc_feature
<222> LOCATION: (12)..(12)
<223> OTHER INFORMATION: Xaa is Asp (D) or Val (V)
<220> FEATURE:
<221> NAME/KEY: misc_feature
<222> LOCATION: (14)..(14)
<223> OTHER INFORMATION: Xaa is Gly (G), Lys (K), Leu (L), Gln (Q), Arg
     (R), Ser (S), or Thr (T)
<220> FEATURE:
<221> NAME/KEY: misc_feature
<222> LOCATION: (15)..(15)
<223> OTHER INFORMATION: Xaa is Ala (A), Gly (G), Pro (P), Arg (R), or
     Tyr (Y)
<220> FEATURE:
<221> NAME/KEY: misc_feature
<222> LOCATION: (16)..(16)
<223> OTHER INFORMATION: Xaa is any amino acid

<400> SEQUENCE: 54

Xaa Tyr Xaa Cys Xaa Xaa Gly Pro Xaa Thr Trp Xaa Cys Xaa Xaa Xaa
 1               5                  10                  15

<210> SEQ ID NO 55
<211> LENGTH: 16
```

```
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (1)..(1)
<223> OTHER INFORMATION: Xaa is Asp (D), Glu (E), Leu (L), Asn (N), Ser
      (S), Thr (T), or Val (V)
<220> FEATURE:
<221> NAME/KEY: misc_feature
<222> LOCATION: (3)..(3)
<223> OTHER INFORMATION: Xaa is Ala (A), His (H), Lys (K), Leu (L), Met
      (M), Ser (S), or Thr (T)
<220> FEATURE:
<221> NAME/KEY: misc_feature
<222> LOCATION: (5)..(5)
<223> OTHER INFORMATION: Xaa is Arg (R) or His (H)
<220> FEATURE:
<221> NAME/KEY: misc_feature
<222> LOCATION: (6)..(6)
<223> OTHER INFORMATION: Xaa is Met (M), Phe (F) or Ile (I)
<220> FEATURE:
<221> NAME/KEY: misc_feature
<222> LOCATION: (9)..(9)
<223> OTHER INFORMATION: Xaa is any amino acid
<220> FEATURE:
<221> NAME/KEY: misc_feature
<222> LOCATION: (12)..(12)
<223> OTHER INFORMATION: Xaa is Asp (D) or Val (V)
<220> FEATURE:
<221> NAME/KEY: misc_feature
<222> LOCATION: (14)..(14)
<223> OTHER INFORMATION: Xaa is Lys (K), Arg (R), Ser (S), or Thr (T)
<220> FEATURE:
<221> NAME/KEY: misc_feature
<222> LOCATION: (15)..(15)
<223> OTHER INFORMATION: Xaa is Pro (P)
<220> FEATURE:
<221> NAME/KEY: misc_feature
<222> LOCATION: (16)..(16)
<223> OTHER INFORMATION: Xaa is any amino acid

<400> SEQUENCE: 55

Xaa Tyr Xaa Cys Xaa Xaa Gly Pro Xaa Thr Trp Xaa Cys Xaa Xaa Xaa
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Structural motif E
<220> FEATURE:
<221> NAME/KEY: misc_feature
<222> LOCATION: (1)..(1)
<223> OTHER INFORMATION: Xaa is Asp (D), Glu (E), Leu (L), Asn (N), Ser
      (S), Thr (T), or Val (V)
<220> FEATURE:
<221> NAME/KEY: misc_feature
<222> LOCATION: (3)..(3)
<223> OTHER INFORMATION: Xaa is Ala (A), His (H), Lys (K), Leu (L), Met
      (M), Ser (S), or Thr (T)
<220> FEATURE:
<221> NAME/KEY: misc_feature
<222> LOCATION: (5)..(5)
<223> OTHER INFORMATION: Xaa is Arg (R) or His (H)
<220> FEATURE:
<221> NAME/KEY: misc_feature
<222> LOCATION: (6)..(6)
<223> OTHER INFORMATION: Xaa is Met (M), Phe (F), or Ile (I)
<220> FEATURE:
<221> NAME/KEY: misc_feature
<222> LOCATION: (9)..(9)
<223> OTHER INFORMATION: Xaa is any amino acid
<220> FEATURE:
<221> NAME/KEY: misc_feature
```

```
<222> LOCATION: (12)..(12)
<223> OTHER INFORMATION: Xaa is Asp (D), or Val (V)
<220> FEATURE:
<221> NAME/KEY: misc_feature
<222> LOCATION: (14)..(14)
<223> OTHER INFORMATION: Xaa is Lys (K), Arg (R), Ser (S), or Thr (T)
<220> FEATURE:
<221> NAME/KEY: misc_feature
<222> LOCATION: (15)..(15)
<223> OTHER INFORMATION: Xaa is Pro (P)
<220> FEATURE:
<221> NAME/KEY: misc_feature
<222> LOCATION: (16)..(16)
<223> OTHER INFORMATION: Xaa is any amino acid

<400> SEQUENCE: 56

Xaa Tyr Xaa Cys Xaa Xaa Gly Pro Xaa Thr Trp Xaa Cys Xaa Xaa Xaa
1               5                   10                  15

<210> SEQ ID NO 57
<211> LENGTH: 20
<212> TYPE: PRT
<213> ORGANISM: Artificial Sequence
<220> FEATURE:
<223> OTHER INFORMATION: Structural motif E, Peptide S

<400> SEQUENCE: 57

Gly Gly Leu Tyr Leu Cys Arg Phe Gly Pro Val Thr Trp Asp Cys Gly
1               5                   10                  15

Tyr Lys Gly Gly
            20

<210> SEQ ID NO 58
<211> LENGTH: 20
<212> TYPE: PRT
<213> ORGANISM: Artificial Sequence
<220> FEATURE:
<223> OTHER INFORMATION: Structural motif E, Peptide T

<400> SEQUENCE: 58

Gly Gly Thr Tyr Ser Cys His Phe Gly Pro Leu Thr Trp Val Cys Lys
1               5                   10                  15

Pro Gln Gly Gly
            20

<210> SEQ ID NO 59
<211> LENGTH: 20
<212> TYPE: PRT
<213> ORGANISM: Artificial Sequence
<220> FEATURE:
<223> OTHER INFORMATION: Structural motif E, Peptide U

<400> SEQUENCE: 59

Gly Gly Asp Tyr His Cys Arg Met Gly Pro Leu Thr Trp Val Cys Lys
1               5                   10                  15

Pro Leu Gly Gly
            20

<210> SEQ ID NO 60
<211> LENGTH: 20
<212> TYPE: PRT
<213> ORGANISM: Artificial Sequence
<220> FEATURE:
<223> OTHER INFORMATION: Structural motif E, Peptide V

<400> SEQUENCE: 60

Val Gly Asn Tyr Met Cys His Phe Gly Pro Ile Thr Trp Val Cys Arg
```

```
                   1               5                  10                 15

Pro Gly Gly Gly
            20

<210> SEQ ID NO 61
<211> LENGTH: 20
<212> TYPE: PRT
<213> ORGANISM: Artificial Sequence
<220> FEATURE:
<223> OTHER INFORMATION: Structural motif E, Peptide W

<400> SEQUENCE: 61

Gly Gly Val Tyr Ala Cys Arg Met Gly Pro Ile Thr Trp Val Cys Ser
1               5                  10                 15

Pro Leu Gly Gly
            20

<210> SEQ ID NO 62
<211> LENGTH: 19
<212> TYPE: PRT
<213> ORGANISM: Artificial Sequence
<220> FEATURE:
<223> OTHER INFORMATION: Structural motif E, Peptide X

<400> SEQUENCE: 62

Val Gly Asn Tyr Met Ala His Met Gly Pro Ile Thr Trp Val Cys Arg
1               5                  10                 15

Pro Gly Gly

<210> SEQ ID NO 63
<211> LENGTH: 18
<212> TYPE: PRT
<213> ORGANISM: Artificial Sequence
<220> FEATURE:
<223> OTHER INFORMATION: Structural motif E, Peptide Y

<400> SEQUENCE: 63

Gly Gly Thr Tyr Ser Cys His Phe Gly Pro Leu Thr Trp Val Cys Lys
1               5                  10                 15

Pro Gln

<210> SEQ ID NO 64
<211> LENGTH: 20
<212> TYPE: PRT
<213> ORGANISM: Artificial Sequence
<220> FEATURE:
<223> OTHER INFORMATION: Structural motif E, Peptide Z

<400> SEQUENCE: 64

Gly Gly Leu Tyr Ala Cys His Met Gly Pro Met Thr Trp Val Cys Gln
1               5                  10                 15

Pro Leu Arg Gly
            20

<210> SEQ ID NO 65
<211> LENGTH: 22
<212> TYPE: PRT
<213> ORGANISM: Artificial Sequence
<220> FEATURE:
<223> OTHER INFORMATION: Structural motif E, Peptide AA

<400> SEQUENCE: 65

Thr Ile Ala Gln Tyr Ile Cys Tyr Met Gly Pro Glu Thr Trp Glu Cys
1               5                  10                 15
```

Arg Pro Ser Pro Lys Ala
            20

<210> SEQ ID NO 66
<211> LENGTH: 13
<212> TYPE: PRT
<213> ORGANISM: Artificial Sequence
<220> FEATURE:
<223> OTHER INFORMATION: Structural motif E, Peptide AB

<400> SEQUENCE: 66

Tyr Ser Cys His Phe Gly Pro Leu Thr Trp Val Cys Lys
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Structural motif E, Peptide AC

<400> SEQUENCE: 67

Tyr Cys His Phe Gly Pro Leu Thr Trp Val Cys
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Structural motif E, Peptide AD

<400> SEQUENCE: 68

Ser Cys His Phe Gly Pro Leu Thr Trp Val Cys Lys
1               5                   10

<210> SEQ ID NO 69
<211> LENGTH: 20
<212> TYPE: PRT
<213> ORGANISM: Artificial Sequence
<220> FEATURE:
<223> OTHER INFORMATION: Structural motif E, Peptide AE

<400> SEQUENCE: 69

Gly Gly Thr Ala Ser Cys His Phe Gly Pro Leu Thr Trp Val Cys Lys
1               5                   10                  15

Pro Gln Gly Gly
            20

<210> SEQ ID NO 70
<211> LENGTH: 20
<212> TYPE: PRT
<213> ORGANISM: Artificial Sequence
<220> FEATURE:
<223> OTHER INFORMATION: Structural motif E, Peptide AF

<400> SEQUENCE: 70

Gly Gly Thr Tyr Ser Cys His Phe Ala Pro Leu Thr Trp Val Cys Lys
1               5                   10                  15

Pro Gln Gly Gly
            20

<210> SEQ ID NO 71
<211> LENGTH: 19
<212> TYPE: PRT

<213> ORGANISM: Artificial Sequence
<220> FEATURE:
<223> OTHER INFORMATION: Structural motif E, Peptide AG

<400> SEQUENCE: 71

Gly Gly Thr Tyr Ser Cys Phe Gly Pro Leu Thr Trp Val Cys Lys Pro
1               5                   10                  15

Gln Gly Gly

<210> SEQ ID NO 72
<211> LENGTH: 18
<212> TYPE: PRT
<213> ORGANISM: Artificial Sequence
<220> FEATURE:
<223> OTHER INFORMATION: Structural motif E, Peptide AH

<400> SEQUENCE: 72

Thr Tyr Ser Cys His Phe Gly Pro Leu Thr Trp Val Cys Lys Pro Gln
1               5                   10                  15

Gly Gly

<210> SEQ ID NO 73
<211> LENGTH: 16
<212> TYPE: PRT
<213> ORGANISM: Artificial Sequence
<220> FEATURE:
<223> OTHER INFORMATION: Structural motif E, Peptide AI

<400> SEQUENCE: 73

Thr Tyr Ser Cys His Phe Gly Pro Leu Thr Trp Val Cys Lys Pro Gln
1               5                   10                  15

<210> SEQ ID NO 74
<211> LENGTH: 14
<212> TYPE: PRT
<213> ORGANISM: Artificial Sequence
<220> FEATURE:
<223> OTHER INFORMATION: Structural motif E, Peptide AJ

<400> SEQUENCE: 74

Tyr Ser Cys His Phe Gly Pro Leu Thr Trp Val Cys Lys Pro
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Structural motif E, Peptide AK

<400> SEQUENCE: 75

Tyr Ser Cys His Phe Gly Pro Leu Thr Trp Val Cys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Structural motif E, Peptide AL

<400> SEQUENCE: 76

Tyr Ser Cys His Phe Gly Ala Leu Thr Trp Val Cys Lys
1               5                   10

```
<210> SEQ ID NO 77
<211> LENGTH: 14
<212> TYPE: PRT
<213> ORGANISM: Artificial Sequence
<220> FEATURE:
<223> OTHER INFORMATION: Structural motif E, Peptide AM

<400> SEQUENCE: 77

Gly Gly Cys Arg Ile Gly Pro Ile Thr Trp Val Cys Gly Gly
1               5                   10

<210> SEQ ID NO 78
<211> LENGTH: 8
<212> TYPE: PRT
<213> ORGANISM: Artificial Sequence
<220> FEATURE:
<223> OTHER INFORMATION: Structural motif E, Peptide AN

<400> SEQUENCE: 78

His Phe Gly Pro Leu Thr Trp Val
1               5

<210> SEQ ID NO 79
<211> LENGTH: 20
<212> TYPE: PRT
<213> ORGANISM: Artificial Sequence
<220> FEATURE:
<223> OTHER INFORMATION: Structural motif E, Peptide AO

<400> SEQUENCE: 79

Gly Gly Thr Thr Ser Cys His Phe Gly Pro Leu Thr Trp Val Cys Lys
1               5                   10                  15

Pro Gln Gly Gly
            20

<210> SEQ ID NO 80
<211> LENGTH: 20
<212> TYPE: PRT
<213> ORGANISM: Artificial Sequence
<220> FEATURE:
<223> OTHER INFORMATION: Structural motif E, Peptide AP

<400> SEQUENCE: 80

Gly Gly Thr Phe Ser Cys His Phe Gly Pro Leu Thr Trp Val Cys Lys
1               5                   10                  15

Pro Gln Gly Gly
            20

<210> SEQ ID NO 81
<211> LENGTH: 20
<212> TYPE: PRT
<213> ORGANISM: Artificial Sequence
<220> FEATURE:
<223> OTHER INFORMATION: Structural motif E, Peptide AQ

<400> SEQUENCE: 81

Gly Gly Thr Tyr Ser Cys His Phe Gly Ala Leu Thr Trp Val Cys Lys
1               5                   10                  15

Pro Gln Gly Gly
            20

<210> SEQ ID NO 82
<211> LENGTH: 20
<212> TYPE: PRT
<213> ORGANISM: Artificial Sequence
<220> FEATURE:
```

<223> OTHER INFORMATION: Structural motif E, Peptide AR

<400> SEQUENCE: 82

Gly Gly Thr Tyr Ser Cys His Phe Gly Pro Ala Thr Trp Val Cys Lys
1               5                   10                  15
Pro Gln Gly Gly
            20

<210> SEQ ID NO 83
<211> LENGTH: 20
<212> TYPE: PRT
<213> ORGANISM: Artificial Sequence
<220> FEATURE:
<223> OTHER INFORMATION: Structural motif E, Peptide AS

<400> SEQUENCE: 83

Gly Gly Thr Tyr Ser Cys His Phe Gly Pro Leu Ala Trp Val Cys Lys
1               5                   10                  15
Pro Gln Gly Gly
            20

<210> SEQ ID NO 84
<211> LENGTH: 20
<212> TYPE: PRT
<213> ORGANISM: Artificial Sequence
<220> FEATURE:
<223> OTHER INFORMATION: Structural motif E, Peptide AT

<400> SEQUENCE: 84

Gly Gly Thr Tyr Ser Cys His Phe Gly Pro Leu Thr Ala Val Cys Lys
1               5                   10                  15
Pro Gln Gly Gly
            20

<210> SEQ ID NO 85
<211> LENGTH: 20
<212> TYPE: PRT
<213> ORGANISM: Artificial Sequence
<220> FEATURE:
<223> OTHER INFORMATION: Structural motif E, Peptide AU

<400> SEQUENCE: 85

Gly Gly Thr Tyr Ser Cys His Phe Gly Pro Leu Thr Phe Val Cys Lys
1               5                   10                  15
Pro Gln Gly Gly
            20

<210> SEQ ID NO 86
<211> LENGTH: 20
<212> TYPE: PRT
<213> ORGANISM: Artificial Sequence
<220> FEATURE:
<223> OTHER INFORMATION: Structural motif E, Peptide AV

<400> SEQUENCE: 86

Gly Gly Thr Tyr Ser Cys His Phe Gly Pro Leu Thr Trp Val Cys Lys
1               5                   10                  15
Ala Gln Gly Gly
            20

<210> SEQ ID NO 87
<211> LENGTH: 20
<212> TYPE: PRT
<213> ORGANISM: Artificial Sequence

```
<220> FEATURE:
<223> OTHER INFORMATION: Structural motif E, Peptide AW
<220> FEATURE:
<221> NAME/KEY: misc_feature
<222> LOCATION: (4)..(4)
<223> OTHER INFORMATION: Xaa is any amino acid

<400> SEQUENCE: 87

Gly Gly Thr Xaa Ser Cys His Phe Gly Pro Leu Thr Trp Val Cys Lys
1               5                   10                  15

Pro Gln Gly Gly
            20

<210> SEQ ID NO 88
<211> LENGTH: 20
<212> TYPE: PRT
<213> ORGANISM: Artificial Sequence
<220> FEATURE:
<223> OTHER INFORMATION: Structural motif E, Peptide AX
<220> FEATURE:
<221> NAME/KEY: misc_feature
<222> LOCATION: (4)..(4)
<223> OTHER INFORMATION: Xaa is any amino acid

<400> SEQUENCE: 88

Gly Gly Thr Xaa Ser Cys His Phe Gly Pro Leu Thr Trp Val Cys Lys
1               5                   10                  15

Pro Gln Gly Gly
            20

<210> SEQ ID NO 89
<211> LENGTH: 20
<212> TYPE: PRT
<213> ORGANISM: Artificial Sequence
<220> FEATURE:
<223> OTHER INFORMATION: Structural motif E, Peptide AY
<220> FEATURE:
<221> NAME/KEY: misc_feature
<222> LOCATION: (4)..(4)
<223> OTHER INFORMATION: Xaa is p-NH2-Phe

<400> SEQUENCE: 89

Gly Gly Thr Xaa Ser Cys His Phe Gly Pro Leu Thr Trp Val Cys Lys
1               5                   10                  15

Pro Gln Gly Gly
            20

<210> SEQ ID NO 90
<211> LENGTH: 20
<212> TYPE: PRT
<213> ORGANISM: Artificial Sequence
<220> FEATURE:
<223> OTHER INFORMATION: Structural motif E, Peptide AZ
<220> FEATURE:
<221> NAME/KEY: misc_feature
<222> LOCATION: (4)..(4)
<223> OTHER INFORMATION: Xaa is p-F-Phe

<400> SEQUENCE: 90

Gly Gly Thr Xaa Ser Cys His Phe Gly Pro Leu Thr Trp Val Cys Lys
1               5                   10                  15

Pro Gln Gly Gly
            20

<210> SEQ ID NO 91
<211> LENGTH: 20
<212> TYPE: PRT
```

-continued

```
<213> ORGANISM: Artificial Sequence
<220> FEATURE:
<223> OTHER INFORMATION: Structural motif E, Peptide BA
<220> FEATURE:
<221> NAME/KEY: misc_feature
<222> LOCATION: (4)..(4)
<223> OTHER INFORMATION: Xaa is p-I-Phe

<400> SEQUENCE: 91

Gly Gly Thr Xaa Ser Cys His Phe Gly Pro Leu Thr Trp Val Cys Lys
1               5                   10                  15

Pro Gln Gly Gly
            20

<210> SEQ ID NO 92
<211> LENGTH: 20
<212> TYPE: PRT
<213> ORGANISM: Artificial Sequence
<220> FEATURE:
<223> OTHER INFORMATION: Structural motif E, Peptide BB
<220> FEATURE:
<221> NAME/KEY: misc_feature
<222> LOCATION: (4)..(4)
<223> OTHER INFORMATION: Xaa is 3,5-dibromo-Tyr

<400> SEQUENCE: 92

Gly Gly Thr Xaa Ser Cys His Phe Gly Pro Leu Thr Trp Val Cys Lys
1               5                   10                  15

Pro Gln Gly Gly
            20

<210> SEQ ID NO 93
<211> LENGTH: 20
<212> TYPE: PRT
<213> ORGANISM: Artificial Sequence
<220> FEATURE:
<223> OTHER INFORMATION: Structural motif E, Peptide BC
<220> FEATURE:
<221> NAME/KEY: MOD_RES
<222> LOCATION: (1)..(1)
<223> OTHER INFORMATION: Xaa is modified Gly with ACETYLATION,
      N-terminal

<400> SEQUENCE: 93

Xaa Gly Thr Tyr Ser Cys His Phe Gly Pro Leu Thr Trp Val Cys Lys
1               5                   10                  15

Pro Gln Gly Gly
            20

<210> SEQ ID NO 94
<211> LENGTH: 20
<212> TYPE: PRT
<213> ORGANISM: Artificial Sequence
<220> FEATURE:
<223> OTHER INFORMATION: Structural motif E, Peptide BD

<400> SEQUENCE: 94

Gly Gly Leu Tyr Ala Cys His Met Gly Pro Met Thr Trp Val Cys Gln
1               5                   10                  15

Pro Leu Gly Gly
            20

<210> SEQ ID NO 95
<211> LENGTH: 22
<212> TYPE: PRT
<213> ORGANISM: Artificial Sequence
<220> FEATURE:
```

-continued

```
<223> OTHER INFORMATION: Structural motif E, Peptide BE

<400> SEQUENCE: 95

Leu Gly Arg Lys Tyr Ser Cys His Phe Gly Pro Leu Thr Trp Val Cys
1               5                   10                  15

Gln Pro Ala Lys Lys Asp
            20

<210> SEQ ID NO 96
<211> LENGTH: 20
<212> TYPE: PRT
<213> ORGANISM: Artificial Sequence
<220> FEATURE:
<223> OTHER INFORMATION: Structural motif E, Peptide BF

<400> SEQUENCE: 96

Gly Gly Thr Tyr Ser Glu His Phe Gly Pro Leu Thr Trp Val Lys Lys
1               5                   10                  15

Pro Gln Gly Gly
            20

<210> SEQ ID NO 97
<211> LENGTH: 17
<212> TYPE: PRT
<213> ORGANISM: Artificial Sequence
<220> FEATURE:
<223> OTHER INFORMATION: Structural motif F, Peptide BG
<220> FEATURE:
<221> NAME/KEY: MOD_RES
<222> LOCATION: (1)..(1)
<223> OTHER INFORMATION: Xaa is modified Ala with N-terminal D-biotin

<400> SEQUENCE: 97

Xaa Glu His Cys Ser Leu Asn Glu Asn Ile Thr Val Pro Asp Thr Lys
1               5                   10                  15

Val

<210> SEQ ID NO 98
<211> LENGTH: 13
<212> TYPE: PRT
<213> ORGANISM: Artificial Sequence
<220> FEATURE:
<223> OTHER INFORMATION: Structural motif F, Peptide BH
<220> FEATURE:
<221> NAME/KEY: MOD_RES
<222> LOCATION: (1)..(1)
<223> OTHER INFORMATION: Xaa is modified Ala with N-terminal D-biotin

<400> SEQUENCE: 98

Xaa Glu His Cys Ser Leu Asn Glu Asn Ile Thr Val Pro
1               5                   10

<210> SEQ ID NO 99
<211> LENGTH: 17
<212> TYPE: PRT
<213> ORGANISM: Artificial Sequence
<220> FEATURE:
<223> OTHER INFORMATION: Structural motif F, Peptide BI
<220> FEATURE:
<221> NAME/KEY: MOD_RES
<222> LOCATION: (17)..(17)
<223> OTHER INFORMATION: Xaa is modified Lys with C-terminal biotin

<400> SEQUENCE: 99

Ala Glu His Cys Ser Leu Asn Glu Asn Ile Thr Val Pro Asp Thr Lys
1               5                   10                  15
```

```
Xaa

<210> SEQ ID NO 100
<211> LENGTH: 13
<212> TYPE: PRT
<213> ORGANISM: Artificial Sequence
<220> FEATURE:
<223> OTHER INFORMATION: Structural motif F, Peptide BJ
<220> FEATURE:
<221> NAME/KEY: MOD_RES
<222> LOCATION: (13)..(13)
<223> OTHER INFORMATION: Xaa is modified Pro with C-terminal D-biotin

<400> SEQUENCE: 100

Ala Glu His Cys Ser Leu Asn Glu Asn Ile Thr Val Xaa
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Formula I of structural motif F
<220> FEATURE:
<221> NAME/KEY: misc_feature
<222> LOCATION: (1)..(1)
<223> OTHER INFORMATION: Xaa is any amino acid containing a sulfhydral
      group
<220> FEATURE:
<221> NAME/KEY: misc_feature
<222> LOCATION: (5)..(5)
<223> OTHER INFORMATION: Xaa is a any amino acid containing a sulfhydral
      group

<400> SEQUENCE: 101

Xaa Ala Glu His Xaa Ser
1               5

<210> SEQ ID NO 102
<211> LENGTH: 20
<212> TYPE: PRT
<213> ORGANISM: Artificial Sequence
<220> FEATURE:
<223> OTHER INFORMATION: Structural motif F, Peptide BK

<400> SEQUENCE: 102

Thr Thr Gly Cys Ala Glu His Cys Ser Leu Asn Glu Asn Ile Thr Val
1               5                   10                  15

Pro Asp Thr Lys
            20

<210> SEQ ID NO 103
<211> LENGTH: 18
<212> TYPE: PRT
<213> ORGANISM: Artificial Sequence
<220> FEATURE:
<223> OTHER INFORMATION: Structural motif F, Peptide BL

<400> SEQUENCE: 103

Cys Ala Glu His Cys Ser Leu Asn Glu Asn Ile Thr Val Pro Asp Thr
1               5                   10                  15

Lys Val

<210> SEQ ID NO 104
<211> LENGTH: 6
<212> TYPE: PRT
<213> ORGANISM: Artificial Sequence
<220> FEATURE:
```

<223> OTHER INFORMATION: Structural motif F, Peptide BM

<400> SEQUENCE: 104

Cys Ala Glu His Cys Ser
1               5

<210> SEQ ID NO 105
<211> LENGTH: 8
<212> TYPE: PRT
<213> ORGANISM: Artificial Sequence
<220> FEATURE:
<223> OTHER INFORMATION: Structural motif F, Peptide BN

<400> SEQUENCE: 105

Gly Cys Ala Glu His Cys Ser Leu
1               5

<210> SEQ ID NO 106
<211> LENGTH: 19
<212> TYPE: PRT
<213> ORGANISM: Artificial Sequence
<220> FEATURE:
<223> OTHER INFORMATION: Structural motif F, Peptide BO

<400> SEQUENCE: 106

Gly Cys Ala Glu His Cys Ser Leu Asn Glu Asn Ile Thr Val Pro Asp
1               5                   10                  15

Thr Lys Val

<210> SEQ ID NO 107
<211> LENGTH: 14
<212> TYPE: PRT
<213> ORGANISM: Artificial Sequence
<220> FEATURE:
<223> OTHER INFORMATION: Structural motif F, Peptide BP

<400> SEQUENCE: 107

Cys Ala Glu His Cys Ser Leu Asn Glu Asn Ile Thr Val Pro
1               5                   10

<210> SEQ ID NO 108
<211> LENGTH: 21
<212> TYPE: PRT
<213> ORGANISM: Artificial Sequence
<220> FEATURE:
<223> OTHER INFORMATION: Structural motif F, Peptide BQ

<400> SEQUENCE: 108

Thr Thr Gly Cys Ala Glu His Cys Ser Leu Asn Glu Asn Ile Thr Val
1               5                   10                  15

Pro Asp Thr Lys Val
            20

<210> SEQ ID NO 109
<211> LENGTH: 17
<212> TYPE: PRT
<213> ORGANISM: Artificial Sequence
<220> FEATURE:
<223> OTHER INFORMATION: Structural motif F, Peptide BR

<400> SEQUENCE: 109

Thr Thr Gly Cys Ala Glu His Cys Ser Leu Asn Glu Asn Ile Thr Val
1               5                   10                  15

Pro

```
<210> SEQ ID NO 110
<211> LENGTH: 20
<212> TYPE: PRT
<213> ORGANISM: Artificial Sequence
<220> FEATURE:
<223> OTHER INFORMATION: Structural motif F, Peptide BS

<400> SEQUENCE: 110

Cys Ala Glu His Cys Ser Leu Asn Lys Asn Ile Asn Leu Asp Ser Val
1               5                   10                  15

Asp Gly Val Pro
            20

<210> SEQ ID NO 111
<211> LENGTH: 6
<212> TYPE: PRT
<213> ORGANISM: Artificial Sequence
<220> FEATURE:
<223> OTHER INFORMATION: Formula II of structural motif F
<220> FEATURE:
<221> NAME/KEY: misc_feature
<222> LOCATION: (1)..(1)
<223> OTHER INFORMATION: Xaa is any amino acid containing a sulfhydral
      group
<220> FEATURE:
<221> NAME/KEY: misc_feature
<222> LOCATION: (5)..(5)
<223> OTHER INFORMATION: Xaa is any amino acid containing a sulfhydral
      group

<400> SEQUENCE: 111

Xaa Ala Glu His Xaa Ser
1               5

<210> SEQ ID NO 112
<211> LENGTH: 16
<212> TYPE: PRT
<213> ORGANISM: Artificial Sequence
<220> FEATURE:
<223> OTHER INFORMATION: Structural motif F, Peptide BT

<400> SEQUENCE: 112

Ala Glu His Cys Ser Leu Met Glu Asn Asn Leu Arg Arg Pro Asn Leu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Structural motif F, Peptide BU
<220> FEATURE:
<221> NAME/KEY: MOD_RES
<222> LOCATION: (1)..(1)
<223> OTHER INFORMATION: Xaa is modified Ala with N-terminal D-biotin

<400> SEQUENCE: 113

Xaa Glu His Cys Ser Leu Met Glu Asn Asn Leu Arg Arg Pro Asn Leu
1               5                   10                  15

<210> SEQ ID NO 114
<211> LENGTH: 14
<212> TYPE: PRT
<213> ORGANISM: Artificial Sequence
<220> FEATURE:
<223> OTHER INFORMATION: Structural motif A, Peptide BV

<400> SEQUENCE: 114
```

```
Trp Glu His Val Asn Ala Ile Gln Glu Ala Arg Arg Leu Leu
1               5                   10
```

```
<210> SEQ ID NO 115
<211> LENGTH: 12
<212> TYPE: PRT
<213> ORGANISM: Artificial Sequence
<220> FEATURE:
<223> OTHER INFORMATION: Structural motif A, Peptide BW

<400> SEQUENCE: 115

Leu Ser Lys Leu Leu Arg Asp Ser His Val Leu His
1               5                   10
```

```
<210> SEQ ID NO 116
<211> LENGTH: 16
<212> TYPE: PRT
<213> ORGANISM: Artificial Sequence
<220> FEATURE:
<223> OTHER INFORMATION: Structural motif A, Peptide BX

<400> SEQUENCE: 116

Lys Ile Arg Ser Asp Leu Thr Ala Leu Thr Glu Ser Tyr Val Lys His
1               5                   10                  15
```

```
<210> SEQ ID NO 117
<211> LENGTH: 17
<212> TYPE: PRT
<213> ORGANISM: Artificial Sequence
<220> FEATURE:
<223> OTHER INFORMATION: Structural motif A, Peptide BY

<400> SEQUENCE: 117

Gly Thr Glu Lys Ala Lys Leu Val Glu Leu Tyr Arg Ile Val Val Tyr
1               5                   10                  15

Leu
```

```
<210> SEQ ID NO 118
<211> LENGTH: 18
<212> TYPE: PRT
<213> ORGANISM: Artificial Sequence
<220> FEATURE:
<223> OTHER INFORMATION: Structural motif A, Peptide BZ

<400> SEQUENCE: 118

Ser Ile Met Ile Asp Glu Ile Ile His His Leu Lys Arg Pro Pro Asn
1               5                   10                  15

Pro Leu
```

```
<210> SEQ ID NO 119
<211> LENGTH: 19
<212> TYPE: PRT
<213> ORGANISM: Artificial Sequence
<220> FEATURE:
<223> OTHER INFORMATION: Formula V of structural motif A
<220> FEATURE:
<221> NAME/KEY: misc_feature
<222> LOCATION: (1)..(1)
<223> OTHER INFORMATION: Xaa is Try (W), Val (V), Ala (A), Ile (I), Pro
      (P), Leu (L), Ser (S), Asp (D), or Thr (T)
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is any amino acid
```

```
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: misc_feature
<222> LOCATION: (6)..(6)
<223> OTHER INFORMATION: Xaa is any amino acid
<220> FEATURE:
<221> NAME/KEY: misc_feature
<222> LOCATION: (7)..(7)
<223> OTHER INFORMATION: Xaa is any amino acid
<220> FEATURE:
<221> NAME/KEY: misc_feature
<222> LOCATION: (8)..(8)
<223> OTHER INFORMATION: Xaa is Ile (I), Phe (F), Leu (L), Val (V), Pro
      (P), Tyr (Y), or Gly (G)
<220> FEATURE:
<221> NAME/KEY: misc_feature
<222> LOCATION: (9)..(9)
<223> OTHER INFORMATION: Xaa is a negatively charged amino acid
<220> FEATURE:
<221> NAME/KEY: misc_feature
<222> LOCATION: (10)..(10)
<223> OTHER INFORMATION: Xaa is a negatively charged amino acid
<220> FEATURE:
<221> NAME/KEY: misc_feature
<222> LOCATION: (11)..(11)
<223> OTHER INFORMATION: Xaa is Ile (I), Leu (L), Ala (A), Gly (G), Phe
      (F), Val (V), or Pro (P)
<220> FEATURE:
<221> NAME/KEY: misc_feature
<222> LOCATION: (12)..(12)
<223> OTHER INFORMATION: Xaa is Ile (I), Met (M), Tyr (Y), Ser (S), Val
      (V), Phe (F), Lys (K), Leu (L), Glu (E), or Asp (D)
<220> FEATURE:
<221> NAME/KEY: misc_feature
<222> LOCATION: (13)..(13)
<223> OTHER INFORMATION: Xaa is any amino acid
<220> FEATURE:
<221> NAME/KEY: misc_feature
<222> LOCATION: (14)..(14)
<223> OTHER INFORMATION: Xaa is His (H), Leu (L), Pro (P), Thr (T), Arg
      (R), Cys (C), Ile (I), Tyr (Y), Gln (Q), or Ala (A)
<220> FEATURE:
<221> NAME/KEY: misc_feature
<222> LOCATION: (15)..(15)
<223> OTHER INFORMATION: Xaa is Leu (L), Lys (K), Thr (T), Val (V), Phe
      (F), Ala (A), or Gln (Q)
<220> FEATURE:
<221> NAME/KEY: misc_feature
<222> LOCATION: (16)..(16)
<223> OTHER INFORMATION: Xaa is Lys (K), Glu (E), Met (M), Gly (G), Asn
      (N), Gln (Q), Thr (T), or Val (V)
<220> FEATURE:
<221> NAME/KEY: misc_feature
<222> LOCATION: (17)..(17)
<223> OTHER INFORMATION: Xaa is any amino acid
<220> FEATURE:
<221> NAME/KEY: misc_feature
<222> LOCATION: (18)..(18)
<223> OTHER INFORMATION: Xaa is Pro (P), Lys (K), Arg (R), Ile (I), Asn
      (N), Ser (S), Gln (Q), or Phe (F)
<220> FEATURE:
<221> NAME/KEY: misc_feature
<222> LOCATION: (19)..(19)
<223> OTHER INFORMATION: Xaa is Pro (P), Ile (I), Tyr (Y), Leu (L), Phe
      (F), Ser (S), Ala (A), Asp (D), Asn (N), or Lys (K)

<400> SEQUENCE: 119

Xaa Xaa Xaa Xaa Xaa Xaa Xaa Xaa Xaa Xaa Xaa Xaa Xaa Xaa Xaa Xaa
1               5                   10                  15

Xaa Xaa Xaa
```

```
<210> SEQ ID NO 120
<211> LENGTH: 24
<212> TYPE: PRT
<213> ORGANISM: Artificial Sequence
<220> FEATURE:
<223> OTHER INFORMATION: Structural motif A, Peptide CA

<400> SEQUENCE: 120

Lys Thr Ser Trp Val Asn Cys Ser Asn Met Ile Asp Glu Ile Ile Thr
1               5                   10                  15

His Leu Lys Gln Pro Pro Leu Pro
            20

<210> SEQ ID NO 121
<211> LENGTH: 24
<212> TYPE: PRT
<213> ORGANISM: Artificial Sequence
<220> FEATURE:
<223> OTHER INFORMATION: Structural motif A, Peptide CB

<400> SEQUENCE: 121

Leu Leu Gln Val Ala Ala Phe Ala Tyr Gln Ile Glu Glu Leu Met Ile
1               5                   10                  15

Leu Leu Glu Tyr Lys Ile Pro Arg
            20

<210> SEQ ID NO 122
<211> LENGTH: 24
<212> TYPE: PRT
<213> ORGANISM: Artificial Sequence
<220> FEATURE:
<223> OTHER INFORMATION: Structural motif A, Peptide CC

<400> SEQUENCE: 122

His Gln Leu Ala Phe Asp Thr Tyr Gln Glu Phe Glu Glu Ala Tyr Ile
1               5                   10                  15

Pro Lys Glu Gln Lys Tyr Ser Phe
            20

<210> SEQ ID NO 123
<211> LENGTH: 24
<212> TYPE: PRT
<213> ORGANISM: Artificial Sequence
<220> FEATURE:
<223> OTHER INFORMATION: Structural motif A, Peptide CD

<400> SEQUENCE: 123

Asp Ser Asn Val Tyr Asp Leu Leu Lys Asp Leu Glu Glu Gly Ile Gln
1               5                   10                  15

Thr Leu Met Gly Arg Leu Glu Asp
            20

<210> SEQ ID NO 124
<211> LENGTH: 24
<212> TYPE: PRT
<213> ORGANISM: Artificial Sequence
<220> FEATURE:
<223> OTHER INFORMATION: Structural motif A, Peptide CE

<400> SEQUENCE: 124

Glu Glu Gly Ile Gln Thr Leu Met Gly Arg Leu Glu Asp Gly Ser Pro
1               5                   10                  15

Arg Thr Gly Gln Ile Phe Lys Gln
```

```
                20

<210> SEQ ID NO 125
<211> LENGTH: 11
<212> TYPE: PRT
<213> ORGANISM: Artificial Sequence
<220> FEATURE:
<223> OTHER INFORMATION: Structural motif A, Peptide CF

<400> SEQUENCE: 125

Ser Asn Val Asp Lys Glu Thr Gly Glu Asp Gly
1               5                   10

<210> SEQ ID NO 126
<211> LENGTH: 24
<212> TYPE: PRT
<213> ORGANISM: Artificial Sequence
<220> FEATURE:
<223> OTHER INFORMATION: Structural motif A, Peptide CG

<400> SEQUENCE: 126

Tyr Ser Ile Ile Asp Lys Leu Val Asn Ile Val Asp Asp Leu Val Glu
1               5                   10                  15

Cys Val Lys Glu Asn Ser Ser Lys
                20

<210> SEQ ID NO 127
<211> LENGTH: 24
<212> TYPE: PRT
<213> ORGANISM: Artificial Sequence
<220> FEATURE:
<223> OTHER INFORMATION: Structural motif A, Peptide CH

<400> SEQUENCE: 127

Phe Lys Ser Pro Glu Pro Arg Leu Phe Thr Pro Glu Glu Phe Phe Arg
1               5                   10                  15

Ile Phe Asn Arg Ser Ile Asp Ala
                20

<210> SEQ ID NO 128
<211> LENGTH: 24
<212> TYPE: PRT
<213> ORGANISM: Artificial Sequence
<220> FEATURE:
<223> OTHER INFORMATION: Structural motif A, Peptide CI

<400> SEQUENCE: 128

Leu Asp Asn Leu Leu Leu Lys Glu Ser Leu Leu Glu Asp Phe Lys Gly
1               5                   10                  15

Tyr Leu Gly Cys Gln Ala Leu Ser
                20

<210> SEQ ID NO 129
<211> LENGTH: 24
<212> TYPE: PRT
<213> ORGANISM: Artificial Sequence
<220> FEATURE:
<223> OTHER INFORMATION: Structural motif A, Peptide CJ

<400> SEQUENCE: 129

Gln Ala Leu Ser Glu Met Ile Gln Phe Tyr Leu Glu Glu Val Met Pro
1               5                   10                  15

Gln Ala Glu Asn Gln Asp Pro Asp
                20
```

<210> SEQ ID NO 130
<211> LENGTH: 24
<212> TYPE: PRT
<213> ORGANISM: Artificial Sequence
<220> FEATURE:
<223> OTHER INFORMATION: Structural motif A, Peptide CK

<400> SEQUENCE: 130

Leu Gln Cys Leu Glu Glu Glu Leu Lys Pro Leu Glu Glu Val Leu Asn
1               5                   10                  15

Leu Ala Gln Ser Lys Asn Phe His
            20

<210> SEQ ID NO 131
<211> LENGTH: 24
<212> TYPE: PRT
<213> ORGANISM: Artificial Sequence
<220> FEATURE:
<223> OTHER INFORMATION: Structural motif A, Peptide CL

<400> SEQUENCE: 131

Ala Gln Asp Leu Glu Arg Ser Gly Leu Asn Ile Glu Asp Leu Glu Lys
1               5                   10                  15

Leu Gln Met Ala Arg Pro Asn Ile
            20

<210> SEQ ID NO 132
<211> LENGTH: 24
<212> TYPE: PRT
<213> ORGANISM: Artificial Sequence
<220> FEATURE:
<223> OTHER INFORMATION: Structural motif A, Peptide CM

<400> SEQUENCE: 132

Val Pro Pro Ser Thr Ala Leu Arg Glu Leu Ile Glu Glu Leu Val Asn
1               5                   10                  15

Ile Thr Gln Asn Gln Lys Ala Pro
            20

<210> SEQ ID NO 133
<211> LENGTH: 24
<212> TYPE: PRT
<213> ORGANISM: Artificial Sequence
<220> FEATURE:
<223> OTHER INFORMATION: Structural motif A, Peptide CN

<400> SEQUENCE: 133

Ile Phe Leu Asp Gln Asn Met Leu Ala Val Ile Asp Glu Leu Met Gln
1               5                   10                  15

Ala Leu Asn Phe Asn Ser Glu Thr
            20

<210> SEQ ID NO 134
<211> LENGTH: 24
<212> TYPE: PRT
<213> ORGANISM: Artificial Sequence
<220> FEATURE:
<223> OTHER INFORMATION: Structural motif A, Peptide CO

<400> SEQUENCE: 134

Asn Ser Glu Thr Val Pro Gln Lys Ser Ser Leu Glu Glu Pro Asp Phe
1               5                   10                  15

Tyr Lys Thr Lys Ile Lys Leu Cys
            20

```
<210> SEQ ID NO 135
<211> LENGTH: 24
<212> TYPE: PRT
<213> ORGANISM: Artificial Sequence
<220> FEATURE:
<223> OTHER INFORMATION: Structural motif A, Peptide CP

<400> SEQUENCE: 135

Phe Met Met Ala Leu Cys Leu Ser Ser Ile Tyr Glu Asp Leu Lys Met
1               5                   10                  15

Tyr Gln Val Glu Phe Lys Thr Met
            20

<210> SEQ ID NO 136
<211> LENGTH: 24
<212> TYPE: PRT
<213> ORGANISM: Artificial Sequence
<220> FEATURE:
<223> OTHER INFORMATION: Structural motif A, Peptide CQ

<400> SEQUENCE: 136

Cys Leu Lys Asp Arg Met Asn Phe Asp Ile Pro Glu Glu Ile Lys Gln
1               5                   10                  15

Leu Gln Gln Phe Gln Lys Glu Asp
            20

<210> SEQ ID NO 137
<211> LENGTH: 9
<212> TYPE: PRT
<213> ORGANISM: Artificial Sequence
<220> FEATURE:
<223> OTHER INFORMATION: Formula VI of structural motif A
<220> FEATURE:
<221> NAME/KEY: misc_feature
<222> LOCATION: (1)..(1)
<223> OTHER INFORMATION: Xaa is Phe (F), Val (V), Ala (A), Gly (G), Pro
      (P), Leu (L), Tyr (Y), Ile (I), Cys (C) or Met (M)
<220> FEATURE:
<221> NAME/KEY: misc_feature
<222> LOCATION: (2)..(2)
<223> OTHER INFORMATION: Xaa is a negatively charged amino acid
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (4)..(7)
<223> OTHER INFORMATION: Xaa is any amino acid or is absent
<220> FEATURE:
<221> NAME/KEY: misc_feature
<222> LOCATION: (8)..(8)
<223> OTHER INFORMATION: Xaa is a negatively charged amino acid
<220> FEATURE:
<221> NAME/KEY: misc_feature
<222> LOCATION: (9)..(9)
<223> OTHER INFORMATION: Xaa is Pro (P), Met (M), Val (V), Ile (I), Phe
      (F), Gly (G), Leu (L), Ala (A), Tyr (Y), and Trp (W)

<400> SEQUENCE: 137

Xaa Xaa Xaa Xaa Xaa Xaa Xaa Xaa Xaa
1               5

<210> SEQ ID NO 138
<211> LENGTH: 26
<212> TYPE: PRT
<213> ORGANISM: Artificial Sequence
<220> FEATURE:
<223> OTHER INFORMATION: Structural motif A, Peptide CR
```

```
<400> SEQUENCE: 138

Asn Glu Thr Val Glu Val Ile Ser Glu Met Phe Asp Leu Gln Glu Pro
1               5                  10                  15

Thr Cys Leu Gln Thr Arg Leu Glu Leu Tyr
            20                  25

<210> SEQ ID NO 139
<211> LENGTH: 19
<212> TYPE: PRT
<213> ORGANISM: Artificial Sequence
<220> FEATURE:
<223> OTHER INFORMATION: Structural motif A, Peptide CS

<400> SEQUENCE: 139

Asn Leu Lys Asp Phe Leu Leu Val Ile Pro Phe Asp Cys Trp Glu Pro
1               5                  10                  15

Val Gln Glu

<210> SEQ ID NO 140
<211> LENGTH: 27
<212> TYPE: PRT
<213> ORGANISM: Artificial Sequence
<220> FEATURE:
<223> OTHER INFORMATION: Structural motif A, Peptide CT

<400> SEQUENCE: 140

Arg Asp Thr Ala Ala Glu Met Asn Glu Thr Val Glu Val Ile Ser Glu
1               5                  10                  15

Met Phe Asp Leu Gln Glu Pro Thr Cys Leu Gln
            20                  25

<210> SEQ ID NO 141
<211> LENGTH: 29
<212> TYPE: PRT
<213> ORGANISM: Artificial Sequence
<220> FEATURE:
<223> OTHER INFORMATION: Structural motif A, Peptide CU

<400> SEQUENCE: 141

Arg Leu Leu Asn Leu Ser Arg Asp Thr Ala Ala Glu Met Asn Glu Thr
1               5                  10                  15

Val Glu Val Ile Ser Glu Met Phe Asp Leu Gln Glu Pro
            20                  25

<210> SEQ ID NO 142
<211> LENGTH: 26
<212> TYPE: PRT
<213> ORGANISM: Artificial Sequence
<220> FEATURE:
<223> OTHER INFORMATION: Structural motif A, Peptide CV

<400> SEQUENCE: 142

Leu Pro Leu Leu Asp Phe Asn Asn Leu Asn Gly Glu Asp Gln Asp Ile
1               5                  10                  15

Leu Met Glu Asn Asn Leu Arg Arg Pro Asn
            20                  25

<210> SEQ ID NO 143
<211> LENGTH: 26
<212> TYPE: PRT
<213> ORGANISM: Artificial Sequence
<220> FEATURE:
<223> OTHER INFORMATION: Structural motif A, Peptide CW
```

<400> SEQUENCE: 143

Pro Thr Arg His Pro Ile His Ile Lys Asp Gly Asp Trp Asn Glu Phe
1               5                   10                  15

Arg Arg Lys Leu Thr Phe Tyr Leu Lys Thr
            20                  25

<210> SEQ ID NO 144
<211> LENGTH: 28
<212> TYPE: PRT
<213> ORGANISM: Artificial Sequence
<220> FEATURE:
<223> OTHER INFORMATION: Structural motif A, Peptide CX

<400> SEQUENCE: 144

His Val Gly His Val Asp Val Thr Tyr Gly Pro Asp Thr Ser Gly Lys
1               5                   10                  15

Asp Val Phe Gln Lys Lys Lys Leu Gly Cys Gly Leu
            20                  25

<210> SEQ ID NO 145
<211> LENGTH: 26
<212> TYPE: PRT
<213> ORGANISM: Artificial Sequence
<220> FEATURE:
<223> OTHER INFORMATION: Structural motif A, Peptide CY

<400> SEQUENCE: 145

Lys His Gln Gly Leu Asn Lys Asn Ile Asn Leu Asp Ser Ala Asp Gly
1               5                   10                  15

Met Pro Val Ala Ser Thr Asp Gln Trp Ser
            20                  25

<210> SEQ ID NO 146
<211> LENGTH: 18
<212> TYPE: PRT
<213> ORGANISM: Artificial Sequence
<220> FEATURE:
<223> OTHER INFORMATION: Structural motif A, Peptide CZ

<400> SEQUENCE: 146

Trp Ser Glu Leu Thr Ala Glu Gln Leu Gln Arg Val Ala Arg Glu
1               5                   10                  15

Val His

<210> SEQ ID NO 147
<211> LENGTH: 27
<212> TYPE: PRT
<213> ORGANISM: Artificial Sequence
<220> FEATURE:
<223> OTHER INFORMATION: Structural motif A, Peptide DA

<400> SEQUENCE: 147

Leu Arg Ala His Arg Leu His Gln Leu Ala Phe Asp Thr Tyr Gln Glu
1               5                   10                  15

Phe Glu Glu Ala Tyr Ile Pro Lys Glu Gln Lys
            20                  25

<210> SEQ ID NO 148
<211> LENGTH: 27
<212> TYPE: PRT
<213> ORGANISM: Artificial Sequence
<220> FEATURE:
<223> OTHER INFORMATION: Structural motif A, Peptide DB

<400> SEQUENCE: 148

Leu Val Tyr Gly Ala Ser Asp Ser Asn Val Tyr Asp Leu Leu Lys Asp
1               5                   10                  15

Leu Glu Glu Gly Ile Gln Thr Leu Met Gly Arg
            20                  25

<210> SEQ ID NO 149
<211> LENGTH: 11
<212> TYPE: PRT
<213> ORGANISM: Artificial Sequence
<220> FEATURE:
<223> OTHER INFORMATION: Structural motif A, Peptide DC

<400> SEQUENCE: 149

Ser Asn Val Asp Lys Glu Thr Gly Glu Asp Gly
1               5                   10

<210> SEQ ID NO 150
<211> LENGTH: 27
<212> TYPE: PRT
<213> ORGANISM: Artificial Sequence
<220> FEATURE:
<223> OTHER INFORMATION: Structural motif A, Peptide DD

<400> SEQUENCE: 150

Gln Glu Glu Arg Arg Arg Val Asn Gly Phe Leu Asp Tyr Leu Gln Glu
1               5                   10                  15

Phe Leu Gly Val Met Asn Thr Glu Trp Ile Ile
            20                  25

<210> SEQ ID NO 151
<211> LENGTH: 27
<212> TYPE: PRT
<213> ORGANISM: Artificial Sequence
<220> FEATURE:
<223> OTHER INFORMATION: Structural motif A, Peptide DE

<400> SEQUENCE: 151

Glu Glu Phe Phe Arg Ile Phe Asn Arg Ser Ile Asp Ala Phe Lys Asp
1               5                   10                  15

Phe Val Val Ala Ser Glu Thr Ser Asp Cys Val
            20                  25

<210> SEQ ID NO 152
<211> LENGTH: 27
<212> TYPE: PRT
<213> ORGANISM: Artificial Sequence
<220> FEATURE:
<223> OTHER INFORMATION: Structural motif A, Peptide DF

<400> SEQUENCE: 152

Ser Arg Asn Val Ile Gln Ile Ser Asn Asp Leu Glu Asn Leu Arg Asp
1               5                   10                  15

Leu Leu His Val Leu Ala Phe Ser Lys Ser Cys
            20                  25

<210> SEQ ID NO 153
<211> LENGTH: 12
<212> TYPE: PRT
<213> ORGANISM: Artificial Sequence
<220> FEATURE:
<223> OTHER INFORMATION: Structural motif A, Peptide DG

<400> SEQUENCE: 153

```
Tyr Ser Thr Val Ser Gly Asp Trp Gln Leu Asp Leu
1               5                   10

<210> SEQ ID NO 154
<211> LENGTH: 26
<212> TYPE: PRT
<213> ORGANISM: Artificial Sequence
<220> FEATURE:
<223> OTHER INFORMATION: Structural motif A, Peptide DH

<400> SEQUENCE: 154

Gln Phe Tyr Leu Glu Glu Val Met Pro Gln Ala Glu Asn Gln Asp Pro
1               5                   10                  15

Asp Ile Lys Ala His Val Asn Ser Leu Gly
            20                  25

<210> SEQ ID NO 155
<211> LENGTH: 28
<212> TYPE: PRT
<213> ORGANISM: Artificial Sequence
<220> FEATURE:
<223> OTHER INFORMATION: Structural motif A, Peptide DI

<400> SEQUENCE: 155

Gln Phe Tyr Leu Glu Glu Val Met Pro Gln Ala Glu Asn Gln Asp Pro
1               5                   10                  15

Asp Ile Lys Ala His Val Asn Ser Leu Gly Glu Asn
            20                  25

<210> SEQ ID NO 156
<211> LENGTH: 25
<212> TYPE: PRT
<213> ORGANISM: Artificial Sequence
<220> FEATURE:
<223> OTHER INFORMATION: Structural motif A, Peptide DJ

<400> SEQUENCE: 156

Lys Ala Thr Glu Leu Lys His Leu Gln Cys Leu Glu Glu Glu Leu Lys
1               5                   10                  15

Pro Leu Glu Glu Val Leu Asn Leu Ala
            20                  25

<210> SEQ ID NO 157
<211> LENGTH: 28
<212> TYPE: PRT
<213> ORGANISM: Artificial Sequence
<220> FEATURE:
<223> OTHER INFORMATION: Structural motif A, Peptide DK

<400> SEQUENCE: 157

Ser Ser Ser Thr Lys Lys Thr Gln Leu Gln Leu Glu His Leu Leu Leu
1               5                   10                  15

Asp Leu Gln Met Ile Leu Asn Gly Ile Asn Asn Tyr
            20                  25

<210> SEQ ID NO 158
<211> LENGTH: 28
<212> TYPE: PRT
<213> ORGANISM: Artificial Sequence
<220> FEATURE:
<223> OTHER INFORMATION: Structural motif A, Peptide DL

<400> SEQUENCE: 158

Phe Lys Asp Asp Gln Ser Ile Gln Lys Ser Val Glu Thr Ile Lys Glu
```

```
                 1               5                  10                 15
Asp Met Asn Val Lys Phe Phe Asn Ser Asn Lys Lys
                20                  25
```

<210> SEQ ID NO 159
<211> LENGTH: 26
<212> TYPE: PRT
<213> ORGANISM: Artificial Sequence
<220> FEATURE:
<223> OTHER INFORMATION: Structural motif A, Peptide DM

<400> SEQUENCE: 159

```
Val Glu Ile Glu Glu Gln Thr Lys Arg Leu Leu Glu Gly Met Glu Leu
1               5                  10                 15

Ile Val Ser Gln Val His Pro Glu Thr Lys
                20                  25
```

<210> SEQ ID NO 160
<211> LENGTH: 28
<212> TYPE: PRT
<213> ORGANISM: Artificial Sequence
<220> FEATURE:
<223> OTHER INFORMATION: Structural motif A, Peptide DN

<400> SEQUENCE: 160

```
Gly Met Glu Leu Ile Val Ser Gln Val His Pro Glu Thr Lys Glu Asn
1               5                  10                 15

Glu Ile Tyr Pro Val Trp Ser Gly Leu Pro Ser Leu
                20                  25
```

<210> SEQ ID NO 161
<211> LENGTH: 13
<212> TYPE: PRT
<213> ORGANISM: Artificial Sequence
<220> FEATURE:
<223> OTHER INFORMATION: Structural motif A, Peptide DO

<400> SEQUENCE: 161

```
Pro Glu Ala Ile Val Glu Glu Arg Glu Leu Ser Gln Val
1               5                  10
```

<210> SEQ ID NO 162
<211> LENGTH: 20
<212> TYPE: PRT
<213> ORGANISM: Artificial Sequence
<220> FEATURE:
<223> OTHER INFORMATION: Structural motif A, Peptide DP

<400> SEQUENCE: 162

```
His Lys Cys Asp Ile Thr Leu Gln Glu Ile Ile Lys Thr Leu Asn Ser
1               5                  10                 15

Leu Thr Glu Gln
                20
```

<210> SEQ ID NO 163
<211> LENGTH: 25
<212> TYPE: PRT
<213> ORGANISM: Artificial Sequence
<220> FEATURE:
<223> OTHER INFORMATION: Structural motif A, Peptide DQ

<400> SEQUENCE: 163

```
Ala Glu Asn Asn Leu Asn Leu Pro Lys Met Ala Glu Lys Asp Gly Cys
1               5                  10                 15
```

Phe Gln Ser Gly Phe Asn Glu Glu Thr
            20                  25

<210> SEQ ID NO 164
<211> LENGTH: 25
<212> TYPE: PRT
<213> ORGANISM: Artificial Sequence
<220> FEATURE:
<223> OTHER INFORMATION: Structural motif A, Peptide DR

<400> SEQUENCE: 164

Thr Cys Leu Val Lys Ile Ile Thr Gly Leu Leu Glu Phe Glu Val Tyr
1               5                   10                  15

Leu Glu Tyr Leu Gln Asn Arg Phe Glu
            20                  25

<210> SEQ ID NO 165
<211> LENGTH: 20
<212> TYPE: PRT
<213> ORGANISM: Artificial Sequence
<220> FEATURE:
<223> OTHER INFORMATION: Structural motif A, Peptide DS

<400> SEQUENCE: 165

Val Pro Pro Gly Glu Asp Ser Lys Asp Val Ala Ala Pro His Arg Gln
1               5                   10                  15

Pro Leu Thr Ser
            20

<210> SEQ ID NO 166
<211> LENGTH: 27
<212> TYPE: PRT
<213> ORGANISM: Artificial Sequence
<220> FEATURE:
<223> OTHER INFORMATION: Structural motif A, Peptide DT

<400> SEQUENCE: 166

Arg Lys Glu Thr Cys Asn Lys Ser Asn Met Cys Glu Ser Ser Lys Glu
1               5                   10                  15

Ala Leu Ala Glu Asn Asn Leu Asn Leu Pro Lys
            20                  25

<210> SEQ ID NO 167
<211> LENGTH: 27
<212> TYPE: PRT
<213> ORGANISM: Artificial Sequence
<220> FEATURE:
<223> OTHER INFORMATION: Structural motif A, Peptide DU

<400> SEQUENCE: 167

Leu Val Lys Ile Ile Thr Gly Leu Leu Glu Phe Glu Val Tyr Leu Glu
1               5                   10                  15

Tyr Leu Gln Asn Arg Phe Glu Ser Ser Glu Glu
            20                  25

<210> SEQ ID NO 168
<211> LENGTH: 29
<212> TYPE: PRT
<213> ORGANISM: Artificial Sequence
<220> FEATURE:
<223> OTHER INFORMATION: Structural motif A, Peptide DV

<400> SEQUENCE: 168

Thr Cys Leu Val Lys Ile Ile Thr Gly Leu Leu Glu Phe Glu Val Tyr
1               5                   10                  15

```
Leu Glu Tyr Leu Gln Asn Arg Phe Glu Ser Ser Glu Glu
            20                  25

<210> SEQ ID NO 169
<211> LENGTH: 29
<212> TYPE: PRT
<213> ORGANISM: Artificial Sequence
<220> FEATURE:
<223> OTHER INFORMATION: Structural motif A, Peptide DW

<400> SEQUENCE: 169

Ile Gln Phe Leu Gln Lys Lys Ala Lys Asn Leu Asp Ala Ile Thr Thr
1               5                   10                  15

Pro Asp Pro Thr Thr Asn Ala Ser Leu Leu Thr Lys Leu
            20                  25

<210> SEQ ID NO 170
<211> LENGTH: 29
<212> TYPE: PRT
<213> ORGANISM: Artificial Sequence
<220> FEATURE:
<223> OTHER INFORMATION: Structural motif A, Peptide DX

<400> SEQUENCE: 170

Arg Asn Asn Ile Tyr Cys Met Ala Gln Leu Leu Asp Asn Ser Asp Thr
1               5                   10                  15

Ala Glu Pro Thr Lys Ala Gly Arg Gly Ala Ser Gln Pro
            20                  25

<210> SEQ ID NO 171
<211> LENGTH: 28
<212> TYPE: PRT
<213> ORGANISM: Artificial Sequence
<220> FEATURE:
<223> OTHER INFORMATION: Structural motif A, Peptide DY

<400> SEQUENCE: 171

Pro Leu Pro Thr Pro Val Leu Leu Pro Ala Val Asp Phe Ser Leu Gly
1               5                   10                  15

Glu Trp Lys Thr Gln Met Glu Glu Thr Lys Ala Gln
            20                  25

<210> SEQ ID NO 172
<211> LENGTH: 29
<212> TYPE: PRT
<213> ORGANISM: Artificial Sequence
<220> FEATURE:
<223> OTHER INFORMATION: Structural motif A, Peptide DZ

<400> SEQUENCE: 172

Asp Phe Ser Leu Gly Glu Trp Lys Thr Gln Met Glu Glu Thr Lys Ala
1               5                   10                  15

Gln Asp Ile Leu Gly Ala Val Thr Leu Leu Leu Glu Gly
            20                  25

<210> SEQ ID NO 173
<211> LENGTH: 16
<212> TYPE: PRT
<213> ORGANISM: Artificial Sequence
<220> FEATURE:
<223> OTHER INFORMATION: Structural motif A, Peptide EA

<400> SEQUENCE: 173

Leu Glu Trp Lys Thr Gln Thr Asp Gly Leu Glu Gly Ala Ala Gly Gln
```

```
                1               5                   10                  15
```

<210> SEQ ID NO 174
<211> LENGTH: 28
<212> TYPE: PRT
<213> ORGANISM: Artificial Sequence
<220> FEATURE:
<223> OTHER INFORMATION: Structural motif A, Peptide EB

<400> SEQUENCE: 174

```
Thr Val Ala Gly Ser Lys Met Gln Gly Leu Leu Glu Arg Val Asn Thr
1               5                   10                  15

Glu Ile His Phe Val Thr Lys Cys Ala Phe Gln Pro
            20                  25
```

<210> SEQ ID NO 175
<211> LENGTH: 26
<212> TYPE: PRT
<213> ORGANISM: Artificial Sequence
<220> FEATURE:
<223> OTHER INFORMATION: Structural motif A, Peptide EC

<400> SEQUENCE: 175

```
Leu Glu Phe Tyr Pro Cys Thr Ser Glu Glu Ile Asp His Glu Asp Ile
1               5                   10                  15

Thr Lys Asp Lys Thr Ser Thr Val Glu Ala
            20                  25
```

<210> SEQ ID NO 176
<211> LENGTH: 26
<212> TYPE: PRT
<213> ORGANISM: Artificial Sequence
<220> FEATURE:
<223> OTHER INFORMATION: Structural motif A, Peptide ED

<400> SEQUENCE: 176

```
Asn Ser Glu Thr Val Pro Gln Lys Ser Ser Leu Glu Glu Pro Asp Phe
1               5                   10                  15

Tyr Lys Thr Lys Ile Lys Leu Cys Ile Leu
            20                  25
```

<210> SEQ ID NO 177
<211> LENGTH: 29
<212> TYPE: PRT
<213> ORGANISM: Artificial Sequence
<220> FEATURE:
<223> OTHER INFORMATION: Structural motif A, Peptide EE

<400> SEQUENCE: 177

```
Glu Asp Ile Thr Lys Asp Lys Thr Ser Thr Val Glu Ala Cys Leu Pro
1               5                   10                  15

Leu Glu Leu Thr Lys Asn Glu Ser Cys Leu Asn Ser Arg
            20                  25
```

<210> SEQ ID NO 178
<211> LENGTH: 26
<212> TYPE: PRT
<213> ORGANISM: Artificial Sequence
<220> FEATURE:
<223> OTHER INFORMATION: Structural motif A, Peptide EF

<400> SEQUENCE: 178

```
Thr Thr Asn Asp Val Pro His Ile Gln Cys Gly Asp Gly Cys Asp Pro
1               5                   10                  15
```

```
Gln Gly Leu Arg Asp Asn Ser Gln Phe Cys
            20                  25

<210> SEQ ID NO 179
<211> LENGTH: 27
<212> TYPE: PRT
<213> ORGANISM: Artificial Sequence
<220> FEATURE:
<223> OTHER INFORMATION: Structural motif A, Peptide EG

<400> SEQUENCE: 179

Ala Trp Ser Ala His Pro Leu Val Gly His Met Asp Leu Arg Glu Glu
1               5                   10                  15

Gly Asp Glu Glu Thr Thr Asn Asp Val Pro His
            20                  25

<210> SEQ ID NO 180
<211> LENGTH: 29
<212> TYPE: PRT
<213> ORGANISM: Artificial Sequence
<220> FEATURE:
<223> OTHER INFORMATION: Structural motif A, Peptide EH

<400> SEQUENCE: 180

Leu Val Gly His Met Asp Leu Arg Glu Glu Gly Asp Glu Glu Thr Thr
1               5                   10                  15

Asn Asp Val Pro His Ile Gln Cys Gly Asp Gly Cys Asp
            20                  25

<210> SEQ ID NO 181
<211> LENGTH: 29
<212> TYPE: PRT
<213> ORGANISM: Artificial Sequence
<220> FEATURE:
<223> OTHER INFORMATION: Structural motif A, Peptide EI

<400> SEQUENCE: 181

Leu Gln Arg Ile His Gln Gly Leu Ile Phe Tyr Glu Lys Leu Leu Gly
1               5                   10                  15

Ser Asp Ile Phe Thr Gly Glu Pro Ser Leu Leu Pro Asp
            20                  25

<210> SEQ ID NO 182
<211> LENGTH: 26
<212> TYPE: PRT
<213> ORGANISM: Artificial Sequence
<220> FEATURE:
<223> OTHER INFORMATION: Structural motif A, Peptide EJ

<400> SEQUENCE: 182

Asn His Leu Lys Thr Val Leu Glu Glu Lys Leu Glu Lys Glu Asp Phe
1               5                   10                  15

Thr Arg Gly Lys Leu Met Ser Ser Leu His
            20                  25

<210> SEQ ID NO 183
<211> LENGTH: 27
<212> TYPE: PRT
<213> ORGANISM: Artificial Sequence
<220> FEATURE:
<223> OTHER INFORMATION: Structural motif A, Peptide EK

<400> SEQUENCE: 183

Leu Glu Tyr Cys Leu Lys Asp Arg Met Asn Phe Asp Ile Pro Glu Glu
1               5                   10                  15
```

Ile Lys Gln Leu Gln Gln Phe Gln Lys Glu Asp
            20                  25

<210> SEQ ID NO 184
<211> LENGTH: 4
<212> TYPE: PRT
<213> ORGANISM: Artificial Sequence
<220> FEATURE:
<223> OTHER INFORMATION: Type-1 cytokine derived peptides exhibiting
      structural motif B
<220> FEATURE:
<221> NAME/KEY: misc_feature
<222> LOCATION: (1)..(1)
<223> OTHER INFORMATION: Xaa is Leu (L), Ile (I), Gly (G), Val (V), Phe
      (F), Pro (P), or Ala (A)
<220> FEATURE:
<221> NAME/KEY: misc_feature
<222> LOCATION: (2)..(2)
<223> OTHER INFORMATION: Xaa is a positively charged amino acid
<220> FEATURE:
<221> NAME/KEY: misc_feature
<222> LOCATION: (3)..(3)
<223> OTHER INFORMATION: Xaa is a negatively charged amino acid
<220> FEATURE:
<221> NAME/KEY: misc_feature
<222> LOCATION: (4)..(4)
<223> OTHER INFORMATION: Xaa is Phe (F), Gly (G), Val (V), Leu (L), Ala
      (A), or Tyr (Y)

<400> SEQUENCE: 184

Xaa Xaa Xaa Xaa
1

<210> SEQ ID NO 185
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EL

<400> SEQUENCE: 185

Ile Ile Thr Phe Glu Ser Phe Lys Glu Asn Leu Lys Asp Phe Leu Leu
1               5                   10                  15

Val Ile Pro Phe Asp Cys Trp Glu
            20

<210> SEQ ID NO 186
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EM

<400> SEQUENCE: 186

Thr Ala Ala Pro Thr Arg His Pro Ile His Ile Lys Asp Gly Asp Trp
1               5                   10                  15

Asn Glu Phe Arg Arg Lys Leu Thr
            20

<210> SEQ ID NO 187
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EN

<400> SEQUENCE: 187

Val Asp Val Thr Tyr Gly Pro Asp Thr Ser Gly Lys Asp Val Phe Gln
1 5 10 15

Lys Lys Lys Leu Gly Cys Gln Leu
20

<210> SEQ ID NO 188
<211> LENGTH: 14
<212> TYPE: PRT
<213> ORGANISM: Artificial Sequence
<220> FEATURE:
<223> OTHER INFORMATION: Type-1 cytokine derived peptides exhibiting structural motif B, Peptide EO

<400> SEQUENCE: 188

Ser Gly Lys Asp Val Phe Gln Lys Gln Gly Gln Ser Val Gln
1 5 10

<210> SEQ ID NO 189
<211> LENGTH: 24
<212> TYPE: PRT
<213> ORGANISM: Artificial Sequence
<220> FEATURE:
<223> OTHER INFORMATION: Type-1 cytokine derived peptides exhibiting structural motif B, Peptide EP

<400> SEQUENCE: 189

Gln Glu Leu Ser Gln Trp Thr Val Arg Ser Ile His Asp Leu Arg Phe
1 5 10 15

Ile Ser Ser His Gln Thr Gly Ile
20

<210> SEQ ID NO 190
<211> LENGTH: 18
<212> TYPE: PRT
<213> ORGANISM: Artificial Sequence
<220> FEATURE:
<223> OTHER INFORMATION: Type-1 cytokine derived peptides exhibiting structural motif B, Peptide EQ

<400> SEQUENCE: 190

Trp Ser Glu Leu Thr Ala Glu Gln Glu Leu Gln Arg Val Ala Arg Glu
1 5 10 15

Val His

<210> SEQ ID NO 191
<211> LENGTH: 24
<212> TYPE: PRT
<213> ORGANISM: Artificial Sequence
<220> FEATURE:
<223> OTHER INFORMATION: Type-1 cytokine derived peptides exhibiting structural motif B, Peptide ER

<400> SEQUENCE: 191

Gly Ala Ser Asp Ser Asn Val Tyr Asp Leu Leu Lys Asp Leu Glu Glu
1 5 10 15

Gly Ile Gln Thr Leu Met Gly Arg
20

<210> SEQ ID NO 192
<211> LENGTH: 24
<212> TYPE: PRT
<213> ORGANISM: Artificial Sequence
<220> FEATURE:
<223> OTHER INFORMATION: Type-1 cytokine derived peptides exhibiting structural motif B, Peptide ES

<400> SEQUENCE: 192

Gly Ile Cys Arg Asn Arg Val Thr Asn Asn Val Lys Asp Val Thr Lys
1               5                   10                  15

Leu Val Ala Asn Leu Pro Lys Asp
            20

<210> SEQ ID NO 193
<211> LENGTH: 25
<212> TYPE: PRT
<213> ORGANISM: Artificial Sequence
<220> FEATURE:
<223> OTHER INFORMATION: Type-1 cytokine derived peptides exhibiting
      structural motif B, Peptide ET

<400> SEQUENCE: 193

Phe Arg Ile Phe Asn Arg Ser Ile Asp Ala Phe Lys Asp Phe Val Val
1               5                   10                  15

Ala Ser Glu Glu Thr Ser Asp Cys Val
            20                  25

<210> SEQ ID NO 194
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EU

<400> SEQUENCE: 194

Val Ile Gln Ile Ser Asn Asp Leu Glu Asn Leu Arg Asp Leu Leu His
1               5                   10                  15

Val Leu Ala Phe Ser Lys Ser Cys
            20

<210> SEQ ID NO 195
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EV

<400> SEQUENCE: 195

Thr His Phe Pro Gly Asn Leu Pro Asn Met Leu Arg Asp Leu Arg Asp
1               5                   10                  15

Ala Phe Ser Arg Val Lys Thr Phe
            20

<210> SEQ ID NO 196
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EW

<400> SEQUENCE: 196

Pro Gly Asn Leu Pro Asn Met Leu Arg Asp Leu Arg Asp Ala Phe Ser
1               5                   10                  15

Arg Val Lys Thr Ph

```
<210> SEQ ID NO 197
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EX

<400> SEQUENCE: 197

Leu Ala Gln Ser Lys Asn Phe His Leu Arg Pro Arg Asp Leu Ile Ser
1               5                   10                  15

Asn Ile Asn Val Ile Val Leu Glu
            20

<210> SEQ ID NO 198
<211> LENGTH: 18
<212> TYPE: PRT
<213> ORGANISM: Artificial Sequence
<220> FEATURE:
<223> OTHER INFORMATION: Type-1 cytokine derived peptides exhibiting
      structural motif B, Peptide EY

<400> SEQUENCE: 198

Gln Asp Pro Tyr Val Lys Glu Ala Glu Asn Leu Lys Lys Tyr Phe Asn
1               5                   10                  15

Ala Gly

<210> SEQ ID NO 199
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide EZ

<400> SEQUENCE: 199

Val Thr Asp Leu Asn Val Gln Arg Lys Ala Ile His Glu Leu Ile Gln
1               5                   10                  15

Val Met Ala Glu Leu Ser Pro Ala
            20

<210> SEQ ID NO 200
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FA

<400> SEQUENCE: 200

Pro Gly Gly Ala Ala Arg Cys Gln Val Thr Leu Arg Asp Leu Phe Asp
1               5                   10                  15

Arg Ala Val Val Leu Ser His Tyr
            20

<210> SEQ ID NO 201
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FB

<400> SEQUENCE: 201

Trp Gly Leu Ala Gly Leu Asn Ser Cys Pro Val Lys Glu Ala Asn Gln
1               5                   10                  15
```

Ser Thr Leu Glu Asn Phe Leu Glu
            20

<210> SEQ ID NO 202
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FC

<400> SEQUENCE: 202

Asp Met Thr Thr His Leu Ile Leu Arg Ser Phe Lys Glu Phe Leu Gln
1               5                   10                  15

Ser Ser Leu Arg Ala Leu Arg Gln
            20

<210> SEQ ID NO 203
<211> LENGTH: 22
<212> TYPE: PRT
<213> ORGANISM: Artificial Sequence
<220> FEATURE:
<223> OTHER INFORMATION: Type-1 cytokine derived peptides exhibiting
      structural motif B, Peptide FD

<400> SEQUENCE: 203

Gly Pro Val Pro Pro Ser Thr Ala Leu Arg Glu Leu Ile Glu Glu Leu
1               5                   10                  15

Val Asn Ile Thr Gln Asn
            20

<210> SEQ ID NO 204
<211> LENGTH: 17
<212> TYPE: PRT
<213> ORGANISM: Artificial Sequence
<220> FEATURE:
<223> OTHER INFORMATION: Type-1 cytokine derived peptides exhibiting
      structural motif B, Peptide FE

<400> SEQUENCE: 204

Lys Asp Leu Leu Leu His Leu Lys Lys Leu Phe Arg Glu Gly Arg Phe
1               5                   10                  15

Asn

<210> SEQ ID NO 205
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FF

<400> SEQUENCE: 205

Arg Asp Thr Lys Ile Glu Val Ala Gln Phe Val Lys Asp Leu Leu Leu
1               5                   10                  15

His Leu Lys Lys Leu Phe Arg Glu
            20

<210> SEQ ID NO 206
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FG

<400> SEQUENCE: 206

Leu Asp Gln Ile Pro Gly Tyr Leu Asn Arg Ile His Glu Leu Leu Asn
1               5                   10                  15

Gly Thr Arg Gly Leu Phe Pro Gly
            20

<210> SEQ ID NO 207
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FH

<400> SEQUENCE: 207

Ser Pro Ile Ser Ser Asp Phe Ala Val Lys Ile Arg Glu Leu Ser Asp
1               5                   10                  15

Tyr Leu Leu Gln Asp Tyr Pro Val
            20

<210> SEQ ID NO 208
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FI

<400> SEQUENCE: 208

Tyr Tyr Gly Arg Ile Leu His Tyr Leu Lys Ala Lys Glu Tyr Ser His
1               5                   10                  15

Cys Ala Trp Thr Ile Val Arg Val
            20

<210> SEQ ID NO 209
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, structural formula VIII
<220> FEATURE:
<221> NAME/KEY: misc_feature
<222> LOCATION: (1)..(1)
<223> OTHER INFORMATION: Xaa is Ala (A), Thr (T), Ser (S), Tyr (Y), Leu
      (L), Val (V), Ile (I), Phe (F), or Glu (E)
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is Ser (S), Gln (Q), Asp (D), Leu (L), Glu
      (E), Cys (C), Asn (N), Arg (R), or Ala (A)
<220> FEATURE:
<221> NAME/KEY: misc_feature
<222> LOCATION: (4)..(4)
<223> OTHER INFORMATION: Xaa is Pro (P), Gly (G), Gln (Q), Leu (L), Thr
      (T), Asn (N), Ser (S), Phe (F), or Ile (I)
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: misc_feature
<222> LOCATION: (6)..(6)
<223> OTHER INFORMATION: Xaa is Pro (P), Ser (S), Cys (C), Val (V), Lys
      (K), Thr (T), Leu (L), Ile (I), or Gln (Q)

```
<220> FEATURE:
<221> NAME/KEY: misc_feature
<222> LOCATION: (7)..(7)
<223> OTHER INFORMATION: Xaa is any amino acid
<220> FEATURE:
<221> NAME/KEY: misc_feature
<222> LOCATION: (8)..(8)
<223> OTHER INFORMATION: Xaa is Thr (T), Pro (P), Leu (L), Arg (R), Gly
      (G), Tyr (Y), Gln (Q), Glu (E), Ile (I) or Ala (A)
<220> FEATURE:
<221> NAME/KEY: misc_feature
<222> LOCATION: (9)..(9)
<223> OTHER INFORMATION: Xaa is any amino acid
<220> FEATURE:
<221> NAME/KEY: misc_feature
<222> LOCATION: (10)..(10)
<223> OTHER INFORMATION: Xaa is Pro (P), Asn (N), Glu (E), Asp (D), Thr
      (T), Leu (L), Ile (I), Gln (Q), Phe (F), or Trp (W)
<220> FEATURE:
<221> NAME/KEY: misc_feature
<222> LOCATION: (11)..(11)
<223> OTHER INFORMATION: Xaa is Trp (W), Leu (L), Ala (A), Met (M), Val
      (V), Ile (I), Phe (F), or Tyr (Y)
<220> FEATURE:
<221> NAME/KEY: misc_feature
<222> LOCATION: (12)..(12)
<223> OTHER INFORMATION: Xaa is a negatively charged amino acid
<220> FEATURE:
<221> NAME/KEY: misc_feature
<222> LOCATION: (13)..(13)
<223> OTHER INFORMATION: Xaa is a positively charged amino acid
<220> FEATURE:
<221> NAME/KEY: misc_feature
<222> LOCATION: (14)..(14)
<223> OTHER INFORMATION: Xaa is Val (V), Leu (L), or Ala (A)
<220> FEATURE:
<221> NAME/KEY: misc_feature
<222> LOCATION: (15)..(20)
<223> OTHER INFORMATION: Xaa is any amino acid
<220> FEATURE:
<221> NAME/KEY: misc_feature
<222> LOCATION: (21)..(21)
<223> OTHER INFORMATION: Xaa is Arg (R), Asp (D), Tyr (Y), Val (V), Ile
      (I), Leu (L), Lys (K), Ser (S), or Thr (T)
<220> FEATURE:
<221> NAME/KEY: misc_feature
<222> LOCATION: (22)..(23)
<223> OTHER INFORMATION: Xaa is any amino acid
<220> FEATURE:
<221> NAME/KEY: misc_feature
<222> LOCATION: (24)..(24)
<223> OTHER INFORMATION: Xaa is Leu (L), Pro (P), Phe (F), Arg (R), Tyr
      (Y), Cys (C), Gly (G), Val (V), or Lys (K)

<400> SEQUENCE: 209

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 210
<211> LENGTH: 24
<212> TYPE: PRT
<213> ORGANISM: Artificial Sequence
<220> FEATURE:
<223> OTHER INFORMATION: Type-1 cytokines derived peptides exhibiting
      structural motifl B, Peptide FJ

<400> SEQUENCE: 210

Ala Arg Ser Pro Ser Pro Ser Thr Gln Pro Trp Glu His Val Asn Ala
1               5                   10                  15

Ile Gln Glu Ala Arg Arg Leu Leu
            20
```

-continued

```
<210> SEQ ID NO 211
<211> LENGTH: 9
<212> TYPE: PRT
<213> ORGANISM: Artificial Sequence
<220> FEATURE:
<223> OTHER INFORMATION: Type-1 cytokine derived peptides exhibiting
      structural motif B, Peptide FK

<400> SEQUENCE: 211

Ile Thr Phe Glu Lys Leu Val Ile Pro
1               5

<210> SEQ ID NO 212
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FL

<400> SEQUENCE: 212

Thr Ala Gln Gly Glu Pro Phe Pro Asn Asn Leu Asp Lys Leu Cys Gly
1               5                   10                  15

Pro Asn Val Thr Asp Phe Pro Pro
            20

<210> SEQ ID NO 213
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FM

<400> SEQUENCE: 213

Ser Thr Asp Gln Trp Ser Glu Leu Thr Glu Ala Glu Arg Leu Gln Glu
1               5                   10                  15

Asn Leu Gln Ala Tyr Arg Thr Phe
            20

<210> SEQ ID NO 214
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FN

<400> SEQUENCE: 214

Tyr Gly Leu Leu Tyr Cys Phe Arg Lys Asp Met Asp Lys Val Glu Thr
1               5                   10                  15

Phe Leu Arg Ile Val Gln Cys Arg
            20

<210> SEQ ID NO 215
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FO

<400> SEQUENCE: 215

Leu Glu Ser Gln Thr Val Gln Gly Gly Thr Val Glu Arg Leu Phe Lys
1               5                   10                  15
```

```
Asn Leu Ser Leu Ile Lys Lys Tyr
            20

<210> SEQ ID NO 216
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FP

<400> SEQUENCE: 216

Val Gln Leu Ser Asp Ser Leu Thr Asp Leu Leu Asp Lys Phe Ser Asn
1               5                   10                  15

Ile Ser Glu Gly Leu Ser Asn Tyr
            20

<210> SEQ ID NO 217
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FQ

<400> SEQUENCE: 217

Ile Ser Glu Gly Leu Ser Asn Tyr Ser Ile Ile Asp Lys Leu Val Asn
1               5                   10                  15

Ile Val Asp Asp Leu Val Glu Cys
            20

<210> SEQ ID NO 218
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FR

<400> SEQUENCE: 218

Ser Ser Ser Thr Lys Lys Thr Gln Leu Gln Leu Glu His Leu Leu Leu
1               5                   10                  15

Asp Leu Gln Met Ile Leu Asn Gly
            20

<210> SEQ ID NO 219
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FS

<400> SEQUENCE: 219

Phe Asn Ser Asn Lys Lys Lys Arg Asp Asp Phe Glu Lys Leu Thr Asn
1               5                   10                  15

Tyr Ser Val Thr Asp Leu Asn Val
            20

<210> SEQ ID NO 220
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide FT
```

<400> SEQUENCE: 220

Ala Arg Cys Gln Val Thr Leu Arg Asp Leu Phe Asp Arg Ala Val Val
1 5 10 15

Leu Ser His Tyr Ile His Asn Leu
20

<210> SEQ ID NO 221
<211> LENGTH: 13
<212> TYPE: PRT
<213> ORGANISM: Artificial Sequence
<220> FEATURE:
<223> OTHER INFORMATION: Type-1 cytokine derived peptides exhibiting structural motif B, Peptide FU

<400> SEQUENCE: 221

Leu Asp Arg Val Tyr Asn Glu Glu Lys Arg Tyr Thr His
1 5 10

<210> SEQ ID NO 222
<211> LENGTH: 24
<212> TYPE: PRT
<213> ORGANISM: Artificial Sequence
<220> FEATURE:
<223> OTHER INFORMATION: Type-1 cytokine derived peptides exhibiting structural motif B, Peptide FV

<400> SEQUENCE: 222

Glu Ala Asn Gln Ser Thr Leu Glu Asn Phe Leu Glu Arg Leu Lys Thr
1 5 10 15

Ile Met Arg Glu Lys Tyr Ser Lys
20

<210> SEQ ID NO 223
<211> LENGTH: 24
<212> TYPE: PRT
<213> ORGANISM: Artificial Sequence
<220> FEATURE:
<223> OTHER INFORMATION: Type-1 cytokine derived peptides exhibiting structural motif B, Peptide FW

<400> SEQUENCE: 223

Leu Glu Arg Ser Gly Leu Asn Ile Glu Asp Leu Glu Lys Leu Gln Met
1 5 10 15

Ala Arg Pro Asn Ile Leu Gly Leu
20

<210> SEQ ID NO 224
<211> LENGTH: 24
<212> TYPE: PRT
<213> ORGANISM: Artificial Sequence
<220> FEATURE:
<223> OTHER INFORMATION: Type-1 cytokine derived peptides exhibiting structural motif B, Peptide FX

<400> SEQUENCE: 224

Leu Trp Arg Leu Val Leu Ala Gln Arg Trp Met Glu Arg Leu Lys Thr
1 5 10 15

Val Ala Gly Ser Lys Met Gln Gly
20

<210> SEQ ID NO 225
<211> LENGTH: 24
<212> TYPE: PRT
<213> ORGANISM: Artificial Sequence -continued

```
<220> FEATURE:
<223> OTHER INFORMATION: Type-1 cytokine derived peptides exhibiting
      structural motif B, Peptide FY

<400> SEQUENCE: 225

Thr Val Ala Gly Ser Lys Met Gln Gly Leu Leu Glu Arg Val Asn Thr
1               5                   10                  15

Glu Ile His Phe Val Thr Lys Cys
            20

<210> SEQ ID NO 226
<211> LENGTH: 21
<212> TYPE: PRT
<213> ORGANISM: Artificial Sequence
<220> FEATURE:
<223> OTHER INFORMATION: Type-1 cytokine derived peptides exhibiting
      structural motif B, Peptide FZ

<400> SEQUENCE: 226

Leu His Ala Phe Arg Ile Arg Ala Val Thr Ile Asp Arg Val Met Ser
1               5                   10                  15

Tyr Leu Asn Ala Ser
            20

<210> SEQ ID NO 227
<211> LENGTH: 24
<212> TYPE: PRT
<213> ORGANISM: Artificial Sequence
<220> FEATURE:
<223> OTHER INFORMATION: Type-1 cytokine derived peptides exhibiting
      structural motif B, Peptide GA

<400> SEQUENCE: 227

Leu Gln Arg Ile His Gln Gly Leu Ile Phe Tyr Glu Lys Leu Leu Gly
1               5                   10                  15

Ser Asp Ile Phe Thr Gly Glu Pro
            20

<210> SEQ ID NO 228
<211> LENGTH: 25
<212> TYPE: PRT
<213> ORGANISM: Artificial Sequence
<220> FEATURE:
<223> OTHER INFORMATION: Type-1 cytokine derived peptides exhibiting
      structural motif B, Formula IX
<220> FEATURE:
<221> NAME/KEY: misc_feature
<222> LOCATION: (1)..(1)
<223> OTHER INFORMATION: Xaa is Cys (C), Tyr (Y), or Ala (A)
<220> FEATURE:
<221> NAME/KEY: misc_feature
<222> LOCATION: (2)..(2)
<223> OTHER INFORMATION: Xaa is Ser (S), Leu (L), or Glu (E)
<220> FEATURE:
<221> NAME/KEY: misc_feature
<222> LOCATION: (3)..(3)
<223> OTHER INFORMATION: Xaa is Arg (R), Gln (Q), or Asn (N)
<220> FEATURE:
<221> NAME/KEY: misc_feature
<222> LOCATION: (4)..(4)
<223> OTHER INFORMATION: Xaa is Ser (S) or Leu (L)
<220> FEATURE:
<221> NAME/KEY: misc_feature
<222> LOCATION: (5)..(5)
<223> OTHER INFORMATION: Xaa is Ile (I), Leu (L), or Lys (K)
<220> FEATURE:
<221> NAME/KEY: misc_feature
<222> LOCATION: (6)..(6)
<223> OTHER INFORMATION: Xaa is Trp (W), Leu (L), or Lys (K)
<220> FEATURE:
```

```
<221> NAME/KEY: misc_feature
<222> LOCATION: (7)..(7)
<223> OTHER INFORMATION: Xaa is Leu (L), Phe (F), or Tyr (Y)
<220> FEATURE:
<221> NAME/KEY: misc_feature
<222> LOCATION: (8)..(8)
<223> OTHER INFORMATION: Xaa is Ala (A), Asn (N), or Phe (F)
<220> FEATURE:
<221> NAME/KEY: misc_feature
<222> LOCATION: (9)..(9)
<223> OTHER INFORMATION: Xaa is Arg (R), Pro (P), or Asn (N);
<220> FEATURE:
<221> NAME/KEY: misc_feature
<222> LOCATION: (10)..(10)
<223> OTHER INFORMATION: Xaa is Lys (K), Leu (L), or Ala (A);
<220> FEATURE:
<221> NAME/KEY: misc_feature
<222> LOCATION: (11)..(11)
<223> OTHER INFORMATION: Xaa is Ile (I), Val (V), or Gly (G)
<220> FEATURE:
<221> NAME/KEY: misc_feature
<222> LOCATION: (12)..(12)
<223> OTHER INFORMATION: Xaa is a positively charged amino acid
<220> FEATURE:
<221> NAME/KEY: misc_feature
<222> LOCATION: (13)..(13)
<223> OTHER INFORMATION: Xaa is a polar amino acid
<220> FEATURE:
<221> NAME/KEY: misc_feature
<222> LOCATION: (14)..(14)
<223> OTHER INFORMATION: Xaa is a negatively charged amino acid
<220> FEATURE:
<221> NAME/KEY: misc_feature
<222> LOCATION: (15)..(15)
<223> OTHER INFORMATION: Xaa is Leu (L), Gly (G), or Val (V)
<220> FEATURE:
<221> NAME/KEY: misc_feature
<222> LOCATION: (16)..(16)
<223> OTHER INFORMATION: Xaa is Thr (T), Ile (I), or Ala (A)
<220> FEATURE:
<221> NAME/KEY: misc_feature
<222> LOCATION: (17)..(17)
<223> OTHER INFORMATION: Xaa is Ala (A), Cys (C), or Asp (D)
<220> FEATURE:
<221> NAME/KEY: misc_feature
<222> LOCATION: (18)..(18)
<223> OTHER INFORMATION: Xaa is Leu (L), Arg (R) or Asn (N)
<220> FEATURE:
<221> NAME/KEY: misc_feature
<222> LOCATION: (19)..(19)
<223> OTHER INFORMATION: Xaa is Thr (T), Asn (N), or Gly (G)
<220> FEATURE:
<221> NAME/KEY: misc_feature
<222> LOCATION: (20)..(20)
<223> OTHER INFORMATION: Xaa is Glu (E), Arg (R), or Thr (T)
<220> FEATURE:
<221> NAME/KEY: misc_feature
<222> LOCATION: (21)..(21)
<223> OTHER INFORMATION: Xaa is Ser (S), Val (V), or Leu (L)
<220> FEATURE:
<221> NAME/KEY: misc_feature
<222> LOCATION: (22)..(22)
<223> OTHER INFORMATION: Xaa is Tyr (Y), Thr (T), Phe (F)
<220> FEATURE:
<221> NAME/KEY: misc_feature
<222> LOCATION: (23)..(23)
<223> OTHER INFORMATION: Xaa is Asn (N) or Leu (L)
<220> FEATURE:
<221> NAME/KEY: misc_feature
<222> LOCATION: (24)..(24)
<223> OTHER INFORMATION: Xaa is Asn (N) or Gly (G)
<220> FEATURE:
<221> NAME/KEY: misc_feature
<222> LOCATION: (25)..(25)
<223> OTHER INFORMATION: Xaa is Val (V) or Ile (I)

<400> SEQUENCE: 228

Xaa Xaa Xaa Xaa Xaa Xaa Xaa Xaa Xaa Xaa Xaa Xaa Xaa Xaa Xaa Xaa
```

```
1               5                   10                  15
Xaa Xaa Xaa Xaa Xaa Xaa Xaa Xaa
            20                  25

<210> SEQ ID NO 229
<211> LENGTH: 25
<212> TYPE: PRT
<213> ORGANISM: Artificial Sequence
<220> FEATURE:
<223> OTHER INFORMATION: Type-1 cytokine derived peptides exhibiting
      structural motif B, Peptide GB

<400> SEQUENCE: 229

Cys Ser Arg Ser Ile Trp Leu Ala Arg Lys Ile Arg Ser Asp Leu Thr
1               5                   10                  15

Ala Leu Thr Glu Ser Tyr Val Lys His
            20                  25

<210> SEQ ID NO 230
<211> LENGTH: 25
<212> TYPE: PRT
<213> ORGANISM: Artificial Sequence
<220> FEATURE:
<223> OTHER INFORMATION: Type-1 cytokine derived peptides exhibiting
      structural motif B, Peptide GC

<400> SEQUENCE: 230

Glu Leu Met Ile Leu Leu Glu Tyr Lys Ile Pro Arg Asn Glu Ala Asp
1               5                   10                  15

Gly Met Pro Ile Asn Val Gly Asp Gly
            20                  25

<210> SEQ ID NO 231
<211> LENGTH: 25
<212> TYPE: PRT
<213> ORGANISM: Artificial Sequence
<220> FEATURE:
<223> OTHER INFORMATION: Type-1 cytokine derived peptides exhibiting
      structural motif B, Peptide GD

<400> SEQUENCE: 231

Tyr Leu Gln Leu Leu Leu Phe Asn Pro Leu Val Lys Thr Glu Gly Ile
1               5                   10                  15

Cys Arg Asn Arg Val Thr Asn Asn Val
            20                  25

<210> SEQ ID NO 232
<211> LENGTH: 25
<212> TYPE: PRT
<213> ORGANISM: Artificial Sequence
<220> FEATURE:
<223> OTHER INFORMATION: Type-1 cytokine derived peptides exhibiting
      structural motif B, Peptide GE

<400> SEQUENCE: 232

Ala Glu Asn Leu Lys Lys Tyr Phe Asn Ala Gly His Ser Asp Val Ala
1               5                   10                  15

Asp Asn Gly Thr Leu Phe Leu Gly Ile
            20                  25

<210> SEQ ID NO 233
<211> LENGTH: 25
<212> TYPE: PRT
<213> ORGANISM: Artificial Sequence
<220> FEATURE:
```

<223> OTHER INFORMATION: Type-1 cytokine derived peptides exhibiting
      structural motif B, structural formula X
<220> FEATURE:
<221> NAME/KEY: misc_feature
<222> LOCATION: (1)..(1)
<223> OTHER INFORMATION: Xaa is Leu (L)
<220> FEATURE:
<221> NAME/KEY: misc_feature
<222> LOCATION: (2)..(2)
<223> OTHER INFORMATION: Xaa is Gly (G)
<220> FEATURE:
<221> NAME/KEY: misc_feature
<222> LOCATION: (3)..(3)
<223> OTHER INFORMATION: Xaa is Cys (C)
<220> FEATURE:
<221> NAME/KEY: misc_feature
<222> LOCATION: (4)..(4)
<223> OTHER INFORMATION: Xaa is Val (V)
<220> FEATURE:
<221> NAME/KEY: misc_feature
<222> LOCATION: (5)..(5)
<223> OTHER INFORMATION: Xaa is Leu (L)
<220> FEATURE:
<221> NAME/KEY: misc_feature
<222> LOCATION: (6)..(6)
<223> OTHER INFORMATION: Xaa is His (H)
<220> FEATURE:
<221> NAME/KEY: misc_feature
<222> LOCATION: (7)..(7)
<223> OTHER INFORMATION: Xaa is Arg (R)
<220> FEATURE:
<221> NAME/KEY: misc_feature
<222> LOCATION: (8)..(8)
<223> OTHER INFORMATION: Xaa is Leu (L)
<220> FEATURE:
<221> NAME/KEY: misc_feature
<222> LOCATION: (9)..(9)
<223> OTHER INFORMATION: Xaa is Ala (A)
<220> FEATURE:
<221> NAME/KEY: misc_feature
<222> LOCATION: (10)..(10)
<223> OTHER INFORMATION: Xaa is Asp (D)
<220> FEATURE:
<221> NAME/KEY: misc_feature
<222> LOCATION: (11)..(11)
<223> OTHER INFORMATION: Xaa is Leu (L)
<220> FEATURE:
<221> NAME/KEY: misc_feature
<222> LOCATION: (12)..(12)
<223> OTHER INFORMATION: Xaa is negatively charged amino acid
<220> FEATURE:
<221> NAME/KEY: misc_feature
<222> LOCATION: (13)..(13)
<223> OTHER INFORMATION: Xaa is a polar amino acid
<220> FEATURE:
<221> NAME/KEY: misc_feature
<222> LOCATION: (14)..(14)
<223> OTHER INFORMATION: Xaa is a positively charged amino acid
<220> FEATURE:
<221> NAME/KEY: misc_feature
<222> LOCATION: (15)..(15)
<223> OTHER INFORMATION: Xaa is Leu (L)
<220> FEATURE:
<221> NAME/KEY: misc_feature
<222> LOCATION: (16)..(16)
<223> OTHER INFORMATION: Xaa is Pro (P)
<220> FEATURE:
<221> NAME/KEY: misc_feature
<222> LOCATION: (17)..(17)
<223> OTHER INFORMATION: Xaa is Lys (K)
<220> FEATURE:
<221> NAME/KEY: misc_feature
<222> LOCATION: (18)..(18)
<223> OTHER INFORMATION: Xaa is Ala (A)
<220> FEATURE:
<221> NAME/KEY: misc_feature
<222> LOCATION: (19)..(19)
<223> OTHER INFORMATION: Xaa is Gln (Q)
<220> FEATURE:

```
<221> NAME/KEY: misc_feature
<222> LOCATION: (20)..(20)
<223> OTHER INFORMATION: Xaa is Asp (D)
<220> FEATURE:
<221> NAME/KEY: misc_feature
<222> LOCATION: (21)..(21)
<223> OTHER INFORMATION: Xaa is Leu (L)
<220> FEATURE:
<221> NAME/KEY: misc_feature
<222> LOCATION: (22)..(22)
<223> OTHER INFORMATION: Xaa is Glu (E)
<220> FEATURE:
<221> NAME/KEY: misc_feature
<222> LOCATION: (23)..(23)
<223> OTHER INFORMATION: Xaa is Arg (R)
<220> FEATURE:
<221> NAME/KEY: misc_feature
<222> LOCATION: (24)..(24)
<223> OTHER INFORMATION: Xaa is Ser (S)
<220> FEATURE:
<221> NAME/KEY: misc_feature
<222> LOCATION: (25)..(25)
<223> OTHER INFORMATION: Xaa is Gly (G)

<400> SEQUENCE: 233

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 234
<211> LENGTH: 25
<212> TYPE: PRT
<213> ORGANISM: Artificial Sequence
<220> FEATURE:
<223> OTHER INFORMATION: Type-1 cytokines derived peptides exhibiting
      structural motif B, Peptide GF

<400> SEQUENCE: 234

Leu Gly Cys Val Leu His Arg Leu Ala Asp Leu Glu Gln Arg Leu Pro
1               5                   10                  15

Lys Ala Gln Asp Leu Glu Arg Ser Gly
            20                  25

<210> SEQ ID NO 235
<211> LENGTH: 14
<212> TYPE: PRT
<213> ORGANISM: Artificial Sequence
<220> FEATURE:
<223> OTHER INFORMATION: Human thrombopoietin derived Peptide GG

<400> SEQUENCE: 235

Asp Leu Arg Val Leu Ser Lys Leu Leu Arg Asp Ser His Val
1               5                   10

<210> SEQ ID NO 236
<211> LENGTH: 20
<212> TYPE: PRT
<213> ORGANISM: Artificial Sequence
<220> FEATURE:
<223> OTHER INFORMATION: Human thrombopoietin derived Peptide GH

<400> SEQUENCE: 236

Pro Thr Pro Val Leu Leu Pro Ala Val Asp Phe Ser Leu Gly Glu Trp
1               5                   10                  15

Lys Thr Gln Met
            20
```

```
<210> SEQ ID NO 237
<211> LENGTH: 24
<212> TYPE: PRT
<213> ORGANISM: Artificial Sequence
<220> FEATURE:
<223> OTHER INFORMATION: Human Thrombopoietin derived Peptide GI

<400> SEQUENCE: 237

Thr Ala His Lys Asp Pro Asn Ala Ile Phe Leu Ser Phe Gln His Leu
1               5                   10                  15

Leu Arg Gly Lys Val Arg Phe Leu
            20

<210> SEQ ID NO 238
<211> LENGTH: 15
<212> TYPE: PRT
<213> ORGANISM: Artificial Sequence
<220> FEATURE:
<223> OTHER INFORMATION: Human thromboietin derived Peptide GJ

<400> SEQUENCE: 238

Pro Asn Arg Thr Ser Gly Leu Leu Glu Thr Asn Phe Thr Ala Ser
1               5                   10                  15

<210> SEQ ID NO 239
<211> LENGTH: 17
<212> TYPE: PRT
<213> ORGANISM: Artificial Sequence
<220> FEATURE:
<223> OTHER INFORMATION: GM-CSF derived Peptide GK

<400> SEQUENCE: 239

Pro Ser Thr Gln Pro Trp Glu His Val Asn Ala Ile Gln Glu Ala Arg
1               5                   10                  15

Arg

<210> SEQ ID NO 240
<211> LENGTH: 9
<212> TYPE: PRT
<213> ORGANISM: Artificial Sequence
<220> FEATURE:
<223> OTHER INFORMATION: GM-CSF derived Peptide GL

<400> SEQUENCE: 240

Asn Glu Thr Val Glu Val Ile Ser Glu
1               5

<210> SEQ ID NO 241
<211> LENGTH: 24
<212> TYPE: PRT
<213> ORGANISM: Artificial Sequence
<220> FEATURE:
<223> OTHER INFORMATION: GM-CSF derived Peptide GM

<400> SEQUENCE: 241

Gln Thr Arg Leu Glu Leu Tyr Lys Gln Gly Leu Arg Gly Ser Leu Thr
1               5                   10                  15

Lys Leu Lys Gly Pro Leu Thr Met
            20

<210> SEQ ID NO 242
<211> LENGTH: 17
<212> TYPE: PRT
<213> ORGANISM: Artificial Sequence
<220> FEATURE:
<223> OTHER INFORMATION: GM-CSF derived Peptide GN
```

<400> SEQUENCE: 242

Lys Asp Phe Leu Leu Val Ile Pro Phe Asp Cys Trp Glu Pro Val Gln
1               5                   10                  15

Glu

<210> SEQ ID NO 243
<211> LENGTH: 14
<212> TYPE: PRT
<213> ORGANISM: Artificial Sequence
<220> FEATURE:
<223> OTHER INFORMATION: CNFT derived Peptide GO

<400> SEQUENCE: 243

Cys Ser Arg Ser Ile Trp Leu Ala Arg Lys Ile Arg Ser Asp
1               5                   10

<210> SEQ ID NO 244
<211> LENGTH: 18
<212> TYPE: PRT
<213> ORGANISM: Artificial Sequence
<220> FEATURE:
<223> OTHER INFORMATION: CNFT derived Peptide GP

<400> SEQUENCE: 244

Asn Lys Asn Ile Asn Leu Asp Ser Ala Asp Gly Met Pro Val Ala Ser
1               5                   10                  15

Thr Asp

<210> SEQ ID NO 245
<211> LENGTH: 21
<212> TYPE: PRT
<213> ORGANISM: Artificial Sequence
<220> FEATURE:
<223> OTHER INFORMATION: CNFT derived Peptide GQ

<400> SEQUENCE: 245

Leu Leu Gln Val Ala Ala Phe Ala Tyr Gln Ile Glu Glu Leu Met Ile
1               5                   10                  15

Leu Leu Glu Tyr Lys
            20

<210> SEQ ID NO 246
<211> LENGTH: 18
<212> TYPE: PRT
<213> ORGANISM: Artificial Sequence
<220> FEATURE:
<223> OTHER INFORMATION: CNFT derived Peptide GR

<400> SEQUENCE: 246

Glu Leu Ser Gln Trp Thr Val Arg Ser Ile His Asp Leu Arg Phe Ile
1               5                   10                  15

Ser Ser

<210> SEQ ID NO 247
<211> LENGTH: 16
<212> TYPE: PRT
<213> ORGANISM: Artificial Sequence
<220> FEATURE:
<223> OTHER INFORMATION: IL-6 derived Peptide GS

<400> SEQUENCE: 247

Ser Glu Arg Ile Asp Lys Gln Ile Arg Tyr Ile Leu Asp Gly Ile Ser
1               5                   10                  15

<210> SEQ ID NO 248
<211> LENGTH: 14
<212> TYPE: PRT
<213> ORGANISM: Artificial Sequence
<220> FEATURE:
<223> OTHER INFORMATION: IL-6 derived Peptide GT

<400> SEQUENCE: 248

Ala Glu Asn Asn Leu Asn Leu Pro Lys Met Ala Glu Lys Asp
1               5                   10

<210> SEQ ID NO 249
<211> LENGTH: 16
<212> TYPE: PRT
<213> ORGANISM: Artificial Sequence
<220> FEATURE:
<223> OTHER INFORMATION: IL-6 derived Peptide GU

<400> SEQUENCE: 249

Glu Glu Gln Ala Arg Ala Val Gln Met Ser Thr Lys Val Leu Ile Gln
1               5                   10                  15

<210> SEQ ID NO 250
<211> LENGTH: 12
<212> TYPE: PRT
<213> ORGANISM: Artificial Sequence
<220> FEATURE:
<223> OTHER INFORMATION: IL-6 derived Peptide GV

<400> SEQUENCE: 250

Arg Ser Phe Lys Glu Phe Leu Gln Ser Ser Leu Arg
1               5                   10

<210> SEQ ID NO 251
<211> LENGTH: 14
<212> TYPE: PRT
<213> ORGANISM: Artificial Sequence
<220> FEATURE:
<223> OTHER INFORMATION: IL-3 derived Peptide GW

<400> SEQUENCE: 251

Ser Cys Asn Met Ile Asp Glu Ile Ile Thr His Leu Lys Gln
1               5                   10

<210> SEQ ID NO 252
<211> LENGTH: 18
<212> TYPE: PRT
<213> ORGANISM: Artificial Sequence
<220> FEATURE:
<223> OTHER INFORMATION: IL-3 derived Peptide GX

<400> SEQUENCE: 252

Glu Asn Asn Leu Arg Arg Pro Asn Leu Glu Ala Phe Asn Arg Ala Val
1               5                   10                  15

Lys Ser

<210> SEQ ID NO 253
<211> LENGTH: 20
<212> TYPE: PRT
<213> ORGANISM: Artificial Sequence
<220> FEATURE:
<223> OTHER INFORMATION: IL-3 derived Peptide GY

<400> SEQUENCE: 253

His Ile Lys Asp Gly Asp Trp Asn Glu Phe Arg Arg Lys Leu Thr Phe

```
1               5                   10                  15

Tyr Leu Lys Thr
            20

<210> SEQ ID NO 254
<211> LENGTH: 21
<212> TYPE: PRT
<213> ORGANISM: Artificial Sequence
<220> FEATURE:
<223> OTHER INFORMATION: Human interferon alpha derived Peptide GZ

<400> SEQUENCE: 254

Ser Ser Cys Leu Met Asp Arg His Asp Phe Gly Phe Pro Gln Glu Glu
1               5                   10                  15

Phe Asp Gly Asn Gln
            20

<210> SEQ ID NO 255
<211> LENGTH: 18
<212> TYPE: PRT
<213> ORGANISM: Artificial Sequence
<220> FEATURE:
<223> OTHER INFORMATION: Human interferon alpha derived Peptide HA

<400> SEQUENCE: 255

Gln Gln Ile Phe Asn Leu Phe Thr Thr Lys Asp Ser Ser Ala Ala Trp
1               5                   10                  15

Asp Glu

<210> SEQ ID NO 256
<211> LENGTH: 20
<212> TYPE: PRT
<213> ORGANISM: Artificial Sequence
<220> FEATURE:
<223> OTHER INFORMATION: Human interferon alpha derived Peptide HB

<400> SEQUENCE: 256

Leu Met Asn Ala Asp Ser Ile Leu Ala Val Lys Lys Tyr Phe Arg Arg
1               5                   10                  15

Ile Thr Leu Tyr
            20

<210> SEQ ID NO 257
<211> LENGTH: 25
<212> TYPE: PRT
<213> ORGANISM: Artificial Sequence
<220> FEATURE:
<223> OTHER INFORMATION: Human interferon beta derived Peptide HC

<400> SEQUENCE: 257

Met Ser Tyr Asn Leu Leu Gly Phe Leu Gln Arg Ser Ser Asn Phe Gln
1               5                   10                  15

Cys Gln Lys Leu Leu Trp Gln Leu Asn
            20                  25

<210> SEQ ID NO 258
<211> LENGTH: 19
<212> TYPE: PRT
<213> ORGANISM: Artificial Sequence
<220> FEATURE:
<223> OTHER INFORMATION: Human interferon beta derived Peptide HD

<400> SEQUENCE: 258

Asp Arg Met Asn Phe Asp Ile Pro Glu Glu Ile Lys Gln Leu Gln Gln
```

```
1               5                   10                  15
Phe Gln Lys

<210> SEQ ID NO 259
<211> LENGTH: 20
<212> TYPE: PRT
<213> ORGANISM: Artificial Sequence
<220> FEATURE:
<223> OTHER INFORMATION: Human interferon beta derived Peptide HE

<400> SEQUENCE: 259

Lys Leu Glu Lys Glu Asp Phe Thr Arg Gly Lys Leu Met Ser Ser Leu
1               5                   10                  15

His Leu Lys Arg
            20

<210> SEQ ID NO 260
<211> LENGTH: 11
<212> TYPE: PRT
<213> ORGANISM: Artificial Sequence
<220> FEATURE:
<223> OTHER INFORMATION: Human interferon beta derived Peptide HF

<400> SEQUENCE: 260

Phe Ile Asn Arg Leu Thr Gly Tyr Leu Arg Asn
1               5                   10

<210> SEQ ID NO 261
<211> LENGTH: 20
<212> TYPE: PRT
<213> ORGANISM: Artificial Sequence
<220> FEATURE:
<223> OTHER INFORMATION: Human interferon gamma derived Peptide HG

<400> SEQUENCE: 261

Cys Tyr Cys Gln Asp Pro Tyr Val Lys Glu Ala Glu Asn Leu Lys Lys
1               5                   10                  15

Tyr Phe Asn Ala
            20

<210> SEQ ID NO 262
<211> LENGTH: 20
<212> TYPE: PRT
<213> ORGANISM: Artificial Sequence
<220> FEATURE:
<223> OTHER INFORMATION: Human interferon gamma  derived Peptide HH

<400> SEQUENCE: 262

Ala Asp Asn Gly Thr Leu Phe Leu Gly Ile Leu Lys Asn Trp Lys Glu
1               5                   10                  15

Glu Ser Asp Arg
            20

<210> SEQ ID NO 263
<211> LENGTH: 20
<212> TYPE: PRT
<213> ORGANISM: Artificial Sequence
<220> FEATURE:
<223> OTHER INFORMATION: Human interferon gamma derived Peptide HI

<400> SEQUENCE: 263

Asn Ser Asn Lys Lys Lys Arg Asp Asp Phe Glu Lys Leu Thr Asn Tyr
1               5                   10                  15

Ser Val Thr Asp
```

<210> SEQ ID NO 264
<211> LENGTH: 11
<212> TYPE: PRT
<213> ORGANISM: Artificial Sequence
<220> FEATURE:
<223> OTHER INFORMATION: Human interferon gamma derived Peptide HJ

<400> SEQUENCE: 264

Glu Leu Ser Pro Ala Ala Lys Thr Gly Lys Arg
1               5                   10

<210> SEQ ID NO 265
<211> LENGTH: 20
<212> TYPE: PRT
<213> ORGANISM: Artificial Sequence
<220> FEATURE:
<223> OTHER INFORMATION: Human stem cell factor derived Peptide HK

<400> SEQUENCE: 265

Ser Leu Ile Ile Gly Phe Ala Ala Gly Ala Leu Tyr Trp Lys Lys Arg
1               5                   10                  15

Gln Pro Ser Leu
            20

<210> SEQ ID NO 266
<211> LENGTH: 15
<212> TYPE: PRT
<213> ORGANISM: Artificial Sequence
<220> FEATURE:
<223> OTHER INFORMATION: Human stem cell factor derived Peptide HL

<400> SEQUENCE: 266

Arg Asn Arg Val Thr Asn Asn Val Lys Asp Val Thr Lys Leu Val
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Human stem cell factor derived Peptide HM

<400> SEQUENCE: 267

Asp Lys Leu Val Asn Ile Val Asp Asp Leu Val Glu Cys Val Lys Glu
1               5                   10                  15

<210> SEQ ID NO 268
<211> LENGTH: 19
<212> TYPE: PRT
<213> ORGANISM: Artificial Sequence
<220> FEATURE:
<223> OTHER INFORMATION: Human stem cell factor derived Peptide HN

<400> SEQUENCE: 268

Ser Glu Thr Ser Asp Cys Trp Ser Ser Thr Leu Ser Pro Glu Lys Asp
1               5                   10                  15

Ser Arg Val

<210> SEQ ID NO 269
<211> LENGTH: 19
<212> TYPE: PRT
<213> ORGANISM: Artificial Sequence
<220> FEATURE:
<223> OTHER INFORMATION: Human multiple coagulation factor deficiency protein 2 derived Peptide HO

<400> SEQUENCE: 269

Asp Glu Leu Ile Asn Ile Ile Asp Gly Val Leu Arg Asp Asp Asp Lys
1               5                   10                  15

Asn Asn Asp

<210> SEQ ID NO 270
<211> LENGTH: 20
<212> TYPE: PRT
<213> ORGANISM: Artificial Sequence
<220> FEATURE:
<223> OTHER INFORMATION: Human multiple coagulation factor deficiency
      protein 2 derived Peptide HP

<400> SEQUENCE: 270

Gly Leu Asp Lys Asn Thr Val His Asp Gln Glu His Ile Met Glu His
1               5                   10                  15

Leu Glu Gly Val
            20

<210> SEQ ID NO 271
<211> LENGTH: 16
<212> TYPE: PRT
<213> ORGANISM: Artificial Sequence
<220> FEATURE:
<223> OTHER INFORMATION: Human multiple coagulation factor deficiency
      protein 2 derived Peptide HQ

<400> SEQUENCE: 271

Gln Leu His Tyr Phe Lys Met His Asp Tyr Asp Gly Asn Asn Leu Leu
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: hIL-6 AB loop derived Peptide HT

<400> SEQUENCE: 272

Glu Ala Leu Ala Glu Asn Asn Leu Asn Leu Pro Lys Met Ala Gly
1               5                   10                  15

<210> SEQ ID NO 273
<211> LENGTH: 17
<212> TYPE: PRT
<213> ORGANISM: Artificial Sequence
<220> FEATURE:
<223> OTHER INFORMATION: hIL-2 AB loop derived Peptide HU

<400> SEQUENCE: 273

Leu Gln Met Ile Leu Asn Gly Ile Asn Asn Tyr Lys Asn Pro Lys Leu
1               5                   10                  15

Thr

<210> SEQ ID NO 274
<211> LENGTH: 12
<212> TYPE: PRT
<213> ORGANISM: Artificial Sequence
<220> FEATURE:
<223> OTHER INFORMATION: hIL-3 AB loop derived Peptide HV

<400> SEQUENCE: 274

Ile Leu Met Glu Asn Asn Leu Arg Arg Pro Asn Leu

```
<210> SEQ ID NO 275
<211> LENGTH: 13
<212> TYPE: PRT
<213> ORGANISM: Artificial Sequence
<220> FEATURE:
<223> OTHER INFORMATION: hIL-gamma AB loop derived Peptide HW

<400> SEQUENCE: 275

Phe Tyr Leu Arg Asn Asn Gln Leu Val Ala Gly Thr Leu
1               5                   10

<210> SEQ ID NO 276
<211> LENGTH: 19
<212> TYPE: PRT
<213> ORGANISM: Artificial Sequence
<220> FEATURE:
<223> OTHER INFORMATION: hLIF AB loop derived Peptide HX

<400> SEQUENCE: 276

Tyr Thr Ala Gln Gly Glu Pro Phe Pro Asn Asn Val Glu Leu Lys Leu
1               5                   10                  15

Cys Ala Pro

<210> SEQ ID NO 277
<211> LENGTH: 15
<212> TYPE: PRT
<213> ORGANISM: Artificial Sequence
<220> FEATURE:
<223> OTHER INFORMATION: hIL-1.beta helix C derived Peptide HY

<400> SEQUENCE: 277

Phe Asn Lys Ile Glu Ile Asn Asn Lys Leu Glu Phe Glu Ser Ala
1               5                   10                  15

<210> SEQ ID NO 278
<211> LENGTH: 18
<212> TYPE: PRT
<213> ORGANISM: Artificial Sequence
<220> FEATURE:
<223> OTHER INFORMATION: hONC-M helix C derived Peptide HZ

<400> SEQUENCE: 278

Arg Pro Asn Ile Leu Gly Leu Arg Asn Asn Ile Tyr Cys Met Ala Gln
1               5                   10                  15

Leu Leu

<210> SEQ ID NO 279
<211> LENGTH: 20
<212> TYPE: PRT
<213> ORGANISM: Artificial Sequence
<220> FEATURE:
<223> OTHER INFORMATION: hCNTF derived Peptide IA
<220> FEATURE:
<221> NAME/KEY: MOD_RES
<222> LOCATION: (20)..(20)
<223> OTHER INFORMATION: Xaa is modified Pro with C-terminal biotin

<400> SEQUENCE: 279

Tyr Val Lys His Gln Gly Leu Asn Lys Asn Ile Asn Leu Asp Ser Val
1               5                   10                  15

Asp Gly Val Xaa
            20
```

```
<210> SEQ ID NO 280
<211> LENGTH: 12
<212> TYPE: PRT
<213> ORGANISM: Artificial Sequence
<220> FEATURE:
<223> OTHER INFORMATION: hIL-3 derived Peptide IB
<220> FEATURE:
<221> NAME/KEY: MOD_RES
<222> LOCATION: (1)..(1)
<223> OTHER INFORMATION: Xaa is modified Ile with N-terminal D-biotin

<400> SEQUENCE: 280

Xaa Leu Met Glu Asn Asn Leu Arg Arg Pro Asn Leu
 1               5                  10

<210> SEQ ID NO 281
<211> LENGTH: 11
<212> TYPE: PRT
<213> ORGANISM: Artificial Sequence
<220> FEATURE:
<223> OTHER INFORMATION: Helix B amino acids derived Peptide IC

<400> SEQUENCE: 281

Gln Glu Gln Leu Glu Arg Ala Leu Asn Ser Ser
 1               5                  10

<210> SEQ ID NO 282
<211> LENGTH: 11
<212> TYPE: PRT
<213> ORGANISM: Artificial Sequence
<220> FEATURE:
<223> OTHER INFORMATION: Helix B amino acids derived Peptide ID
<220> FEATURE:
<221> NAME/KEY: misc_feature
<222> LOCATION: (1)..(1)
<223> OTHER INFORMATION: Xaa is pyroglutamate

<400> SEQUENCE: 282

Xaa Glu Gln Leu Glu Arg Ala Leu Asn Ser Ser
 1               5                  10

<210> SEQ ID NO 283
<211> LENGTH: 12
<212> TYPE: PRT
<213> ORGANISM: Artificial Sequence
<220> FEATURE:
<223> OTHER INFORMATION: Calcitonin derived Peptide IE

<400> SEQUENCE: 283

Ala Leu Ser Ile Leu Val Leu Leu Gln Ala Gly Ser
 1               5                  10

<210> SEQ ID NO 284
<211> LENGTH: 11
<212> TYPE: PRT
<213> ORGANISM: Artificial Sequence
<220> FEATURE:
<223> OTHER INFORMATION: Corticotropin releasing hormone derived
      Peptide IF

<400> SEQUENCE: 284

Val Ala Leu Leu Pro Cys Pro Pro Cys Arg Ala
 1               5                  10

<210> SEQ ID NO 285
<211> LENGTH: 11
<212> TYPE: PRT
<213> ORGANISM: Artificial Sequence
<220> FEATURE:
```

<223> OTHER INFORMATION: Beta endorphin derived Peptide IG

<400> SEQUENCE: 285

Asn Ala Ile Ile Lys Asn Ala Tyr Lys Lys Gly
1               5                   10

<210> SEQ ID NO 286
<211> LENGTH: 11
<212> TYPE: PRT
<213> ORGANISM: Artificial Sequence
<220> FEATURE:
<223> OTHER INFORMATION: Glucagon derived Peptide IH

<400> SEQUENCE: 286

Gly Ser Trp Gln Arg Ser Leu Gln Asp Thr Glu
1               5                   10

<210> SEQ ID NO 287
<211> LENGTH: 10
<212> TYPE: PRT
<213> ORGANISM: Artificial Sequence
<220> FEATURE:
<223> OTHER INFORMATION: Secretin derived Peptide II

<400> SEQUENCE: 287

Gly Gly Ser Ala Ala Arg Pro Ala Pro Pro
1               5                   10

<210> SEQ ID NO 288
<211> LENGTH: 11
<212> TYPE: PRT
<213> ORGANISM: Artificial Sequence
<220> FEATURE:
<223> OTHER INFORMATION: Vasointestinal peptide derived Peptide IJ

<400> SEQUENCE: 288

Asn Ala Leu Ala Glu Asn Asp Thr Pro Tyr Tyr
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Neuropeptide Y derived Peptide IK

<400> SEQUENCE: 289

Gly Ala Leu Ala Glu Ala Tyr Pro Ser Lys Pro
1               5                   10

<210> SEQ ID NO 290
<211> LENGTH: 11
<212> TYPE: PRT
<213> ORGANISM: Artificial Sequence
<220> FEATURE:
<223> OTHER INFORMATION: Gonadotropin releasing hormone derived
      Peptide IL

<400> SEQUENCE: 290

Gly Cys Ser Ser Gln His Trp Ser Tyr Gly Leu
1               5                   10

<210> SEQ ID NO 291
<211> LENGTH: 11
<212> TYPE: PRT
<213> ORGANISM: Artificial Sequence
<220> FEATURE:

<223> OTHER INFORMATION: Parathyroid hormone derived Peptide IM

<400> SEQUENCE: 291

Val Met Ile Val Met Leu Ala Ile Cys Phe Leu
1               5                   10

<210> SEQ ID NO 292
<211> LENGTH: 11
<212> TYPE: PRT
<213> ORGANISM: Artificial Sequence
<220> FEATURE:
<223> OTHER INFORMATION: Pancreatic polypeptide derived Peptide IN

<400> SEQUENCE: 292

Leu Arg Arg Tyr Ile Asn Met Leu Thr Arg Pro
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Calcitonin gene related peptide derived
      Peptide IO

<400> SEQUENCE: 293

Leu Ala Leu Ser Ile Leu Val Leu Tyr Gln Ala
1               5                   10

<210> SEQ ID NO 294
<211> LENGTH: 23
<212> TYPE: PRT
<213> ORGANISM: Artificial Sequence
<220> FEATURE:
<223> OTHER INFORMATION: Carboxy terminus of the amphipathic helix;
      sequence TR derived Peptide IQ

<400> SEQUENCE: 294

Gln Glu Gln Leu Glu Arg Ala Leu Asn Ser Ser Leu Arg Arg Tyr Ile
1               5                   10                  15

Asn Met Leu Thr Arg Thr Arg
            20

<210> SEQ ID NO 295
<211> LENGTH: 7
<212> TYPE: PRT
<213> ORGANISM: Artificial Sequence
<220> FEATURE:
<223> OTHER INFORMATION: Helix-B exterior-presenting amino acids linked
      to the beta pleated sheet derived Peptide IR

<400> SEQUENCE: 295

Cys Ser Leu Asn Glu Asn Ile
1               5

<210> SEQ ID NO 296
<211> LENGTH: 18
<212> TYPE: PRT
<213> ORGANISM: Artificial Sequence
<220> FEATURE:
<223> OTHER INFORMATION: Chimeric peptide derived Peptide IS

<400> SEQUENCE: 296

Cys Ser Leu Asn Glu Asn Ile Gln Glu Gln Leu Glu Arg Ala Leu Asn
1               5                   10                  15

Ser Ser

```
<210> SEQ ID NO 297
<211> LENGTH: 5
<212> TYPE: PRT
<213> ORGANISM: Artificial Sequence
<220> FEATURE:
<223> OTHER INFORMATION: Terminal portion of Helix C derived Peptide IT

<400> SEQUENCE: 297

Ala Leu Gly Lys Ala
1               5

<210> SEQ ID NO 298
<211> LENGTH: 11
<212> TYPE: PRT
<213> ORGANISM: Artificial Sequence
<220> FEATURE:
<223> OTHER INFORMATION: Loop CD-partial derived Peptide IW
<220> FEATURE:
<221> NAME/KEY: misc_feature
<222> LOCATION: (1)..(1)
<223> OTHER INFORMATION: Xaa is PEG-Gln

<400> SEQUENCE: 298

Xaa Glu Gln Leu Glu Arg Ala Leu Asn Ser Ser
1               5                   10

<210> SEQ ID NO 299
<211> LENGTH: 27
<212> TYPE: PRT
<213> ORGANISM: Artificial Sequence
<220> FEATURE:
<223> OTHER INFORMATION: Peptide IV

<400> SEQUENCE: 299

Ala Leu Gly Lys Ala Leu Gly Ala Gln Lys Glu Ala Ile Ser Pro Pro
1               5                   10                  15

Asp Ala Ala Ser Ala Ala Pro Leu Arg Thr Ile
            20                  25

<210> SEQ ID NO 300
<211> LENGTH: 11
<212> TYPE: PRT
<213> ORGANISM: Artificial Sequence
<220> FEATURE:
<223> OTHER INFORMATION: Retro inverso peptide IC, Peptide IZ

<400> SEQUENCE: 300

Ser Ser Asn Leu Ala Arg Glu Leu Gln Glu Gln
1               5                   10

<210> SEQ ID NO 301
<211> LENGTH: 11
<212> TYPE: PRT
<213> ORGANISM: Artificial Sequence
<220> FEATURE:
<223> OTHER INFORMATION: Scrambled peptide IC, Peptide IX
      220>
<221> NAME/KEY: misc_feature
<222> LOCATION: (1)..(1)
<223> OTHER INFORMATION: Xaa is D-Leu
      220>
<221> NAME/KEY: misc_feature
<222> LOCATION: (2)..(2)
<223> OTHER INFORMATION: Xaa is D-Ser
      220>
<221> NAME/KEY: misc_feature
<222> LOCATION: (3)..(3)
<223> OTHER INFORMATION: Xaa is D-Glu
```

```
           220>
<221> NAME/KEY: misc_feature
<222> LOCATION: (4)..(4)
<223> OTHER INFORMATION: Xaa is D-Gln
           220>
<221> NAME/KEY: misc_feature
<222> LOCATION: (5)..(5)
<223> OTHER INFORMATION: Xaa is D-Ala
           220>
<221> NAME/KEY: misc_feature
<222> LOCATION: (6)..(6)
<223> OTHER INFORMATION: Xaa is D-Arg
           220>
<221> NAME/KEY: misc_feature
<222> LOCATION: (7)..(7)
<223> OTHER INFORMATION: Xaa is D-Asn
           220>
<221> NAME/KEY: misc_feature
<222> LOCATION: (8)..(8)
<223> OTHER INFORMATION: Xaa is D-Gln
           220>
<221> NAME/KEY: misc_feature
<222> LOCATION: (9)..(9)
<223> OTHER INFORMATION: Xaa is D-Ser
           220>
<221> NAME/KEY: misc_feature
<222> LOCATION: (10)..(10)
<223> OTHER INFORMATION: Xaa is D-Glu
           220>
<221> NAME/KEY: misc_feature
<222> LOCATION: (11)..(11)
<223> OTHER INFORMATION: Xaa is D-Leu

<400> SEQUENCE: 301

Xaa Xaa Xaa Xaa Xaa Xaa Xaa Xaa Xaa Xaa Xaa
1               5                   10

<210> SEQ ID NO 302
<211> LENGTH: 6
<212> TYPE: PRT
<213> ORGANISM: Artificial Sequence
<220> FEATURE:
<223> OTHER INFORMATION: Type-1 cytokine derived peptide, structural
      formula VII(a)
<220> FEATURE:
<221> NAME/KEY: misc_feature
<222> LOCATION: (1)..(1)
<223> OTHER INFORMATION: Xaa is Leu (L), Ile (I), Gly (G), Val (V), Phe
      (F), Pro (P), or Ala (A)
<220> FEATURE:
<221> NAME/KEY: misc_feature
<222> LOCATION: (2)..(2)
<223> OTHER INFORMATION: Xaa is a positively charged amino acid
<220> FEATURE:
<221> NAME/KEY: misc_feature
<222> LOCATION: (3)..(3)
<223> OTHER INFORMATION: Xaa is a negatively charged amino acid
<220> FEATURE:
<221> NAME/KEY: misc_feature
<222> LOCATION: (4)..(4)
<223> OTHER INFORMATION: Xaa is Phe (F), Gly (G), Val (V), Leu (L), Ala
      (A), or Tyr (Y)
<220> FEATURE:
<221> NAME/KEY: misc_feature
<222> LOCATION: (5)..(5)
<223> OTHER INFORMATION: Xaa is Arg (R), Asp (D), Glu (E), Asn (N), Ser
      (S), Thr (T), Phe (F), Val (V), or Tyr (Y)
<220> FEATURE:
<221> NAME/KEY: misc_feature
<222> LOCATION: (6)..(6)
<223> OTHER INFORMATION: Xaa is His (H), Lys (K), Asp (D), Glu (E), Gln
      (Q), Asn (N), Ser (S), Leu (L), Trp (W), or Phe (F)

<400> SEQUENCE: 302

Xaa Xaa Xaa Xaa Xaa Xaa
1               5
```

```
<210> SEQ ID NO 303
<211> LENGTH: 16
<212> TYPE: PRT
<213> ORGANISM: Artificial Sequence
<220> FEATURE:
<223> OTHER INFORMATION: Structural motif A, derived Peptide E

<400> SEQUENCE: 303

Arg Tyr Leu Leu Glu Ala Lys Glu Ala Glu Asn Ile Thr Thr Gly Cys
1               5                   10                  15

<210> SEQ ID NO 304
<211> LENGTH: 12
<212> TYPE: PRT
<213> ORGANISM: Artificial Sequence
<220> FEATURE:
<223> OTHER INFORMATION: Scrambled peptide, Peptide IY
<220> FEATURE:
<221> NAME/KEY: MOD_RES
<222> LOCATION: (3)..(3)
<223> OTHER INFORMATION: Xaa is modified Leu with N-terminal phosphate

<400> SEQUENCE: 304

Gly Leu Xaa Ser Glu Ala Arg Asn Gln Ser Glu Leu
1               5                   10

<210> SEQ ID NO 305
<211> LENGTH: 11
<212> TYPE: PRT
<213> ORGANISM: Artificial sequence
<220> FEATURE:
<223> OTHER INFORMATION: Peptide IW
<220> FEATURE:
<221> NAME/KEY: MOD_RES
<222> LOCATION: (1) .. (1)
<223> OTHER INFORMATION: Xaa is a modified Gln with 5-terminal
      polyethlene glycol

<400> SEQUENCE: 305

Xaa Glu Gln Leu Glu Arg Ala Leu Asn Ser Ser
1               5                   10

<210> SEQ ID NO 306
<211> LENGTH: 22
<212> TYPE: PRT
<213> ORGANISM: Artificial Sequence
<220> FEATURE:
<223> OTHER INFORMATION: Peptide IP

<400> SEQUENCE: 306

Gln Glu Gln Leu Glu Arg Ala Leu Asn Ser Ser Leu Arg Arg Tyr Ile
1               5                   10                  15

Asn Met Leu Thr Arg Pro
            20

<210> SEQ ID NO 307
<211> LENGTH: 22
<212> TYPE: PRT
<213> ORGANISM: Artificial Sequence
<220> FEATURE:
<223> OTHER INFORMATION: Loop CD-partial corresponding to amino acids
      112-133 of EPO

<400> SEQUENCE: 307

Leu Gly Ala Gln Lys Glu Ala Ile Ser Pro Pro Asp Ala Ala Ser Ala
1               5                   10                  15
```

```
Ala Pro Leu Arg Thr Ile
            20

<210> SEQ ID NO 308
<211> LENGTH: 13
<212> TYPE: PRT
<213> ORGANISM: Artificial Sequence
<220> FEATURE:
<223> OTHER INFORMATION: Structural motif D
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (7)..(7)
<223> OTHER INFORMATION: Xaa is Ala (A), Asn (N), Asp (D), Cys (C), Gln
      (Q), Glu (E), Gly (G), His (H), Ile (I), Lys (K), Met (M), Phe
      (F), Pro (P), Ser (S), Thr (T), Trp (W), Tyr (Y), or Val (V)
<220> FEATURE:
<221> NAME/KEY: misc_feature
<222> LOCATION: (9)..(9)
<223> OTHER INFORMATION: Xaa is Arg (R), His (H), Lys (K), Asp (D), or
      Glu (E)
<220> FEATURE:
<221> NAME/KEY: misc_feature
<222> LOCATION: (10)..(10)
<223> OTHER INFORMATION: Xaa is Arg (R), His (H), Lys (K), Asp (D), Glu
      (E) or absent
<220> FEATURE:
<221> NAME/KEY: misc_feature
<222> LOCATION: (11)..(11)
<223> OTHER INFORMATION: Xaa is Arg (R), His (H), Lys (K), Asp (D), or
      Glu (E)
<220> FEATURE:
<221> NAME/KEY: misc_feature
<222> LOCATION: (12)..(12)
<223> OTHER INFORMATION: Xaa is any amino acid or is absent
<220> FEATURE:
<221> NAME/KEY: misc_feature
<222> LOCATION: (13)..(13)
<223> OTHER INFORMATION: Xaa is any amino acid or is absent

<400> SEQUENCE: 308

Leu Ile Arg Xaa Asn Asn Xaa Thr Xaa Xaa Xaa Xaa Xaa
1               5                   10
```

TISSUE PROTECTIVE PEPTIDES AND PEPTIDE ANALOGS FOR PREVENTING AND TREATING DISEASES AND DISORDERS ASSOCIATED WITH TISSUE DAMAGE

The instant application is a divisional of U.S. patent application Ser. No. 12/863,973, filed Jul. 21, 2010, which is a 35 U.S.C. §371 U.S. National Stage application of International Patent Application No. PCT/US2009/000424, filed Jan. 22, 2009, and claims the benefit under 35 U.S.C. §119(e) of U.S. Provisional Application No. 61/062,012, filed Jan. 22, 2008, 61/062,022, filed Jan. 22, 2008; 61/062,045, filed Jan. 22, 2008; 61/133,912, filed Jul. 3, 2008; and 61/203,890, filed Dec. 30, 2008, the contents of which are hereby incorporated by reference in their entireties.

1. INTRODUCTION

The invention provides tissue protective peptides and peptide analogs for preventing or treating a disease or disorder associated with tissue damage and/or damage, an effect, or a symptom thereof, including, but not limited to, cancer, inflammation, and exposure to a toxic agent. In particular, the invention provides tissue protective peptides and peptide analogs that share consensus sequences with fragments of Type I cytokine receptor ligands that have little or no potentially undesirable hematopoietic effects of the full length ligands.

These peptides also include fragments, chimeras, as well as peptides designed to mimic the spatial localization of key amino acid residues within the tissue protective receptor ligands, e.g., EPO. This invention further provides methods and uses of these peptides to modulate a subject's response and/or a symptom resulting from a disease or disorder associated with tissue damage for the purposes of treating, preventing or ameliorating the disease or disorder.

Additionally, the present invention provides pharmaceutical compositions comprising a peptide and a pharmaceutically acceptable carrier, excipient or diluent for the treatment of a disease or disorder associated with tissue damage; or damage, an effect or a symptom thereof, including, but not limited to, cancer, inflammation and exposure to a toxic agent, in a subject in need thereof.

2. BACKGROUND OF THE INVENTION

Tissue damage can be caused by a substantive loss of tissue due to ischemic, traumatic, toxic, or inflammatory injuries in which cells within the tissue are destroyed by apoptosis or necrosis. Tissue damage can occur in a number of acute and chronic diseases and conditions. The degree to which tissue damage occurs is mediated by many factors, including the type of disease or injury, the level of or severity of inflammation or trauma associated with the disease or injury, the location of the tissue damage, and the vascular sufficiency of the tissue.

Recent evidence suggests that erythropoietin (EPO), a member of the Type-1 cytokine family, commonly associated with the maintenance of hematocrit may also play an important role in attenuating tissue damage through the interaction with its receptor, EPOR (Brines et al., 2004, Proc. Natl. Acad. Sci. USA, 101(41):14907-12). Although it is hypothesized that EPO may provide compensatory responses that serve to improve hypoxic cellular environment and modulate programmed cell death caused by metabolic stress, the underlying molecular mechanism is yet to be clearly understood.

Based upon this observation, investigators have explored the use of EPO in various indications. As an example, investigators have explored the use of EPO as a potential treatment for cancers based upon the observation that EPO used to treat anemia in oncology patients not only rectified the anemia but resulted in an enhancement of the well-being of the oncology patient as well. (see U.S. Pat. No. 6,579,525 and Blau C. A., 2007, Stem Cells 25(8):2094-7). U.S. Pat. No. 6,579,525 to Haran-Ghera et al. relates to the use of recombinant EPO for the treatment of multiple myelomas and hypothesizes that EPO induces an immune response to the tumor. Additionally, U.S. patent application Ser. No. 11/093,177, publication no. US 2005/0267027, discloses the use of EPO to inhibit angiogenesis in tumors by reducing HIF-1α and/or VEGF expression in the tumors.

However, EPO as a potential tissue protective agent suffers from serious disadvantages due to its erythropoietic effect. In particular with chronic dosing, such as would be envisioned in indications such as cancer and inflammation, the frequent applications of therapeutic doses of EPO may significantly increase a subject's hematocrit, which may lead to hypertension, seizures, and vascular thrombosis.

Further, with regard to cancer, the potential of EPO as a therapeutic has not been realized. It has been determined that several types of cancer, such as breast cancers, express, and tend to over-express, erythropoietin receptors. This has led to concerns that the therapeutic use of EPO to treat cancer would lead to further growth of the tumor as opposed to a regression of the tumor's development (see Blau, 2007, supra, and U.S. patent application Ser. No. 10/432,899, published as US 2005/0260580). This concern has been borne out in the clinic as several trials of EPO within various cancer indications have been halted due to an increase in mortality due to tumor growth (Blau). In light of these adverse clinical outcomes the FDA has attached a Black Box warning on approved EPO products cautioning against their use in unapproved cancer indications.

Additionally, mature human EPO protein is a 165 amino acid protein having a molecular weight of about 30.4 kDa measured by mass spectroscopy. The recombinant protein can be produced in Chinese hamster ovary cells in an expensive and labor intensive process that is highly regulated. Further, EPO must be stored under stringent conditions to maintain its activity. Given these limitations EPO is not an ideal candidate to address public emergencies, such as the release of a toxic agent such as radiation or a chemical agent, either through an industrial accident or act of terrorism or war that would require the rapid mass production of the therapeutic for wide distribution.

Accordingly, there is a need for tissue protective treatments that have little or no potentially detrimental effects and can be made readily available to the public.

3. SUMMARY

The present invention provides isolated peptides and peptide analogs that have tissue protective activity in a responsive cell, tissue, or organ. In certain embodiments, the peptides and peptide analogs have little or no potentially undesirable hematopoietic effects. In particular, the invention provides tissue protective peptides and peptide analogs that share consensus sequences with portions of EPO and Type I cytokine receptor ligands. In certain embodiments, an isolated peptide or peptide analog comprises a 9 to 29-residue amino acid sequence featuring a core structural motif selected from (1) two negatively charged amino acids and (2) one positively charged amino acid and one negatively charged amino acid. The core charged amino acids are flanked by 7 to 27 amino acids as described herein. In certain embodiments the core charged amino acids are immediately adjacent to each other. In certain embodiments, the charged amino acids are separated by 1 to 5 amino acids or by a single polar amino acid.

In certain aspects, the invention provides isolated peptides and peptide analogs that have at least one tissue protective activity. Exemplary tissue protective activities include, but are not limited to, protecting, maintaining, enhancing, and restoring the function or viability of a responsive mammalian cell, tissue, or organ. Accordingly, in one aspect, the present invention provides the use of an isolated peptides and peptide analogs of the present invention for the preparation of pharmaceutical compositions for protecting, maintaining, enhancing, or restoring the function or viability of responsive mammalian cells and their associated cells, tissues, and organs. In related embodiments, the compositions are for administration to a subject in need thereof.

In other aspects, the isolated peptides and peptide analogs of the invention also have little or no erythropoietic activity, e.g. they do not significantly increase hemoglobin or hematocrit in a subject, or more generally have little or no hematopoietic activity, e.g. they do not significantly increase blood cellular components such as erythroid, lymphoid, and myeloid cells. In specific embodiments, the isolated peptides and peptide analogs have little or no activity selected from vasoactive action (e.g., vasoconstriction), hyperactivating platelets, pro-coagulant activities, and stimulating proliferation or production of thrombocytes or erythropoietic-dependent cells (see, Coleman et al., 2006, Proc. Natl. Acad. Sci. USA 103:5965-5970).

The invention also provides pharmaceutical compositions comprising such tissue protective peptides and peptide analogs and a pharmaceutically acceptable carrier excipient or diluent, as well as methods for preparing such compositions and their use to treat diseases and disorders associated with tissue damage. In other aspects, the present invention provides methods of using an isolated peptide or peptide analog described herein for the preparation of a pharmaceutical composition for the protection against or prevention of a responsive tissue injury, for the restoration of, or for the rejuvenation of responsive tissue or responsive tissue function in a subject in need thereof. In one particular aspect, the responsive mammalian cells and their associated cells, tissues, or organs are distal to the vasculature by virtue of a tight endothelial cell barrier. In another particular aspect, the cells, tissues, organs or other bodily parts are isolated from a mammalian body, such as those intended for transplant. In certain aspects of the invention, the excitable tissue is central nervous system tissue, peripheral nervous system tissue, cardiac tissue or retinal tissue. In another aspect, the responsive cell or its associated cells, tissues, or organs are not excitable cells, tissues, or organs, nor do they predominantly comprise excitable cells or tissues.

In another embodiment the invention is drawn to a method of preventing, treating, ameliorating or managing inflammation, cancer or neoplastic disorders, or exposure to a toxic agent in a patient in need thereof by administering an effective amount of a peptide.

In certain embodiments, the invention relates to methods of modulating the activity of a mediator of cancer, the body's response to toxic agents, and inflammation. In particular, the invention relates to modulating the activity of an inflammatory mediator. Preferably, the peptides of the current invention are capable of modulating the effects of one or more inflammatory mediators.

In another embodiment, the invention relates to methods of arresting the growth of a cell comprising contacting a cell in need of growth arrestment with an effective amount of a peptide.

In another embodiment, the invention relates to methods of causing the death of a cancer or neoplastic cell comprising contacting a cancer or neoplastic cell with an effective amount of a peptide.

In another embodiment, the invention relates to methods of inhibiting blood vessel generation to the cancerous or neoplastic cells or reducing the production of molecules causing mitosis or angiogenesis.

In another embodiment, the invention relates to methods for treating or preventing the side-effects associated with chemotherapy or radiation therapy, comprising administering to a patient in need of such treatment or prevention an effective amount of a peptide. Side-effects associated with chemotherapy or radiation therapy include cachexia, low blood count, nausea, diarrhea, oral lesions, and alopecia.

In another embodiment, the invention relates to methods for treating or preventing cancer or neoplastic disease in a patient comprising contacting a cancer or neoplastic cell with an effective amount of a peptide.

In another embodiment, the invention relates to methods of treating or preventing cancer or neoplastic disease in a patient comprising administering to a patient in need of such treatment or prevention an effective amount of a peptide.

In certain embodiments, the invention relates to the use of the peptide for the preparation of a pharmaceutical composition for the prevention, treatment, amelioration, or management of cancer or neoplastic disorder in a subject in need thereof.

In another embodiment, the invention relates to methods of treating or preventing the symptoms associated with inflammation or an inflammatory condition. In a further embodiment, the invention relates to methods of treating or preventing inflammation or an inflammatory condition in a patient in need thereof. Amongst the inflammatory conditions treatable by the current method are allergies and allergic diseases, rheumatic diseases, and sports related injuries.

In another embodiment, the invention relates to methods of treating, preventing, ameliorating or managing the effects of exposure to a toxic agent in a person in need of treatment. Amongst the toxic agents considered are biological, chemical and radioactive agents.

In certain embodiments, the invention is also directed to pharmaceutical compositions comprising the aforementioned isolated peptides for administration to a subject in need thereof. In specific aspects in accordance with this embodiment, the pharmaceutical composition of the invention further comprises a pharmaceutically acceptable carrier. Such pharmaceutical compositions may be formulated for oral, intranasal, ocular, inhalational, transdermal, rectal, sublingual, vaginal, or parenteral administration, or in the form of a perfusate solution for maintaining the viability of cells, tissues, or organs ex vivo. In related embodiments of the invention the subject is a mammalian animal, preferably a human.

These and other features, aspects, and advantages of the present invention will become better understood with reference to the following description and appended claims.

4. ABBREVIATIONS AND TERMINOLOGY

4.1 Abbreviations

As used herein, the abbreviations for the genetically encoded L-enantiomeric amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Pyroglutamate | U | pGlu (Glp) |

4.2 Terminology

Unless defined otherwise, all technical and scientific terms used herein have the meaning commonly understood by a person skilled in the art to which this invention belongs. As used herein, the following terms have the meanings ascribed to them unless specified otherwise.

(i) As used herein, the terms "about" or "approximately" when used in conjunction with a number refer to any number within 1, 5, 10, 15 or 20% of the referenced number.

(ii) The term "administered in conjunction with" in the context of the methods of the invention means administering a compound prior to, at the same time as, and/or subsequent to the onset of a disease, disorder, or condition.

(iii) The term "allergen" refers to an antigenic substance capable of producing immediate type hypersensitivity (allergy). Common allergens include, but are not limited to bacteria, viruses, animal parasites, insects and insect stings, chemicals (latex), dust, dust mites, molds, animal dander, drugs (such as antibiotics, serums, sulfa drugs, anti-convulsants, insulin preparations, local anesthetics, iodine, and aspirin), foods (such as milk, chocolate, strawberries, eggs, soy, nuts, fish, shellfish, wheat), perfumes, plants, pollens, and smoke.

(iv) The term "allergic disease" refers to a condition or disease caused by or relating to an allergy. Allergic diseases include, but are not limited to, asthma, hypersensitivity lung diseases, rhinitis, rhinosinusitis, atopic eczema, contact dermatitis, allergic conjunctivitis (intermittent and persistent), vernal conjunctivitis (hayfever), atopic keratoconjunctivitis, giant papillary conjunctivitis, urticaria (hives), angioedema, hypersensitivity pneumonitis, eosinophilic bronchitis, vasculitis, hypersensitivity vasculitis, antineutrophil cytoplasmic antibody (ANCA) associated vasculitis, Wegner's granulomatosis, Churg Strauss vasculitis, microscopic polyangiitis, temporal arteritis, celiac disease, mastocytosis, and anaphylaxis.

(v) The term "allergy symptom" or "allergic reaction" refers to the body's response to an allergen. The allergic reaction can be localized to one area (skin that came into contact with allergen) or generalized. Allergic reactions may include, but are not limited to, rash, itching, hives, swelling, difficulty breathing, wheezing, angioedema, difficulty swallowing, nasal congestion, runny nose, shortness of breath, nausea, stomach cramps, abdominal pain, vomiting and/or low blood pressure.

(vi) The term "allergy" refers to a state of hypersensitivity induced by exposure to a particular antigen (allergen) resulting in harmful immunological reactions on subsequent exposures.

(vii) The term "amino acid" or any reference to a specific amino acid is meant to include naturally occurring proteogenic amino acids as well as non-naturally occurring amino acids such as amino acid analogs. Those skilled in the art would know that this definition includes, unless otherwise specifically noted, naturally occurring proteogenic (L)-amino acids, their optical (D)-isomers, chemically modified amino acids, including amino acid analogs such as penicillamine (3-mercapto-D-valine), naturally occurring non-proteogenic amino acids such as norleucine and chemically synthesized amino acids that have properties known in the art to be characteristic of an amino acid. Additionally, the term "amino acid equivalent" refers to compounds that depart from the structure of the naturally occurring amino acids, but which have substantially the structure of an amino acid, such that they can be substituted within a peptide, which retains its biological activity despite the substitution. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents. Amino acids may also be classified into the following groups as is commonly known in the art: (1) acidic=Asp, Glu; (2) basic=Lys, Arg, His; (3) nonpolar (hydrophobic)=Cys, Ala, Val, Leu, Ile, Pro, Phe, Met, Trp, Gly, Tyr; and (4) uncharged polar=Asn, Gln, Ser, Thr. Non-polar may be subdivided into: strongly hydrophobic=Ala, Val, Leu, Ile, Met, Phe; and moderately hydrophobic=Gly, Pro, Cys, Tyr, Trp. In alternative fashion, the amino acid repertoire can be grouped as (1) acidic=Asp, Glu; (2) basic=Lys, Arg, His, (3) aliphatic=Gly, Ala, Val, Leu, Ile, Ser, Thr, with Ser and Thr optionally be grouped separately as aliphatic-hydroxyl; (4) aromatic=Phe, Tyr, Trp; (5) amide=Asp, Glu; and (6) sulfur-containing=Cys and Met. (See, for example, Biochemistry, 4th ed., Ed. by L. Stryer, WH Freeman and Co., 1995, which is incorporated by reference herein in its entirety).

(viii) The term "biological agent" as used herein refers to living organisms or the materials derived from them (such as bacteria, viruses, fungi, and toxins) that cause disease in or harm to humans, animals, or plants, or cause deterioration of materials. These biological agents are ubiquitous in nature and may be designed or optimized for use in warfare or terrorism (bioterrorism). These biological agents may consist of prions, viruses, microorganisms (bacteria and fungi), and some unicellular and multicellular eukaryotes (i.e., parasites). In particular, the biological agents (identified by their common name, biologic name and the NATO Standard Reference letter code, where available) may include, but are not limited to, mycotic agents (*Coccidioides mycosis*, OC, *Coccidioides posadasil, Coccidioides immitis*), bacterial agents (anthrax (cutaneous, inhalation, gastrointestinal) (*Bacillus anthracis*, N and TR), plague (bubonic, pneumonic) (*Yersinia pestis*, LE), tularemia (*Francisella tularensis*, UL (schu S4), TT (wet type), ZZ (dry type) and SR and JT (425)), cholera (*Vibrio cholerae*, HO), bovine brucellosis (AB), porcine brucellosis (US and NX), caprine brucellosis (AM and BX), *Brucella abortus, Brucella melitenis, Brucella suis*, bacterial dysentery (shigellosis, campylobacteriosis, salmonellosis) (Y), glanders (*Burkholderia mallei*, LA), melioidosis (*Burkholderia pseudomallei*, HI), diphtheria (*Corynebacterium diphtheriae*, DK), listeriosis (*Listeria monocytogenes*, TQ)), chlamydial agents (psittacosis "Parrot Fever" (*Chlamydophilia psittici*, SI), rickettsial agents (rocky mountain spotted fever (*Rickettsia rickettsii*, RI and UY), Q fever (*Coxiella burnetti*, OU, MN (wet type), and NT (dry type)), human typhus (*Rickettsia prowazekii*, YE), murine typhus (*Rickettsia typhi*, AV)), viral agents (yellow fever (Arbovirus flavivirdae, OJ, UT, and LU), rift valley fever (RVF Phlebovirus bunyaviridae, FA), alphaviruses (e.g.: eastern equine encephalitis (ZX), western equine encephalitis, Venezuelan equine encephalitis (NU, TD, and FX)), smallpox (ZL), Japanese B Encephalitis (AN), Cercopithecine herpesvirus 1 (Herpes B virus), Crimean-Congo haemorrhagic fever virus, viral hemorrhagic fever (Filoviridae (ebola and Marburg virus) and Arenaviridae (Lassa and Machupo)), monkey pox virus, Reconstructed 1918 influenza virus, South American Haemorrhagic Fever viruses (Flexal, Guanarito, Junin, Machupo, Sabia), tick borne meningoencephalitis (TEBV) viruses (Central European Tick-borne encephalitis, Far Eastern Tick-borne encephalitis, Kyasanur Forest disease, Omsk Hemorrhagic fever, Russian Spring and Summer virus), Hendra virus, Nipah virus, hantaviruses (Korean hemorrhagic fever), African horse sickness virus, optimized swine fever virus, Akabane virus, avian influenza virus, bluetongue virus, camel pox virus, classical swine fever virus, foot-and-mouth disease virus, goat pox virus, lumpy skin disease virus, malignant catarrhal fever virus (Alcelaphine herpesvirus type 1), Menangle virus, New Castle disease virus, Pestes des petits ruminants virus, rabies virus, rinderpest virus, sheep pox virus, swine vescular disease virus, vesicular somatitis virus), toxins (botulinum toxin (*Clostridium*, X and XR), ricin (*Ricinus communis*, W and WA), Staphylococcal enterotoxin B (UC and PG), Saxitoxin (paralytic shellfish poisoning) (TZ and SS), tetrodotoxin (PP), conotoxins, *clostridium perfringens* epsilon toxin, tricothecene mycotoxins (T-2 toxins), shigatoxin), and simuants (molasis residium (MR), *Bacillus globigii* (BG, BS, and U), *Serratia marescens* (SM and P), *Aspergillus fumigatus* mutant C-2 (AF), *E. Coli* (EC), *Bacillus thursidius* (BT), *Erwinia herbicola* (EH), fluorescent particle (FP)), rye ergot, leprosy, rabies, intestinal typhoid, *clostridium perfringens* (gas gangrene), aflatoxins, *Salmonella typhimurium*, enterotoxins, Argentinian hemorrhagic fever, multi-drug resistant Tuberculosis (MTB), Bolivian hemorrhagic fever, *legionella pneumophilia*, marine toxins, beriberi, malaria, pellagra, dengue fever, *sclerotium rolfoil*, neurotrophic encephalitis, *Shigella* (Y), SEB (UC), and mycotoxins, Diaacetoxyscirpenol, *Cowdria ruminantium, Mycoplasma capricolum* M.F38/M. *Mycoides capri, Mycoplasma mycoides mycoides*, abrin. The biological agents may be targeted against humans (e.g. Small pox, Ebola virus, Reconstructed 1918 influenza virus, ricin, etc.), animals such as livestock (e.g. African horse sickness virus, African swine fever virus, foot-and-mouth disease, etc.) or both (Eastern equine encephalitis virus, etc.) Further, even non-lethal biological agents may pose a threat given that they may be re-engineered for greater lethality for use as a biological weapon. Thus even the viruses responsible for the common cold may pose a risk.

(ix) The term "cancer" as used herein refers to any abnormal growth exhibiting malignant properties: the ability (1) to grow and divide without respect to normal limits, (2) to invade and destroy adjacent tissues, and (3) in some instances, spread to other locations in the body. Cancer includes cancers or neoplastic disorders of the central nervous system, peripheral nervous system, gastrointestinal/digestive system, genitourinary system, gynecological, head and neck, hematological/blood, musculoskeletal/soft tissue, respiratory, and breast. Further examples of cancers or neoplastic disorders include, but are not limited to, those of the brain (astrocytoma, gliobastoma, glioma), spinal cord, pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), Lymph node cancer, Lung (Adenocarcinoma, Oat Cell, Non-small Cell, Small Cell, Squamous Cell, Mesothelioma), skin (melanoma, basal cell, squamous cell, Kapsosis Sarcoma), Bone Cancer (Ewings Sarcoma, Osteosarcoma, Chondrosarcoma), head and neck (laryngeal, pharyngeal (nasal cavity & sinus cavity), and esophageal cancers), oral (jaw, salivary gland, throat, thyroid, tongue, and tonsil cancers), eye, gynecological (Cervical, Endometrial, Fallopian, Ovarian, Uterine, Vaginal, and Vulvar), genitourinary (bladder, kidney, penile, prostate, testicular, and urinary cancers), adrenal (cortical adenoma, cortical carcinoma, pheochromocytoma) and gastrointestinal (appendix, bile duct (extrahepatic bile duct) colon, gallbladder, gastric, intestinal, colon, liver, pancreatic, rectal, and stomach cancers) as well as those listed below: (for a review of such disorders, see Fishman et al., 1985, Medicine, 2d Ed., J.B. Lippincott Co., Philadelphia): Leukemia: acute leukemia, acute lymphocytic leukemia, acute myelocytic leukemia, myeloblastic, promyelocytic, myelomonocytic, monocytic erythroleukemia, chronic leukemia, chronic myelocytic (granulocytic) leukemia, chronic lymphocytic leukemia, Polycythemia vera, Gastric carcinoma, Lymphoma (malignant and non-malignant): Hodgkin's disease, non-Hodgkin's disease, Multiple myeloma, Waldenstrom's macroglobulinemia, Heavy chain disease, Solid tumors sarcomas and carcinomas: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, oral squamous cell carcinoma, hepatocellular carcinoma, basal cell carcinoma, adenocarcinoma, sweat gland carcinoma, sebaceous gland carcinoma, papillary carcinoma, papillary adenocarcinomas: cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, cervix adenocarcinoma, uterine cancer, testicular tumor, lung carcinoma, small cell lung carcinoma, non-small cell lung adenocarcinoma, bladder carcinoma, epithelial carcinoma, glioma, malignant glioma, glioblastoma, multiforme astrocytic gliomas, medulloblastoma, craniopharyngioma, ependymoma, pinealoma, hemangioblastoma, acoustic neuroma, oligodendroglioma, meningioma, melanoma, neuroblastoma, or retinoblastoma.

(x) The term "chemical agent" as used herein refers chemical substances that cause severe death or harm to people or animals. To the extent that the chemical agent has been optimized to be delivered using munitions or a dispersal device, the agent is a chemical weapon. In general, chemical agents used as weapons can be classified by their method of action such as: blood agents, blister agents, nerve agents, pulmonary agents, and incapacitating agents. Each of the chemical agents below are identified by their NATO standard Reference letter code where available.

(xi) "Blood agents" refer to those chemical agents that prevent cells from using oxygen. Chemical agents within this category include, but are not limited to Arsine (adamsite (diphenylaminechloroarsine), Clark I (diphenylchloroarsine), Clark II (diphenylcyanoarsine)) and Cyanide (cyanogen chloride (CK), hydrogen cyanide (AC), etc.) compounds. Arsine compounds cause intravascular hemolysis that leads to renal failure. Cyanide compounds prevent the cells from using oxygen and the cells then resort to anaerobic respiration creating an excess of lactic acid leading to metabolic acidosis. Victims of blood agents may exhibit symptoms including, but not limited to, headaches, dizziness, nausea, vomiting, mucosal irritation, dysponea, impaired consciousness, coma, convulsions, tachy- and brady-dysrhythmias, hypotension, cardiovascular collapse, and acyanosis.

(A) "Nerve agents" refer to those chemical agents that inactivate the enzyme acetylcholinesterase. The resulting buildup of the neurotransmitter acetylcholine in the victim's synapses leads to muscarinic and nicotinic effects. Compounds within this category include, but are not limited to, cyclosarin (cyclohexylmethylphosphofluoridate, GF), sarin (isopropyl methylphosphanofluoridate, GB), thiosarin, soman (pinacolylmethylphosphanofluoridate, GC), tabun (ethyl N, N-dimethylphosphoramidocyanidate, GA), VX (O-ethyl[s]-[2-diisopropylaminoethyl-methylphosphonothiolate), VR (N,N-diethyl-2-(methyl-(2-methylpropoxy)phosphoryl)sulfanylethanamine), VE (O-ethyl-S-[2-(diethylamino)ethyl]phosphonothioate), VG (O,O-diethyl-S-[2-(diethylamino)ethyl]phosphorothioate), VM (O-ethyl-S-[2-(diethylamino)ethyl]methylphosphonothioate), ethyl sarin (isopropylethylphosphonofluoridate, GE), EDMP (ethyl-2-diisopropylaminoethylmethylphosphonate), DF (methylphosphonyl difluoride), Novichok Agents, GV (P[2-(dimethylamino)ethyl]-N,N-dimethylphosphonamidic fluoride), Gd42, Gd83, Tammelin Esters, fluorophosphocholines, phosphothiocholates, DFP, and insecticides (phenothiazines, organophosphates (dichorous, malathion, parathion, fenthion, amidon, paraoxon, chloropyrifos, systox, pyrophosphate, TOCP)). Victims of nerve agents may exhibit symptoms including, but not limited to, bradycardia, myosis, excessive salivation, vomiting, diarrhea, involuntary micturition, muscle fasciculation, initial depolarizing flaccid paralysis, spike discharges and convulsions, intermediate syndrome, neurotoxic esterase inhibition, and organophosphate-induced delayed neuropathy.

(B) "Blister Agents" refer to agents that are acid-forming compounds that damage the victim's skin and respiratory system resulting in burns and respiratory problems. Chemical agents within this category include, but are not limited to, sulfur mustards (1,2 bis(2-chloroethylthio)ethane (Sesquimustard, Q), 1,3 bis(2-chloroethylthio)-n-propane, 1,4-bis (2-chloroethylthio)-n-butane, 1,5-bis(2-chloroethylthio)-n-pentane, 2-Chloroethylchloromethylsulfide, Bis(2-chloroethyl)sulfide (HD), Bis(2-chloroethylthio) methane, Bis(2-chloroethylthiomethyl) ether, Bis(2-chloroethylthioethyl) ether, di-2'-chloroethylsulfide and combinations thereof (HT, HL, HQ)), nitrogen mustards (Bis(2-chloroethyl)ethylamine (HN1), Bis(2-chloroethyl)methylamine (HN2), Tris(2-chloroethyl)amine (HN3), 2-chloro-N-(2-chloroethyl)-N-methylethanamine-N-oxide hydrochloride, cyclophosphamide, chlorambucil, uramustine, melphalan), lewisites (2-Chlorovinyldichloroarsine, Bis(2-chlorovinyl) chloroarsine, Tris(2-chlorovinyl)arsine, dichloro(2-chlorovinyl)arsine), ethyldichloroarsine, methyldichloroarsine, phenyldichloroarsine, and phosgene oxime (dichloroformoxime). Victims of blister agents may exhibit symptoms including, but not limited to, erythema, edema, necrosis and vesicles, melanoderma, tracheobronchitis, bronchospasms, bronchial obstruction, hemorrhagic pulmonary edema, respiratory failure, bacterial pneumonia, eye erythema, lachrymation, discomfort of the eyes, severe pain in the eyes, blepharospasm, iritis, blindness, nausea, vomiting, bone marrow suppression, lewisite shock, hepatic necrosis, and renal failure secondary to hypoperfusion.

(D) "Pulmonary Agents" refer to agents that are similar to blister agents but have a more pronounced effect on the respiratory system resulting in the respiratory system being flooded and the victim suffocating. Chemical agents within this category include, but are not limited to, adamsite, Acrolein, Bis(chloromethyl)ether, chlorine, Chloropicrin, diphosphogene, methyl chlorosulfate, stannic chloride, hydrogen chloride, nitrogen oxides, and phosgene. Victims of pulmonary agents may exhibit symptoms including, but not limited to, burning sensations (eyes, nasopharynx, oropharynx), profuse tearing, rhinorrhoea, coughing hoarseness, dyspnoea, odynophagia, conjunctivitis, corneal injury, naso-orophangyal injury/edema, respiratory distress due to inflammation of the glottic structures, secretions, and/or laryngospasms, acute respiratory syndromes, and reactive airway dysfunction syndrome.

(E) "Incapacitating agents" refer to agents that are less lethal and are intended largely to incapacitate through physiological or mental effects or both. A common class of incapacitating agents is lachrymatory agents, chemical agents that irritate the eyes causing tearing, pain, and even temporary blindness. Lachrymatory agents include, but are not limited to, a-chlorotoluene, benzyl bromide, Bromoacetone (BA), Bromobenzylcyanide (CA), Bromomethyl ethyl ketone, Capsaicin (OC), Chloracetophenone (CN), chloromethyl chloroformate, Dibenzoxazepine (CR), Ethyl iodoacetate, Ortho-chlorobenzylidene malonitrile (CS), Trichloromethyl chloroformate, and xylyl bromide. Additional incapacitating agents include, but are not limited to, 3-Quinuclidinyl benzilate (psychedelic; BZ), hydrocyanic acid (paralytic), diphenylchloroarsine (sternutatory; DA), diphenylcyanoarsine (DC), KOLOKOL-1 (fentanyl derivative), *Datura stramonium*, Hellborne, *Belladonna, Hyoscyamus* falezlez, indoles (lysergic acid diethylamide (LSD-25)), marijuana derivatives (DMHP), amphetamines, cocaine, caffeine, nicotine, strychnine, metrazole, barbiturates (methohexital), opioids, antipsychotics (haloperidol), benzodiazepines, fentanyl congeners, psilocybin, ibogaine, harmine, ectasy, PCP, atropine, scopolamine, oxybutynin, ditropan, anticholinergic antihistamines, benactyzine, and tranquilizers.

Many of the above noted chemicals have uses beyond their use as weapons and are used within manufacturing. Thus, the accidental or intentional release of these chemical agents from manufacturing or chemical plants will pose a risk to the employees of the plant as well as the populations living in the vicinity of these plants. Examples of toxic industrial manufacturing chemicals include, but are not limited to, ammonia, arsine, boron trichloride, boron trifluoride, carbon disulfide, chlorine, diborane, ethylene oxide, fluorine, formaldehyde, hydrogen bromide, hydrogen chloride, hydrogen cyanide, hydrogen fluoride, hydrogen sulfide, nitric acid, phosgene, phosphorous trichloride, sulfur dioxide, sulfuric acid, tungsten hexafluoride, acetone cyanohydrin, acrolein, acrylotrile, allyl alcohol, allyl amine, allyl chlorocarbonate, boron tribromide, carbon monoxide, carbonyl sulfide, chloroacetone, chloroacetylnitrile, chloro sulfonic acid, diketone, 1,2-dimethyl hydrazine, ethylene dibromide, hydrogen selenide, methane sulfonyl chloride, methyl bromide, methyl chloroformate, methyl chlorosilane, methyl hydrazine, methyl isocyanate, methyl mercapatan, nitrogen dioxide, phosphine, phosphorous oxychloride, phosphorous pentafluoride, selenium hexafluoride, silicone tetrafluoride, stiloine, sulfur trioxide, sulfuryl chloride, sulfuryl fluoride, tellurium hexafluoride, n-octyl mercaptan, titanium tetrachloride, trichloroacetyl chloride, trifluoroacetyl chloride, allyl isothiocyanate, arsenic trichloride, bromine, bromine chloride, bromine penta fluoride, bromine trifluoride, carbonyl fluoride, chlorine penta fluoride, chlorine trifluoride, chloroacetylaldehyde, chloroacetylchloride, crotonaldehyde, cyanogens chloride, dimethyl sulfate, diphenylmethane-4,4'-diisocyanate, ethyl chloroformate, ethyl chlorothioformate, ethyl phosphonothioic dichloride, ethyl phosphonic dichloride, ethyleneimine, hexachlorocyclopentadiene, hydrogen iodine, iron pentcarbonyl, isobutyl chloroformate, isopropyl chloroformate, isopropyl isocyanate, n-butyl chloroformate, n-butyl isocyanate, nitric oxide, n-propyl chloroformate, parathion, perchloromethyl mercaptan, sec-butyl isocyanate, tert-butyl isocyanate, tetraethyl lead, tetraethyl pyrophosphate, tetra methyl lead, toluene 2,4-diisocyanate, and toluene 2,6-diisocyanate.

(xi) As used herein, an "effective amount" includes that amount of a peptide sufficient to modulate any disease or disorder associated with tissue damage or the damage, effects, or symptoms thereof, preferably to inhibit, suppress, or moderate the deleterious effects of the body's response to the disease or disorder associated with the tissue damage including, but not limited to, the body's response to cancer, inflammation, or exposure to toxic agents. Additionally, an "effective amount" includes the amount of the peptide sufficient to mitigate, ameliorate, diminish or prevent any disease or disorder associated with tissue damage or provide a therapeutic benefit in a patient afflicted with a disease or disorder associated with tissue damage.

(xii) As used herein, "erythropoietic activity" means any significant increase in the levels of hemoglobin or hematocrit in a subject. "Little or no erythropoietic activity" means that an increased level of a subject's hemoglobin or hematocrit meets the criteria accepted in the art as an insufficient increase to cause an adverse effect in a subject. "Significantly increased erythropoietic activity" means that the a difference in the level of a subject's hemoglobin or hematocrit compared to a control meets the criteria accepted in the art as significant, which may, inter alia, increase the likelihood of hypertension, seizures, and vascular thrombosis.

(xiii) "Excitable tissue" means tissue that contains excitable cells. Excitable cells are cells that respond actively to an electric stimulus and have an electrical charge differential across their cellular membranes. Excitable cells are generally capable of undergoing an action potential. Such cells typically express channels, such as voltage-gated, ligand-gated, and stretch channels, which allow flow of ions (potassium, sodium, calcium, chloride, etc.) across the membrane. Excitable tissue includes neuronal tissue, muscle tissue, and glandular tissue. Excitable tissue includes, but is not limited to, neuronal tissues such as tissue of the peripheral nervous system (ear and retina) and central nervous system (brain and spinal cord); cardiovascular tissue such as the cells of the heart and associated nerves; and glandular tissue such as the pancreas where T-type calcium channels along with cell-to-cell gap junctions participate in secretion of insulin. An exemplary list of excitable tissue includes organs and tissues that include nerves, skeletal muscle, smooth muscle, cardiac muscle, uterus, central nervous system, spinal cord, brain, retina, olfactory system, auditory system, etc.

(xiv) The term "hematopoietic activity" means any significant increase in blood cellular components such as erythroid, lymphoid, and myeloid cells. Further hematopoietic activity refers to whether an isolated peptide or peptide analog posses activity selected from vasoactive action (e.g., vasoconstriction), hyperactivating platelets, pro-coagulant activities, and stimulating proliferation or production of thrombocytes or erythropoietin-dependent cells.

(xv) The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

(xvi) The term "inflammatory conditions" as used herein refers to various diseases or traumas, whether mechanically or chemically induced, that have an inflammatory component. It includes conditions giving rise to inflammation in one or more organs or tissues including, but not limited to, the brain, spinal cord, connective tissue, heart, lung, kidney, urinary tract, pancreas, eyes and prostate. Non-limiting examples of such conditions include, but are not limited to, appendicitis, blepharitis, bronchitis, bursitis, cervicitis, cholangitis, cholecystitis, chorioamnionitis, conjunctivitis, cystitis, dacryoadenitis, dermatitis, endocarditis, endometritis, epicondylitis, epididymitis, fibrositis, gastritis, gingivitis, glossitis, hidradenitis suppurativa, iritis, laryngitis, mastitis, myocarditis, myositis, nephritis, omphalitis, oophoritis, orchitis, osteitis, otitis, parotitis, pericarditis, peritonitis, pharyngitis, pleuritis, phlebitis, pneumonitis (pneumonia), prostatitis, pyelonephritis, rhinitis, salpingitis, sinusitis, stomatitis, synovitis, tonsillitis, uveitis, urethritis, vaginitis, vulvitis, asthma, systemic lupus erythematosus, myasthenia gravis, tendonitis, angiitis, chronic bronchitis, pancreatitis, osteomyelitis, arthritis (rheumatoid and psoriatic), glumeronephritis, optic neuritis, temporal arteritis, encephalitis, meningitis, traverse myelitis, dermatomyositis, polymyositis, necrotizing fasciitis, hepatitis, necrotizing entercolitis, pelvic inflammatory disease, inflammatory bowel disease (ulcerative colitis, Crohn's disease, ileitis, and enteritis), proctitis, vasculitis, vascular stenosis, restenosis, hypotension, Type-1 diabetes, Kawasaki disease, Decum's disease, chronic obstructive pulmonary disease, psoriasis, artherosclerosis, scleroderma, Sjogren's syndrome, mixed connective tissue disease, rosacea, gastric ulcers, duodenal ulcers, Alzheimer's disease, adult onset Still's disease, acute retinal pigment epitheliitis, Tietze's syndrome, Bechçet's disease, white dot syndrome (acute posterior multifocal placoid pigment epitheliopathy, serpiginous choroiditis, birdshot chorioretinopathy, multifocal choroiditis with panuveitis, diffuse subretinal fibrosis syndrome, punctuate inner chorioidopathy, multiple evanescent white dot syndrome, and diffuse unilateral subacute neuroretinitis), granuloma annulare, irritable bowel syndrome, gastroenteritis, Grave's disease, multiple sclerosis, Dupuytren's contracture, graft rejection diseases (including allograft rejection and graft-v-host disease), e.g. skin graft rejection, solid organ transplant rejection, bone marrow transplant rejection, inflammatory dermatoses, viral cutaneous pathologies such as those derived from human papilloma virus, HIV, or RLV infection, bacterial, fungal and or other parasital cutaneous pathologies, cutaneous lupus erythematosus, and Hyper IgG4 disease. Further "Inflammatory condition" may refer to inflammation resulting from ischemic or non-ischemic conditions, including but not limited to, blunt trauma, contusions, allergies and allergic diseases, rheumatic disease (childhood arthritis, rheumatoid arthritis, Churg-Strauss syndrome, fibromyalgia, giant cell (temporal) arteritis, gout, Henoch-Schoenlin purpura, hypersensitivity vasculitis, ankylosing spondylitis, capsulitis, rheumatic fever, rheumatic heart disease, systemic lupus erythematosus, polymyalgia rheumatica, osteoarthritis (hand, hip, knee, etc.) polyarteritis nodosa, Reiter's syndrome), sports related injuries (runner's knee, tennis elbow, frozen shoulder, Achilles tendonitis, plantar fasciitis, bursitis, Osgood-Schlatter disease), repetitive stress injuries (cumulative trauma diseases, focal dystonia, carpal tunnel syndrome, intersection syndrome, reflex sympathetic dystrophy syndrome, stenosing tenosynovitis (De Quervain's syndrome, trigger finger/trigger thumb), thoracic outlet syndrome, tendonitis, tenosynovitis, radial tunnel syndrome, Raynaud's disease, ganglion, gamer's thumb, Wii-itis, etc.) infections including viral, fungal and bacterial. The "inflammatory condition" may be acute or chronic.

(xvii) An "isolated" or "purified" peptide is substantially free of cellular material or other contaminating proteins from the cell or tissue source from which the protein or peptide is derived, or substantially free of chemical precursors or other chemicals when chemically synthesized. The language "substantially free of cellular material" includes preparations of a peptide in which the peptide is separated from cellular components of the cells from which it is isolated or recombinantly produced. Thus, a peptide that is substantially free of cellular material includes preparations of peptides having less than about 30%, 20%, 10%, or 5% (by dry weight) of heterologous protein (also referred to herein as a "contaminating protein"). When the peptide is recombinantly produced, it is also preferably substantially free of culture medium, i.e., culture medium represents less than about 20%, 10%, or 5% of the volume of the protein preparation. When the peptide is produced by chemical synthesis, it is preferably substantially free of chemical precursors or other chemicals, i.e., it is separated from chemical precursors or other chemicals which are involved in the synthesis of the protein. Accordingly such preparations of the peptide have less than about 30%, 20%, 10%, 5% (by dry weight) of chemical precursors or compounds other than the peptide of interest. In a preferred embodiment, peptides of the invention are isolated or purified.

(xviii) An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding a peptide of the invention is isolated or purified.

(xix) As used herein, the term "management" includes the provision of one or more beneficial side effects that a patient derives from a peptide which, in one embodiment, does not reverse the damage, effects or symptoms of a disease or disorder associated with tissue damage. In certain embodiments, a patient is administered a peptide to "manage" the symptoms of a disease or disorder associated with tissue damage so as to prevent the progression or worsening of the symptoms.

(xx) The terms "modulate," "modulations" and the like refer to the ability of a compound to increase or decrease the function and/or expression of mediators of the body's response to a disease or disorder associated with tissue damage, including transcription of regulatory activity and/or protein binding. Modulation, as described herein, includes the inhibition, antagonism, partial antagonism, activation, agonism or partial agonism of a function or characteristic associated with the mediator, either directly or indirectly, and/or the upregulation or downregulation of the expression of the mediator. In a preferred embodiment, the modulation is direct, and more preferably the modulation occurs through an inhibitor or antagonist of the mediator, a compound that binds to, partially or totally blocks stimulation, decreases, prevents, inhibits, delays activation, inactivates, desensitizes, or downregulates signal transduction. The ability of a particular peptide useful in the method of the current invention to inhibit the function of a mediator can be demonstrated in a biochemical assay, e.g. binding assay, cell based assay, e.g. transient transfection assay, or in vivo assay, e.g. animal model of neuronal injury, cancer, inflammation, or chemical or radiation injury such as a rat or murine model.

(xxi) As used herein in reference to a structure within a peptide, the term "motif" refers either to a set of consecutive amino acids within the amino acid sequence of the peptide chain and/or to a set of linearly or spatially adjacent amino acids within the secondary and/or tertiary structure of said peptide. Because the motif may be formed all or in part as a result of protein folding, amino acids that are adjacent in the described motif may be separated by 0, 1 or more, 5 or more, 10 or more, 15 or more or 20 or more amino acids within the linear amino acid sequence of the peptide.

(xxii) As used herein, the terms "peptide," "polypeptide" and "protein" are used interchangeably and in their broadest sense to refer to constrained (that is, having some element of structure as, for example, the presence of amino acids which initiate a 0 turn or (3 pleated sheet, or for example, cyclized by the presence of disulfide bonded Cys residues) or unconstrained (e.g., linear) amino acid sequences. In certain embodiments, the peptide of the invention consists of less than 30 amino acids. However, upon reading the instant disclosure, the skilled artisan will recognize that it is not the length of a particular peptide but its ability to bind a tissue protective receptor complex and/or compete with the binding of a peptide described herein that distinguishes the peptides useful in the method of the current invention. The terms "peptide," "polypeptide," and "protein" also refer to compounds containing amino acid equivalents or other non-amino acid groups, while still retaining the desired functional activity of a peptide or protein. Peptide equivalents can differ from conventional peptides by the replacement of one or more amino acids with related organic acids (such as PABA), amino acid equivalents or the like or the substitution or modification of side chains or functional groups.

(xxiii) The term "preventing the damages, effects or symptoms of a disease or disorder associated with tissue damage" means delaying the onset, hindering the progress, hindering the appearance, protection against, inhibiting or eliminating the emergence, or reducing the incidence, of such damages, effects or symptoms. Use of the term "prevention" is not meant to imply that all patients in a patient population administered a preventative therapy will never be affected by or develop symptoms in response to the disease or disorder associated with tissue damage targeted for prevention, but rather that the patient population will exhibit a reduction in the damage, effects, or symptoms of the disease or disorder. For example, many flu vaccines are not 100% effective at preventing flu in those administered the vaccine. One skilled in the art can readily identify patients and situations for whom preventative therapy would be beneficial, such as, but not limited to, individuals about to engage in activities that may expose them to various toxic agents or traumas (e.g., soldiers engaging in military operations, chemical or food processing workers, emergency personnel or first responders, etc.), or individuals that may be subjected to exposure to a toxic agent (e.g., individuals living in the vicinity of chemical, nuclear, or manufacturing facilities, or individuals under threat of military or terrorist attack).

(xxiv) As used herein, a "prophylactically effective amount" refers to that amount of a peptide sufficient to result in the prevention of the damage, effects or symptoms resulting from a disease or disorder associated with tissue damage. A prophylactically effective amount can refer to the amount of a peptide sufficient to prevent the damage, effects or symptoms resulting from a disease or disorder associated with tissue damage. Further, a prophylactically effective amount with respect to another prophylactic agent means that amount of that prophylactic agent in combination with a peptide that provides a prophylactic benefit in the prevention of damage, effects or symptoms resulting from a disease or disorder associated with tissue damage. Used in connection with an amount of a peptide, the term "prophylactically effective amount" can encompass an amount that improves overall prophylaxis or enhances the prophylactic efficacy of or provides a synergistic affect with another prophylactic agent.

(xxv) The term "neoplasm" refers to abnormal growths that lack the malignant properties of cancerous tumors, and are generally mild and non-progressive tumors. Neoplasms, include but are not limited to moles, uterine fibroids, thyroid adenomas, adrenocortical adenomas, pituitary adenomas, and teratomas.

(xxvi) The term "radiation agent" as used herein means any radioactive material that may kill or injure a subject, and may be used to cause disruption upon a city or nation. Exposure to a radiation agent may occur through deployment of a weapon (nuclear bomb (fission, fusion, neutron, boosted fission, or salted bombs), shells containing depleted uranium), terrorist device ("dirty bomb"), or fallout resulting from the detonation of a nuclear weapon or failure of a nuclear plant. Radioactive agents may include, but are not limited to, $^{137}$Cs, $^{60}$Co, $^{241}$Am, $^{252}$Cf, $^{192}$Ir, $^{238}$Pu, $^{90}$Sr, $^{226}$Ra, $^{91}$Sr, $^{92}$Sr, $^{95}$Zr, $^{99}$Mo, $^{106}$Ru, $^{131}$Sb, $^{132}$Te, $^{139}$Te, $^{140}$Ba, $^{141}$La, $^{144}$Ce, $^{233}$U, $^{235}$U, $^{238}$U, $^{228}$P, $^{229}$P, $^{230}$P, $^{231}$P, $^{232}$P, $^{233}$P, $^{234}$P, $^{235}$P, $^{236}$P, $^{237}$P, $^{238}$P, $^{239}$P, $^{240}$P, $^{241}$P, $^{242}$P, $^{243}$P, $^{244}$P, $^{245}$P, $^{246}$P, $^{247}$P, and $^{131}$I. Exposure to the radioactive agents can result in carcinogenesis, sterilization, cataract formation, radiodermatitis, beta burns, gamma burns, loss of cells (in particular bone marrow, digestive tract cells), damage to the hematopoietic, gastrointestinal, central nervous, cardiovascular, skin, and/or reproductive systems, acute radiation syndrome, chronic radiation syndrome, and cutaneous radiation syndrome. Acute radiation syndrome generally results from large doses of radiation to a subject's body occurring in a short period of time. The syndrome has a predictable course starting with a feeling of nausea, vomiting, general illness and fatigue, immune system depression, loss of hair, uncontrollable bleeding (mouth, under the skin, kidneys), massive diarrhea, delirium, coma and death. Cutaneous radiation syndrome is a subset of acute radiation syndrome and refers to radiations effects on the skin, which include, but are not limited to, inflammation, erythema, dry or moist desquamation, hair loss, blistering, reddening, ulceration, damage to sebaceous and sweat glands, atrophy, fibrosis, decreased or increased skin pigmentation, and necrosis.

(xxvii) As used herein, the terms "subject," "patient" and "victim" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, ape, or a human), and more preferably a human.

(xxviii) As used herein, the term "syndromes associated with neoplasms or cancers" refers to syndromes resulting from the direct action of the tumors through "mass effect" (compression of vital organs due to tumor) or "functional tumors" (overproduction of hormones by organ afflicted with tumor). Such syndromes include, but are not limited to, Beckwith-Wiedmann syndrome, SBLA syndrome, Li-Fraumeni syndrome, Familial Adenomatous Polyposis syndrome (Gardner syndrome), Hereditary Nonpolyposis Colorectal Cancer, Turcot syndrome, Cowden syndrome, Carney Triad syndrome, Multiple Endocrine Neoplasia syndromes (Wermer (MEN-1), Sipple (MEN-2a, MEN-2b), Von Hipple-Lindau syndrome, Cushing's syndrome, Addison's syndrome, Verner Morrison syndrome, Zollinger-Ellison syndrome, WDHA syndrome, Pancreatic Cholera, Isaac's syndrome, Rippling muscle syndrome, Stiffman syndrome, Paraneoplastic Ataxia, Yo syndrome, Tr syndrome, Hu syndrome, CV-2 syndrome, CRMP-5 syndromes, Opsoclonus/Myoclonus, Ma syndromes, Morvan's fibrillary chorea, Bannayan-Riley-Runalcaba syndrome, Peutz-Jegher syndrome, Muir-Tone syndrome, Hirschsprung disease, Lynch syndrome, Lambert-Eaton Myastenic syndrome, Myasthenia Gravis, Neuromyotonia, Paraneoplastic Cerebellat Degeneration, Paraneoplastic Limbic Encephalitis, Sweets syndrome, Birt-Hogg-Dube syndrome, Naevoid Basal Cell Carcinoma syndrome, Generalized Basaloid Follicular syndrome, Hamartoma syndrome, Bazex syndrome, Brooke Spiegler syndrome, Familial Cylindromatosis, Multiple Familial Trichoepitheliomas, Androgen Deprivation syndrome, Therapy Related Myelodysplastic syndrome, Somnolence syndrome, Gulf War syndrome, and Somatostatinoma syndrome.

(xxix) As used herein, the term "tissue protective activity" or "tissue protection" refers to the effect of inhibiting or delaying damage or death of a cell, tissue, or organ. Unless otherwise noted, the "delay" in damage or death of a cell, tissue or organ is evaluated relative to a control condition in the absence of a peptide of the invention. Tissue protective activity is specific to tissue, cells, and/or organs expressing a tissue protective receptor complex (i.e., a responsive tissue cell, and/or organ, respectively), such as, but not limited to, the tissues of the central nervous system. In specific embodiments, the responsive cells are not erythrocyte progenitor cells.

(xxx) The term "tissue protective receptor complex" as used herein means a complex comprising at least one erythropoietin receptor subunit and at least one beta common receptor subunit. The tissue protective receptor complex may contain multiple erythropoietin receptor subunits and/or beta common receptor subunits, as well as other types of receptors or proteins. See WO 2004/096148, which is hereby incorporated by reference herein in its entirety.

(xxxi) The term "toxic agent" as used herein refers to the biological, chemical and radiation agents mentioned above.

(xxxii) To determine the percent identity of two amino acid sequences, the sequences are aligned for optimal comparison purposes. The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical overlapping positions× 100/total number of positions). In one embodiment, the two sequences are the same length. In an alternate embodiment, the sequences are of different length and, accordingly, the percent identity refers to a comparison of the shorter sequence to a portion of the longer sequence, wherein said portion is the same length as said shorter sequence.

(xxxiii) As used herein, the term "treatment" includes the elimination, reduction, management or control of damage, effects or symptoms resulting from a disease or disorder associated with tissue damage or the damage, effects, or symptoms thereof.

5. BRIEF DESCRIPTION OF THE FIGURES

Figure 3A:
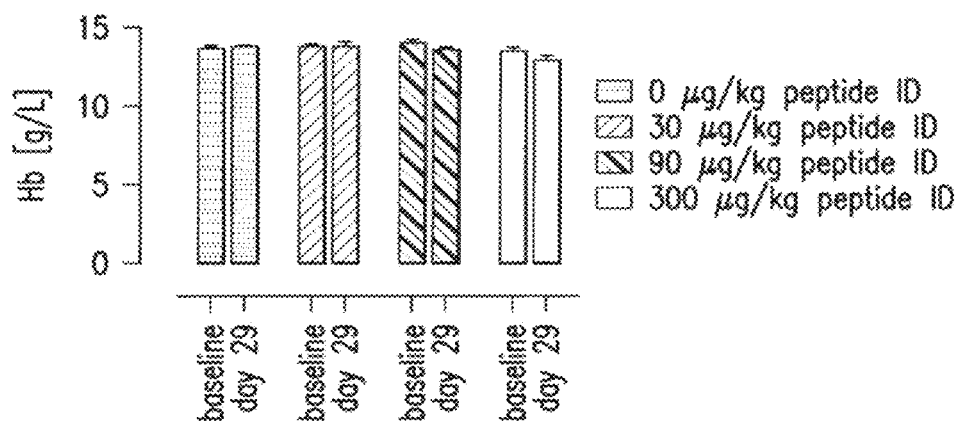
Figure 3B:
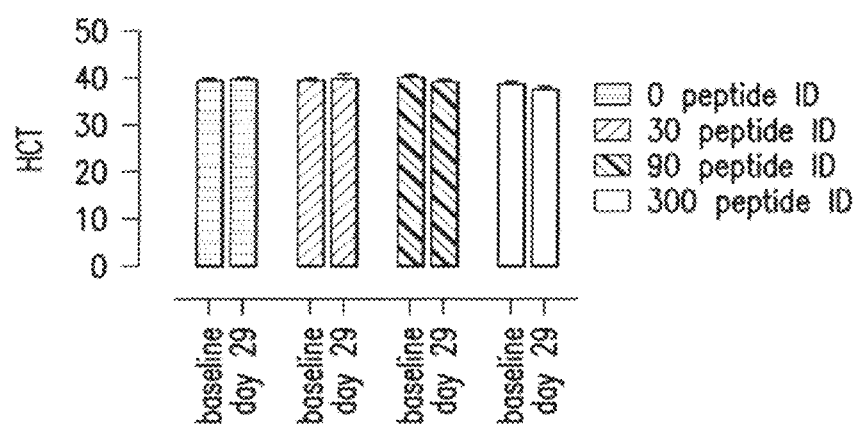
Figure 3C:
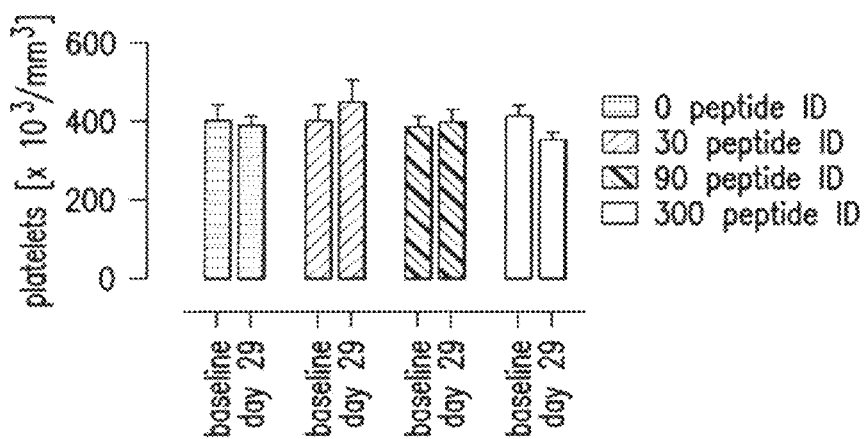

FIG. 3A-3C is a series of bar graphs illustrating the (a) hemoglobin concentration, (b) hematocrit, and (c) platelet count in blood samples taken from New Zealand White Rabbits administered various doses of Peptide ID twice daily i.v. for a period of 28 days. As shown in the graphs, the administration of Peptide ID, at all doses, had no effect on the hemoglobin concentration, hematocrit, or platelet count of the animals.

Figure 4:
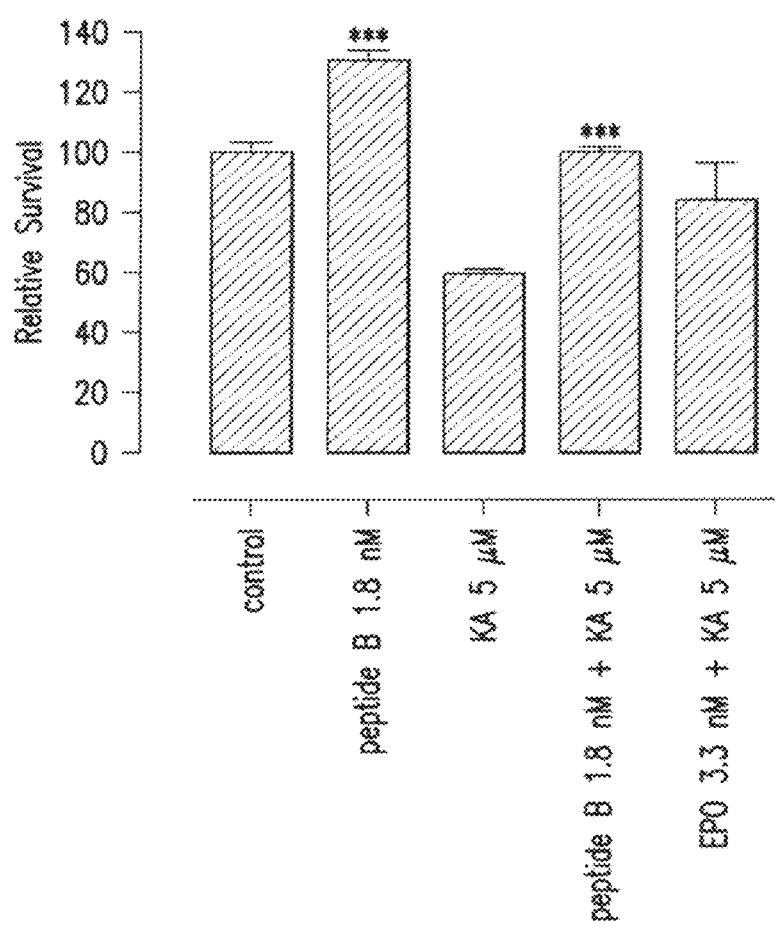

FIG. 4 is a bar graph indicating the relative survival of motorneurons subjected to kainic acid. As is shown in the graph, those cells pretreated with either Peptide B (SEQ ID NO: 3) or EPO exhibited improved survival rates.

Figure 5:
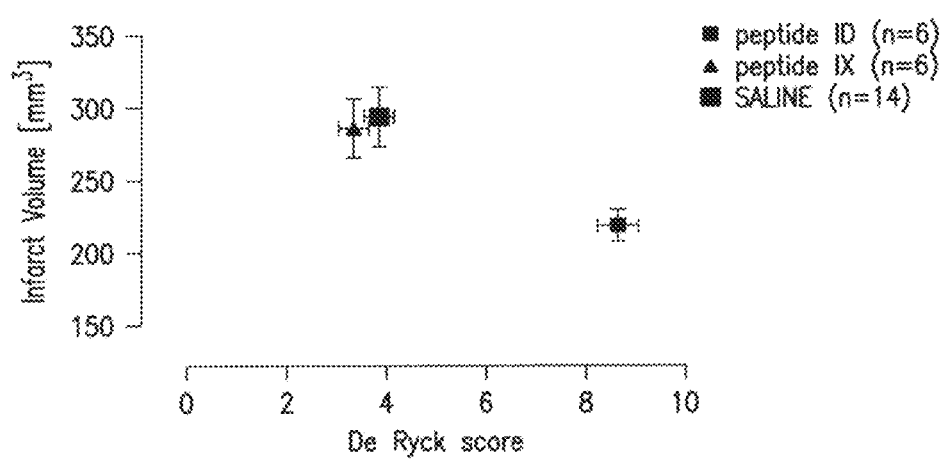

FIG. 5 is a chart illustrating the De Ryck scores of rats subjected to a foot fault test following middle cerebral artery occlusion and treatment with either saline, Peptide ID or Peptide IX (SEQ ID NO: 301). As shown in the chart, Peptide ID significantly improved the rats performance in the foot fault protocol (11.2±1.1 foot faults) in comparison to the saline treated rats (20.2±0.8 foot faults) and Peptide IX treated rats (20.1±2.1 foot faults).

Figure 6A:
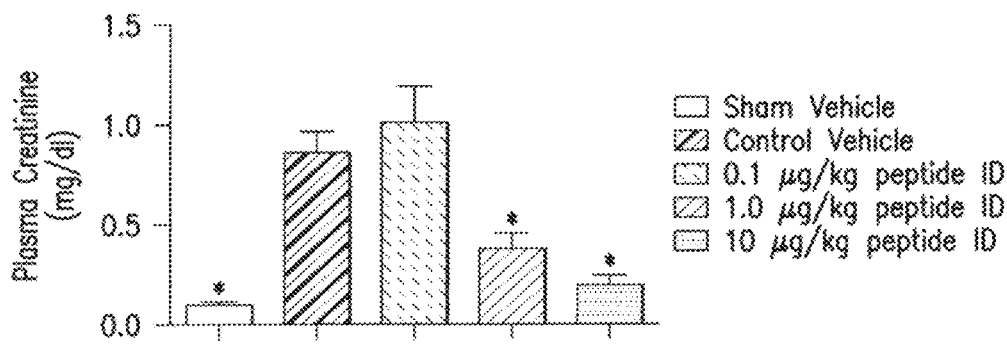
Figure 6B:
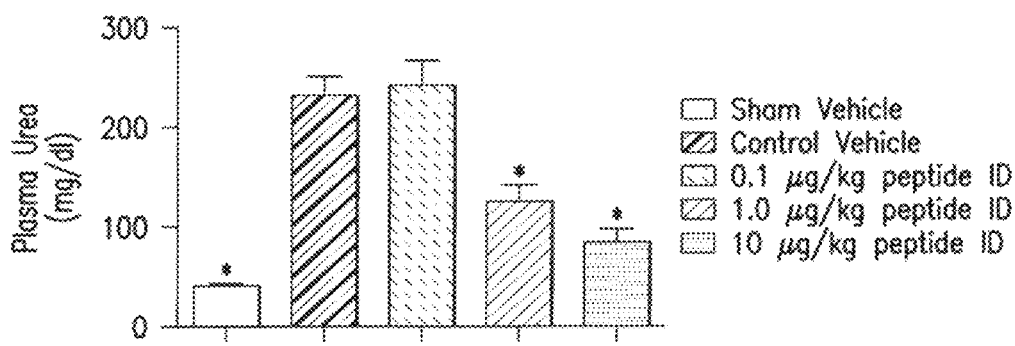
Figure 6C:
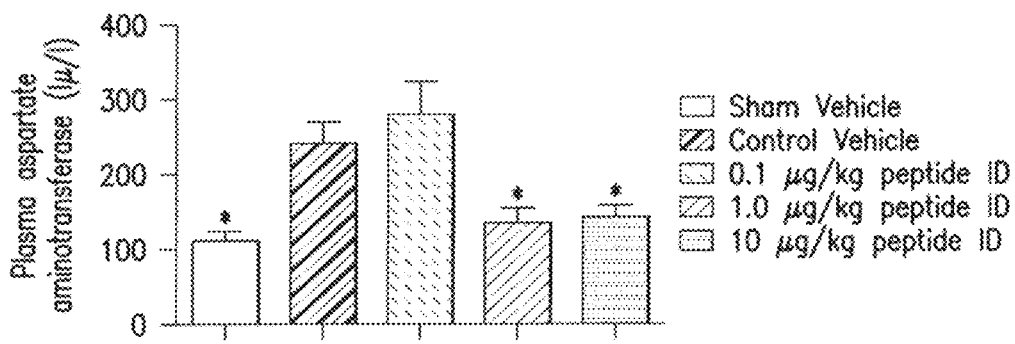

FIG. 6A-6C is a series of graphs relating to the concentration of creatinine (Graph A), urea (Graph B), and aspartate aminotransferase (AST) (Graph C) in the serum of mice that had been subjected to 30 minutes of bilateral renal ischemia followed by a period of 24 hrs of reperfusion and received either a control (PBS), 1 µg/kg of Peptide IH at 1 minute into reperfusion, 1 µg/kg of Peptide IH at 30 minutes into reperfusion, 1 µg/kg of Peptide IH at 6 hours into reperfusion, or 10 µg/kg of Peptide IH at 6 hours into reperfusion. As shown in each graph, 1 µg/kg of Peptide IH at 6 hours into reperfusion or 10 µg/kg of Peptide IH at 6 hours into reperfusion resulted in a reduction in these biochemical markers of renal dysfunction.

Figure 7A:
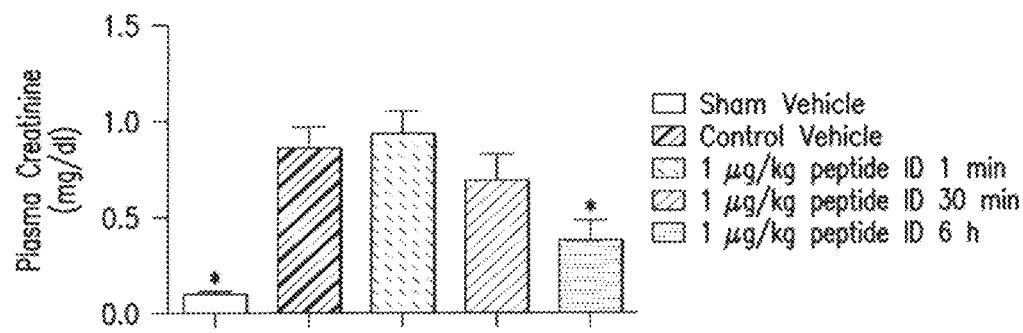
Figure 7B:
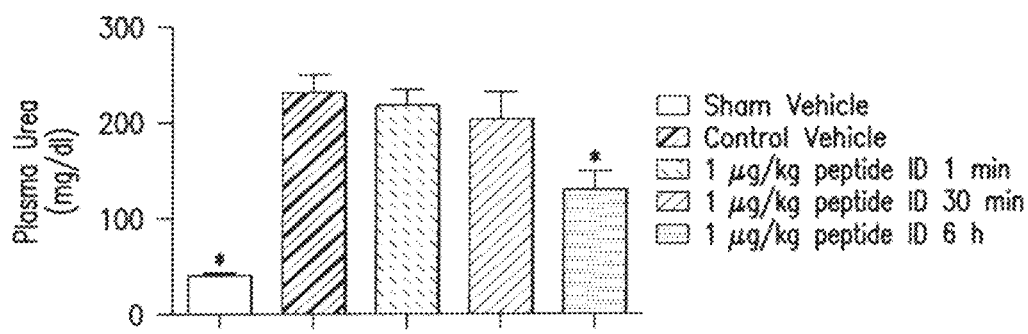
Figure 7C:
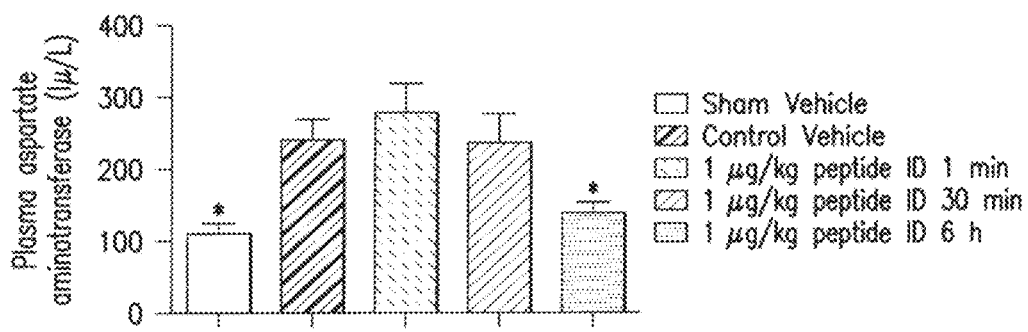

FIG. 7A-7C is series of graphs relating to the concentration of creatinine (Graph A), urea (Graph B), and aspartate aminotransferase (AST) (Graph C) in the serum of mice that had been subjected to 30 minutes of bilateral renal ischemia followed by a period of 24 hrs of reperfusion and received either multiple doses of a control (PBS), 0.1 µg/kg of Peptide IH, 1 µg/kg of Peptide IH, or 10 µg/kg of Peptide IH at 1 minute, 6 hours and 12 hours into reperfusion. As shown in each graph, 1 µg/kg of Peptide IH or 10 µg/kg of Peptide IH resulted in a reduction in these biochemical markers of renal dysfunction.

Figure 8:
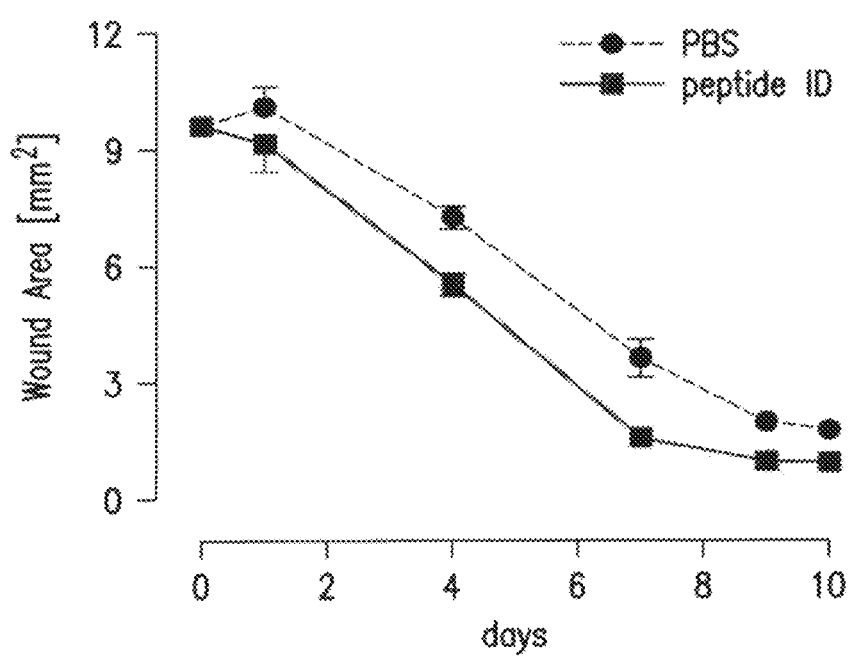

FIG. 8 is a chart illustrating the reduction in wound area over a period of treatment in a full thickness punch biopsy wound assay in rats receiving Peptide ID (24 nmol/kg of bw) daily s.c. As shown in the chart, the wounds on rats receiving Peptide ID healed more rapidly.

Figure 9:
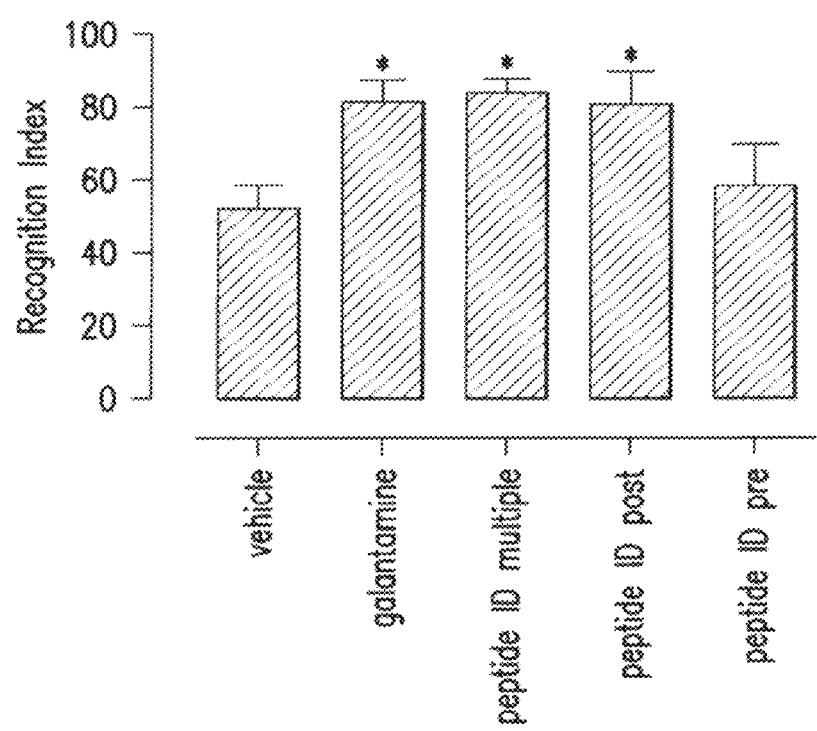

FIG. 9 is a bar graph showing the results from a novel object recognition test performed on adult Wistar rats that received saline, positive control galantamine (3 mg/kg of bw), or Peptide ID (24 nmol/kg of bw) at various time points. As shown in the graph, galantamine and Peptide ID increased the rats recognition of the novel objects.

Figure 10:
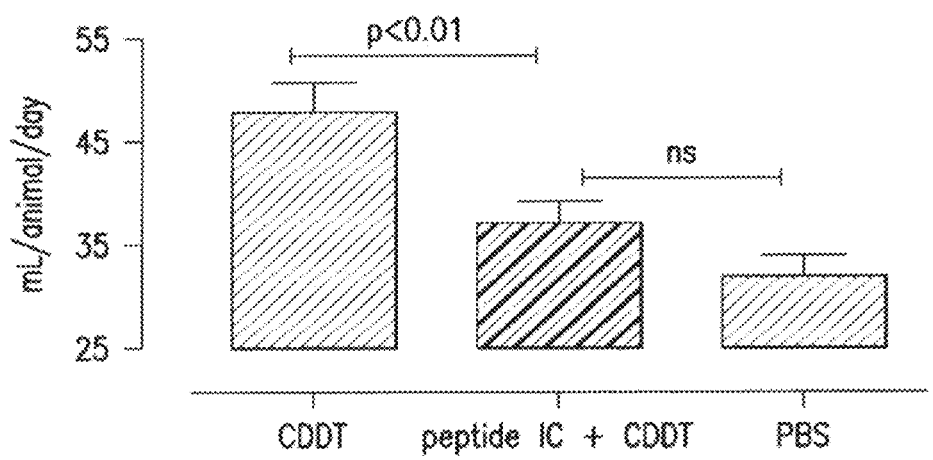

FIG. 10 is a graph comparing the volume of urine produced by rats treated with cisplatin, cisplatin and peptide IC (SEQ ID NO: 281), or control (PBS). The graph illustrates that the urine volume of the cisplatin and Peptide IC treated rats was substantially like that of the control (PBS) group. Thus the graph demonstrates that in a model of cisplatin induced nephropathy in rats that Peptide IC administered three times weekly at a dose of 0.4 µg/kg over a 5 week period protected the treated rats against renal damage due to the cisplatin.

Figure 11:
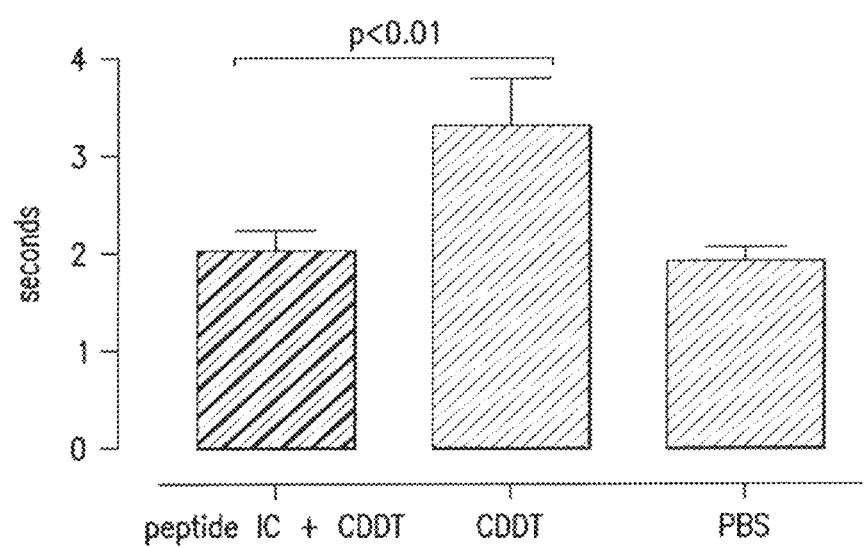

FIG. 11 is a graph comparing the times it took a rat to withdraw a paw from the hot plate in rats treated with cisplatin, cisplatin with Peptide IC or control (PBS). The graph illustrates that the time it took the rats treated with cisplatin and Peptide IC to withdraw their paw from the hotplate was substantially similar to the control group (PBS). Thus the graph demonstrates that in a model of cisplatin induced neuropathy in rats that Peptide IC administered three times weekly at a dose of 0.4 µg/kg over a 5 week period protected the treated rats against peripheral neuropathy due to the cisplatin.

Figure 12:
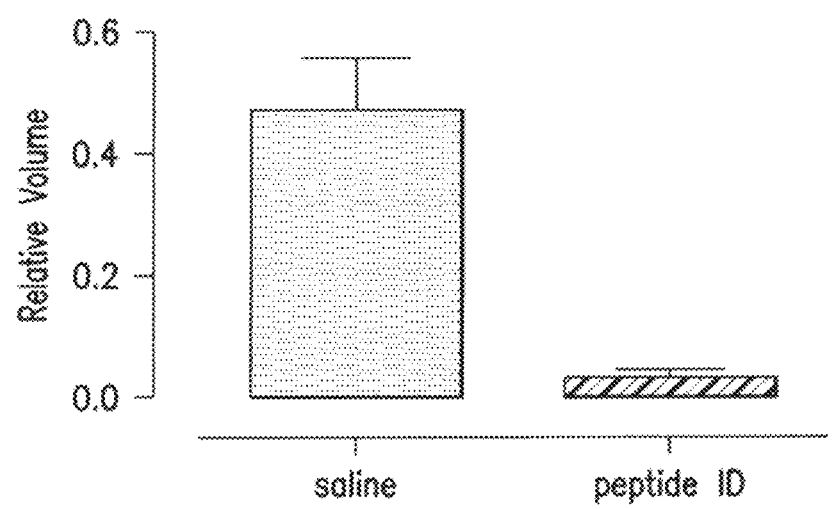

FIG. 12 is a graph comparing relative volume of a cortical tumor implanted in a rat's brain in accordance with the protocol of Lampson L. A. et al., 193, *Cancer Res.* 53(1): 176-82 after 25 days. The graph shows that the relative volume of the tumors in the rats treated by saline increased by slightly greater than 0.4 cm$^2$ whereas the rats treated with Peptide ID following implantation showed no increase in the relative volume of the tumor.

Figure 13:
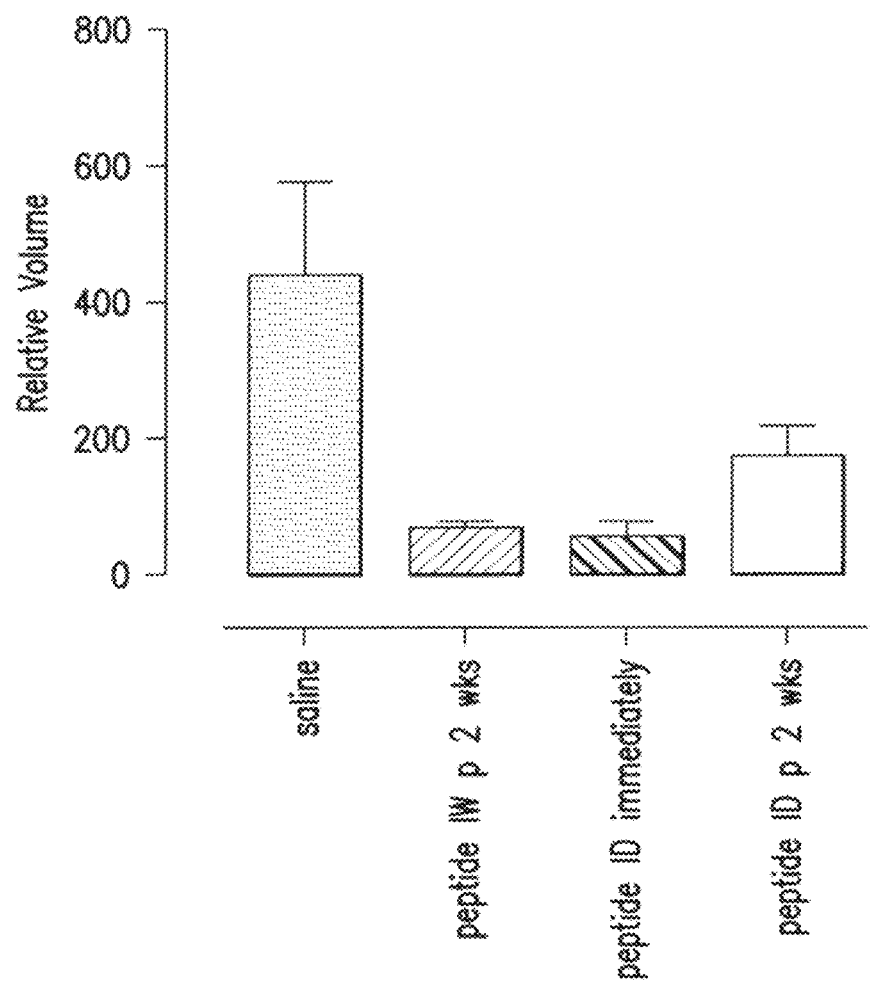

FIG. 13 is a graph comparing the relative volume of a cortical tumor implanted in a rat's brain in accordance with the protocol of Lampson L. A. et al., 193, *Cancer Res.* 53(1):176-82 after 25 days. The graph shows that the relative volume of the tumors in the rats treated by saline starting two weeks after implantation is about 300 mm$^2$ greater whereas treatment with Peptide ID and Peptide 1W (an extended half-life peptide, SEQ ID NO: 305) starting two weeks after implantation reduced the size of tumor in both cases. Administration of Peptide IW at two weeks resulted in a reduction in size of the tumor equivalent to that achieved by immediate treatment with Peptide ID.

Figure 14:
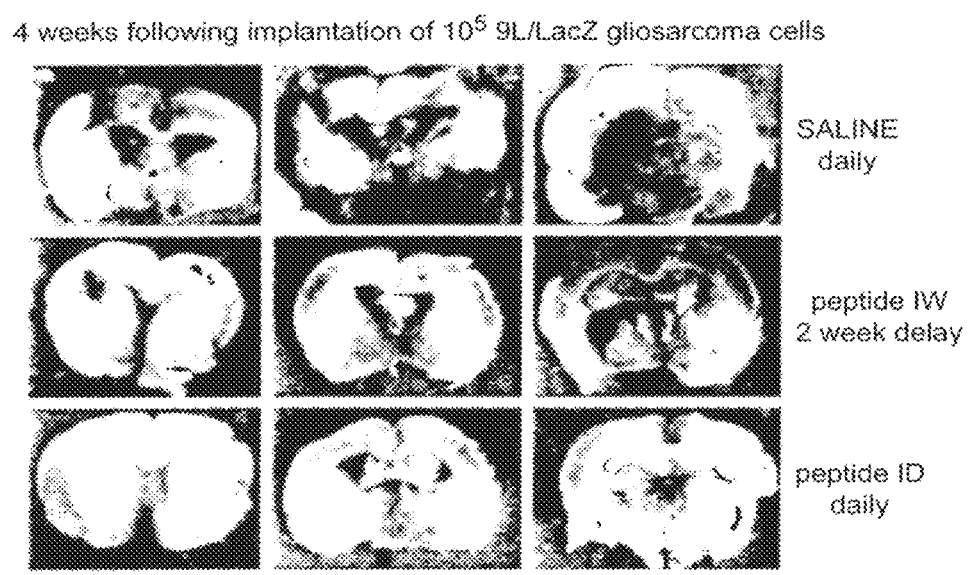

FIG. 14 is a comparison of cortical tumor size in rats treated with saline daily, Peptide ID, or Peptide IW after a two week delay. The darkened areas on the photograph illustrate the presence of the tumor. The comparative photos clearly demonstrate that the administration of Peptide IW after two weeks led to a similar reduction in size of the tumor as administration of Peptide ID immediately after implantation of the tumor.

Figure 15:
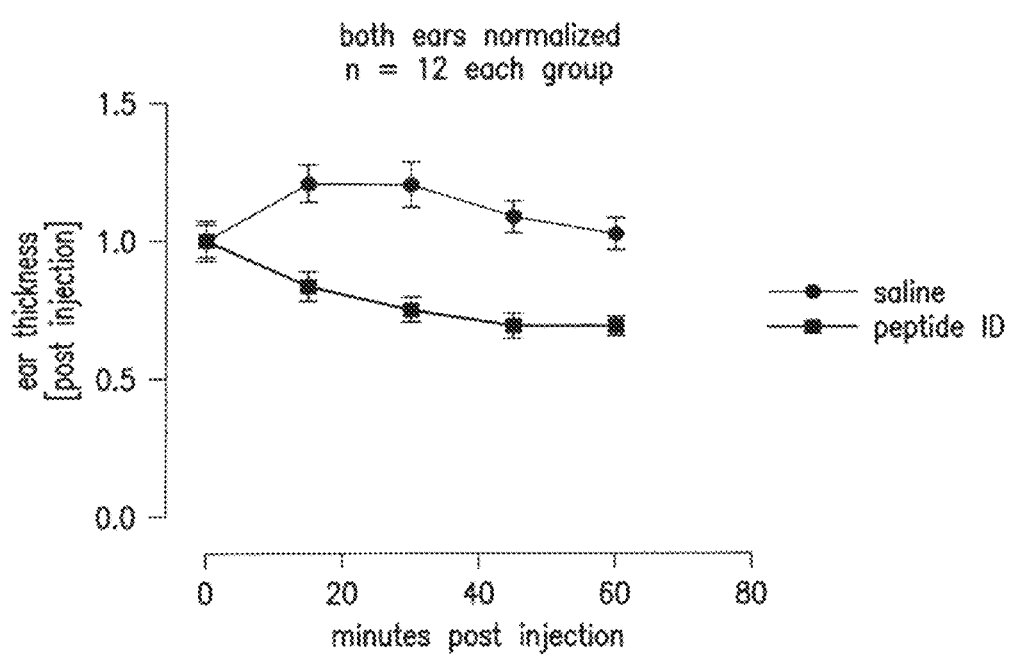

FIG. 15 difference in ear thickness in the ears of Sprague Dawley rats intradermally injected with histamine diphosphate. The rats were treated either with Peptide ID intravenously or saline. The ears of the rats treated with Peptide ID, exhibited less inflammation in response to the histamine challenge than the ears of the rats treated with saline.

Figure 16:
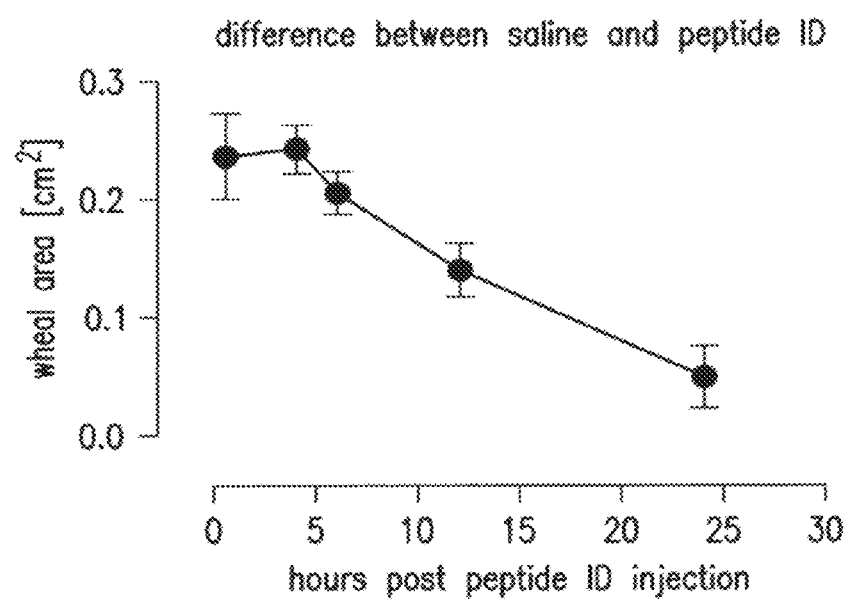

FIG. 16 is a chart demonstrating the difference in wheal (hive) size on rat abdomens in response to intradermally administered histamine in those rats pretreated with saline and those pretreated with Peptide ID. The chart illustrates the anti-inflammatory effects of Peptide ID up to 24 hours following the histamine injection.

Figure 17:
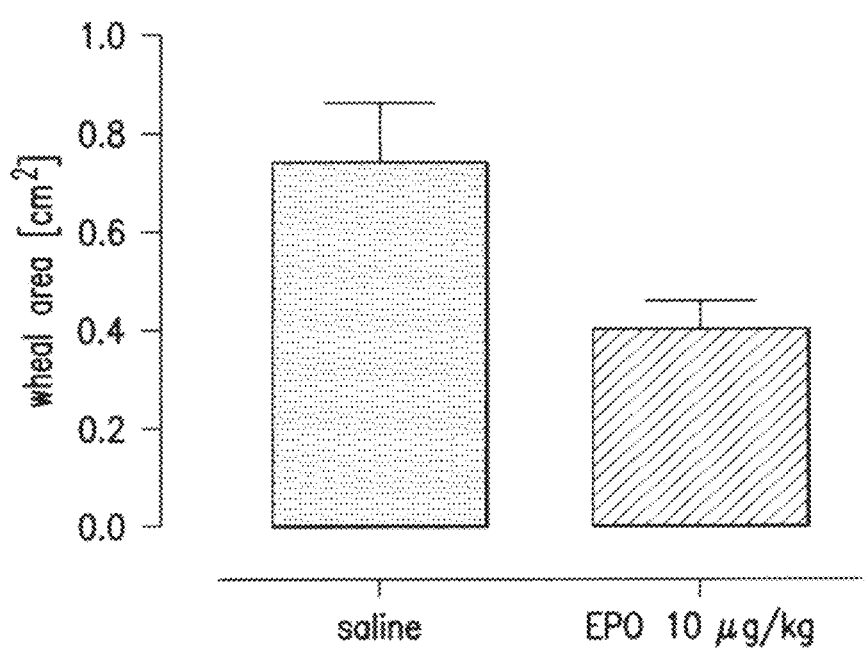

FIG. 17 is a chart demonstrating the difference in wheal (hive) area in response to a histamine challenge in rats between those rats treated with EPO and those rats treated with saline. The wheal area after fifteen (15) minutes was less in those treated with EPO than those rats treated with saline.

Figure 18:
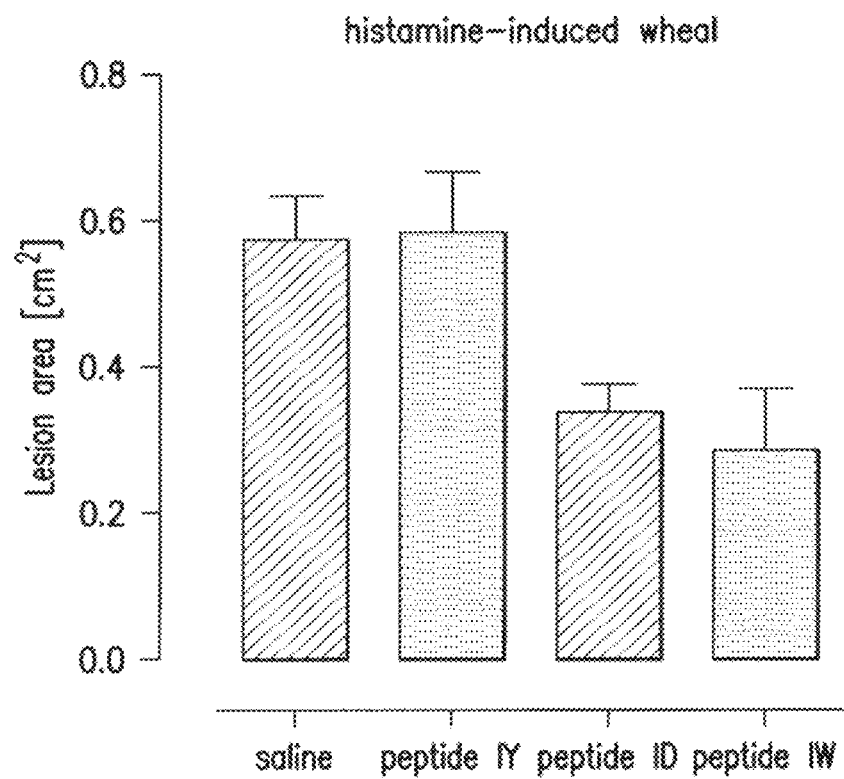

FIG. 18 is a chart comparing the difference in wheal (hive) size (lesion area) in rats challenged with histamine and treated using saline, Peptide IY (SEQ ID NO: 304), Peptide ID and Peptide IW. Animals treated with either Peptide ID or Peptide IW exhibited nearly half the lesion area (about 0.35 cm$^2$ and 0.3 cm$^2$ respectively) of the lesions on the saline and Peptide IY treated animals (about 0.6 cm$^2$).

Figure 19:
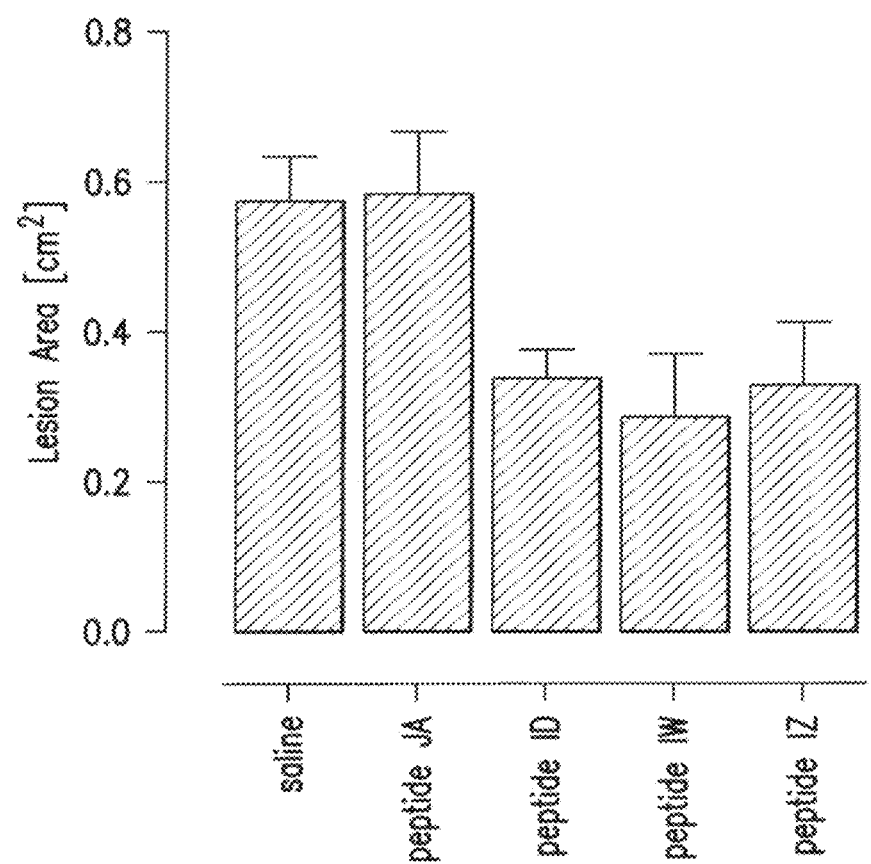

FIG. 19 is a chart comparing the difference in wheal (hive) size (lesion area) in rats challenged with histamine and treated using saline, Peptide JA (SEQ ID NO: 301), Peptide IW, Peptide IZ (SEQ ID NO: 300), and Peptide ID. Animals treated with either peptide IW, IZ, or ID exhibited a smaller lesion area (0.3 cm$^2$, 0.35$^2$, and 0.4 cm$^2$ respectively) in comparison to the saline and peptide JA treated animals (both about 0.6 cm$^2$).

Figure 20:
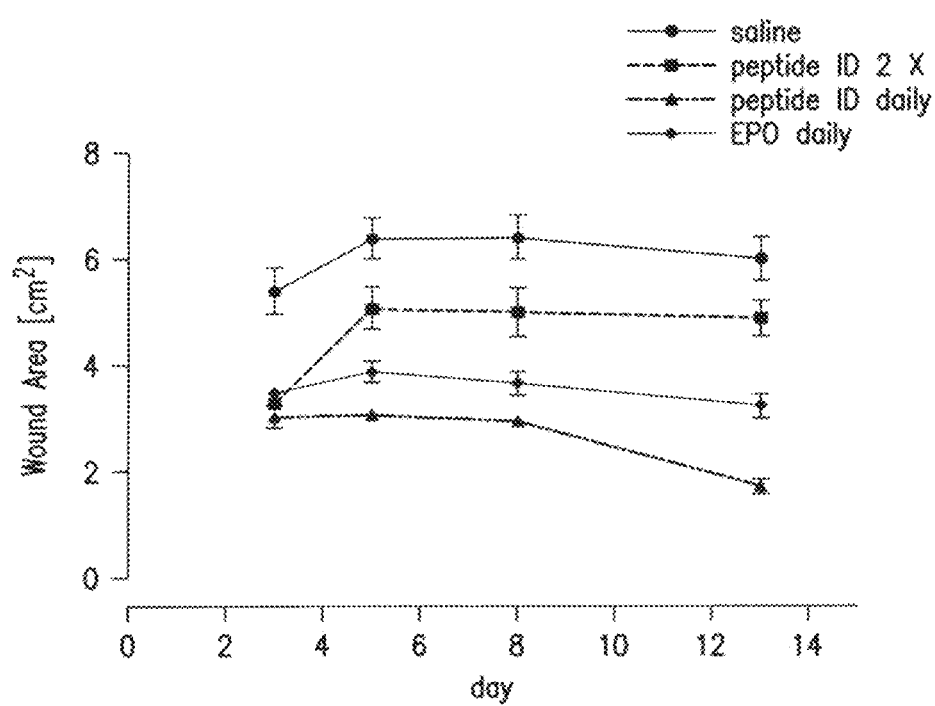

FIG. 20 is a chart comparing the difference in wound (ulcer) size (area) in rats subjected to a pressure ulcer and treated using saline, Peptide ID dosed twice, Peptide ID dosed daily or EPO administered daily. The chart demonstrates that the Peptide ID and EPO treated rats exhibited better wound healing than the saline treated rats. With the Peptide ID daily treated animals had the smallest wound size.

Figure 21:
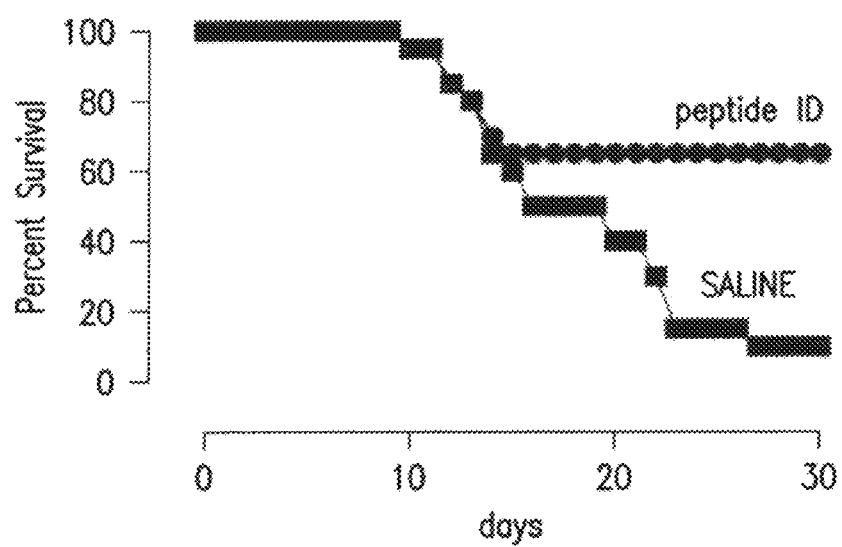

FIG. 21 shows Kaplan Meier Survival Curves for mice irradiated with 796 cGy (A) or 831 cGy (B) and then treated with Peptide ID subcutaneously daily for 29 days following irradiation or with PBS subcutaneously for 29 days. At both doses of radiation, Peptide ID significantly increased the overall survival time of the mice at day 30 (45% survival at day 30 at 796 cGy, 20% survival at day 30 at 831 cGy)

Figure 22:
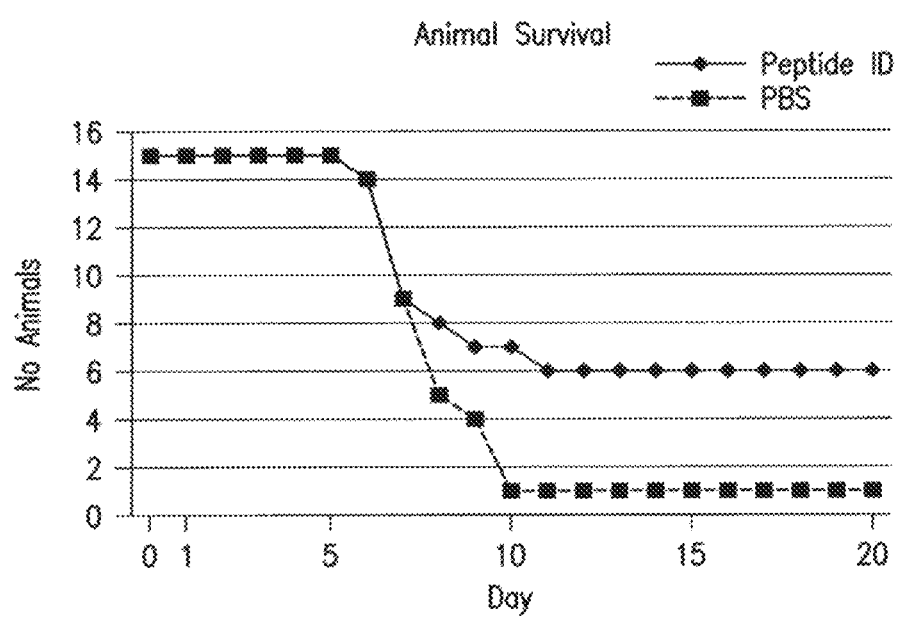

FIG. 22 is a chart showing the survival rate of mice that received partial body irradiation of 15 Gy and then were treated with Peptide ID at day 1 and daily thereafter or PBS at day one and daily thereafter. As the chart shows, the number of mice surviving to day 20 was substantially greater amongst those receiving Peptide ID in comparison to those receiving PBS (6 peptide treated mice vs. 1 PBS treated mouse).

6. DETAILED DESCRIPTION OF THE INVENTION

6.1 Isolated Polypeptides

The current invention provides a method of modulating the effects of the body's response to a disease or disorder associated with tissue damage. Further, the current invention provides a method of preventing, treating, ameliorating, or managing damage, effects or symptoms in a patient afflicted with a disease or disorder associated with tissue damage by administering a peptide that is derived from erythropoietin or another Type-1 cytokine Preferably, the peptide used in the current method is tissue protective, neuroprotective, neuritogenic, or anti-apoptotic.

Several peptides derived from Type-1 cytokines, such as EPO, have been disclosed in the art, such as: (a) and (b) Brines et al. in PCT/US2006/031061, published as WO 2007/019545, and US Patent Applications: "Tissue Protective Peptides and Peptide Analogs for Preventing and Treating Diseases and Disorders Associated with Tissue Damage," Ser. No. 61/062,012, filed Jan. 22, 2008; "EPO-derived Tissue Protective Peptides and Peptide Analogs for Preventing and Treating Disorders Associated with Tissue Damage," Ser. No. 61/062,022, filed Jan. 22, 2008; and "Method of Treating Inflammation or Inflammatory Conditions and Symptoms Thereof with Peptides," Ser. No. 61/133,912, filed Jul. 3, 2008 ("Brines"); (c) Bock et al. in PCT Application No. DK2006/000246 published as WO 2006/119767 and WO 2007/071248 ("Bock"); (d) O'Brien et al. in U.S. Pat. Nos. 5,571,787, 5,700,909, 5,696,080, 5,714,459, 6,590,074, 6,559,124, 6,271,196, 6,268,347, and 6,849,602 ("O'Brien"); (e) Smith-Swintowsky et al. in U.S. Pat. No. 7,259,146 and U.S. Publication No. 20030130197 ("Smith-Swintowsky"), and (f) Yuan et al. in PCT/IB2006/003581 published as WO/2007/052154 ("Yuan") each of these inventions is hereby incorporated in their entirety.

For purposes of discussing the above-motifs, the three dimensional structure of EPO is accepted as described by Cheetham et al., 1998, Nat. Struct. Biol. 5; 861-866, hereby incorporated by reference in its entirety, and as set forth in SEQ ID NO:1 (also available as data deposited in the Protein Data Bank of the National Center for Biotechnology Information as entry "1BUY").

As stated above, peptides useful for the modulation of the body's response to a disease or disorder associated with tissue damage and/or useful in the prevention, treatment, amelioration and management of damage, effects or symptoms in a subject afflicted with a disease or disorder associated with tissue damage have a motif based in one embodiment on fragments of the amino acid sequences of EPO, derived from the three dimensional structure of the EPO protein, and in particular, were derived from those regions of EPO facing away from the ligand binding sites and/or the internal portion of the EPOR homodimer. These fragments are derived from the following EPO structures: (1) loop AB and N-terminal portion of helix B (Peptide A: NITVPDT-KVNFYAWKRMEVG, SEQ ID NO:2, corresponding to amino acids 38-57 of SEQ ID NO:1); (2) C-terminal portion of helix B (Peptide B: QQAVEVWQGLALLSEAVL-RGQALLV, SEQ ID NO:3, corresponding to amino acids 58-82 of SEQ ID NO:1), and (3) a portion of the A-B loop consisting of a small cysteine loop and a B-pleated sheet (Peptide C: GCAEHCSLNENITVPDTKVN, SEQ ID NO:4, corresponding to amino acids 28-47 of SEQ ID NO:1).

Specifically, these motifs may be:

(a) Structural Motif A.

In this structural motif, the peptide useful for the prevention, treatment, amelioration, or management of a disease or disorder associated with tissue damage or damages, effects or symptoms resulting therefrom possesses two negatively charged amino acids, which can be separated by up to 5 amino acids, flanked by hydrophobic amino acids. Structurally this can be represented as $H_1$-$N_1$-$(X)_n$-$N_2$-$H_2$, wherein n is 0-5, SEQ ID NO: 5; or alternatively as:

```
(a1)      HNNH,        SEQ ID NO: 6;
(a2)      HNXNH,       SEQ ID NO: 7;
(a3)      HNXXNH,      SEQ ID NO: 8;
(a4)      HNXXXNH,     SEQ ID NO: 9;
(a5)      HNXXXXH,     SEQ ID NO: 10;
or
(a6)      HNXXXXXH,    SEQ ID NO: 11,
``` where H represents hydrophobic amino acids (e.g., the moderately hydrophobic amino acids: Gly (G), Pro (P), Cys (C), Tyr (Y), and Trp (W), and preferably the highly hydrophobic amino acids: Ala (A), Val (V), Ile (I), Met (M), Leu (L), Phe (F)), N represents a negatively charged amino acid such as Glu (E) or Asp (D), and X represents any amino acid, although preferably a hydrophilic one.

A variation of this structural motif, structurally represented as $H_1$-$N_1$-$(X)_n$-$N_2$-$L_1$, wherein $n$ is 0-5, SEQ ID NO: 12, or $L_1$-$N_1$-$(X)_n$-$N_2$-$H_1$, wherein $n$ is 0-5, SEQ ID NO: 13, is disclosed where one of the flanking hydrophobic amino acids has been replaced with a polar amino acid such as Ser (S), Thr (T), Asn (N), or Gln (Q).

Examples of this motif are:

```
Peptide D
                                    (SEQ ID NO: 14)
APPRLICDSRVLERYLLEAKEAE;

Peptide A
                                    (SEQ ID NO: 2)
NITVPDTKVNFYAWKRMEVG;
and Peptide B
                                    (SEQ ID NO: 3)
QQAVEVWQGLALLSEAVLRGQALLV.
```

In a particular embodiment of Structural Motif A, a class of the isolated peptides and peptide analogs useful for the prevention, treatment, amelioration, management of a disease or disorder associated with tissue damage or damages, effects or symptoms resulting therefrom may have the structural Formula I (SEQ ID NO. 15):

$$X_1-X_2-X_3-X_4-X_5-X_6-X_7-X_8-X_9-X_{10}-X_{11}-X_{12}-(Z)_n-X_{13}-$$
$$X_{14}-X_{15}-X_{16}-X_{17}-X_{18}-X_{19}-X_{20}-X_{21}-X_{22}-X_{23}-X_{24}$$

wherein:
$X_1$ is Cys (C) or Pro (P);
$X_2$ is Asp (D) or Pro (P);
$X_3$ is Ser (S) or Arg (R);
$X_4$ is Arg (R) or Leu (L);
$X_5$ is Val (V) or Ile (I);
$X_6$ is Leu (L) or Cys (C);
$X_7$ is Glu (E) or Asp (D);
$X_8$ is Arg (R) or Ser (S);
$X_9$ is Tyr (Y) or Arg (R);
$X_{10}$ is Leu (L) or Val (V);
$X_{11}$ is Leu (L) or Ala (A);
$X_{12}$ is a negatively charged amino acid;
$(Z)_n$ is an amino acid, wherein $n$ is 1-5;
$X_{13}$ is a negatively charged amino acid;
$X_{14}$ is Ala (A) or Leu (L);
$X_{15}$ is Glu (E) or Lys (K);
$X_{16}$ is Asn (N), Glu (E), or Lys (K);
$X_{17}$ is Ile (I) or Ala (A);
$X_{18}$ is Thr (T), Glu (E), or Gly (G);
$X_{19}$ is Thr (T), Asn (N), or Ala (A);
$X_{20}$ is Gly (G) or Ile (I);
$X_{21}$ is Cys (C) or Thr (T);
$X_{22}$ is Ala (A) or Thr (T);
$X_{23}$ is Glu (E) or Gly (G);
$X_{24}$ is His (H) or Cys (C).

In certain embodiments, isolated peptides and peptide analogs of Formula I may not include Peptide D, APPRLICDSRVLERYLLEAKEAE (SEQ ID NO:14); Peptide A, NITVPDTKVNFYAWKRMEVG (SEQ ID NO: 2); Peptide B, QQAVEVWQGLALLSEAVLRGQALLV (SEQ ID NO: 3), Peptide C, GCAEHCSLNENITVPDTKVN (SEQ ID NO: 4) or Peptide E, RYLLEAKEAENITTGC (SEQ ID NO:303).

In certain embodiments, the isolated peptides and peptide analogs can contain fewer than 24 amino acid residues. Indeed truncated or internally deleted forms of structural Formula I containing as few as 23, 22, 21, 20, 19, 18, 17, 16, 15, 14, 13, 12, 11, or even 10 amino acid residues that substantially retain the overall characteristics and tissue protective properties of the isolated peptides and peptide analogs of structural Formula I.

Due to the surmised importance of the spatially compact charge configuration at the internal residues of the isolated peptides and peptide analogs of structural Formula I, in certain embodiments of the invention, residues comprising the polar, negatively and positively charged, and immediately adjacent amino acids are not deleted. Thus, in certain embodiments, residues $X_{11}$, $X_{12}$, $X_{13}$, and $X_{14}$ are not deleted.

The isolated peptides and peptide analogs of Formula I can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 25, 26, 27, 28, or 29 amino acid residues and are considered to be within the scope of the present invention. Preferably, such extended peptides will substantially retain the tissue protective properties of the peptide analogs of Formula I.

Certain amino acid residues in the core peptides and peptide analogs of Formula I can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula I wherein at least one and up to eight amino acid residues in the formula are conservatively substituted with another amino acid residue. In certain embodiments, seven, six, five, four, three, two, or one amino acid is conservatively substituted.

In specific embodiments, the isolated peptides and peptide analogs consists of the amino acid sequence:

```
Peptide F
                                    (SEQ ID NO: 16)
CDSRVLERYLLEAKEAENITTGCAEH;

Peptide G
                                    (SEQ ID NO: 17)
PPRLICDSRVLERYLLEAKEAENITTGC;
and
```

```
Peptide H
                                    (SEQ ID NO: 18)
    ADRELEKIGA.
```

(b) Structural Motif B.

In this structural motif, the peptide has a positive amino acid next to a negative amino acid and both charged amino acids are flanked by single hydrophobic amino acids. Structurally this can be represented as:

```
    (b1)        HNPH,       SEQ ID NO: 19;
    or
    (b2)        HPNH,       SEQ ID NO: 20,
``` where P represents positively charged amino acids such as arginine, lysine or histidine and N represents the negatively charged amino acids glutamate or aspartate.

In a variation of this particular motif, the negative and positive amino acids can be separated by a polar amino acid, e.g.,

```
    (b3)        HNLPH,      SEQ ID NO: 21;
    (b4)        HPLNH,      SEQ ID NO: 22,
``` wherein L represents a polar amino acid such as serine, threonine, asparagine, or glutamine. Alternatively, the above structural motifs may be represented as $H_1$-$N_1$-$(L)_n$-$P_1$-$H_2$, wherein $n$ is 0-1, SEQ ID NO: 23, or $H_1$-$P_1$-$(L)_n$-$N_1$-$H_2$, wherein $n$ is 0-1, SEQ ID NO: 24, as well. An example of this motif is peptide C (GCAEHCSLNENITVPDTKVN, SEQ ID NO:4).

In certain embodiments, isolated peptides and peptide analogs of the particular embodiments of Structural Motif B disclosed below in Formulas II-IV may not include Peptide D, APPRLICDSRVLERYLLEAKEAE (SEQ ID NO:14); Peptide A, NITVPDTKVNFYAWKRMEVG (SEQ ID NO: 2); Peptide B, QQAVEVWQGLALLSEAVLRGQALLV (SEQ ID NO: 3), Peptide C, GCAEHCSLNENITVPDTKVN (SEQ ID NO: 4) or Peptide E, RYLLEAKEAENITTGC (SEQ ID NO:303).

In a particular embodiment of Structural Motif B, a class of the isolated peptides and peptide analogs useful for the prevention, treatment, amelioration, management of a disease or disorder associated with tissue damage or damages, effects or symptoms resulting therefrom may comprise 10 to 28 consecutive amino acid residues, which have the structural Formula II (SEQ ID NO:25):

$$X_1-X_2-X_3-X_4-X_5-X_6-X_7-X_8-X_9-X_{10}-X_{11}-X_{12}-X_{13}-X_{14}-$$

$$X_{15}-X_{16}-X_{17}-X_{18}-X_{19}-X_{20}-X_{21}-X_{22}-X_{23}-X_{24}$$

wherein:
$X_1$ is Ser (S);
$X_2$ is Arg (R);
$X_3$ is Val (V);
$X_4$ is Leu (L);
$X_5$ is Glu (E);
$X_6$ is Arg (R);
$X_7$ is Tyr (Y);
$X_8$ is Leu (L);
$X_9$ is Leu (L);
$X_{10}$ is Glu (E);
$X_{11}$ is Ala (A);
$X_{12}$ is a positively charged amino acid;
$X_{13}$ is a negatively charged amino acid;
$X_{14}$ is Ala (A);
$X_{15}$ is Glu (E);
$X_{16}$ is Asn (N);
$X_{17}$ is Ile (I);
$X_{18}$ is Thr (T);
$X_{19}$ is Thr (T);
$X_{20}$ is Gly (G);
$X_{21}$ is Cys (C);
$X_{22}$ is Ala (A);
$X_{23}$ is Glu (E);
$X_{24}$ is His (H).

In certain embodiments, the isolated peptides and peptide analogs can contain fewer than 24 amino acid residues. Indeed, truncated or internally deleted forms of structural Formula II containing as few as 23, 22, 21, 20, 19, 18, 17, 16, 15, 14, 13, 12, 11, or even 10 amino acid residues that substantially retain the overall characteristics and tissue protective properties of the isolated peptides and peptide analogs of structural Formula II.

Due to the surmised importance of the spatially compact charge configuration at the internal residues of the isolated peptides and peptide analogs of structural Formula II, in certain embodiments of the invention, residues comprising the negatively and positively charged and immediately adjacent amino acids are not deleted. Thus, in certain embodiments, residues $X_{11}$, $X_{12}$, $X_{13}$, and $X_{14}$ are not deleted.

The isolated peptides and peptide analogs of Formula II can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 25, 26, 27, 28, or 29 amino acid residues and are considered to be within the scope of the present invention. Preferably, such extended peptides will substantially retain the tissue protective properties of the peptide analogs of Formula II.

Certain amino acid residues in the core peptides and peptide analogs of Formula II can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula II wherein at least one and up to eight amino acid residues in the formula are conservatively substituted with another amino acid residue. In certain embodiments, seven, six, five, four, three, two, or one amino acid is conservatively substituted.

In specific embodiments, the isolated peptide or peptide analog consists of the amino acid sequence:

```
    Peptide I
                                    (SEQ ID NO: 26)
    SRVLERYLLEAKEAENITTGCAEH.
```

In a further embodiment of Structural Motif B, a class of the isolated peptides and peptide analogs useful for the prevention, treatment, amelioration, management of a disease or disorder associated with tissue damage or damages, effects or symptoms resulting therefrom, have the structural Formula III (SEQ ID NO:27):

$X_1-X_2-X_3-X_4-X_5-X_6-X_7-X_8-X_9-X_{10}-X_{11}-X_{12}-X_{13}-X_{14}-$
$X_{15}-X_{16}-X_{17}-X_{18}-X_{19}-X_{20}-X_{21}-X_{22}-X_{23}-X_{24}$ wherein:
$X_1$ is Pro (P), Lys (K), or Ser (S);
$X_2$ is Pro (P), Glu (E), or Gln (Q);
$X_3$ is Arg (R), Ala (A), or Pro (P);
$X_4$ is Leu (L), Glu (E), or Trp (W);
$X_5$ is Ile (I), Asn (N), or Glu (E);
$X_6$ is Cys (C), Ile (I), or Pro (P);
$X_7$ is Asp (D), Thr (T), Leu (L), or Ala (A);
$X_8$ is Ser (S), Thr (T), Gln (Q), or Asp (D);
$X_9$ is Arg (R), Gly (G), or Leu (L);
$X_{10}$ is Val (V), Cys (C), His (H), or Glu (E);
$X_{11}$ is Leu (L), Ala (A), Val (V);
$X_{12}$ is a negatively charged amino acid;
$X_{13}$ is a positively charged amino acid;
$X_{14}$ is Tyr (Y), Cys (C), Ala (A), or Ile (I);
$X_{15}$ is Leu (L), Ser (S), Val (V), or Gly (G);
$X_{16}$ is Leu (L), Ser (S), or Ala (A);
$X_{17}$ is Glu (E), Asn (N), or Gly (G);
$X_{18}$ is Ala (A), Glu (E), or Leu (L);
$X_{19}$ is Lys (K), Asn (N), or Arg (R);
$X_{20}$ is Glu (E), Ile (I), or Ser (S);
$X_{21}$ is Ala (A), Thr (T), or Leu (L);
$X_{22}$ is Glu (E), Val (V), or Thr (T);
$X_{23}$ is Asn (N), Pro (P), or Thr (T);
$X_{24}$ is Ile (I), Asp (D), or Leu (L).

In certain embodiments, the isolated peptides and peptide analogs can contain fewer than 24 amino acid residues. Indeed, truncated or internally deleted forms of structural Formula III containing as few as 23, 22, 21, 20, 19, 18, 17, 16, 15, 14, 13, 12, 11, or even 10 amino acid residues that substantially retain the overall characteristics and tissue protective properties of the isolated peptides and peptide analogs of structural Formula III.

Due to the surmised importance of the spatially compact charge configuration at the internal residues of the isolated peptides and peptide analogs of structural Formula III, in certain embodiments of the invention, residues comprising the negatively and positively charged and immediately adjacent amino acids are not deleted. Thus, in certain embodiments, residues $X_{11}$, $X_{12}$, $X_{13}$, and $X_{14}$ are not deleted.

The isolated peptides and peptide analogs of Formula III can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 25, 26, 27, 28, or 29 amino acid residues and are considered to be within the scope of the present invention. Preferably, such extended peptides will substantially retain the tissue protective properties of the peptide analogs of Formula III.

Certain amino acid residues in the core peptides and peptide analogs of Formula III can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula III wherein at least one and up to eight amino acid residues in the formula are conservatively substituted with another amino acid residue. In certain embodiments, seven, six, five, four, three, two, or one amino acid is conservatively substituted.

In specific embodiments, the isolated peptides and peptide analogs are selected from the group of peptides set forth below:

```
Peptide J
                                  (SEQ ID NO: 28)
PPRLICDSRVLERYLLEAKEAENI;

Peptide K
                                  (SEQ ID NO: 29)
KEAENITTGCAEHCSLNENITVPD;

Peptide L
                                  (SEQ ID NO: 30)
SQPWEPLQLHVDKAVSGLRSLTTL;
and Peptide H
                                  (SEQ ID NO: 18)
ADRELEKIGA.
```

In yet another embodiment of Structural Motif B, a class of the isolated peptides and peptide analogs useful for the prevention, treatment, amelioration, management of a disease or disorder associated with tissue damage or damages, effects or symptoms resulting therefrom, the isolated peptides and peptide analogs have the structural Formula IV (SEQ ID NO:31):

$X_1-X_2-X_3-X_4-X_5-X_6-X_7-X_8-X_9-X_{10}-X_{11}-X_{12}-X_{13}-X_{14}-$
$X_{15}-X_{16}-X_{17}-X_{18}-X_{19}-X_{20}-X_{21}-X_{22}-X_{23}-X_{24}-X_{25}$ wherein:
$X_1$ is His (H);
$X_2$ is Cys (C);
$X_3$ is Ser (S);
$X_4$ is Leu (L);
$X_5$ is Ala (A) or Asn (N);
$X_6$ is Pro (P) or Glu (E);
$X_7$ is Pro (P) or Asn (N);
$X_8$ is Arg (R) or Ile (I);
$X_9$ is Leu (L) or Thr (T);
$X_{10}$ is Ile (I) or Val (V);
$X_{11}$ is Cys (C) or Pro (P);
$X_{12}$ is a negatively charged amino acid;
$X_{13}$ is a polar amino acid;
$X_{14}$ is a positively charged amino acid;
$X_{15}$ is Val (V);
$X_{16}$ is Leu (L) or Asn (N);
$X_{17}$ is Glu (E) or Phe (F);
$X_{18}$ is Arg (R) or Tyr (Y);
$X_{19}$ is Tyr (Y) or Ala (A);
$X_{20}$ is Leu (L) or Trp (W);
$X_{21}$ is Leu (L) or Lys (K);
$X_{22}$ is Glu (E) or Arg (R);
$X_{23}$ is Ala (A) or Met (M);
$X_{24}$ is Lys (K) or Glu (E);
$X_{25}$ is Glu (E) or Val (V).

In certain embodiments, the isolated peptides and peptide analogs can contain fewer than 25 amino acid residues. Indeed, truncated or internally deleted forms of structural Formula IV containing as few as 24, 23, 22, 21, 20, 19, 18, 17, 16, 15, 14, 13, 12, 11, or even 10 amino acid residues that substantially retain the overall characteristics and tissue protective properties of the isolated peptides and peptide analogs of structural Formula IV.

Due to the surmised importance of the spatially compact charge configuration at the internal residues of the isolated peptides and peptide analogs of structural Formula IV, in certain embodiments of the invention, residues comprising the polar, negatively and positively charged, and immediately adjacent amino acids are not deleted. Thus, in certain embodiments, residues $X_{11}$, $X_{12}$, $X_{13}$, $X_{14}$, and $X_{is}$ are not deleted.

The isolated peptides and peptide analogs of Formula IV can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 26, 27, 28, or 29 amino acid residues and are considered to be within the scope of the present invention. Preferably, such extended peptides will substantially retain the tissue protective properties of the peptide analogs of Formula IV.

Certain amino acid residues in the core peptides and peptide analogs of Formula IV can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula IV wherein at least one and up to eight amino acid residues in the formula are conservatively substituted with another amino acid residue. In certain embodiments, seven, six, five, four, three, two, or one amino acid is conservatively substituted.

In specific embodiments, the isolated peptides and peptide analogs are selected from the group of peptides set forth below:

```
Peptide M
                                        (SEQ ID NO: 32)
APPRLICDSRVLERYLLEAKE;
and Peptide N
                                        (SEQ ID NO: 33)
HCSLNENITVPDTKVNFYAWKRMEV.
```

One of ordinary skill in the art will recognize that it is the above noted structural motifs A and B that is important to the current invention. Thus one of ordinary skill in the art would recognize that the isolated peptide may have less than 90%, less than 85%, less than 80%, less than 75%, less than 70%, less than 65%, less than 60%, less than 55%, less than 50%, less than 45%, less than 40%, less than 35%, less than 30%, or less than 20 percent sequence identity with any portion of the amino acid sequence of mature human EPO set forth in SEQ ID NO:1, wherein said portion of EPO contains the same number of amino acid residues as said peptide.

Applicants further propose that the tissue protective activity of structural motifs A and B is due to an appropriate, spatially compact charge configuration generated by the motifs. The proximity of these charges may occur via the linear structure imposed by peptide bonding i.e., the structure may be formed by consecutive amino acids in a polypeptide chain, or alternatively, proximity can also occur via a spatial relationship between different parts of the EPO molecule (or other related Type 1 cytokine molecules) imparted by the protein's secondary and/or tertiary structure, i.e., three dimensional structure. Not wishing to be bound to any specific theory, Applicants believe that, in general, this requirement dictates that a tissue protective peptide will have a distinct tertiary structure (e.g., helices or pleated sheets) that provides for the required spatial location of the pair of charged amino acids (i. e., the two negatively charged amino acids and/or the 'positively and negatively charged amino acid). A simple exception is a linear peptide wherein the amino acid pair is immediately adjacent to each other, with the required rigidity imparted by the peptide backbone. Accordingly, the structural motif A, is encompassed by a linear sequence of amino acid residues, e.g., H1-N1-N1-H2 (SEQ ID NO:6), or by a linear sequence of amino acid residues wherein N1 and N2 are separated by 1, 2, 3, 4, 5, 6, or more intervening residues, e.g., H-N-X-X-X-X-N-H (SEQ ID NO: 11).

Not wishing to be bound by any particular theory, Applicants believe that for tissue protection, the pair of charged amino acids in the peptide must be spatially oriented such that the carbamyl carbons are about 3 angstroms (Å) to about 5 Å apart, preferably, about 4 Å to about 5 Å apart, and more preferably about 4.4 Å to about 4.8 Å apart. This can be accomplished in a number of ways, for example, by adjacent charged amino acids in a simple linear peptide or for peptides that can form an alpha helix, charged amino acids separated by an intervening amino acid residue. It is to be noted that tertiary structure (e.g., an alpha helix in amphipathic peptides) can also be imparted when the peptide is within a specific microenvironment, such as at the extracellular-cell surface membrane interface (see, Segrest, 1990, *Proteins* 8:103-117, hereby incorporated by reference in its entirety).

Further, tissue protective activity is predicted for peptides that contain pairs of charged amino acids such that the charged side-chains (either positive and negative or two negatives) be confined spatially to within about 6.5 Å to about 9 Å of each other. This can be provided for in an alpha helix by the charged pair being separated by one or two amino acids, which will provide for the charges to be more or less on the same side of the helix with the required about 6.5 Å to about 9 Å separation. One skilled in the art can devise a tertiary structure for the peptide that is generally required to obtain the appropriate three dimensional location of the charged amino acids, as well as the design of small molecules to mimic the charge separation within the peptide.

The spatial distances between the carbamyl carbons of any two amino acids or between the side chains of any two amino acids can be deduced by any method known in the art or described herein. For example, where the three-dimensional structure of the protein is known, the charge separation of two side chains or the spatial distance between two carbamyl carbons within a portion of interest of said protein can be calculated based on the published, or otherwise art-accepted, three-dimensional coordinates of the amino acid residues in said portion of interest. Where the three-dimensional structure of the protein and, therefore, the portion of interest is unknown, or wherein a fully synthetic peptide is constructed based on the teachings herein, whose three dimensional structure is unknown, the charge separation of two side chains or the spatial distance between two carbamyl carbons within said peptide can be estimated using the three-dimensional structure predicted by protein modeling software as is known in the art. Non-limiting examples of such software are MOE™ by Chemical Computing Group (Quebec, Canada) and Modeler by Accelrys (San Diego, Calif.). Similarly such predictive software, available from the above-noted companies as well, is also known in the art for the design of small molecules as and, accordingly, one of ordinary skill in the art, based upon the teachings herein, would be able to make small molecules that emulate the disclosed structural motifs.

c. Structural Motif C.

Another structural motif exhibited by peptides useful for the prevention, treatment, amelioration and management of a disease or disorder associated with tissue damage or damage, effects or symptoms resulting therefrom of the current invention is:

$X_1-X_2-X_3-X_4-X_5-X_6$ (SEQ ID NO: 34)

wherein $X_1$ is a charged amino acid residue, $X_6$ is a hydrophobic amino acid residue or A, and $X_2$, $X_3$, $X_4$ and $X_5$ is any amino acid residue.

Beyond the presence of the charged residue in position $X_1$ of the motif, preferably the negatively charged residue, and a hydrophobic amino acid residues in position $X_6$, preferably Leu (L), Val (V) or Tyr (Y), the sequence may further comprise i) a Ser (S) in position $X_2$ and/or ii) a hydrophobic residue in position $X_2$ and/or hydrophobic residue in position $X_3$ of the motif. Examples of such preferred motifs may be the sequences (i) R-S-$X_3$-$X_4$-$X_5$-L (SEQ ID NO:35), and (ii) R-V-$X_3$-$X_4$-$X_5$-A (SEQ ID NO:36), R-V-L-$X_4$-$X_5$-Y (SEQ ID NO:37), K-A-V-$X_4$-$X_5$-L (SEQ ID NO:38), R-$X_2$-L-$X_4$-$X_5$-L (SEQ ID NO:39), or R-S-L-$X_4$-$X_5$-L (SEQ ID NO:40). Yet, Ser (S) or Thr (T) is in some cases preferred in position $X_4$ independently of the presence of a hydrophobic residue in position $X_2$ and/or $X_3$.

A group of peptides useful in the prevention, treatment, amelioration, or management of a disease or disorder associated with tissue damage or damages, effects or symptoms resulting therefrom that exhibit Structural Motif C are:

```
Peptide O
                                    (SEQ ID NO: 41)
DSRVLERYLLEAKE;

Peptide P
                                    (SEQ ID NO: 42)
NENITVPDTKVNFYAWKR;

Peptide Q
                                    (SEQ ID NO: 43)
QLHVDKAVSGLRSLTTLLRA;
and Peptide R
                                    (SEQ ID NO: 44)
RVYSNFLRGKLKLYTGEA.
``` d. Structural Motif D.

A further motif for peptides useful in the prevention, treatment, amelioration, or management of a disease or disorder associated with tissue damage or damage, effects or symptoms resulting therefrom, is based on a neurotrophic peptide consensus sequence found in a number of neurotrophic and hematopoietic cytokines which will stimulate both neurite outgrowth and mimic the activity of prosaposin. This consensus sequence is derived from a comparison of the active 22-mer peptide derived from saposin C has the amino acid sequence set forth in SEQ ID NO:45 (CE-FLVKEVTKLIDNNKTEKEIL) and a 20-mer CNTF peptide with the amino acid sequence set forth in SEQ ID NO:46 (YVKHQGLNKNINLDSVDGVP) with various cytokines and growth factors revealed sequence similarity to EPO.

The consensus sequence is:

$A(X)_nN(X)_oN(X)_pB(X)_qC$, (SEQ ID NO: 47)

wherein N is Asn (N), A is a Leu (L) or Ile (I), X is independently any amino acid, n is 2-3, o is 0-1, p is 1-7, B is one or more charged amino acids (Asp (D), Lys (K), Glu (E), or Arg (R)), q is 4-7, and C is one or more hydrophobic amino acids (Ala (A), Leu (L), Ile (I) or Val (V), wherein C is 6-10 amino acids from the second asparagine residue. An example of a peptide exhibiting Structural Motif D is Peptide U: AEHCSLNENITVPDTKV (SEQ ID NO: 48) derived from the EPO AB-Loop. A further sequence in accordance with Structural Motif D is LIRX$_1$NNX$_2$TX$_3$X$_4$X$_3$X$_1$X$_1$ (SEQ ID NO: 308) wherein $X_1$ is any amino acid, $X_2$ is any amino acid but not Leu (L) or Arg (R), $X_3$ is a charged amino acid, and $X_4$ when present is a charged amino acid.

e. Structural Motif E.

Further, peptides comprising a core amino acid sequence of $X_3$-$X_4$-$X_5$-G-P-$X_6$-T-W-$X_7$$X_8$ (SEQ ID NO:49) wherein $X_3$ can be Cys (C), Glu (E), Ala (A), α-amino-γ-bromobutyric acid, or Hoc, where Hoc is homocysteine; $X_4$ can be Arg (R), His (H), Tyr (Y), Leu (L), or Trp (W), or $X_4$ is a bond; $X_5$ can be Met (M), Phe (F), or Ile (I); $X_6$ is independently anyone of the 20 genetically coded L-amino acids or the stereoisomeric D amino acids; $X_7$ can be Asp (D), Glu (E), Ile (I), Leu (L), or Val (V); and $X_8$ can be Cys (C), Lys (K), Ala (A), α-amino-γ-bromobutyric acid, or Hoc, where Hoc is homocysteine, provided that either $X_3$ or $X_8$ is Cys (C) or Hoc are useful in the prevention, treatment, amelioration, or management of a disease or disorder associated with tissue damage or damage, effects or symptoms resulting therefrom in accordance with the current invention. A variation of the motif in which the monomeric peptide unit of the dimer or multimer comprises a core sequence YX$_2$X$_3$X$_4$X$_5$GPX$_6$TWX$_7$X$_8$ (SEQ ID NO:50) wherein each $X_2$ and $X_6$ is independently selected from the 20 genetically coded L-amino acids; $X_3$ can be Cys (C), Glu (E), Ala (A), α-amino-γ-bromobutyric acid, or Hoc, where Hoc is homocysteine; $X_4$ can be Arg (R), His (H), Tyr (Y), Leu (L), or Trp (W), or $X_4$ is a bond; $X_5$ can be Met (M), Phe (F), or Ile (I); $X_7$ can be Asp (D), Glu (E), Ile (I), Leu (L), or Val (V); and $X_8$ can be Cys (C), Lys (K), Ala (A), α-amino-γ-bromobutyric acid, or Hoc, where Hoc is homocysteine. More preferably, either $X_3$ or $X_8$ is Cys (C) or Hoc. A further variation of the motif is disclosed in which the monomeric peptide unit of the dimer or multimer comprises a core peptide sequence of amino acids YX$_2$X$_3$X$_4$X$_5$GPX$_6$TWX$_7$X$_8$ (SEQ ID NO:51), wherein each of $X_2$ and $X_6$ is independently anyone of the 20 genetically coded L-amino acids; $X_3$ is Cys (C); and $X_8$ is Cys (C). Another variation of the motif is disclosed wherein the monomeric peptide unit of the dimer comprises a core sequence of amino acids $X_1$YX$_2$X$_3$X$_4$X$_5$GPX$_6$TWX$_7$X$_8$X$_9$X$_{10}$X$_{11}$ (SEQ ID NO:52), wherein each of $X_1$, $X_2$, $X_6$, $X_9$, $X_{10}$, and $X_{11}$ is independently selected from the 20 genetically coded L-amino acids. Particularly, $X_3$ can be Cys (C), Glu (E), Ala (A); $X_4$ can be Arg (R), His (H), or Tyr (Y), or $X_4$ is a bond; $X_5$ can be Met (M), Phe (F), or Ile (I); $X_7$ can be Asp (D) or Val (V); and Xg can be Cys (C), Lys (K), or Ala (A). In another variation of the motif, both X3 and Xg are Cys (C) and thus, the monomeric peptide unit of the dimer comprises a core sequence of amino acids $X_1$YX$_2$CX$_4$X$_5$GPX$_6$TWX$_7$CX$_9$X$_{10}$X$_{11}$ (SEQ ID NO:53). The motif may also be a core sequence of amino acids $X_1$YX$_2$CX$_4$X$_5$GPX$_6$TWX$_7$CX$_9$X$_{10}$X$_{11}$ (SEQ ID NO:54), where $X_4$ can be Arg (R) or His (H); Xs can be Phe (F) or Met (M); $X_6$ can be Ile (I), Leu (L), Thr (T), Met (M), or Val (V); $X_7$ is Asp (D) or Val (V); $X_9$ can be Gly (G), Lys (K), Leu (L), Gln (Q), Arg (R), Ser (S), or Thr (T); and XIO can be Ala (A), Gly (G), Pro (P), Arg (R), or Tyr (Y). Or the motif may comprise a core sequence of amino acids $X_1YX_2CX_4X_5GPX_6TWX_7CX_9X_{10}X_{11}$ (SEQ ID NO:55), where $X_1$ can be Asp (D), Glu (E), Leu (L), Asn (N), Ser (S), Thr (T), or Val (V); $X_2$ can be Ala (A), His (H), Lys (K), Leu (L), Met (M), Ser (S), or Thr (T); $X_4$ is Arg (R) or His (H); $X_9$ can be Lys (K), Arg (R), Ser (S), or Thr (T); and XIO is Pro (P). Alternatively, the motif will comprise a core sequence of amino acids $X_1YX_2CX_4X_5GPX_6TWX_7CX_9X_{10}X_{11}$ (SEQ ID NO:56), where $X_1$ can be Asp (D), Glu (E), Leu (L), Asn (N), Ser (S), Thr (T), or Val (V); $X_2$ can be Ala (A), His (H), Lys (K), Leu (L), Met (M), Ser (S), or Thr (T); $X_4$ is Arg (R) or His (H); $X_9$ can be Lys (K), Arg (R), Ser (S), or Thr (T); and $X_{10}$ is Pro (P).

Particular peptides in accordance with the Structural Motif E that are useful in the prevention, treatment, amelioration, and management of a disease or disorder associated with tissue damage or damages, effects or symptoms resulting therefrom are:

```
Peptide S
                                          (SEQ ID NO: 57)
GGLYLCRFGPVTWDCGYKGG Peptide T
                                          (SEQ ID NO: 58)
GGTYSCHFGPLTWVCKPQGG Peptide U
                                          (SEQ ID NO: 59)
GGDYHCRMGPLTWVCKPLGG Peptide V
                                          (SEQ ID NO: 60)
VGNYMCHFGPITWVCRPGGG Peptide W
                                          (SEQ ID NO: 61)
GGVYACRMGPITWVCSPLGG Peptide X
                                          (SEQ ID NO: 62)
VGNYMAHMGPITWVCRPGG Peptide Y
                                          (SEQ ID NO: 63)
GGTYSCHFGPLTWVCKPQ Peptide Z
                                          (SEQ ID NO: 64)
GGLYACHMGPMTWVCQPLRG Peptide AA
                                          (SEQ ID NO: 65)
TIAQYICYMGPETWECRPSPKA Peptide AB
                                          (SEQ ID NO: 66)
YSCHFGPLTWVCK Peptide AC
                                          (SEQ ID NO: 67)
YCHFGPLTWVC Peptide AD
                                          (SEQ ID NO: 68)
SCHFGPLTWVCK Peptide AE
                                          (SEQ ID NO: 69)
GGTASCHFGPLTWVCKPQGG Peptide AF
                                          (SEQ ID NO: 70)
GGTYSCHFAPLTWVCKPQGG Peptide AG
                                          (SEQ ID NO: 71)
GGTYSCFGPLTWVCKPQGG Peptide AH
                                          (SEQ ID NO: 72)
TYSCHFGPLTWVCKPQGG Peptide AI
                                          (SEQ ID NO: 73)
TYSCHFGPLTWVCKPQ Peptide AJ
                                          (SEQ ID NO: 74)
YSCHFGPLTWVCKP Peptide AK
                                          (SEQ ID NO: 75)
YSCHFGPLTWVC Peptide AL
                                          (SEQ ID NO: 76)
YSCHFGALTWVCK Peptide AM
                                          (SEQ ID NO: 77)
GGCRIGPITWVCGG Peptide AN
                                          (SEQ ID NO: 78)
HFGPLTWV Peptide AO
                                          (SEQ ID NO: 79)
GGTTSCHFGPLTWVCKPQGG Peptide AP
                                          (SEQ ID NO: 80)
GGTFSCHFGPLTWVCKPQGG Peptide AQ
                                          (SEQ ID NO: 81)
GGTYSCHFGALTWVCKPQGG Peptide AR
                                          (SEQ ID NO: 82)
GGTYSCHFGPATWVCKPQGG Peptide AS
                                          (SEQ ID NO: 83)
GGTYSCHFGPLAWVCKPQGG Peptide AT
                                          (SEQ ID NO: 84)
GGTYSCHFGPLTAVCKPQGG Peptide AU
                                          (SEQ ID NO: 85)
GGTYSCHFGPLTFVCKPQGG Peptide AV
                                          (SEQ ID NO: 86)
GGTYSCHFGPLTWVCKAQGG Peptide AW
                                          (SEQ ID NO: 87)
GGTXSCHFGPLTWVCKPQGG Peptide AX
                                          (SEQ ID NO: 88)
GGTXSCHFGPLTWVCKPQGG Peptide AY
                                          (SEQ ID NO: 89)
GGTXSCHFGPLTWVCKPQGG;
(X = p-NH2-Phe)
```

```
Peptide AZ
                                          (SEQ ID NO: 90)
GGTXSCHFGPLTWVCKPQGG;
(X = p-F-Phe)

Peptide BA
                                          (SEQ ID NO: 91)
GGTXSCHFGPLTWVCKPQGG;
(X = p-I-Phe)

Peptide BB
                                          (SEQ ID NO: 92)
GGTXSCHFGPLTWVCKPQGG;
(X = 3,5-dibromo-Tyr)

Peptide BC
                                          (SEQ ID NO: 93)
Ac-GGTYSCHFGPLTWVCKPQGG Peptide BD
                                          (SEQ ID NO: 94)
GGLYACHMGPMTWVCQPLGG Peptide BE
                                          (SEQ ID NO: 95)
LGRKYSCHFGPLTWVCQPAKKD;
and Peptide BF
                                          (SEQ ID NO: 96)
GGTYSEHFGPLTWVKKPQGG.
``` f. Structural Motif F.

Further peptides derived from the AB loop of EPO are contemplated as well. This AB loop peptide may further be stabilized by chemically adding a small bicyclic molecule to at least one of the N-terminal end or the C-terminal end of the peptide's amino acid sequence.

Particular peptides in accordance with the Structural Motif F that are useful in the prevention, treatment, amelioration, and management of a disease or disorder associated with tissue damage or damage, effects or symptoms resulting therefrom are:

```
Peptide BG
                                          (SEQ ID NO: 97)
D-biotin-AEHCSLNENITVPDTKV;

Peptide BH
                                          (SEQ ID NO: 98)
D-Biotin-AEHCSLNENITVP;

Peptide BI
                                          (SEQ ID NO: 99)
AEHCSLNENITVPDTKK-biotin;
and Peptide BJ
                                          (SEQ ID NO: 100)
AEHCSLNENITVP-D-biotin.
```

Moreover, the peptides may be stabilized by a disulfide bond formed between a sulfhydryl group of a first amino acid residue and a sulfhydryl group of a second amino acid residue along the peptide sequence. A particular embodiment of the peptide has at least 6 amino acids having the peptide sequence XAEHYS (SEQ ID NO: 101), wherein X is a first amino acid residue containing a sulfhydryl group and Y is a second amino acid residue containing a sulfhydryl group, and wherein the sulfhydryl group of the first amino acid residue is at an appropriate distance from the sulfhydryl group of the second amino acid residue to form the disulfide bond with the sulfhydryl group of the second amino acid residue within the peptide sequence, thus stabilizing the peptide (Formula I).

Particular peptides in accordance with the Structural Motif F, Formula I, that are useful in the prevention, treatment, amelioration, and management of a disease or disorder associated with tissue damage or damage, effects or symptoms resulting therefrom are:

```
Peptide BK
                                          (SEQ ID NO: 102)
TTGCAEHCSLNENITVPDTK;

Peptide BL
                                          (SEQ ID NO; 103)
CAEHCSLNENITVPDTKV;

Peptide BM
                                          (SEQ ID NO: 104)
CAEHCS;

Peptide BN
                                          (SEQ ID NO: 105)
GCAEHCSL;

Peptide BO
                                          (SEQ ID NO: 106)
GCAEHCSLNENITVPDTKV;

Peptide BP
                                          (SEQ ID NO: 107)
CAEHCSLNENITVP;

Peptide BQ
                                          (SEQ ID NO: 108)
TTGCAEHCSLNENITVPDTKV;

Peptide BR
                                          (SEQ ID NO: 109)
TTGCAEHCSLNENITVP;
and Peptide BS
                                          (SEQ ID NO: 110)
CAEHCSLNKNINLDSVDGVP
```

In another embodiment, the disulfide bond-stabilized isolated EPO-derived peptide is further stabilized by chemically adding a small bicyclic molecule to at least one of the N-terminal end or the C-terminal end of the peptide's amino acid sequence.

The peptide may also exhibit the following motif of at least 7 amino acids having the peptide sequence XAEHYS (SEQ ID NO:111), wherein X is a first amino acid residue containing a sulfhydryl group and Y is a second amino acid residue containing a sulfhydryl group, and wherein the sulfhydryl group of the first amino acid residue is at an appropriate distance from the sulfhydryl group of the second amino acid residue to form the disulfide bond with the sulfhydryl group of the second amino acid residue within the peptide sequence, thus stabilizing the peptide (Formula II).

Particular peptides in accordance with the Structural Motif F, Formula II, that are useful in the prevention, treatment, amelioration, and management of a disease or disorder associated with tissue damage or damage, effects or symptoms resulting therefrom are:

```
Peptide BT
                                          (SEQ ID NO: 112)
AEHCSLMENNLRRPNL;
and Peptide BU
                                          (SEQ ID NO: 113)
D-Biotin-AEHCSLMENNLRRPNL.
```

G. Other EPO Derived EPO Peptides.

In addition to the above-noted EPO peptides and EPO derived motifs, EPO peptides, fragments or mimetics disclosed in U.S. Pat. Nos. 5,106,954, 5,952,293, 6,004,758, 6,346,390, 6,932,968, 5,835,382, 7,037,902, 7,084,245, and 7,272,508; U.S. Patent Application No. 20050191301; WO2005/021579; Skelton et al. "Amino Acid Determinants of Beta-hairpin Confirmation in Erythropoietin Receptor Agonist Peptides Derived From A Phage Display Library," Journal of Molecular Biology Vol. 316, Issue 8, 2002, pages 1111-1125; Livnah et al., Functional Mimicry of a Protein Hormone by a Peptide Agonist: the EPO Receptor Complex at 2 Å, Science 26, July 1996 vol. 273, no. 5274, pp. 464-471; Johnson and Joliffe, "Erythropoietin Mimetic Peptides and the Future," Nephrol. Dial. Transplant (2000) 15:1274-1277, Wrighton et al. (1996) Science 273: 458-463; Johnson et al. (1998) Biochemistry, 37: 3699-3710 may also be useful in the methods of modulating the effects of body's response to a disease or disorder of the current invention.

6.2 Type 1 Cytokine Fragments.

The above motifs are not only useful in identifying EPO derived peptides or EPO agonist fragments but fragments of Type-1 cytokines that also exhibit the ability to inhibit or retard a disease or disorder associated with tissue damage or damage, effects or symptoms resulting therefrom and are therefore therapeutically effective at preventing, treating, ameliorating or maintaining a disease or disorder associated with tissue damage or damage, effects or symptoms resulting therefrom. The Type-1 cytokine family includes, but is not limited to, interleukin (IL)-2, IL-3, IL-4, IL-5, IL-6, IL-7, IL-9, IL-10, or IL-11, granulocyte macrophage-colony stimulating factor (GM-CSF), leptin, granulocyte colony stimulating factor (G-CSF), leukemia inhibiting factor (LIF), ciliary neurotrophic factor (CNTF), thrombopoietin (TPO), growth hormone, macrophage colony stimulating factor (M-CSF), erythropoietin (EPO) and prolactin.

Consideration of the secondary structure of EPO provides guidance for the preparation of a candidate peptide via the spatial arrangement of amino acids derived from homologous amino acids located within homologous secondary structures within other Type-1 cytokine receptor ligands: e.g., GM-CSF and IL-3 (Kannan, 2000, Neuroimmunomod. 8:132-141, hereby incorporated by reference in its entirety), among others, have been shown to possess potent neurotrophic and neuroprotective activities, due in large part, the Applicants believe, by stimulating a tissue protective receptor. For example, considering helix B of these type I cytokines: Homologous amino acids in thrombopoietin (TPO; Protein Data Bank (PDB) accession 1V7M) comprise D62, G65, T68, L69, E72, A76 and Q80, where these amino acids are spatially adjacent to one another in a linear arrangement; homologous amino acids in leukemia inhibitory factor (LIF; PDB accession 1EMR) comprise E61, R64, Y68, S72, N75, and D79; homologous amino acids in ciliary neurotrophic factor (CNTF; PDB accession 1CNT) comprise E71, E75. These all are examples of Structural Motif A described above wherein the underlined amino acids are negatively charged.

In certain embodiments of Structural Motif A disclosed below as Formulas V-VI, isolated peptides and peptide analogs may not include Peptide BV, WEHVNAIQEARRLL (SEQ ID NO:114); Peptide BW, LSKLLRDSHVLH (SEQ ID NO: 115); Peptide BX, KIRSDLTALTESYVKH (SEQ ID NO: 116), Peptide BY, GTEKAKLVELYRIVVYL (SEQ ID NO: 117) or Peptide BZ, SIMIDEIIHHLKRPP-NPL (SEQ ID NO: 118).

In an embodiment of Structural Motif A, Type-1 cytokine derived peptides and peptide analogues have the structural Formula (V) (SEQ ID NO:119):

$$X_1-X_2-X_3-X_4-X_5-X_6-X_7-X_8-X_9-X_{10}-X_{11}-X_{12}-X_{13}-X_{14}-$$
$$X_{15}-X_{16}-X_{17}-X_{18}-X_{19}$$

wherein:
$X_1$ is Trp (W), Val (V), Ala (A), Ile (I), Pro (P), Leu (L), Ser (S), Asp (D), or Thr (T);
$X_2$ is any amino acid;
$X_3$ is any amino acid;
$X_4$ is any amino acid;
$X_5$ is any amino acid;
$X_6$ is any amino acid;
$X_7$ is any amino acid;
$X_8$ is Ile (I), Phe (F), Leu (L), Val (V), Pro (P), Tyr (Y), or Gly (G);
$X_9$ is a negatively charged amino acid;
$X_{10}$ is a negatively charged amino acid;
$X_{11}$ is Ile (I), Leu (L), Ala (A), Gly (G), Phe (F), Val (V), or Pro (P);
$X_{12}$ is Ile (I), Met (M), Tyr (Y), Ser (S), Val (V), Phe (F), Lys (K), Leu (L), Glu (E), or Asp (D);
$X_{13}$ is any amino acid;
$X_{14}$ is His (H), Leu (L), Pro (P), Thr (T), Arg (R), Cys (C), Ile (I), Tyr (Y), Gln (Q), or Ala (A);
$X_{15}$ is Leu (L), Lys (K), Thr (T), Val (V), Phe (F), Ala (A), or Gln (Q);
$X_{16}$ is Lys (K), Glu (E), Met (M), Gly (G), Asn (N), Gln (Q), Thr (T), or Val (V);
$X_{17}$ is any amino acid;
$X_{18}$ is Pro (P), Lys (K), Arg (R), Ile (I), Asn (N), Ser (S), Gln (Q), or Phe (F);
$X_{19}$ is Pro (P), Ile (I), Tyr (Y), Leu (L), Phe (F), Ser (S), Ala (A), Asp (D), Asn (N), or Lys (K).

In certain embodiments, the isolated peptides and peptide analogs can contain fewer than 19 amino acid residues. Indeed, truncated or internally deleted forms of structural formula V containing as few as 18, 17, 16, 15, 14, 13, 12, 11, or even 10 amino acid residues that substantially retain the overall characteristics and tissue protective properties of the isolated peptides and peptide analogs of structural Formula V.

Due to the surmised importance of the spatially compact charge configuration at the internal residues of the isolated peptides and peptide analogs of Formula (V) in tissue protective activity, in certain embodiments of the invention, residues comprising the polar, negatively and positively charged, and immediately adjacent amino acids are not deleted. Thus, in certain embodiments, residues $X_8$, $X_9$, $X_{10}$, and $X_{11}$ are not deleted.

The isolated peptides and peptide analogs of Formula V can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 20, 21, 22, 23, 24, 25, 26, 27, 28, or 29 amino acid residues and are considered to be within the scope of the present invention. Preferably, such extended peptides will substantially retain the tissue protective properties of the peptide analogs of Formula V.

Certain amino acid residues in the core peptides and peptide analogs of Formula V can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula V wherein at least one and up to eight amino acid residues in the formula are conservatively substituted with another amino acid residue. In certain embodiments, seven, six, five, four, three, two, or one amino acid is conservatively substituted.

In specific embodiments, the isolated peptides and peptide analogs of Formula V are selected from the group of peptides set forth below:

```
Peptide CA
                                      (SEQ ID NO: 120)
KTSWVNCSNMIDEIITHLKQPPLP;

Peptide CB
                                      (SEQ ID NO: 121)
LLQVAAFAYQIEELMILLEYKIPR;

Peptide CC
                                      (SEQ ID NO: 122)
HQLAFDTYQEFEEAYIPKEQKYSF;

Peptide CD
                                      (SEQ ID NO: 123)
DSNVYDLLKDLEEGIQTLMGRLED;

Peptide CE
                                      (SEQ ID NO: 124)
EEGIQTLMGRLEDGSPRTGQIFKQ;

Peptide CF
                                      (SEQ ID NO: 125)
SNVDKETGEDG;

Peptide CG
                                      (SEQ ID NO: 126)
YSIIDKLVNIVDDLVECVKENSSK;

Peptide CH
                                      (SEQ ID NO: 127)
FKSPEPRLFTPEEFFRIFNRSIDA;

Peptide CI
                                      (SEQ ID NO: 128)
LDNLLLKESLLEDFKGYLGCQALS;

Peptide CJ
                                      (SEQ ID NO: 129)
QALSEMIQFYLEEVMPQAENQDPD;

Peptide CK
                                      (SEQ ID NO: 130)
LQCLEEELKPLEEVLNLAQSKNFH;

Peptide CL
                                      (SEQ ID NO: 131)
AQDLERSGLNIEDLEKLQMARPNI;

Peptide CM
                                      (SEQ ID NO: 132)
VPPSTALRELIEELVNITQNQKAP;

Peptide CN
                                      (SEQ ID NO: 133)
IFLDQNMLAVIDELMQALNFNSET;

Peptide CO
                                      (SEQ ID NO: 134)
NSETVPQKSSLEEPDFYKTKIKLC;
```

```
-continued
Peptide CP
                                      (SEQ ID NO: 135)
FMMALCLSSIYEDLKMYQVEFKTM;
and Peptide CQ
                                      (SEQ ID NO: 136)
CLKDRMNFDIPEEIKQLQQFQKED.
```

In another embodiment of Structural Motif A, the isolated peptides and peptide analogs based on Type-1 cytokines and useful in the method of the current invention have the structural Formula VI (SEQ ID NO:137):

$$X_1 - X_2 - (Z)_n - X_3 - X_4$$

wherein:

$X_1$ is Phe (F), Val (V), Ala (A), Gly (G), Pro (P), Leu (L), Tyr (Y), Ile (I), Cys (C) or Met (M);

$X_2$ is a negatively charged amino acid;

$(Z)_n$ is an amino acid, wherein $n$ is 1-5;

$X_3$ is a negatively charged amino acid;

$X_4$ is Pro (P), Met (M), Val (V), Ile (I), Phe (F), Gly (G), Leu (L), Ala (A), Tyr (Y), and Trp (W).

In certain embodiments, the isolated peptides and peptide analogs can contain fewer than 9 amino acid residues. Indeed, truncated or internally deleted forms of structural formula VI containing as few as 8, 7, 6, or even 5 amino acid residues that substantially retain the overall characteristics and tissue protective properties of the isolated peptides and peptide analogs of structural formula VI.

Due to the surmised importance of the spatially compact charge configuration at the internal residues of the isolated peptides and peptide analogs of Formula VI, in certain embodiments of the invention, residues comprising the negatively and positively charged and immediately adjacent amino acids are not deleted. Thus, in certain embodiments, residues $X_1$, $X_2$, $X_3$, and $X_4$ are not deleted.

The isolated peptides and peptide analogs of Formula VI can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 10, 11, 12, 13, 14, 15, 16, 17, 18, 19, 20, 21, 22, 23, 24, 25, 26, 27, 28, or 29 amino acid residues and are considered to be within the scope of the present invention. Preferably, such extended peptides will substantially retain the tissue protective properties of the peptide analogs of Formula VI.

Certain amino acid residues in the core peptides and peptide analogs of Formula VI can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula VI wherein at least one and up to five amino acid residues in the formula are conservatively substituted with another amino acid residue. In certain embodiments, four, three, two or one amino acids are conservatively substituted.

In specific embodiments, the isolated peptides and peptide analogs of Formula VI are selected from the group of peptides set forth below:

Peptide CR
(SEQ ID NO: 138)
NETVEVISEMFDLQEPTCLQTRLELY;

Peptide CS
(SEQ ID NO: 139)
NLKDFLLVIPFDCWEPVQE;

Peptide CT
(SEQ ID NO: 140)
RDTAAEMNETVEVISEMFDLQEPTCLQ;

Peptide CU
(SEQ ID NO: 141)
RLLNLSRDTAAEMNETVEVISEMFDLQEP;

Peptide CV
(SEQ ID NO: 142)
LPLLDFNNLNGEDQDILMENNLRRPN;

Peptide CW
(SEQ ID NO: 143)
PTRHPIHIKDGDWNEFRRKLTFYLKT;

Peptide CX
(SEQ ID NO: 144)
HVGHVDVTYGPDTSGKDVFQKKKLGCGL;

Peptide CY
(SEQ ID NO: 145)
KHQGLNKNINLDSADGMPVASTDQWS;

Peptide CZ
(SEQ ID NO: 146)
WSELTAEQELQRVAREVH;

Peptide DA
(SEQ ID NO: 147)
LRAHRLHQLAFDTYQEFEEAYIPKEQK;

Peptide DB
(SEQ ID NO: 148)
LVYGASDSNVYDLLKDLEEGIQTLMGR;

Peptide DC
(SEQ ID NO: 149)
SNVDKETGEDG;

Peptide DD
(SEQ ID NO: 150)
QEERRRVNGFLDYLQEFLGVMNTEWII;

Peptide DE
(SEQ ID NO: 151)
EEFFRIFNRSIDAFKDFVVASETSDCV;

Peptide DF
(SEQ ID NO: 152)
SRNVIQISNDLENLRDLLHVLAFSKSC;

Peptide DG
(SEQ ID NO: 153)
YSTVSGDWQLDL;

Peptide DH
(SEQ ID NO: 154)
QFYLEEVMPQAENQDPDIKAHVNSLG;

Peptide DI
(SEQ ID NO: 155)
QFYLEEVMPQAENQDPDIKAHVNSLGEN;

Peptide DJ
(SEQ ID NO: 156)
KATELKHLQCLEEELKPLEEVLNLA;

Peptide DK
(SEQ ID NO: 157)
SSSTKKTQLQLEHLLLDLQMILNGINNY;

Peptide DL
(SEQ ID NO: 158)
FKDDQSIQKSVETIKEDMNVKFFNSNKK;

Peptide DM
(SEQ ID NO: 159)
VEIEEQTKRLLEGMELIVSQVHPETK;

Peptide DN
(SEQ ID NO: 160)
GMELIVSQVHPETKENEIYPVWSGLPSL;

Peptide DO
(SEQ ID NO: 161)
PEAIVEERELSQV;

Peptide DP
(SEQ ID NO: 162)
HKCDITLQEIIKTLNSLTEQ;

Peptide DQ
(SEQ ID NO: 163)
AENNLNLPKMAEKDGCFQSGFNEET;

Peptide DR
(SEQ ID NO: 164)
TCLVKIITGLLEFEVYLEYLQNRFE;

Peptide DS
(SEQ ID NO: 165)
VPPGEDSKDVAAPHRQPLTS;

Peptide DT
(SEQ ID NO: 166)
RKETCNKSNMCESSKEALAENNLNLPK;

Peptide DU
(SEQ ID NO: 167)
LVKIITGLLEFEVYLEYLQNRFESSEE;

Peptide DV
(SEQ ID NO: 168)
TCLVKIITGLLEFEVYLEYLQNRFESSEE;

Peptide DW
(SEQ ID NO: 169)
IQFLQKKAKNLDAITTPDPTTNASLLTKL;

Peptide DX
(SEQ ID NO: 170)
RNNIYCMAQLLDNSDTAEPTKAGRGASQP;

Peptide DY
(SEQ ID NO: 171)
PLPTPVLLPAVDFSLGEWKTQMEETKAQ;

Peptide DZ
(SEQ ID NO: 172)
DFSLGEWKTQMEETKAQDILGAVTLLLEG;

Peptide EA
(SEQ ID NO: 173)
LEWKTQTDGLEGAAGQ;

Peptide EB
(SEQ ID NO: 174)
TVAGSKMQGLLERVNTEIHFVTKCAFQP;

Peptide EC
(SEQ ID NO: 175)
LEFYPCTSEEIDHEDITKDKTSTVEA;

Peptide ED
(SEQ ID NO: 176)
NSETVPQKSSLEEPDFYKTKIKLCIL;

Peptide EE
(SEQ ID NO: 177)
EDITKDKTSTVEACLPLELTKNESCLNSR;

-continued

Peptide EF
(SEQ ID NO: 178)
TTNDVPHIQCGDGCDPQGLRDNSQFC;

Peptide EG
(SEQ ID NO: 179)
AWSAHPLVGHMDLREEGDEETTNDVPH;

Peptide EH
(SEQ ID NO: 180)
LVGHMDLREEGDEETTNDVPHIQCGDGCD;

Peptide EI
(SEQ ID NO: 181)
LQRIHQGLIFYEKLLGSDIFTGEPSLLPD;

Peptide EJ
(SEQ ID NO: 182)
NHLKTVLEEKLEKEDFTRGKLMSSLH;
and

Peptide EK
(SEQ ID NO: 183)
LEYCLKDRMNFDIPEEIKQLQQFQKED.

Further examples of tissue protective peptides useful in the methods of treatment of the current invention derived from the Type-1 cytokines that exemplify Structural Motif B described herein above, and disclosed within PCT/US2006/031061, include, but are not limited to, GM-CSF helix A fragment, Peptide BV: WEHVNAIQEARRLL (SEQ ID NO:114); TPO helix A fragment, Peptide BW: LSKLLRDSHVLH (SEQ ID NO:115); TPO helix B fragment: E56, K59; CNTF helix A fragment, Peptide BX: K IRSDLTALTESYVKH (SEQ ID NO:116); CNTF helix B fragment: R89, E92. LIF helix B fragment, Peptide BY: G TEKAKLVELYRIVVYL (SEQ ID NO:117); and interleukin 3 (IL-3) helix A fragment, Peptide BZ: SIM IDEIIHHLKRPPNPL (SEQ ID NO: 118).

In certain embodiments of Structural Motif B disclosed below as Formulas VII-X, isolated peptides and peptide analogs may not include Peptide BV, WEHVNAIQEARRLL (SEQ ID NO:114); Peptide BW, LSKLLRDSHVLH (SEQ ID NO: 115); Peptide BX, KIRSDLTALTESYVKH (SEQ ID NO: 116), Peptide BY, GTEKAKLVELYRIVVYL (SEQ ID NO: 117) or Peptide BZ, SIMIDEIIHHLKRPPNPL (SEQ ID NO: 118).

Further Type-1 cytokine derived peptides exhibiting structural motif B that are useful in the current method of preventing, treating, ameliorating and managing a disease or disorder associated with tissue damage or damage, effects or symptoms resulting therefrom are those that exhibit structural Formula VII: (SEQ ID NO: 184)

$$X_1-X_2-X_3-X_4$$

wherein:
$X_1$ is Leu (L), Ile (I), Gly (G), Val (V), Phe (F), Pro (P), or Ala (A);
$X_2$ is a positively charged amino acid;
$X_3$ is a negatively charged amino acid;
$X_4$ is Phe (F), Gly (G), Val (V), Leu (L), Ala (A), or Tyr (Y);
In one embodiment of the invention, Type-I cytokine derived peptides have the structural Formula VII(a): (SEQ ID NO:302)

$$X_1-X_2-X_3-X_4-X_5-X_6$$

wherein:
$X_1$ is Leu (L), Ile (I), Gly (G), Val (V), Phe (F), Pro (P), or Ala (A);
$X_2$ is a positively charged amino acid;
$X_3$ is a negatively charged amino acid;
$X_4$ is Phe (F), Gly (G), Val (V), Leu (L), Ala (A), or Tyr (Y);
$X_5$ is Arg (R), Asp (D), Glu (E), Asn (N), Ser (S), Thr (T), Phe (F), Val (V), or Tyr (Y);
$X_6$ is His (H), Lys (K), Asp (D), Glu (E), Gln (Q), Asn (N), Ser (S), Leu (L), Trp (W), or Phe (F).

In certain embodiments, the isolated peptides and peptide analogs can contain fewer than 5 or even 4 amino acid residues. Indeed, truncated or internally deleted forms of structural Formulas VII or VIIa containing as few as 6 or even 5 amino acid residues that substantially retain the overall characteristics and tissue protective properties of the isolated peptides and peptide analogs.

Due to the surmised importance of the spatially compact charge configuration at the internal residues of the isolated peptides and peptide analogs of structural Formulas VII or VIIa, in certain embodiments of the invention, residues comprising the negatively and positively charged and immediately adjacent amino acids are not deleted. Thus, in certain embodiments, residues $X_1$, $X_2$, $X_3$, and $X_4$ are not deleted.

The isolated peptides and peptide analogs of Formula VII and Formula IIa can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 7, 8, 9, 10, 11, 12, 13, 14, 15, 16, 17, 18, 19, 20, 21, 22, 23, 24, 25, 26, 27, 28, or 29 amino acid residues and are considered to be within the scope of the present invention. Preferably, such extended peptides will substantially retain the tissue protective properties of the peptide analogs of Formula VII or Formula IIa.

Certain amino acid residues in the core peptides and peptide analogs of Formula VII or Formula IIa can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula VII wherein at least one and up to two amino acid residues in the formula are conservatively substituted with another amino acid residue.

In specific embodiments, the isolated peptides and peptide analogs of Formula VII or Formula IIa are selected from the group of peptides set forth below:

Peptide EL
(SEQ ID NO: 185)
IITFESFKENLKDFLLVIPFDCWE;

Peptide EM
(SEQ ID NO: 186)
TAAPTRHPIHIKDGDWNEFRRKLT;

Peptide EN
(SEQ ID NO: 187)
VDVTYGPDTSGKDVFQKKKLGCQL;

Peptide EO
(SEQ ID NO: 188)
SGKDVFQKQGQSVQ;

-continued

Peptide EP (SEQ ID NO: 189)
QELSQWTVRSIHDLRFISSHQTGI;

Peptide EQ (SEQ ID NO: 190)
WSELTAEQELQRVAREVH;

Peptide ER (SEQ ID NO: 191)
GASDSNVYDLLKDLEEGIQTLMGR;

Peptide ES (SEQ ID NO: 192)
GICRNRVTNNVKDVTKLVANLPKD;

Peptide ET (SEQ ID NO: 193)
FRIFNRSIDAFKDFVVASEETSDCV;

Peptide EU (SEQ ID NO: 194)
VIQISNDLENLRDLLHVLAFSKSC;

Peptide EV (SEQ ID NO: 195)
THFPGNLPNMLRDLRDAFSRVKTF;

Peptide EW (SEQ ID NO: 196)
PGNLPNMLRDLRDAFSRVKTFFQM;

Peptide EX (SEQ ID NO: 197)
LAQSKNFHLRPRDLISNINVIVLE;

Peptide EY (SEQ ID NO: 198)
QDPYVKEAENLKKYFNAG;

Peptide EZ (SEQ ID NO: 199)
VTDLNVQRKAIHELIQVMAELSPA;

Peptide FA (SEQ ID NO: 200)
PGGAARCQVTLRDLFDRAVVLSHY;

Peptide FB (SEQ ID NO: 201)
WGLAGLNSCPVKEANQSTLENFLE;

Peptide FC (SEQ ID NO: 202)
DMTTHLILRSFKEFLQSSLRALRQ;

Peptide FD (SEQ ID NO: 203)
GPVPPSTALRELIEELVNITQN;

Peptide FE (SEQ ID NO: 204)
KDLLLHLKKLFREGRFN;

Peptide FF (SEQ ID NO: 205)
RDTKIEVAQFVKDLLLHLKKLFRE;

Peptide FG (SEQ ID NO: 206)
LDQIPGYLNRIHELLNGTRGLFPG;

Peptide FH (SEQ ID NO: 207)
SPISSDFAVKIRELSDYLLQDYPV;
and

Peptide FI (SEQ ID NO: 208)
YYGRILHYLKAKEYSHCAWTIVRV.

In yet another embodiment of the peptides useful in the prevention, treatment, amelioration, or management of a disease or disorder associated with tissue damage or damage, effects or symptoms resulting therefrom, the isolated peptides or peptide analogs derived from Type-1 cytokines and exhibiting Structural Motif B have the structural formula (VIII) (SEQ ID NO:209):

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}$$
$$X_{15}\text{-}X_{16}\text{-}X_{17}\text{-}X_{18}\text{-}X_{19}\text{-}X_{20}\text{-}X_{21}\text{-}X_{22}\text{-}X_{23}\text{-}X_{24}$$

wherein:
$X_1$ is Ala (A), Thr (T), Ser (S), Tyr (Y), Leu (L), Val (V), Ile (I), Phe (F), or Glu (E);
$X_2$ is any amino acid;
$X_3$ is Ser (S), Gln (Q), Asp (D), Leu (L), Glu (E), Cys (C), Asn (N), Arg (R), or Ala (A);
$X_4$ is Pro (P), Gly (G), Gln (Q), Leu (L), Thr (T), Asn (N), Ser (S), Phe (F), or Ile (I);
$X_5$ is any amino acid;
$X_6$ is Pro (P), Ser (S), Cys (C), Val (V), Lys (K), Thr (T), Leu (L), Ile (I), or Gln (Q);
$X_7$ is any amino acid;
$X_8$ is Thr (T), Pro (P), Leu (L), Arg (R), Gly (G), Tyr (Y), Gln (Q), Glu (E), Ile (I) or Ala (A);
$X_9$ is any amino acid;
$X_{10}$ is Pro (P), Asn (N), Glu (E), Asp (D), Thr (T), Leu (L), Ile (I), Gln (Q), Phe (F), or Trp (W);
$X_{11}$ is Trp (W), Leu (L), Ala (A), Met (M), Val (V), Ile (I), Phe (F), or Tyr (Y);
$X_{12}$ is a negatively charged amino acid;
$X_{13}$ is a positively charged amino acid;
$X_{14}$ is Val (V), Leu (L), or Ala (A);
$X_{15}$ is any amino acid;
$X_{16}$ is any amino acid;
$X_{17}$ is any amino acid;
$X_{18}$ is any amino acid;
$X_{19}$ is any amino acid;
$X_{20}$ is any amino acid;
$X_{21}$ Arg (R), Asp (D), Tyr (Y), Val (V), Ile (I), Leu (L), Lys (K), Ser (S), or Thr (T);
$X_{22}$ is any amino acid;
$X_{23}$ is any amino acid;
$X_{24}$ is Leu (L), Pro (P), Phe (F), Arg (R), Tyr (Y), Cys (C), Gly (G), Val (V), or Lys (K).

In certain embodiments, the isolated peptides and peptide analogs can contain fewer than 24 amino acid residues. Indeed, truncated or internally deleted forms of structural Formula VIII containing as few as 23, 22, 21, 20, 19, 18, 17, 16, 15, 14, 13, 12, 11, or even 10 amino acid residues that substantially retain the overall characteristics and tissue protective properties of the isolated peptides and peptide analogs of structural formula VIII.

Due to the surmised importance of the spatially compact charge configuration at the internal residues of the isolated peptides and peptide analogs of Formula VIII in tissue protective activity, in certain embodiments of the invention, residues comprising the negatively and positively charged and immediately adjacent amino acids are not deleted. Thus, in certain embodiments, residues $X_{11}$, $X_{12}$, $X_{13}$, and $X_{14}$ are not deleted.

The isolated peptides and peptide analogs of Formula VIII can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 25, 26, 27, 28, or 29 amino acid residues and are considered to be within the scope of the present invention. Preferably, such extended peptides will substantially retain the tissue protective properties of the peptide analogs of Formula VIII.

Certain amino acid residues in the core peptides and peptide analogs of Formula VIII can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula VIII wherein at least one and up to eight amino acid residues in the formula are conservatively substituted with another amino acid residue. In certain embodiments, seven, six, five, four, three, two, or one amino acid is conservatively substituted.

In specific embodiments, the isolated peptides and peptide analogs of Formula VIII are selected from the group of peptides set forth below:

```
Peptide FJ
                                       (SEQ ID NO: 210)
ARSPSPSTQPWEHVNAIQEARRLL;

Peptide FK
                                       (SEQ ID NO: 211)
ITFEKLVIP;

Peptide FL
                                       (SEQ ID NO: 212)
TAQGEPFPNNLDKLCGPNVTDFPP;

Peptide FM
                                       (SEQ ID NO: 213)
STDQWSELTEAERLQENLQAYRTF;

Peptide FN
                                       (SEQ ID NO: 214)
YGLLYCFRKDMDKVETFLRIVQCR;

Peptide FO
                                       (SEQ ID NO: 215)
LESQTVQGGTVERLFKNLSLIKKY;

Peptide FP
                                       (SEQ ID NO: 216)
VQLSDSLTDLLDKFSNISEGLSNY;

Peptide FQ
                                       (SEQ ID NO: 217)
ISEGLSNYSIIDKLVNIVDDLVEC;

Peptide FR
                                       (SEQ ID NO: 218)
SSSTKKTQLQLEHLLLDLQMILNG;

Peptide FS
                                       (SEQ ID NO: 219)
FNSNKKKRDDFEKLTNYSVTDLNV;

Peptide FT
                                       (SEQ ID NO: 220)
ARCQVTLRDLFDRAVVLSHYIHNL;

Peptide FU
                                       (SEQ ID NO: 221)
LDRVYNEEKRYTH;

Peptide FV
                                       (SEQ ID NO: 222)
EANQSTLENFLERLKTIMREKYSK;

Peptide FW
                                       (SEQ ID NO: 223)
LERSGLNIEDLEKLQMARPNILGL;

Peptide FX
                                       (SEQ ID NO: 224)
LWRLVLAQRWMERLKTVAGSKMQG;

Peptide FY
                                       (SEQ ID NO: 225)
TVAGSKMQGLLERVNTEIHFVTKC;

Peptide FZ
                                       (SEQ ID NO: 226)
LHAFRIRAVTIDRVMSYLNAS;
and Peptide GA
                                       (SEQ ID NO: 227)
LQRIHQGLIFYEKLLGSDIFTGEP.
```

In another embodiment of the invention, the isolated peptides and peptide analogs based on Type-1 cytokines that exhibit Structural Motif B have the structural Formula IX (SEQ ID NO:228):

$X_1-X_2-X_3-X_4-X_5-X_6-X_7-X_8-X_9-X_{10}-X_{11}-X_{12}-X_{13}-X_{14}-$ $X_{15}-X_{16}-X_{17}-X_{18}-X_{19}-X_{20}-X_{21}-X_{22}-X_{23}-X_{24}-X_{25}$ wherein:
$X_1$ is Cys (C), Tyr (Y), or Ala (A);
$X_2$ is Ser (S), Leu (L), or Glu (E);
$X_3$ is Arg (R), Gln (Q), or Asn (N);
$X_4$ is Ser (S) or Leu (L);
$X_5$ is Ile (I), Leu (L), or Lys (K);
$X_6$ is Tip (W), Leu (L), or Lys (K);
$X_7$ is Leu (L), Phe (F), or Tyr (Y);
$X_8$ is Ala (A), Asn (N), or Phe (F);
$X_9$ is Arg (R), Pro (P), or Asn (N);
$X_{10}$ is Lys (K), Leu (L), or Ala (A);
$X_{11}$ is Ile (I), Val (V), or Gly (G);
$X_{12}$ is a positively charged amino acid;
$X_{13}$ is a polar amino acid;
$X_{14}$ is a negatively charged amino acid;
$X_{15}$ is Leu (L), Gly (G), or Val (V);
$X_{16}$ is Thr (T), Ile (I), or Ala (A);
$X_{17}$ is Ala (A), Cys (C), or Asp (D);
$X_{18}$ is Leu (L), Arg (R) or Asn (N);
$X_{19}$ is Thr (T), Asn (N), or Gly (G);
$X_{20}$ is Glu (E), Arg (R), or Thr (T);
$X_{21}$ is Ser (S), Val (V), or Leu (L);
$X_{22}$ is Tyr (Y), Thr (T), Phe (F);
$X_{23}$ is Asn (N) or Leu (L);
$X_{24}$ is Asn (N) or Gly (G);
$X_{25}$ is Val (V) or Ile (I).

In certain embodiments, the isolated peptides and peptide analogs can contain fewer than 25 amino acid residues. Indeed, truncated or internally deleted forms of structural Formula IX containing as few as 24, 23, 22, 21, 20, 19, 18, 17, 16, 15, 14, 13, 12, 11, or even 10 amino acid residues that substantially retain the overall characteristics and tissue protective properties of the isolated peptides and peptide analogs of structural formula IX.

Due to the surmised importance of the spatially compact charge configuration at the internal residues of the isolated peptides and peptide analogs of Formula IX in tissue protective activity, in certain embodiments of the invention, residues comprising the polar, negatively and positively charged, and immediately adjacent amino acids are not deleted. Thus, in certain embodiments, residues $X_{11}$, $X_{12}$, $X_{13}$, $X_{14}$, and $X_{15}$ are not deleted.

The isolated peptides and peptide analogs of Formula IX can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 26, 27, 28, or 29 amino acid residues and are considered to be within the scope of the present invention. Preferably, such extended peptides will substantially retain the tissue protective properties of the peptide analogs of Formula XI.

Certain amino acid residues in the core peptides and peptide analogs of Formula XI can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula XI wherein at least one and up to eight amino acid residues in the formula are conservatively substituted with another amino acid residue. In certain embodiments, seven, six, five, four, three, two, or one amino acid is conservatively substituted.

In specific embodiments, the isolated peptides and peptide analogs are selected from the group of peptides set forth below:

```
Peptide GB
                              (SEQ ID NO: 229)
CSRSIWLARKIRSDLTALTESYVKH;

Peptide GC
                              (SEQ ID NO: 230)
ELMILLEYKIPRNEADGMPINVGDG;

Peptide GD
                              (SEQ ID NO: 231)
YLQLLLFNPLVKTEGICRNRVTNNV;
and Peptide GE
                              (SEQ ID NO: 232)
AENLKKYFNAGHSDVADNGTLFLGI.
```

In another embodiment of the invention, the isolated peptides and peptide analogs of type-1 cytokines that exhibit structural motif B have the structural formula X (SEQ ID NO:233):

$$X_1-X_2-X_3-X_4-X_5-X_6-X_7-X_8-X_9-X_{10}-X_{11}-X_{12}-X_{13}-X_{14}-$$
$$X_{15}-X_{16}-X_{17}-X_{18}-X_{19}-X_{20}-X_{21}-X_{22}-X_{23}-X_{24}-X_{25}$$

wherein:
$X_1$ is Leu (L);
$X_2$ is Gly (G);
$X_3$ is Cys (C);
$X_4$ is Val (V);
$X_5$ is Leu (L);
$X_6$ is His (H);
$X_7$ is Arg (R);
$X_8$ is Leu (L);
$X_9$ is Ala (A);
$X_{10}$ is Asp (D);
$X_{11}$ is Leu (L);
$X_{12}$ is a negatively charged amino acid;
$X_{13}$ is a polar amino acid;
$X_{14}$ is a positively charged amino acid;
$X_{15}$ is Leu (L);
$X_{16}$ is Pro (P);
$X_{17}$ is Lys (K);
$X_{18}$ is Ala (A);
$X_{19}$ is Gln (Q);
$X_{20}$ is Asp (D);
$X_{21}$ is Leu (L);
$X_{22}$ is Glu (E);
$X_{23}$ is Arg (R);
$X_{24}$ is Ser (S);
$X_{25}$ is Gly (G).

In certain embodiments, the isolated peptides and peptide analogs can contain fewer than 25 amino acid residues. Indeed, truncated or internally deleted forms of structural Formula X containing as few as 24, 23, 22, 21, 20, 19, 18, 17, 16, 15, 14, 13, 12, 11, or even 10 amino acid residues that substantially retain the overall characteristics and tissue protective properties of the isolated peptides and peptide analogs of structural Formula X.

Due to the surmised importance of the spatially compact charge configuration at the internal residues of the isolated peptides and peptide analogs of Formula X in tissue protective activity, in certain embodiments of the invention, residues comprising the polar, negatively and positively charged, and immediately adjacent amino acids are not deleted. Thus, in certain embodiments, residues $X_{11}$, $X_{12}$, $X_{13}$, $X_{14}$, and $X_{15}$ are not deleted.

The isolated peptides and peptide analogs of Formula X can also be extended at one or both termini or internally with additional amino acid residues that do not substantially interfere with, and in some embodiments even enhance, the structural and/or functional properties of the peptides or peptide analogs. Indeed, extended core peptides and peptide analogs containing as many as 26, 27, 28, or 29 amino acid residues and are considered to be within the scope of the present invention. Preferably, such extended peptides will substantially retain the tissue protective properties of the peptide analogs of Formula X.

Certain amino acid residues in the core peptides and peptide analogs of Formula X can be replaced with other amino acid residues without significantly deleteriously affecting, and in many cases even enhancing, the activity of the peptides and peptide analogs. Thus, also contemplated by the present invention are altered or mutated forms of the isolated peptides and peptide analogs of Formula X wherein at least one and up to eight amino acid residues in the formula are conservatively substituted with another amino acid residue. In certain embodiments, seven, six, five, four, three, two, or one amino acid is conservatively substituted.

In specific embodiments, the isolated peptides and peptide analogs consists of the amino acid sequence:

```
Peptide GF
                              (SEQ ID NO: 234)
LGCVLHRLADLEQRLPKAQDLERSG.
```

Further examples of peptides derived from the Type-1 cytokines that exemplify Structural Motif C described herein above include, but are not limited to, human thrombopoietin derived, Peptide GG: DLRVLSKLLRDSHV (SEQ ID NO: 235); Peptide GH: PTPVLLPAVDFSLGEWKTQM (SEQ ID NO: 236); Peptide GI: TAHKDPNAIFLSFQHLLRGK-VRFL (SEQ ID NO: 237); and Peptide GJ: PNRTSGLLET-NFTAS (SEQ ID NO: 238); GM-CSF derived, Peptide GK: PSTQPWEHVNAIQEARR (SEQ ID NO: 239); Peptide GL: NETVEVISE (SEQ ID NO: 240); Peptide GM: QTRLELYKQGLRGSLTKLKGPLTM (SEQ ID NO: 241);

and Peptide GN: KDFLLVIPFDCWEPVQE (SEQ ID NO: 242); CNFT derived, Peptide GO: CSRSIWLARKIRSD (SEQ ID NO: 243); Peptide GP: NKNINLDSADGMPV-ASTD (SEQ ID NO: 244); Peptide GQ: LLQVAAFAYQ-IEELMILLEYK (SEQ ID NO: 245); and Peptide GR: ELSQWTVRSIHDLRFISS (SEQ ID NO: 246); IL-6 derived, Peptide GS: SERIDKQIRYILDGIS (SEQ ID NO: 247); Peptide GT: AENNLNLPKMAEKD (SEQ ID NO: 248); Peptide GU: EEQARAVQMSTKVLIQ (SEQ ID NO: 249) and Peptide GV: RSFKEFLQSSLR (SEQ ID NO: 250); IL-3 derived, Peptide GW: SCNMIDEIITHLKQ (SEQ ID NO: 251); Peptide GX: ENNLRRPNLEAFN-RAVKS (SEQ ID NO: 252); and Peptide GY: HIKDGD-WNEFRRKLTFYLKT (SEQ ID NO: 253); human interferon alpha derived, Peptide GZ: SSCLMDRHDFGFPQEEFDGNQ (SEQ ID NO: 254); Peptide HA: QQIFNLFTTKDSSAAWDE (SEQ ID NO: 255); and Peptide HB: LMNADSILAVKKYFRRITLY (SEQ ID NO: 256); human interferon beta derived, Peptide HC: MSYNLLGFLQRSSNFQCQKLLWQLN (SEQ ID NO: 257); Peptide HD: DRMNFDIPEEIKQLQQFQK (SEQ ID NO: 258); Peptide HE: KLEKEDFTRGKLMSSLHLKR (SEQ ID NO: 259) and Peptide HF: FINRLTGYLRN (SEQ ID NO: 260); human interferon gamma derived, Peptide HG: CYCQDPYVKEAENLKKYFNA (SEQ ID NO: 261); Peptide HH: ADNGTLFLGILKNWKEESDR (SEQ ID NO: 262); Peptide HI: NSNKKKRDDFEKLTNYSVTD (SEQ ID NO: 263); and Peptide HJ: ELSPAAKTGKR (SEQ ID NO: 264); human stem cell factor derived, HK: SLIIG-FAAGALYWKKRQPSL (SEQ ID NO: 265); HL: RNRVTNNVKDVTKLV (SEQ ID NO: 266); Peptide HM: DKLVNIVDDLVECVKE (SEQ ID NO: 267); and Peptide HN: SETSDCWSSTLSPEKDSRV (SEQ ID NO: 268); and human multiple coagulation factor deficiency protein 2 derived, Peptide HO: DELINIIDGVLRDDDKNND (SEQ ID NO: 269); Peptide HP: GLDKNTVHDQEHIMEHLEGV (SEQ ID NO: 270); and Peptide HQ: QLHYFKMHDY-DGNNLL (SEQ ID NO: 271).

Further examples of peptides derived from the Type-1 cytokines that exemplify Structural Motif D described herein above include, but are not limited to, Saposin C derived, Peptide HR: CEFLVKEVTKLIDNNKTEKEIL (SEQ ID NO: 45); hCNTF AB loop derived, Peptide HS: YVKHQGLNKNINLDSVDGVP (SEQ ID NO: 46); hIL-6 AB loop derived Peptide HT: EALAENNLNLPKMAG (SEQ ID NO: 272), hIL-2 AB loop derived Peptide HU: LQMILNGINNYKNPKLT (SEQ ID NO: 273), hIL-3 AB loop derived Peptide HV: ILMENNLRRPNL (SEQ ID NO. 274), hIL-.gamma AB loop derived Peptide HW: FYLRN-NQLVAGTL (SEQ ID NO: 275), hLIF AB loop derived, Peptide HX: YTAQGEPFPNNVELKLCAP (SEQ ID NO: 276); hIL-1.beta helix C derived Peptide HY: FNKIEINN-KLEFESA (SEQ ID NO: 277), and hONC-M helix C derived Peptide HZ: RPNILGLRNNIYCMAQLL (SEQ ID NO: 278).

Further examples of peptides derived from the Type-1 cytokines that exemplify Structural Motif F described herein above include, but are not limited to, hCNTF derived, Peptide IA: YVKHQGLNKNINLDSVDGVP-biotin (SEQ ID NO: 279) and hIL-3 derived Peptide IB: D-Biotin-ILMENNLRRPNL (SEQ ID NO: 280).

These aforementioned amino acids are merely exemplary from some members of the cytokine superfamily that signal through Type 1 cytokine receptors, and homologous regions on other members of the cytokine superfamily will be readily identified by the skilled artisan.

6.3 Chimeras

"Chimeric" peptides—linear amino acid sequences that incorporate non-linear structural elements of the externally-facing amino acids of the EPO molecule or other type I cytokines that exhibit the above-noted structural motifs—are also contemplated by the current invention. Chimeric peptides useful in the current invention may consist of combining structural elements of separate amino acid sequences into a single peptide. In other words, a chimeric peptide may be comprised of amino acid sequences derived from non-linear but adjacent structural elements such as a fragment derived from amino acid sequences 110-115, 133-136, and 160-165, of SEQ ID NO:1 which would allow structural elements of the C terminal portion of helix C and N-terminal portion of loop C-D, the β-pleated sheet in loop C-D, and the C-terminal portion of EPO to be contained in a single peptide. Additionally, chimeric peptides may be used to select out the important features of a particular structure, for example the externally-facing amino acids of a particular tertiary structure. Thus, a chimeric peptide useful in the methods of the current invention may consist of a fragment comprised of helix B amino acids 58, 62, 65, 69, 72, 76, 79, 80, 83, 84, and 85 (e.g., peptide IC, QEQLER-ALNSS, SEQ ID NO: 281) or, in other words, all of the exterior-presenting amino acids of helix B of EPO, as disclosed in PCT/US2006/031061. A further chimeric peptide in which the first glutamine is replaced with pyroglutamate (e.g., peptide ID, UEQLERALNSS, SEQ ID NO. 282) is contemplated by the current invention as well.

Further, non-naturally occurring or chimeric peptides can be designed that mimic the critical spatial proximities between carbamyl carbons of any two amino acids or between the side chains of any two amino acids in erythropoietin or another Type-1 cytokine described herein above via a linear sequence of amino acids and may provide a guide in evaluating possible tissue protective chimeras derived from other proteins. The present invention is, therefore, directed to novel chimeric tissue protective peptides, including those that exhibit these structural motifs and critical spatial proximities that trigger tissue protection.

Furthermore, the potency of the current peptides may be increased by attaching an amphipathic peptide helix. Amphipathic peptide helices are well known in the art, e.g. from peptides that signal through the Class B G-protein coupled receptors (e.g., Segrest et al., 1990, Proteins 8: 103, hereby incorporated by reference in its entirety), serving to localize the peptide ligand to the cell membrane. Examples of such helices include, but are not limited to, the highly hydrophobic regions from: calcitonin (Peptide IE: ALSIL-VLLQAGS, SEQ ID NO:283); corticotropin releasing hormone (Peptide IF: VALLPCPPCRA, SEQ ID NO:284); beta endorphin (Peptide IG: NAIIKNAYKKG, SEQ ID NO:285); glucagon (Peptide IH: GSWQRSLQDTE, SEQ ID NO:286); secretin (Peptide II: GGSAARPAPP, SEQ ID NO:287); vasointestinal peptide (Peptide IJ: NALAENDT-PYY, SEQ ID NO:288); neuropeptide Y (Peptide IK: GALAEAYPSKP, SEQ ID NO:289); gonadotropin releasing hormone (Peptide IL: GCSSQHWSYGL, SEQ ID NO:290); parathyroid hormone (Peptide IM: VMIVMLAICFL, SEQ ID NO:291); pancreatic polypeptide (Peptide IN: LRRYIN-MLTRP, SEQ ID NO:292); and calcitonin gene related peptide (Peptide IO: LALSILVLYQA, SEQ ID NO:293) (disclosed in Grace et al., 2004, PNAS 101: 12836, hereby incorporated by reference in its entirety). For example, a chimeric peptide useful in the methods of the current invention may be made from a peptide with the surface charge motif of helix B of EPO (Peptide IC: QEQLERALNSS, SEQ ID NO:281) joined at the carboxy terminus to the amphipathic helix of pancreatic polypeptide (Peptide IN: LRRYINMLTRP, SEQ ID NO:292) for a chimeric peptide (Peptide IP: QEQLERALNSSLRRYINMLTRP, SEQ ID NO. 306), as disclosed in PCT/US2006/031061. Further modifications may be made to the carboxy terminus of the amphipathic helix without affecting its tissue protective properties. Thus, a further example of a peptide useful in the treatment of a disease or disorder associated with tissue damage or damage, effects or symptoms resulting therefrom is generated by replacing the terminal Pro of the above chimeric peptide with the sequence TR (Peptide IQ: QEQLERALNSSLRRYINMLTRTR, SEQ ID NO:294).

Additionally, instead of the above-noted helices, other tertiary structures can be attached to the peptides. For example, the helix B exterior-presenting amino acids can be linked to the beta pleated sheet (Peptide IR: CSLNENI, SEQ ID NO:295) found within the AB loop of EPO to form a chimeric peptide having the sequence Peptide IS: CSLNE-NIQEQLERALNSS (SEQ ID NO:296). Additionally, the presenting amino acids of the terminal portion of helix C (Peptide IT: ALGKA, SEQ ID NO:297, corresponding to amino acids 111, 112, 113, 116, and 118 of SEQ ID NO:1) may be combined with all or part of loop CD-partial (Peptide IU: LGAQKEAISPPDAASAAPLRTI, SEQ ID NO: 307, corresponding to amino acids 112-133 of SEQ ID NO:1) to form Peptide IV: ALGKALGAQKEAISPPDAASAAPLRTI (SEQ ID NO: 299).

Additionally, isolated peptides exhibiting the various motifs disclosed above—Structural Motifs A (including Formulas I-IV), Structural MotifB (including Formulas V-X), Structural MotifC, Structural, MotifD, Structural MotifE and Structural MotifF—may be combined to form various chimeras as well. In certain embodiments, the chimeras will exclude Peptide IC, QEQLERALNSS, SEQ ID NO: 281, Peptide IP: QEQLERALNSSLRRYINMLTRP, SEQ ID NO: 306, Peptide IQ: QEQLERALNSSLRRYINMLTRTR, SEQ ID NO:294, Peptide IS: CSLNENIQEQLERALNSS, SEQ ID NO:296, Peptide IT: ALGKA, SEQ ID NO:297, and Peptide IV: ALGKALGAQKEAISPPDAASAAPLRTI, SEQ ID NO: 299.

Preferably, a linking arm will be present between the fused peptides to provide for flexibility so that the joined peptides can assume the proper structural orientation to bind with the tissue protective receptor complex. Such fusion peptides may have a synergistic effect, obtaining a greater tissue protective effect jointly as opposed to individually possibly through enhanced binding with the tissue protective receptor complex or increased biological half life.

One of ordinary skill in the art will recognize the benefit of combining various desired structural elements in to a single peptide for maximizing the effectiveness of such compounds in the method of preventing, treating, ameliorating or managing damages, effects, or symptoms resulting from exposure to a toxic agent in accordance with the current invention. Such chimeras may comprise amino acids peptides, and non-amino acid elements, such as linkers or bridging atoms or moieties.

6.4 Fusion Peptides

The present invention further contemplates that two or more of the above noted peptides, fragment derived or chimera, may be linked to a related or unrelated protein such as erythropoietin, albumin, etc. Such fusion peptides may be generated in order to achieve synergistic benefits, increase the circulating half-life of the peptide, or increase the ability of the peptide to penetrate endothelial barriers, such as the blood-brain barrier, blood-retina barrier, etc., or vice versa, i.e. to act as a transport mechanism similar to that disclosed in PCT/US01/49479 published as WO 2002/053580 hereby incorporated in its entirety by reference.

6.5 Manufacture of Peptides

Peptides useful in the method of the current invention may be made using recombinant or synthetic techniques well known in the art. In particular, solid phase protein synthesis is well suited to the relatively short length of the peptides and may provide greater yields with more consistent results. Additionally, the solid phase protein synthesis may provide additional flexibility regarding the manufacture of the peptides. For example, desired chemical modifications may be incorporated into the peptide at the synthesis stage: homocitrulline could be used in the synthesis of the peptide as opposed to lysine, thereby obviating the need to carbamylate the peptide following synthesis or amino acids with protected functional groups may be left on the peptide during synthesis.

Synthesis

The isolated peptides and peptide analogs useful in the method of the current invention may be prepared using conventional step-wise solution or solid phase synthesis (see, e.g., Merrifield, R. B., 1963, *J. Am. Chem. Soc.* 85:2149-2154; Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the peptides and peptide analogs useful in the current invention may be prepared by way of segment condensation, as described, for example, in Liu et al., 1996, Tetrahedron Lett. 37(7):933-936; Baca, et al., 1995, *J. Am. Chem. Soc.* 117:1881-1887; Tam et al., 1995, *Int. J. Peptide Protein Res.* 45:209-216; Schnolzer and Kent, 1992, *Science* 256:221-225; Liu and Tam, 1994, *J. Am. Chem. Soc.* 116 (10):4149-4153; Liu and Tam, 1994, *Proc. Natl. Acad. Sci. USA* 91:6584-6588; Yamashiro and Li, 1988, *Int. J. Peptide Protein Res.* 31:322-334). This is particularly the case with Gly (G) containing peptides. Other methods useful for synthesizing the peptides and peptide analogs of the invention are described in Nakagawa et al., 1985, *J. Am. Chem. Soc.* 107:7087-7092.

Recombinant Techniques

A variety of host-expression vector systems may be utilized to produce the peptides and peptide analogues. Such host-expression systems represent vehicles by which the peptide of interest may be produced and subsequently purified, but also represent cells that may, when transformed or transfected with the appropriate nucleotide coding sequences, exhibit the modified erythropoietin gene product in situ. These include but are not limited to, bacteria, insect, plant, mammalian, including human host systems, such as, but not limited to, insect cell systems infected with recombinant virus expression vectors (e.g., baculovirus) containing the peptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing erythropoietin-related molecule coding sequences; or mammalian cell systems, including human cell systems, e.g., HT1080, COS, CHO, BHK, 293, 3T3, PERC6 harboring recombinant expression constructs containing promoters derived from the genome of mammalian cells, e.g., metallothionein promoter, or from mammalian viruses, e.g., the adenovirus late promoter; the vaccinia virus 7.5K promoter.

In addition, a host cell strain may be chosen that modulates the expression of the inserted sequences, or modifies and processes the gene product in the specific fashion desired. Such modifications and processing of protein products may be important for the function of the protein. As known to those of ordinary skill in the art, different host cells have specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant peptides, stable expression is preferred. For example, cell lines that stably express the recombinant tissue protective cytokine-related molecule gene product may be engineered. Rather than using expression vectors that contain viral origins of replication, host cells can be transformed with DNA controlled by appropriate expression control elements, e.g., promoter, enhancer, sequences, transcription terminators, polyadenylation sites, and the like, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the tissue-protective product. Such engineered cell lines may be particularly useful in screening and evaluation of compounds that affect the endogenous activity of the EPO-related molecule gene product.

Further Modifications

Peptides with additional modifications can also be used in the method of the present invention for preventing, treating, ameliorating or managing a disease or disorder associated with tissue damage or damage, effects or symptoms resulting therefrom. For example, the peptides of the above-noted structural motifs may be synthesized with one or more (D)-amino acids. The choice of including an (L)- or (D)-amino acid into a peptide of the present invention depends, in part, upon the desired characteristics of the peptide. For example, the incorporation of one or more (D)-amino acids can confer increasing stability on the peptide in vitro or in vivo. The incorporation of one or more (D)-amino acids can also increase or decrease the binding activity of the peptide as determined, for example, using the bioassays described herein, or other methods well known in the art.

Replacement of all or part of a sequence of (L)-amino acids by the respective sequence of entatiomeric (D)-amino acids renders an optically isomeric structure in the respective part of the peptide chain. Inversion of the sequence of all or part of a sequence of (L)-amino acids renders retro-analogues of the peptide. Combination of the enantiomeric (L to D, or D to L) replacement and inversion of the sequence renders retro-inverso-analogues of the peptide. It is known to those skilled in the art that enantiomeric peptides, their retro-analogues, and their retro-inverso-analogues maintain significant topological relationship to the parent peptide, and especially high degree of resemblance is often obtained for the parent and its retro-inverso-analogues. This relationship and resemblance can be reflected in biochemical properties of the peptides, especially high degrees of binding of the respective peptides and analogs to a receptor protein. The synthesis of the properties of retro-inverso analogues of peptides have been discussed for example in Methods of Organic Chemistry (Houben-Weyl), Synthesis of Peptides and Peptidomimetics Workbench Edition Volume E22c (Editor-in-chief Goodman M.) 2004 (George Thieme Verlag Stuttgart, New York), and in references cited therein, all of which are hereby incorporated by reference herein in their entireties.

Amino acid "modification" refers to the alteration of a naturally occurring amino acid to produce a non-naturally occurring amino acid. Derivatives of the peptides of the present invention with non-naturally occurring amino acids can be created by chemical synthesis or by site specific incorporation of unnatural amino acids into peptides during biosynthesis, as described in Christopher J. Noren, Spencer J. Anthony-Cahill, Michael C. Griffith, Peter G. Schultz, 1989 Science, 244:182-188, hereby incorporated by reference herein in its entirety.

Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —$CH_2NH$—, —$CH_2S$—, —$CH_2CH_2$—, —CH=CH (cis and trans), —$COCH_2$—, —CH(OH)$CH_2$—, and $CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p 267 (1983); Spatola, A. F., Vega Data (March 1983), Vol. 1. Issue 3, "Peptide Backbone Modifications" (general review); Morely, J. S., Trends Pharma Sci (1980) pp. 463-468 (general review); Hudson, D. et al., (1979) Int J Pept Prot Re 14: 177-185 (—$CH_2NH$—, —$CH_2CH_2$—); Spatola, A. F. et al., (1986) Life Sci 38:1243-1249 (—$CH_2S$—); Hann, M. M., (1982) J Chem Soc Perkin Trans I 307-314 (—CH=CH—, cis and trans); Almquist, R. G. et al., (1980) J Med Chem 23: 1392 (—$COCH_2$—); Jennings-White, C et al., (1982) Tetrahedron Lett 23:2533 (—$COCH_2$—); Szelke, M et al., European Appln. EP 45665 (1982) CA: 97: 39405 (1982) (—CH(OH)$CH_2$—); Holladay, M. W. et al., (1983) Tetrahedron Lett 24:4401-4404 (—C(OH)$CH_2$—); and Hruby, V. J., (1982) Life Sci 31:189-199 (—$CH_2S$—); each of which is incorporated herein by reference.

In another embodiment, a particularly preferred non-peptide linkage is —$CH_2NH$—. Such peptide mimetics may have significant advantages over peptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

A variety of designs for peptide mimetics are possible. For example, cyclic peptides, in which the necessary conformation is stabilized by non-peptides, are specifically contemplated, U.S. Pat. No. 5,192,746 to Lobl, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred et al., J. Med. Chem. 37:3882 (1994), hereby incorporated by reference herein in its entirety) describe non-peptide antagonists that mimic the peptide sequence. Likewise, Ku et al., J. Med. Chem 38:9 (1995) (hereby incorporated by reference herein in its entirety) further elucidates the synthesis of a series of such compounds.

Further modifications following synthesis may be implemented. For example, the peptides may be further chemically modified, i.e. carbamylated, acetylated, succinylated, guanidated, nitrated, trinitrophenylated, amidinated, etc., in accordance with U.S. patent application Ser. No. 10/188,905, which published as 20030072737-A1 on Apr. 17, 2003 and discloses chemically modified EPO, and in accordance with U.S. patent application Ser. No. 10/612,665, filed Jul. 1, 2003, and U.S. patent application Ser. No. 09/753,132, filed Dec. 29, 2000, which are incorporated by reference herein in their entirety.

Additionally, the peptides may consist of recombinant peptides—muteins. The disclosed mutations may include substitutions, deletions, including internal deletions, additions, including additions yielding fusion proteins, or conservative substitutions of amino acid residues within and/or adjacent to the amino acid sequence, but that result in a "silent" change, and non-conservative amino acid changes and larger insertions and deletions, as previously disclosed in PCT/US03/20964 entitled Recombinant Tissue Protective Cytokines and Encoding Nucleic Acids Thereof for Protection, Restoration, and Enhancement of Responsive Cells, Tissues, and Organs (which is incorporated by reference herein in its entirety)

Either conservative or non-conservative amino acid substitutions can be made at one or more amino acid residues. Both conservative and non-conservative substitutions can be made. Conservative replacements are those that take place within a family of amino acids that are related in their side chains. Genetically encoded amino acids can be divided into four families: (1) acidic=Asp (D), Glu (G); (2) basic=Lys (K), Arg (R), His (H); (3) nonpolar (hydrophobic)=Cys (C), Ala (A), Val (V), Leu (L), Ile (I), Pro (P), Phe (F), Met (M), Trp (W), Gly (G), Tyr (Y); and (4) uncharged polar=Asn (N), Gln (Q), Ser (S), Thr (T). Non-polar may be subdivided into: strongly hydrophobic=Ala (A), Val (V), Leu (L), Ile (I), Met (M), Phe (F); and moderately hydrophobic=Gly (G), Pro (P), Cys (C), Tyr (Y), Trp (W). In alternative fashion, the amino acid repertoire can be grouped as (1) acidic=Asp (D), Glu (G); (2) basic=Lys (K), Arg (R), His (H), (3) aliphatic=Gly (G), Ala (A), Val (V), Leu (L), Ile (I), Ser (S), Thr (T), with Ser (S) and Thr (T) optionally be grouped separately as aliphatic-hydroxyl; (4) aromatic=Phe (F), Tyr (Y), Tip (W); (5) amide=Asn (N), Glu (Q); and (6) sulfur-containing=Cys (C) and Met (M). (See, for example, Biochemistry, 4th ed., Ed. by L. Stryer, WH Freeman and Co., 1995, which is incorporated by reference herein in its entirety).

Alternatively, mutations can be introduced randomly along all or part of the coding sequence of a peptide, such as by saturation mutagenesis, and the resultant mutants can be screened for biological activity to identify mutants that retain activity. Following mutagenesis, the encoded peptide can be expressed recombinantly and the activity of the recombinant peptide can be determined.

In another embodiment, the peptide may be further modified through the additions of polymers (such as polyethylene glycol), sugars, or additional proteins (such as a fusion construct) in an effort to extend the half-life of the peptide or enhance the peptide's tissue protective effects. Examples of such modifications are disclosed within WO/04022577 A3 and WO/05025606 A1, which are incorporated herein by reference. For example, a polyethylene glycol polymer can be attached to Peptide IC to result in a Peptide IW ((SEQ ID NO. 305) PEG-QEQLERALNSS).

Depending on the conjugation chemistry selected and the number of reactive sites already present or created on the peptide, one, two, or a selected number of polymers can be appended in a reproducible manner. The principal mode of attachment of a PEG, and its derivatives, to peptides is a non-specific bonding through a peptide amino acid residue (see e.g., U.S. Pat. No. 4,088,538, U.S. Pat. No. 4,496,689, U.S. Pat. No. 4,414,147, U.S. Pat. No. 4,055,635, and PCT WO 87/00056). Another mode of attaching PEG to peptides is through the non-specific oxidation of glycosyl residues on a glycopeptide (see e.g., WO 94/05332). In these non-specific methods, PEG is added in a random, non-specific manner to reactive residues on a peptide backbone.

7. ASSAYS FOR TESTING PEPTIDES

Various assays can be used to determine the utility of the above noted peptides for use in the therapeutic methods of the current invention. The peptides tissue protective activity would be confirmed using various assays known in the art and disclosed within U.S. patent application Ser. Nos. 10/554,517, 10/612,665 and 11/997,898. Further, the peptides lack of erythropoietic activity or reduced erythropoietic activity will be confirmed using various in vitro assays, such as EPO dependent cell lines (UT-7), mouse spleen bioassay (Krystal, G (1983) (a simple microassay for erythropoietin based on $^3$H-thymidine incorporation into spleen cells for phenylhydrazine treated mice. *Exp. Hematol.* 11, 649-660)), or clonal assays (Spivak, J. L., Seiber, F. (1983). Erythropoietin. *Horm. Norm. Abnorm. Hum. Tissues* 3, 63-96), and in vivo assays, such as the ex hypoxic polycythemic mouse assay (Cotes P M, Bangham D R, Bio-assay of erythropoietin in mice made polycythemic by exposure to air at a reduced pressure, *Nature*. 1961 Sep. 9; 191:1065-7). Additionally, one of ordinary skill in the art will recognize that the peptide's ability to prevent, mitigate or treat a disease or disorder associated with tissue damage or damage, effects or symptoms resulting therefrom may be confirmed through various assays both in vitro and in vivo, although in certain embodiments in vivo assays may be preferred.

7.1 Tissue Protective Assays and Models

The peptides utilized in the current method exhibit tissue protective properties, i.e. anti-apoptotic, neuritogenic, neuroprotective, etc. Peptides in accordance with the present invention may be tested for tissue protective activity, e.g., protecting cells, tissues or organs. Protective activities may be further tested using in vitro and in vivo assays. In vitro tests that are indicative of tissue protective activity include, for example, cell proliferation assays, cell differentiation assays, or detecting the presence of proteins or nucleic acids upregulated by tissue protective receptor complex, e.g. tissue protective cytokine receptor complex, activity, e.g., nucleolin, neuroglobin, cytoglobin, or frataxin. Neuroglobin, for example, may be involved in facilitating the transport or the short-term storage of oxygen. Therefore, oxygen transport or storage assays may be used as an assay to identify or screen for compounds which modulate tissue protective activity.

Neuroglobin is expressed in cells and tissues of the central nervous system in response to hypoxia or ischemia and may provide protection from injury (Sun et al. 2001, PNAS 98:15306-15311; Schmid et al., 2003, J. Biol. Chem. 276: 1932-1935, each of which is incorporated by reference herein in its entirety). Cytoglobin may play a similar role in protection, but is expressed in a variety of tissues at varying levels (Pesce et al., 2002, *EMBO* 3:1146-1151, which is incorporated by reference herein in its entirety). In one embodiment of the invention, the levels of an upregulated protein in a cell may be measured before and after contacting the peptide to a cell. In certain embodiments, the presence of an upregulated protein associated with tissue protective activity in a cell, may be used to confirm the tissue protective activities of a peptide.

Nucleolin may protect cells from damage. It plays numerous roles in cells including modulation of transcription processes, sequence specific RNA-binding protein, cytokinesis, nucleogenesis, signal transduction, apoptosis induced by T-cells, chromatin remodelling, or replication. It can also function as a cell surface receptor DNA/RNA helicase, DNA-dependent ATPase, protein shuttle, transcription factor component, or transcriptional repressor (Srivastava and Pollard, 1999, *FASEB J.*, 13:1911-1922; and Ginisty et al., 1999, *J. Cell Sci.*, 112:761-772, each of which is incorporated by reference herein in its entirety).

Frataxin is a protein involved with mitochondrial iron metabolism and has previously been shown to be strongly up-regulated by EPO both in vivo and in vitro (Sturm et al. (2005) *Eur J Clin Invest* 35: 711, which is incorporated by reference herein in its entirety)

Expression of an upregulated protein may be detected by detecting mRNA levels corresponding to the protein in a cell. The mRNA can be hybridized to a probe that specifically binds a nucleic acid encoding the upregulated protein. Hybridization may consist of, for example, Northern blot, Southern blot, array hybridization, affinity chromatography, or in situ hybridization.

Tissue protective activity of the peptide of the invention can also be detected using in vitro neuroprotection assays. For example, primary neuronal cultures may be prepared from new born rat hippocampi by trypsinization, and cultured as by any method known in the art and/or described herein e.g. in MEM-II growth medium (Invitrogen), 20 mM D-glucose, 2 mM L-glutamine, 10% Nu-serum (bovine; Becton Dickinson, Franklin Lakes, N.J.), 2% B27 supplement (Invitrogen), 26.2 mM NaHCO3, 100 U/ml penicillin, and 1 mg/ml streptavidin (see, e.g., Leist et al., 2004, Science 305:239-242, hereby incorporated by reference in its entirety). One day after seeding, 1 µM cytosinearabinofuranoside is added. Thirteen day old cultures are then preincubated with increasing doses of the peptide of interest (3-3000 pM) for 24 h. On day 14, the medium is removed and the cultures challenged with 300 µM NMDA in PBS at room temperature (RT). After 5 min, pre-conditioned medium is returned to the cultures which are then returned to the incubator for 24 h. The cells are fixed in paraformaldehyde, stained by Hoechst 33342 (Molecular Probes, Eugene, Oreg.) and condensed apoptotic nuclei may be counted. NGF (50 ng/ml) and MK801 (1 µM) are included as positive controls.

Animal model systems can be used to demonstrate the tissue protective activity of a compound or to demonstrate the safety and efficacy of the compounds identified by the screening methods of the invention described above. The compounds identified in the assays can then be tested for biological activity using animal models for a type of tissue damage, disease, condition, or syndrome of interest. These include animals engineered to contain the tissue protective receptor complex coupled to a functional readout system, such as a transgenic mouse.

Animal models that can be used to test the efficacy of the cell or tissue protective activity of an identified compound are known in the art and include, for example, protection against the onset of acute experimental allergic encephalomyelitis in Lewis rats, restoration or protection from diminished cognitive function in mice after receiving brain trauma, cerebral ischemia ("stroke") or seizures stimulated by excitotoxins (Brines et al., 2000, *PNAS*, 97:10295-10672, which is incorporated by reference herein in its entirety), protection from induced retinal ischemia (Rosenbaum et al., 1997, *Vis. Res.* 37:3443-51 which is incorporated by reference herein in its entirety), protection from injury to the sciatic nerve, and protection from ischemia-reperfusion injury to the heart (in vitro cardiomyocyte studies and in vivo ischemia-reperfusion injury, see, e.g., Calvillo et al., 2003, *PNAS* 100:4802-4806 and Fiordaliso et al., 2005, *PNAS* 102:2046-2051, each of which is hereby incorporated by reference in its entirety). Such assays are described in further detail in Grasso et al. (2004) *Med Sci Monit* 10: BR1-3, PCT publication no. WO02/053580, or PCT application PCT/US2006/031061 each of which is incorporated by reference herein in its entirety. The in vivo methods described therein are directed towards administration of EPO, however, tissue protective proteins administered in place of EPO have been identified to also exhibit similar biologic activity, e.g., Leist et al. (2004) *Science* 305: 239-242, which is incorporated by reference herein in its entirety. Peptides may be substituted for testing as well. Other assays for determining tissue protective activity of a peptide are well known to those of skill in the art.

Alternatively, cell binding assays can be for evaluation of the peptides of the invention. For example, the peptide of interest can be bound to a biological marker such as a fluorescent or radiolabeled marker for ease of detection and tested for binding to transfected BaF3 cells expressing EPOR and/or $\beta_c$ receptor. In a 96 well plate, eight 1:2 serial dilutions of the peptide of interest in growth medium (RPMI 1640, 10% fetal bovine serum, 1 mM sodium pyruvate, 2 mM L-glutamine) are plated, such that the final volume in each well is about 100 µl. The BaF3 parental line and BaF3 cells transfected with EPOR and/or $\beta_c$ receptor can be washed three times in growth media (see above), pellets resuspended in growth medium, and cells counted and diluted in growth media to 5,000 cells/100 µl. 100 µl of diluted cells are then added to each peptide dilution. The assay plate is then incubated in a 37° C. incubator for three to four days. The plate/cells are then washed and the plate is read on a fluorescent plate reader or by other suitable method to detect the level of biomarker associated with the biological activity of the peptide of interest.

Similarly, a competitive assay can be utilized to determine if a peptide is tissue protective. In the competitive assay, a compound known to be tissue protective including, but not limited to, tissue protective cytokines such as those disclosed in U.S. patent application Ser. Nos. 10/188,905 and 10/185,841 (each of which is incorporated by reference herein in its entirety), can be attached to a suitable bio marker.

In a 96 well plate eight 1:2 serial dilutions of a known tissue protective compound/biomarker in suitable growth medium, and the same dilution series of the known tissue protective compound/biomarker and an excess of the peptide of interest are plated. The final volume of each dilution should be about 100 µl. Once again, the BaF3 cells are seeded into the plates as disclosed supra and allowed to incubate. After an appropriate amount of time, the cells are washed and the plate is read on a fluorescent plate reader or by any other suitable method known in the art to detect the biomarker. If the readout of the plates and/or wells containing the known tissue protective compound/biomarker and peptide of interest is less than the readout of the plates containing only the known tissue protective compound/biomarker then the peptide of interest is tissue protective.

Many protein factors discovered to date, including all known cytokines, have exhibited activity in one or more factor-dependent cell proliferation assays, and hence these assays serve as a convenient confirmation of cytokine activity. The activity of a peptide can be evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mole and CMK. These cells are cultured in the presence or absence of a peptide, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, 1983, J. Immunol. Meth. 65:55-63, which is incorporated by reference herein in its entirety).

If a peptide exhibits a tissue protective activity, one of ordinary skill in the art would recognize that it would be beneficial to verify the result using one of the neuroprotective and tissue protective assays known to those skilled in the art, such as, but not limited to, P-19 and PC-12 cell assays. Additionally, various in vivo models such as animal models related to spinal cord injury, ischemic stroke, peripheral nerve damage, wounds, or damage to the heart, eyes, kidneys, etc. would be helpful in further characterizing the peptide. Suitable in vitro and in vivo assays are disclosed in U.S. patent application Ser. Nos. 10/188,905 and 10/185,841, each of which is incorporated by reference herein in its entirety.

7.2 Assays for Specific Indications

A. Toxic Agents.

The isolated peptides to be used within the method of the current invention may be demonstrated to inhibit damage, effects or symptoms resulting from exposure to a toxic agent in vitro or in vivo using a variety of assays known in the art, or described herein.

Further peptides used within the method of the Invention, may be tested in various in vitro assays in the art to determine their ability to prevent, treat, ameliorate, or manage damage, effects or symptoms resulting from exposure to a toxic agent. In general, this is accomplished by selecting an appropriate cell line, subjecting that cell to a toxic agent of interest and treating a portion of the cells with a peptide of interest and determining the cells survival or response in the presence of the toxic agent and in the presence of the toxic agent and the peptide of interest. If the cell exhibits improved survival or a reduction of damage, effects or symptoms in the presence of the peptide, the peptide can be considered to be a possible therapeutic for toxic exposure. Further one of ordinary skill in the art will recognize that the peptides ability as a protectant can be evaluated by treating the cells with the peptide prior to the toxic agent challenge.

For example, suitable assays for toxic agents include, but are not limited to: Chemical Agents: a) skin cell lines such as J-774 (mouse macrophage derived cell line), CHO-K1 (strain of epithelial cell line derived from Chinese hamster ovary cells), and HeLa (human cervical carcinoma) (Sawyer, T. et al., Hypothermia as an adjunct to vesicant-induced skin injury, *Eplasty* 2008; 8:e25); b) corneal cell lines for vesicant agents (Amir, A. et al., The corneal epithelium in sulfur mustard ocular injury—In vitro and ex vivo studies, Proceedings of the U.S. Army Medical Defense Bioscience Review, Aberdeen Proving Ground, MD (2004)); c) macrophages (Amir A., et al., Sulfur mustard toxicity in macrophages: effect of dexamethasone, *J Appl Toxicol,* 20 Suppl 1:S51-8 (2000)); d) upper respiratory tract cell lines (Andrew, D. J. and C. D. Lindsay, Protection of human upper respiratory tract cell lines against sulphur mustard toxicity by gluthione esters, *Hum Exp Toxicol* 17(7):387-95 (1998); Calvet et al., Airway epithelial damage and release of inflammatory mediators in human lung parenchyma after sulfur mustard exposure, *Hum Exp Toxicol* 18(2):77-81 (1999); Langford, A. M. et al., The effect of sulphur mustard on glutathione levels in rat lung slices and the influence of treatment with arylthiols and cysteine esters, *Hum Exp Toxicol* 15(8):619-24); e) skin models (Blaha et al., Effects of CEES on inflammatory mediators, heat shock protein 70A, histology and ultrastructure in two skin models, *J Appl Toxicol* 20 Suppl 1:S101-8 (2000); Henemyre-Harris et al., An in vitro wound healing model to screen pharmacological interventions for the effective treatment of cutaneous sulfur mustard injuries, Proceedings of the U.S. Army Medical Defense Bioscience Review, Aberdeen Proving Ground, MD (2004)) (See generally, www.counteract.rutgers.edu/invitro.html for additional literature on appropriate in vitro studies); Radiation Agents: a) endothelial cells (Abderrahmani, R. et al., Role of plasminogen activator inhibitor type-1 in radiation-induced endothelial cell apoptosis, *Radioprotection* 2008, vol 43, no. 5, b) neuroimmune cells (afferent nerves, enteric sensory nerves, mast cells) (Wang, J. et al., Neuroimmune interactions: potential target for mitigating or treating intestinal radiation injury, *British Journal of Radiology* (2007) 80, S41-S48), c) blood or lymphocyte cultures (Lloyd D C et al., *Phys Med Biol* 18(3):421-31 (1973); Lloyd D C et al., *Mutat. Res.* 179(2): 197-208 (1987); Blakely W F et al., *Stem Cells* 13 (Suppl 1):223-30 (1995); Gotoh E et al., *Int. J. Radiation. Biol.* 81(1):33-40 (2005)); Biological Agents: (a) peripheral blood mononuclear cells (Rasha, H. et al. Modeling of SEB-induced host gene expression to correlate in vitro to in vivo responses: Microarrays for biodefense and environmental applications, *Biosensors and Bioelectrics* (2004) vol. 20, no. 4, 719-727).

Further, suitable in vivo assays are known in the art for evaluating the effect of therapeutics on toxic agent exposure. Animal models using rats, mice, guinea pigs, rabbits, pigs, sheep, ferrets, dogs and non-human primates are contemplated as well as transgenic animals that are particularly susceptible to a toxic agent (CD46 mice). In particular, assays known in the art include, but are not limited to: Chemical Agents: (1) Reid, F. M., Sulfur mustard induced skin burns in weanling swine evaluated clinically and histopathologically, *Journal of applied toxicology*, vol. 20 (51), pages S153-S160 (2001); (2) Isidore, M. A. et al., A dorsal model for cutaneous vesicant injury 2-chloroethyl ethyl sulfide using c57bl/6 mice, *Cutaneous and ocular toxicology*, Vol. 26 (3), 265-276 (2007); (3) See generally, www-.counteract.rutgers.edu/animal.html; (4) Kassa J., et al., The Choice: HI-6, pradoxime or Obidoxime against Nerve Agents?, www.asanlte.com/ASANews-97/Antidot-Choice.html, (5) Shih, T M et al., Organophosphorus nerve agents-induced seizures and efficacy of atropine sulfate as anticonvulsant treatment, *Pharmacol-Biochem-Behav.* 1999 September, 64(1), 147-53, (6) Luo, C et al., Comparison of oxime reactivation and aging of the nerve agent-inhibited monkey and human acetylcholinesterases, *Chemico-Biological Interactions*, 175(1-3), 261-266 (2008); Radiation Agents: (1) W. F. Blakely et al., In Vitro and Animal Models of Partial-Body Dose Exposure: Use of Cytogenic and Molecular Biomarkers for Assessment of Inhomogeneous Dose Exposures and Radiation Injury, PB-Rad-Injury 2008 Workshop, May 5-6, 2008 AFRRI, Bethesda, Md.; (2) Augustine, A et al., Meeting Report: Animal Models of Radiation Injury, Protection and Therapy, *Radiation Research* 164: 100-109 (2005); (3) Houchen, C et al. Pro-survival and antiapoptotic effects of $PGE_2$ in radiation injury are mediated by $EP_2$ receptor in intestine, *Am J Physiol Gastrointest Liver Physiol*, 284: G490-G498, 2003; (4) Jichun Chen, Animal Models for Acquired Bone Marrow Failure Syndromes, *Clinical Medicine & Research* 3(2): 102-108: Biological Agents: (1) Biodefense: Research Methodology and Animal Models, James R. Swearengen (editor) 2006 CRC Press.

B. Inflammation

Additionally, various in vitro models of inflammation may be used to evaluate a peptides ability to protect or treat the damage, symptoms, or effects of inflammation on the body. Initially, the ability of the peptide to modulate an inflammatory mediator can be confirmed by measuring the levels of the inflammatory mediator in an inflammatory assay after treatment with the peptide by known methods, including but not limited to, ELISA, cytometric bead array analysis, high-sensitivity and immunonephelometric assays. For example to determine if the peptide modulates either TNF-α or IL-1, a murine model of LPS-mediated cytokine production would be performed. Some mice in the murine model would be pretreated with the peptide of interest and then challenged with LPS while others would be saline treated. Blood would then be collected and the TNF-α and IL-1 levels in the blood could be determined by an ELISA kit (OPT-EIA mouse TNF-α and IL-1 ELISA kits (BD Biosciences). If the TNF-α levels in the treated animals are lower than the TNF-α levels in the saline treated animals then the peptide could be considered to modulate TNF-α. Preferably, the peptide would be tested for its ability to modulate more than one inflammatory mediator, and more preferably it would be a mediator other than or in addition to TNF-α, and most preferably it would be histamine. Similarly, the peptides may be tested in additional in vitro assays including, but not limited to, those disclosed in Lopata, Andreas L., Specialized in vitro Diagnostic Methods In The Evaluation Of Hypersensitivity—An Overview, *Current Allergy & Clinical Immunology*, March 2006, Vol. 19, No. 1, (histamine and tryptase assays), and Arulmozhi et al., Pharmacological Investigations of *Sapindus trifoliatus* in various in vitro and in vivo models of inflammation, *Indian Journal of Pharmacology*, vol. 37:2, 96-102 (2005) (5-lipoxygenase (5-LO), cyclo-oxygenase (COX), Leukotrine B4 (LTB4) and nitric oxide synthase (NOS)).

Further, in vivo assays of inflammation may be useful in evaluating the peptides utility as a therapeutic against toxic agents. In vivo assays, including, but not limited to, murine EAE models, those utilizing transgenic mice such as MDBiosciences DSS IBD murine model of severe colitis, the MDBioscience TNBS IBD murine model of inflammatory bowel disease, models involving IL-1 knockout mice disclosed within U.S. Pat. No. 6,437,216, or models of transgenic mice involving TNF-α as disclosed within Probert et al. Spontaneous inflammatory demyelinating disease in transgenic mice showing CNS-specific expression of tumor necrosis factor α. *Proc. Natl. Acad. Sci.* 1995 USA 92, 11294-11298, Kontoyiannis et al. Impaired on/off regulation of TNF biosynthesis in mice lacking TNF AU-rich elements: implications for joint and gut-associated immunopathologies. *Immunity* 10:387-398, 1999, Keffer et al. Transgenic mice expressing human tumour necrosis factor: a predictive genetic model of arthritis. *EMBO J.* 1991 December; 10(13): 4025-31, or models using chemical or synthetic challenges to induce the inflammation such as models of asthma and chronic obstructive pulmonary disease disclosed in JPET 307:373-385, 2003, adjuvant arthritis models as disclosed in EP 1 777 234; murine LPS shock models, murine LPS lung models, acute paw inflammation models, or histidine challenge wheal formation model as disclosed in detail below.

Further, the efficacy of the compounds in humans using well-known clinical studies such as the skin prick test and bronchoprovocation test disclosed in Ravensberg et al. "Validated safety predictions of airway responses to house dust mites in asthma," *Clinical and Experimental Allergy*, 37:100-107 (2007); asthma studies as disclosed in Diamant et al. "Methods used in clinical development of novel anti-asthma therapies," *Respiratory Medicine* (2008) 102, 332-338, or nasal allergen challenge as disclosed in Boot et al. "Nasal Nitric Oxide: longitudinal reproducibility and the effects of a nasal allergen challenge in patients with allergic rhinitis," *Allergy* 2007:62:378-384.

C. Cancer.

The isolated peptides to be used within the method of the current invention may be demonstrated to inhibit tumor cell proliferation, cell transformation and tumorigenesis in vitro or in vivo using a variety of assays known in the art, or described herein. Such assays can use cells of a cancer cell line or cells from a patient. Many assays well-known in the art can be used to assess such survival and/or growth; for example, cell proliferation can be assayed by measuring $^3$H-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3 or E). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz, Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides for cell cycle and cell proliferation analysis by a variety of techniques known in the art, including but not limited to the following:

As one example, bromodeoxyuridine ("BRDU") incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, *Int. J. Cancer* 38, 369; Campana et al., 1988, *J. Immunol. Meth.* 107, 79).

Cell proliferation may also be examined using ($^3$H)-thymidine incorporation (see e.g., Chen, J., 1996, *Oncogene* 13:1395 403; Jeoung, J., 1995, *J. Biol. Chem.* 270:18367 73). This assay allows for quantitative characterization of S-phase DNA synthesis. In this assay, cells synthesizing DNA will incorporate $^3$H-thymidine into newly synthesized DNA. Incorporation may then be measured by standard techniques in the art such as by counting of radioisotope in a Scintillation counter (e.g., Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, *Curr. Biol.* 6:189 199; Vassilev et al., 1995, *J. Cell Sci.* 108:1205 15).

Cell proliferation may be measured by counting samples of a cell population over time (e.g., daily cell counts). Cells may be counted using a hemacytometer and light microscopy (e.g., HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g., cells in S-phase) will exhibit a ploidy value higher than 2N and up to 4N DNA content. Ploidy value and cell-cycle kinetics may be further measured using propidium iodide assay (see e.g., Turner, T., et al., 1998, *Prostate* 34:175 81). Alternatively, the DNA ploidy may be determined by quantitation of DNA Feulgen staining (which binds to DNA in a stoichiometric manner) on a computerized microdensitometry staining system (see e.g., Bacus, S., 1989, *Am. J. Pathol.* 135:783 92). In another embodiment, DNA content may be analyzed by preparation of a chromosomal spread (Zabalou, S., 1994, *Hereditas.* 120:127 40; Pardue, 1994, *Meth. Cell Biol.* 44:333 351).

The expression of cell-cycle proteins (e.g., CycA, CycB, CycE, CycD, cdc2, Cdk4/6, Rb, p21 or p27) provide crucial information relating to the proliferative state of a cell or population of cells. For example, identification in an anti-proliferation signaling pathway may be indicated by the induction of p21cip1. Increased levels of p21 expression in cells results in delayed entry into G1 of the cell cycle (Harper et al., 1993, *Cell* 75:805 816; Li et al., 1996, *Curr. Biol.* 6:189 199). p21 induction may be identified by immunostaining using a specific anti-p21 antibody available commercially (e.g., from Santa Cruz, Inc.). Similarly, cell-cycle proteins may be examined by Western blot analysis using commercially available antibodies. In another embodiment, cell populations are synchronized prior to detection of a cell cycle protein. Cell-cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by a peptide of the Invention. In one embodiment the length of the cell cycle is determined by the doubling time of a population of cells (e.g., using cells contacted or not contacted with one or more peptide of the Invention). In another embodiment, FACS analysis is used to analyze the phase of cell cycle progression, or purify G1, S, and G2/M fractions (see e.g., Delia, D. et al., 1997, *Oncogene* 14:2137 47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, *Genetics*, 134:63 80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved detected post-translational modifications (e.g., phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, *Biochem. J.* 250:485 91; Paige, L., 1988, *Biochem J.;* 250:485 91).

Activity of signaling and cell cycle proteins and/or protein complexes is often mediated by a kinase activity. The present invention provides for analysis of kinase activity by assays such as the histone H1 assay (see e.g., Delia, D. et al., 1997, *Oncogene* 14:213747).

The peptides used within the method of the Invention can also be demonstrated to alter cell proliferation in cultured cells in vitro using methods which are well known in the art. Specific examples of cell culture models include, but are not limited to, for lung cancer, primary rat lung tumor cells (Swafford et al., 1997, *Mol. Cell. Biol.*, 17:1366 1374) and large-cell undifferentiated cancer cell lines (Mabry et al., 1991, *Cancer Cells*, 3:53 58); colorectal cell lines for colon cancer (Park and Gazdar, 1996, *J. Cell Biochem. Suppl.* 24:131 141); multiple established cell lines for breast cancer (Hambly et al., 1997, *Breast Cancer Res. Treat.* 43:247 258; Gierthy et al., 1997, *Chemosphere* 34:1495 1505; Prasad and Church, 1997, *Biochem. Biophys. Res. Commun.* 232:14 19); a number of well-characterized cell models for prostate cancer (Webber et al., 1996, *Prostate*, Part 1, 29:386 394; Part 2, 30:58 64; and Part 3, 30:136 142; Boulikas, 1997, *Anticancer Res.* 17:1471 1505); for genitourinary cancers, continuous human bladder cancer cell lines (Ribeiro et al., 1997, *Int. J. Radiat. Biol.* 72:11 20); organ cultures of transitional cell carcinomas (Booth et al., 1997, *Lab Invest.* 76:843 857) and rat progression models (Vet et al., 1997, *Biochim. Biophys Acta* 1360:39 44); and established cell lines for leukemias and lymphomas (Drexler, 1994, *Leuk. Res.* 18:919 927, Tohyama, 1997, *Int. J. Hematol.* 65:309 317).

The peptides of the Invention can also be demonstrated to inhibit cell transformation (or progression to malignant phenotype) in vitro. In this embodiment, cells with a transformed cell phenotype are contacted with one or more peptides of the Invention, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, General Virology, 3d Ed., John Wiley & Sons, New York, pp. 436446).

Loss of invasiveness or decreased adhesion may also be used to demonstrate the anti-cancer effects of the peptides used in the method of the Invention. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464 66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464 66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun. 193:518 25).

The peptides used in the method of the Invention can also be demonstrated to inhibit tumor formation in vivo. A vast number of animal models of hyperproliferative disorders, including tumorigenesis and metastatic spread, are known in the art (see Table 317-1, Chapter 317, "Principles of Neoplasia," in Harrison's Principles of Internal Medicine, 13th Edition, Isselbacher et al., eds., McGraw-Hill, N.Y., p. 1814, and Lovejoy et al., 1997, J. Pathol. 181:130 135). Specific examples include for lung cancer, transplantation of tumor nodules into rats (Wang et al., 1997, Ann. Thorac. Surg. 64:216 219) or establishment of lung cancer metastases in SCID mice depleted of NK cells (Yono and Sone, 1997, Gan To Kagaku Ryoho 24:489 494); for colon cancer, colon cancer transplantation of human colon cancer cells into nude mice (Gutman and Fidler, 1995, World J. Surg. 19:226 234), the cotton top tamarin model of human ulcerative colitis (Warren, 1996, Aliment. Pharmacol. Ther. 10 Supp 12:45 47) and mouse models with mutations of the adenomatous polyposis tumor suppressor (Polakis, 1997, Biochim. Biophys. Acta 1332:F127 F147); for breast cancer, transgenic models of breast cancer (Dankort and Muller, 1996, Cancer Treat. Res. 83:71 88; Amundadittir et al., 1996, Breast Cancer Res. Treat. 39:119 135) and chemical induction of tumors in rats (Russo and Russo, 1996, Breast Cancer Res. Treat. 39:7-20); for prostate cancer, chemically-induced and transgenic rodent models, and human xenograft models (Royai et al., 1996, Semin. Oncol. 23:35 40); for genitourinary cancers, induced bladder neoplasm in rats and mice (Oyasu, 1995, Food Chem. Toxicol 33:747 755) and xenografts of human transitional cell carcinomas into nude rats (Jarrett et al., 1995, J. Endourol. 9:1 7); and for hematopoietic cancers, transplanted allogeneic marrow in animals (Appelbaum, 1997, Leukemia 11 (Suppl. 4):S15 S17). Further, general animal models applicable to many types of cancer have been described, including, but not restricted to, the p53-deficient mouse model (Donehower, 1996, Semin. Cancer Biol. 7:269 278), the Min mouse (Shoemaker et al., 1997, Biochem. Biophys. Acta, 1332:F25 F48), and immune responses to tumors in rat (Frey, 1997, Methods, 12:173 188).

For example, a peptide to be used in the method of the Invention can be administered to a test animal, in one embodiment a test animal predisposed to develop a type of tumor, and the test animal subsequently examined for a decreased incidence of tumor formation in comparison with an animal not administered the peptide of the Invention. Alternatively, a peptide of the Invention can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the peptide of the Invention.

8. THERAPEUTIC USE

A. Modulation of Mediators of the Body's Response

One of ordinary skill in the art would recognize that the peptides of the current invention may be used to modulate the effects of the body's response to a disease or disorder associated with tissue damage. In particular, one example of mediators the peptides noted above may be used to modulate are inflammatory modulators, including but not limited to, plasma derived inflammatory mediators, such as bradykinins, C3, C5a, Factor XII, membrane attack complex, Hageman factor, plasmin, thrombin, lymphokines (macrophage activating factor (MAF), macrophage migration inhibition factor (MMIF), macrophage chemotactic factor (MCF), leukocyte migration inhibition factor (LMIF), histamine releasing factors (HRFs), and transfer factor (TF)); interleukins (IL-1, IL-2, IL-3, IL-4, . . . IL-15); Tumor necrosis factors (TNF-α (cachectin), TNF-β (lymphotoxin)); Interferons (IFN-α, IFN-β, IFN-γ, IFN-ω, IFN-τ); Colony stimulating factors (granulocyte colony stimulating factor (G-CSF), granulocyte-macrophage colony stimulating factor (GM-CSF), macrophage colony stimulating factor (M-CSF), and multi colony stimulating factor (IL-3)); polypeptide growth factors (acidic fibroblast growth factor (aFGF), basic fibroblast growth factor (bFGF), epidermal growth factor (EGF); nerve growth factor (NGF), platelet-derived growth factor (PDGF), and vascular endothelial growth factor (VEGF)); Transforming growth factors (TGF-α and TGF-β), α-Chemokines (IL-8, neutrophil-activating protein 2 (NAP-2), platelet factor-4 (PF-4), and β-thromboglobulin (βTG)); β-Chemokines (monocyte chemoattractant protein 1 (MCP-1), MCP-3, MIP-1α, macrophage inflammatory protein 1β (MIP-1β), regulated upon activation normal T expressed and presumably secreted chemokine (RANTES)) and Stress proteins (heat shock proteins (HSPs), glucose related proteins (GSPs), ubiquitin, and superoxide dismutase (Mn)), leukemia inhibitory factor (LIF), oncostatin (OSM), ciliary neurotrophic factor (CNTF), platelet basic protein (PBP), lysosome granules, histamine, serotonin, leukotriene B4, nitric oxide, and/or prostaglandins. In a preferred embodiment the peptides inhibit or suppress the activity of the mediators and more preferably inhibit the activity of TNF-α, histamine, nitric oxide, and interleukins. Most preferably, the peptides inhibit the activity of two or more inflammatory mediators.

B. Treatment or Prevention of Various Diseases, Disorders, and Conditions

The tissue protective peptides and peptide analogs of the current invention are also useful as therapeutics for treatment or prevention of various diseases, disorders, and conditions. One skilled in the art would also recognize that such peptides and peptide analogs can be used to achieve modulation of a tissue protective receptor complex, e.g., tissue protective cytokine complex. Both in vitro and in vivo techniques that can be used for assessing the therapeutic indications of, for example, the compounds identified by the inventive assays disclosed above are disclosed in PCT Application No. PCT/US01/49479, U.S. patent application Ser. Nos. 10/188,905 and 10/185,841.

The aforementioned tissue protective peptides and peptide analogs of the invention may be useful generally for the prevention, therapeutic treatment, or prophylactic treatment of human diseases or disorders of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, connective tissue diseases, gastrointestinal diseases and endocrine and metabolic abnormalities. Examples of use include, but are not limited to, protection against and repair of injury resulting from trauma and resulting inflammation to the brain (ischemic stroke, blunt trauma, subarachnoid hemorrhage), spinal cord (ischemia, blunt force trauma), peripheral nerves (sciatic nerve injury, diabetic neuropathy, carpal tunnel syndrome), retinal (macular edema, diabetic retinopathy, glaucoma), and heart (myocardial infarct, chronic heart failure). In particular, such diseases, disorders, and conditions include hypoxic conditions, which adversely affect responsive tissues, such as excitable tissues including, but not limited to, those noted above in Section 4.2 (xiii), or those responsive cells tissues or organs, those that express the appropriate Type-1 cytokine receptor, e.g., EPO-R receptor or the tissue protective receptor complex. Therefore, the tissue protective peptides and peptide analogs of the invention can be used to treat or prevent damage to responsive tissue resulting from hypoxic conditions in a variety of conditions and circumstances. Non-limiting examples of such conditions and circumstances are provided in the table herein below.

The tissue protective peptides and peptide analogs are also of interest in the modulation of stem cell activity. It has been established that cytokines exhibiting tissue protective activity, e.g. EPO, are able to mobilize stem cells, stimulating the migration to regions of injury and aiding the repair process, e.g. in a regenerative role. For example, in experimental stroke, EPO mediates the migration of neuroblasts into a region of ischemic injury to regenerate neurons during the period of recovery (Tsai et al, *J. Neurosci* (2006) 26:1269-74). As another example, EPO and carbamylated EPO (CEPO) mobilize endothelial progenitor cells from the bone marrow into the circulation. These cells then home to distance regions and are involved in the formation of new blood vessels (for effect of EPO, see, Bahlmann et al, 2003, *Kidney Int.* 64:1648-1652). While not wishing to be bound to any particular theory, the isolated peptides and peptide analogs disclosed herein are believed to have a similar effect on the migration of stem cells.

In the example of the protection of neuronal tissue pathologies treatable and preventable using tissue protective peptides and peptide analogs of the invention, such pathologies include those which result from reduced oxygenation of neuronal tissues. Any condition which reduces the availability of oxygen to neuronal tissue, resulting in stress, damage, and finally, neuronal cell death, can be treated using tissue protective peptides and peptide analogs of the present invention. Generally referred to as hypoxia and/or ischemia, these conditions arise from or include, but are not limited to, stroke, vascular occlusion, prenatal or postnatal oxygen deprivation, suffocation, choking, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmia, nitrogen narcosis, hypoxemic hypoxia (altitude sickness, high altitude pulmonary edema, high altitude cerebral edema, sleep apnea, hypopnea, respiratory arrest, shunts), methaemoglobinaemia, histotoxic hypoxia, intrauterine hypoxia, and neurological deficits caused by heart-lung bypass procedures.

In one embodiment, for example, the tissue protective peptides and peptide analogs of the present invention identified using the above-noted assays could be administered alone or as part of a composition to prevent injury or tissue damage resulting from risk of injury or tissue damage prior to, during, or subsequent to a surgical procedure or a medical procedure. For example, surgical procedures may include tumor resection or aneurysm repair and medical procedures may include labor or delivery. Other pathologies caused by or resulting from hypoglycemia which are treatable using tissue protective peptides and peptide analogs of the present invention include insulin overdose, also referred to as iatrogenic hyperinsulinemia, insulinoma, growth hormone deficiency, hypocortisolism, drug overdose, and certain tumors.

Other pathologies resulting from excitable neuronal tissue damage include seizure disorders, such as epilepsy, convulsions, or chronic seizure disorders. Other treatable conditions and diseases include, but are not limited to, diseases such as stroke, multiple sclerosis, hypotension, cardiac arrest, chronic heart failure, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, optic nerve damage resulting from glaucoma, and neuronal loss.

The specific tissue protective peptides and peptide analogs of the present invention may be used to treat or prevent inflammation resulting from disease conditions or various traumas, such as physically or chemically induced inflammation. The tissue protective peptides and peptide analogs are also contemplated for the treatment and prevention of inflammatory conditions in one or more organs or tissues including, but not limited to, the brain, spinal cord, connective tissue, heart, lung, kidney and urinary tract, pancreas, eyes and prostate. Non-limiting examples of such trauma include, but are not limited to those listed in Section 4.2 (xvi). Further the tissue protective peptides may used to treat or prevent inflammation resulting from ischemic and non-ischemic conditions including, but not limited to, allergies, allergic diseases, allergic symptoms, rheumatic diseases, sports related injuries, exposure to toxic agents, infections including viral, fungal, and bacterial, further examples of such conditions are disclosed above in Section 4.2(iv), (v) and (xvi). The inflammation may be acute or chronic. Further applications in the field of inflammation are noted within PCT/US2004/031789 filed Sep. 29, 2004 and published as WO 2005/032467.

The specific tissue protective peptides and peptide analogs of the present invention may be used to treat central nervous and peripheral nervous system diseases resulting from demyelination or impairment of the mylin sheath. These diseases are defined as mainly involving inflammatory myelin sheath lesions of unknown origin, with the exception of myelination deficiency diseases, such as leukodystrophy, and diseases due to obvious causes. Multiple sclerosis (MS) is a typical disease among demyelinating diseases, and pathologically, it is characterized by changes, mainly, inflammatory demyelination, and gliosis. Since its etiology is unknown, its diagnosis is made based on its clinical features, i.e., spatial multiplicity and multiplicity over time of central nervous system lesions. Furthermore, acute disseminated encephalomyelitis (ADEM), inflammatory diffuse sclerosis, acute and subacute necrotizing hemorrhagic encephalomyelitis, and transverse myelitis are included in demyelinating diseases. Also, peripheral nervous tissues rely upon Schwann cells to maintain the myelin sheath, if these cells are impaired, peripheral demyelinating disease is caused.

The tissue protective peptides and peptide analogs of the present invention may be used to treat or prevent conditions of, and damage to the heart including any chronic or acute pathological event involving the heart and/or associated tissue (e.g., the pericardium, aorta and other associated blood vessels), including ischemia-reperfusion injury; congestive heart failure; cardiac arrest; myocardial infarction; atherosclerosis, mitral valve leakage, atrial flutter, cardiotoxicity caused by compounds such as drugs (e.g., doxorubicin, herceptin, thioridazine and cisapride); cardiac damage due to parasitic infection (bacteria, fungi, rickettsiae, and viruses, e.g., syphilis, chronic Trypanosoma cruzi infection); fulminant cardiac amyloidosis; heart surgery; heart transplantation; angioplasty, laparoscopic surgery, traumatic cardiac injury (e.g., penetrating or blunt cardiac injury, and aortic valve rupture), surgical repair of a thoracic aortic aneurysm; a suprarenal aortic aneurysm; cardiogenic shock due to myocardial infarction or cardiac failure; neurogenic shock and anaphylaxis. The tissue protective peptides and peptide analogs of the current invention may also be used to treat those individuals at risk for heart disease such as cardiac failure (i.e., where the heart is not able to pump blood at a rate required by the metabolizing tissues, or when the heart can do so only with an elevated filling pressure). Such at risk patients would include patients having or being at risk of having cardiac infarction, coronary artery disease, myocarditis, chemotherapy, cardiomyopathy, hypertension, valvular heart diseases (most often mitral insufficiency and aortic stenosis) and toxin-induced cardiomyopathy (e.g. ethanol, cocaine, etc.) and the like.

The tissue protective peptides and peptide analogs of the present invention may be used to treat or prevent conditions of, and damage to, the eyes, e.g., retinal tissue. Such disorders include, but are not limited to retinal ischemia, macular degeneration, retinal detachment, retinitis pigmentosa, arteriosclerotic retinopathy, hypertensive retinopathy, retinal artery blockage, retinal vein blockage, retinal edema, hypotension, and diabetic retinopathy.

In another embodiment, the tissue protective peptides and peptide analogs of the present invention and principles of the invention may be used to prevent or treat injury resulting from exposure to toxic agents, i.e. radiation or chemical damage to responsive tissue. In one embodiment of the invention the above-noted peptides are useful as therapeutics for modulating the mediators of the body's response to toxic agents, preferably to suppress or inhibit the activity of such modulators. Additionally, the above-noted peptides are useful as therapeutics for the treatment, prevention, amelioration or management of damage, effects or symptoms of exposure to a toxic agent. The peptides may be used to treat exposure to various toxic agents, including biological, chemical or radiation agents.

These peptides may be used to treat the damages, effects, or symptoms due to biological agents such as of prions, viruses, microorganisms (bacteria and fungi), and some unicellular and multicellular eukaryotes (i.e., parasites), including, but not limited to, those biological toxins listed above in Section 4.2 (viii). Further the peptides of the current invention may be used to prevent, treat, ameliorate, or manage the damage, effects or symptoms due to chemical agents. Such agents include, but are not limited to, blood agents, blister agents, nerve agents, pulmonary agents, and incapacitating agents. Additionally, the peptides of the current invention may be used to prevent, treat, ameliorate or manage damage, effects or symptoms due to toxic exposure to industrial chemicals including but not limited to those listed in Section 4.2 (x). Damage, effects or symptoms due to exposure to a radiation agent are preventable, treatable, or manageable using the peptides of the current invention. The peptides can prevent, treat, ameliorate, or manage the damage, effects or symptoms due to radioactive agents that include alpha, beta or gamma radiation, and more particularly may include, but are not limited to, $^{137}$Cs, $^{60}$Co, $^{241}$Am, $^{252}$Cf, $^{192}$Ir, $^{238}$Pu, $^{90}$Sr, $^{226}$Ra, $^{91}$Sr, $^{92}$Sr, $^{95}$Zr, $^{99}$Mo, $^{106}$Ru, $^{131}$Sb, $^{132}$Te, $^{139}$Te, $^{140}$Ba, $^{141}$La, $^{144}$Ce, $^{233}$U, $^{235}$U, $^{238}$U, $^{228}$P, $^{229}$P, $^{230}$P, $^{231}$P, $^{232}$P, $^{233}$P, $^{234}$P, $^{235}$P, $^{236}$P, $^{237}$P, $^{238}$P, $^{239}$P, $^{240}$P, $^{241}$P, $^{242}$P, $^{243}$P, $^{244}$P, $^{245}$P, $^{246}$P, $^{247}$P, and $^{131}$I. Further, one of ordinary skill in the art will recognize that the peptides may also be used to prevent, mediate, treat or ameliorate the damages, effects or symptoms due to the cumulative or synergistic use of these toxic agents (i.e., the use of a radioactive agent prior to dispersing a biological agent so that the victim's will be more susceptible to the biological agent, administering a vesicant agent in conjunction with a nerve agent to prevent the victims from effectively seeking refuge or aid, tainting bullets or shrapnel with biological or radioactive agents to inhibit or complicate the healing process, etc.) Preferably, peptides of the current invention will be able to treat, mediate, ameliorate or prevent toxic effects on several different types of cells, organs, or tissues for example in two or more of the following central nervous, peripheral nervous, ophthalmic, cardiovascular, cardiopulmonary, respiratory, kidney, urinary, reproductive, musculoskeletal, skin, connective tissue, gastrointestinal, hematopoietic, endocrine, and metabolic. Further, a peptide of the current invention would be effective as a therapeutic or preventive for more than one toxic agent within the same class (i.e., against more than one type of chemical, biological or radioactive agent a preventive against a vesicant and nerve agents for example) or different classes of toxic agents (i.e. a therapeutic for exposure to a radioactive agent and a chemical agent). A further utility of the tissue protective peptides and peptide analogs of the present invention is in the treatment of poisoning, such as neurotoxin poisoning (e.g., domoic acid shellfish poisoning), toxins (ethanol, cocaine, etc.), as the result of chemotherapeutic agents of radiation exposure; neurolathyrism; Guam disease; amyotrophic lateral sclerosis; and Parkinson's disease.

As mentioned above, the present invention also provides tissue protective peptides and peptide analogs of the present invention for use in enhancing tissue function in responsive cells, tissues and organs in a mammal by peripheral administration of a tissue protective peptide as described above. Various diseases and conditions are amenable to treatment using this method. For example this method is useful for enhancing function in excitable tissues resulting in an increase in cognitive function even in the absence of any condition or disease. Further, the tissue protective cytokines are useful for improving the quality of wound healing, reducing the time required to heal, improving the quality of the healed tissues and reducing the incidence of adhesions resulting from the wound. See PCT/US2004/031789 filed Sep. 29, 2004 and published as WO 2005/032467. Further the tissue protective peptides of the current invention may be useful in treating, preventing or managing the lesions on the skin or along the respiratory pathways induced by chemical agents such as blistering or vessicant agents or industrial chemicals.

These uses of the peptides of the present invention are describe in further detail below and include enhancement of learning and training in both human and non-human mammals.

In another embodiment, the tissue protective peptides and peptide analogs of the present invention may be useful generally for the prevention, therapeutic treatment, prophylactic treatment or management of various cancers or neoplastic disorders of the central nervous system, peripheral nervous system, gastrointestinal/digestive system, genitourinary system, adrenal, gynecological, head and neck, hematological/blood, musculoskeletal/soft tissue, respiratory, and breast. Examples of use include, but are not limited to, protection against and repair of injury resulting from cancers or neoplastic disorders listed in section 4.2(ix) and (xxv). Further the peptides of the current invention may be used for the prevention, therapeutic treatment, prophylactic treatment or management of various syndromes associated with neoplasms or cancers, including, but not limited to those listed above in Section 4.2 (xxviii). The peptides may be used in accordance with the method of the current invention to address the above-noted syndromes. For example, the peptides may be administered to address hereditary syndromes such as Li Fraumeni, hereditary nonpolyposis colorectal cancer, familial adenomatous polyposis, and Von Hippel-Lindau syndrome by either delaying the onset of the neoplastic aspects of the disease, reducing the number of neoplastic growths associated with the syndrome, or in general enhancing the quality of life or the longevity of those patients afflicted with these conditions. The peptides may also be administered prophylactically to address syndromes related to certain treatment, chemotherapy or radiation therapy, of the neoplastic disorder or cancer, such as androgen deprivation syndrome, therapy related myelodysplastic syndrome or somnolence syndrome, in the hopes of preventing the syndromes or reducing the severity of the syndrome.

Further, the peptides may be used to treat or prevent cachexia and diseases related to cachexia. Such diseases include, but are not limited to cancer cachexia, anorexia, asthenia, anemia, tuberculosis, AIDS, congestive heart failure, renal failure, liver failure, chronic obstructive pulmonary disease, emphysema, muscle atrophy, diabetes, and endotoxinemia.

Conditions and diseases treatable or preventable using tissue protective peptides and peptide analogs of the present invention provides the central nervous system include but are not limited to mood disorders, anxiety disorders, depression, autism, attention deficit hyperactivity disorder, and cognitive dysfunction. These conditions benefit from enhancement of neuronal function. Other disorders treatable in accordance with the teachings of the present invention include sleep disruption, for example, sleep apnea and travel-related disorders; subarachnoid and aneurismal bleeds, hypotensive shock, concussive injury, septic shock, anaphylactic shock, and sequelae of various encephalitides and meningitides, for example, connective tissue disease-related cerebritides such as lupus. Other uses include prevention of or protection from poisoning by neurotoxins, such as domoic acid shellfish poisoning, neurolathyrism, and Guam disease, amyotrophic lateral sclerosis, Parkinson's disease; postoperative treatment for embolic or ischemic injury; whole brain irradiation; sickle cell crisis; and eclampsia.

A further group of conditions treatable or preventable using tissue protective peptides and peptide analogs of the present invention include mitochondrial dysfunction, of either a hereditary or acquired nature, which are the cause of a variety of neurological diseases typified by neuronal injury and death. For example, Leigh disease (subacute necrotizing encephalopathy) is characterized by progressive visual loss and encephalopathy, due to neuronal drop out, and myopathy. In these cases, defective mitochondrial metabolism fails to supply enough high energy substrates to fuel the metabolism of excitable cells. A tissue protective peptide or peptide analog optimizes failing function in a variety of mitochondrial diseases. As mentioned above, hypoxic conditions adversely affect excitable tissues. The excitable tissues include, but are not limited to, neuronal tissues such as tissue of the peripheral nervous system (ear and retina) and central nervous system (brain and spinal cord); cardiovascular tissue such as the cells of the heart and associated nerves; and glandular tissue such as the pancreas where T-type calcium channels along with cell-to-cell gap junctions participate in secretion of insulin. An exemplary list of excitable tissue includes, but is not limited to, organs and tissues that include nerves, skeletal muscle, smooth muscle, cardiac muscle, uterus, central nervous system, spinal cord, brain, retina, olfactory system, and auditory system. In addition to the conditions described above, the tissue protective peptides and peptide analogs of the present invention are useful in the treatment of inhalation poisoning such as carbon monoxide and smoke inhalation, severe asthma, adult respiratory distress syndrome, and choking and near drowning. Further conditions which create hypoxic conditions or by other means induce responsive tissue, such as excitable tissue damage include hypoglycemia that may occur in inappropriate dosing of insulin, or with insulin-producing neoplasms (insulinoma).

Various neuropsychologic disorders which are described to originate from excitable tissue damage are treatable using tissue protective peptides and peptide analogs of the present invention. Chronic disorders in which neuronal damage is involved and for which treatment or preventable by the present invention include disorders relating to the central nervous system and/or peripheral nervous system including age-related loss of cognitive function and senile dementia, chronic seizure disorders, Alzheimer's disease, Parkinson's disease, dementia, memory loss, amyotrophic lateral sclerosis, multiple sclerosis, tuberous sclerosis, Wilson's disease, cerebral and progressive supranuclear palsy, Guam disease, Lewy body dementia, prion diseases, such as spongiform encephalopathies, e.g., Creutzfeldt-Jakob disease, Huntington's disease, myotonic dystrophy, Freidrich's ataxia and other ataxias, as well as Gilles de La Tourette's syndrome, seizure disorders such as epilepsy and chronic seizure disorder, stroke, brain or spinal cord trauma, AIDS dementia, alcoholism, autism, retinal ischemia, glaucoma, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as unipolar and bipolar affective disorders. Additional neuropsychiatric and neurodegenerative disorders include, for example, those listed in the American Psychiatric Association's Diagnostic and Statistical Manual of Mental Disorders (DSM).

A further group of conditions treatable or preventable using tissue protective peptides and peptide analogs of the present invention include kidney diseases such as renal failure, acute and chronic. Blood supply to the kidneys can be cut off due to several causes including shock from infections invading the bloodstream (septicemia), internal or external hemorrhaging, loss of fluid from the body as a result of severe diarrhea or burns, reactions to transfusions, cardiac arrest or arythmias, surgical trauma and kidney transplantations. The reduced flow of blood to the kidneys resulting from the above conditions may reduced blood flow to dangerously low levels for a time period great enough to cause the development of acute renal failure. The depressed blood flow also results in necrosis, or tissue death, in the kidney, damaging the renal tubular cells. Renal failure may also result from diseases (interstitial and diabetic) nephrotic syndromes, infections, injury (CPB-induced), toxins (contrast-induced, chemotherapy-induced, cyclosporine), autoimmune inflammation (e.g. Lupus, erythrocytosis, etc.) The tissue protective peptides and peptide analogs of the current invention assist in the repair or prevention of this damage helping to ameliorate acute renal failure. Further, the peptides of the current invention may be used to treat, prevent or ameliorate diseases or disorders of the urinary tract including, but not limited, urinary tract infections, irritable bladder, and trauma or radiation injury to the bladder.

The following table lists additional exemplary, non-limiting indications as to the various conditions and diseases amenable to treatment by the aforementioned tissue protective peptides and peptide analogs.

TABLE I

DISEASES AND DISORDERS AMENABLE TO TREATMENT BY TISSUE PROTECTIVE PEPTIDES AND PEPTIDE ANALOGS

| Cell, tissue, or organ | Dysfunction or pathology | Condition or disease | Type |
| --- | --- | --- | --- |
| Heart | Ischemia | Coronary artery disease | Acute, chronic Stable, unstable |
| | | Myocardial infarction | Dressler's syndrome |
| | | Angina | |
| | | Congenital heart disease | Valvular Cardiomyopathy |
| | | Prinzmetal angina | |
| | | Cardiac rupture | Aneurysmatic |
| | | Angiitis | |
| | Arrhythmia | Tachy-, bradyarrhythmia | Stable, unstable Hypersensitive |
| | | Supraventricular, ventricular Conduction abnormalities | carotid sinus node |
| | Congestive heart failure | Left, right, bi-ventricular, systolic, diastolic | Cardiomyopathies, such as idiopathic familial, infective, metabolic, storage disease, deficiencies, connective tissue disorder, infiltration and granulomas, neurovascular |
| | | Myocarditis and pericarditis | Autoimmune, infective, idiopathic |
| | | Cor pulmonale | |
| | Radiation injury | | |
| | Blunt and penetrating trauma | Intrathoracal adhesions to surgery, infections, or inflammation | |
| | Toxins | Cocaine toxicity, adriamycin, heavy metals (cobalt) | |
| Vascular | Hypertension | Primary, secondary | |
| | Decompression sickness | | |
| | Fibromuscular hyperplasia | | |
| | Aneurysm | Dissecting, ruptured, enlarging | |
| | Cancer | Hemangioma hemangiopericytoma | Hemangiosarcoma, angiosarcoma |

TABLE I-continued

DISEASES AND DISORDERS AMENABLE TO TREATMENT BY
TISSUE PROTECTIVE PEPTIDES AND PEPTIDE ANALOGS

| Cell, tissue, or organ | Dysfunction or pathology | Condition or disease | Type |
|---|---|---|---|
| Lungs | Obstructive | Asthma<br>Chronic bronchitis,<br>Emphysema and<br>airway obstruction | |
| | Ischemic lung disease | Pulmonary embolism,<br>Pulmonary thrombosis,<br>Fat embolism | |
| | Environmental lung diseases | | |
| | Interstitial lung disease | Idiopathic pulmonary fibrosis | |
| | Congenital | Cystic fibrosis | |
| | Cor pulmonale | | |
| | Trauma | | |
| | Pneumonia and pneumonitides | Infectious (including Avian Flu), parasitic, toxic, traumatic, burn, aspiration | |
| | Sarcoidosis | | |
| | Cancers and precancers | | Bronchial carcinooid, oat cell carcinoma |
| | Radiation injury | | |
| Pancreas | Endocrine | Diabetes mellitus, type I and II | Beta cell failure, dysfunction<br>Diabetic neuropathy |
| | | Other endocrine cell failure of the pancreas | |
| | Exocrine | Exocrine pancreas failure | Pancreatitis |
| | Cancer and precancers | Islet cell adenoma, Insulinoma, gastrinoma | Islet Cell Carcinoma |
| Bone | Osteopenia | Primary<br>Secondary | Hypogonadism<br>Immobilization<br>Postmenopausal<br>Age-related<br>Hyperparathyroidism<br>Hyperthyroidism<br>Calcium, magnesium, phosphorus, and/or vitamin D deficiency |
| | Osteomyelitis | | |
| | Avascular necrosis | | |
| | Trauma | | |
| | Paget's disease | | |
| | Cancer | Osteoma | Osteosarcoma |
| Skin | Alopecia | Areata<br>Totalis | Primary<br>Secondary<br>Male pattern baldness |
| | Vitiligo | Localized<br>Generalized | Primary<br>Secondary |
| | Ulceration | Diabetic<br>Decubitus<br>Ischemia | Pressure sores, pressure ulcers, bed sores |
| | Peripheral vascular disease | Infection, self amputation | |
| | Surgical wounds, lacerations | | |
| | Burn injuries | | |
| | Radiation injuries | Cutaneous radiation syndrome | |
| | Cancers and precancers | Nevus, papilloma, seborrheic keratosis, skin adnexal tumors | Melanoma, squamous cell carcinoma, epidermoid carcinoma, basal cell carcinoma and malignant skin adnexal tumors |
| Autoimmune disorders | Lupus erythematosus, Sjogren's syndrome, Rheumatoid arthritis, Glomerulonephritis, Angiitis, Fibromyalgia, Ankylosing spondylitis Langerhans' histiocytosis | | |

TABLE I-continued

DISEASES AND DISORDERS AMENABLE TO TREATMENT BY
TISSUE PROTECTIVE PEPTIDES AND PEPTIDE ANALOGS

| Cell, tissue, or organ | Dysfunction or pathology | Condition or disease | Type |
|---|---|---|---|
| Eye | Optic neuritis | | |
| | Blunt and penetrating injuries, surgical wounds, infections, Sarcoid, Sickle C disease, Retinal detachment, Temporal arteritis | | |
| | Retinal ischemia, Macular degeneration, Retinitis pigmentosa, Arteriosclerotic retinopathy, Hypertensive retinopathy, Retinal artery blockage, Retinal vein blockage, Hypotension, Diabetic retinopathy, glaucoma and Macular edema | | |
| Embryonic and fetal disorders | Asphyxia | | |
| | Ischemia | | |
| | Cancers and precancers | Myxoma, hydatidiform mole | Myxosarcoma, chordoma, choriocarcinoma |
| CNS | Chronic fatigue syndrome, acute and chronic hypo-osmolar and hyperosmolar syndromes, AIDS Dementia, Electrocution | | |
| | Cerebral malaria | | |
| | Encephalitis | Rabies, Herpes | |
| | Meningitis | | |
| | Subdural hematoma | | |
| | Nicotine addiction | | |
| | Drug abuse and withdrawal | Cocaine, heroin, crack, marijuana, LSD, PCP, poly-drug abuse, ecstasy, opioids, sedative hypnotics, amphetamines, caffeine, alcohol | |
| | Obsessive-compulsive disorders | | |
| | Psychotic and depressive disorders | | |
| | Attention deficit and hyperactivity disorders | | |
| | Spinal stenosis, Transverse myelitis, Guillian Barré, Traumatic injury to peripheral nerves, spinal cord, or brain, Nerve root compression, Compression by tumor or vascular malformations, Heat stroke | | |
| | Cancers and precancers | Ganglioneuroma, meningioma, schwannoma, neurilemmoma | Glioma (grades I-III), anaplastic, glioblastoma multiforme (Grade IV), neuroblastoma, medulloblastoma, malignant meningioma, malignant schwannoma |
| ENT | Tinnitus | | |
| | Meunière's syndrome | | |
| | Hearing loss | | |
| | Traumatic injury, barotraumas | | |

TABLE I-continued

DISEASES AND DISORDERS AMENABLE TO TREATMENT BY
TISSUE PROTECTIVE PEPTIDES AND PEPTIDE ANALOGS

| Cell, tissue, or organ | Dysfunction or pathology | Condition or disease | Type |
|---|---|---|---|
| Kidney | Renal failure | Acute, chronic | Vascular/ischemic, interstitial disease, diabetic kidney disease, nephritic syndromes, infections, injury, contrast-induced, chemotherapy-induced, cyclosporine, radiation-induced Cardio Pulmonary Bypass-induced |
|  | Radiation injury |  |  |
|  | Henoch Schönlein purpura |  |  |
|  | Cancers or precancers | Renal Tubular adenoma | Renal Cell Carcinoma, hypernephroma |
| Striated muscle | Autoimmune disorders | Myasthenia gravis Dermatomyositis Polymyositis |  |
|  | Myopathies | Inherited metabolic, endocrine and toxic |  |
|  | Heat stroke |  |  |
|  | Crush injury |  |  |
|  | Rhabdomyolysis |  |  |
|  | Mitochondrial disease |  |  |
|  | Infection | Necrotizing fasciitis |  |
|  | Cancers or precancers | Rhabdomyoma | Rhabdomyosarcoma |
| Sexual dysfunction | Central and peripheral (e.g. erectile dysfunction) | Impotence secondary to medication, (diabetes) |  |
| Liver | Hepatitis | Viral, bacterial, parasitic |  |
|  | Ischemic disease |  |  |
|  | Cirrhosis, fatty liver |  |  |
|  | Infiltrative/metabolic diseases |  |  |
|  | Cancers or precancers | Hepatic adenoma | Hepatoma: Hepatocellular carcinoma |
| Gastrointestinal | Ischemic bowel disease |  |  |
|  | Inflammatory bowel disease |  |  |
|  | Necrotizing enterocolitis |  |  |
|  | Wound healing post surgical or perforation | abdominal adhesions due to surgery or infections |  |
|  | Cancers or precancers | Carcinoid | Malignant Carcinoid |
| Organ transplantation | Treatment of donor, organ and recipient | Transplant rejection, graft rejection, delayed graft function, graft v. host disease |  |
|  | Growth of cell or tissue cultures for tissue regeration, graft or transplantation |  |  |
| Reproductive tract | Infertility | Vascular Autoimmune Uterine abnormalities Implantation disorders |  |
|  | Cancers or precancers |  | Seminoma, dysgerminoma, choriocarcinoma, embryonal carcinoma, endodermal sinus tumor, teratocarcinoma, |

TABLE I-continued

DISEASES AND DISORDERS AMENABLE TO TREATMENT BY
TISSUE PROTECTIVE PEPTIDES AND PEPTIDE ANALOGS

| Cell, tissue, or organ | Dysfunction or pathology | Condition or disease | Type |
|---|---|---|---|
| | | | Seroli-Leydig tumors, arrhenoblastoma, granulosetheca cell tumors, hilar cell tumors, lipid cell tumors |
| Endocrine | Glandular hyper- and hypofunction | | |
| | Cancers or precancers | Basophilic adenoma, Eosinophilic adenoma, Chromophobe adenoma, Parathyroid adenoma, C cell hyperplasia, Pheochromocytoma | Parathyroid carcinoma, Medullary carcinoma of thyroid, Malignant Pheochromocytoma |
| General | Shock | Septic, hemodynamic | |
| | Cachexia, Cancer Cachexia | Anorexia, Asthenia, Anemia | |
| | Parasitemia | Malaria, trypanosomiasis, Leshmaniasis | |

As mentioned above, these diseases, disorders or conditions are merely illustrative of the range of benefits provided by the tissue protective peptides and peptide analogs of the present invention. Accordingly, this invention generally provides preventative, therapeutic, or prophylactic treatment of the consequences of mechanical trauma or of human diseases. Prevention or therapeutic or prophylactic treatment for diseases, disorders or conditions of the CNS and/or peripheral nervous system are contemplated. Prevention or therapeutic or prophylactic treatment for diseases, disorders or conditions which have a psychiatric component is provided. Prevention or therapeutic or prophylactic treatment for diseases, disorders or conditions including but not limited to those having an ophthalmic, cardiovascular, cardiopulmonary, respiratory, kidney, urinary, reproductive, gastrointestinal, endocrine, or metabolic component is provided. The peptides may be useful for the prevention, therapeutic treatment, prophylactic treatment or management of diseases or disorders associated with tissue damages as well as the damages, effects or symptoms thereof in one or more organs or tissues, preferably at least two, including, but not limited to, the brain, spinal cord, connective tissue, skin, gastrointestinal tract, reproductive organs, liver, heart, lung, kidney, urinary tract, pancreas, eyes and prostate.

In certain embodiments, the methods of the current invention may exclude peptides of the current invention or particular indications. For example, peptides in accordance with Structural Motif C may be excluded in methods of the current invention in the indications disclosed within WO 2006/119767 and WO 2007/071248 including: post-operative nerve damage; traumatic nerve damage; spinal cord injury, impaired myelination of nerve fibers; postischemic damage; stroke; Parkinson's disease; Alzheimer's disease; Huntington's disease; aschizophrenia, dementias; multiple sclerosis, multiinfarct dementias; nerve degeneration associated with diabetes mellitus; neuro-muscular degeneration, disorders affecting the circadian clock or neuro-muscular connections; organ transplantation; genetic or traumatic atrophic muscle disorders; degenerative conditions of the gonads, pancreas, kidney, heart, liver and bowel; diabetes mellitus type I or II; nephrosis; psychoses; neurotic disorders; personality disorders; sexual deviations and disorders; mental retardation; disease in the nerve system and sense organs; cognitive anomalies; inflammatory disease of the central nervous system; cerebral degenerations; stimulation of short or long term memory; extra pyramidal diseases and abnormal movement disorders; motor neuron diseases; diseases of the spinal cord; disorders of the autonomic nervous system, diseases of the peripheral nervous system; neuropathies; disorders affecting multiple structures of the eyes; diseases of the ear and mastoid process; abnormalities of organs and soft tissue in newborns; complications of administration of anesthesia or other sedation in labor and delivery; diseases and injuries of the skin; injury to nerves and spinal cord; poisoning by drugs; medicinal and biological substances; metabolic disorders; disorders of endocrine glands; disorders of purine and pyrimidine metabolism; bone disorders; neoplasms; cancers; viral infections of the brain; Gillian-Bane syndromes; pain syndrome; autism and stimulation of the ability to learn. Also, for example, peptides in accordance with Structural Motif D may be excluded in methods of the current invention in the indications disclosed in U.S. Pat. Nos. 5,571,787, 5,700,909, 5,696,080, 5,714,459, 6,590,074, 6,559,124, 6,271,196, 6,268,347, and 6,849,602 including: neuropathic pain due to neuroma (amputation, nerve transaction), nerve compression (entrapment neuropathies, or tumor compression), nerve trauma (crush, stretch, or incomplete transsection); diabetes mellitus; irradiation, ischemia, vasculitis, post-polio syndrome, alcohol, amyloid, toxins, HIV, hypothyroidism, uremia, vitamin deficiencies, chemotherapy, ddC (Zalcitabine), Fabry's diseases, compression (disk, tumor, scar tissue), root avulsion, inflammation (posttherapeutic neuralgia), spinal cord contusions, spinal cord tumors, spinal cord hemisection, and infarction, tumors or trauma of the brainstem, thalamus or cortex; and demyelenating diseases including multiple sclerosis, acute disseminated leukoencephalitis, progressive multifocal leukoencephalitis, metachromatic leukodystrophy, and adrenal leukodystrophy. For another example, peptides in accordance with Structural Motif E may be excluded in methods of the current invention in the indications disclosed in U.S. Pat. No. 7,259,146 and US Patent Publication No.

20030130197, including: acute neurodegenerative disorders: cerebral ischemia or infarction including embolic occlusion and thrombotic occlusion; reperfusion following acute ischemia; perinatal hypoxic-ischemic injury; cardiac arrest; intracranial hemorrhage; intracranial and intravertebral lesions; and whiplash shake infant syndrome; chronic neurodegenerative disorders: Alzheimer's disease, Pick's disease, diffuse Lewy body disease, progressive supranuclear palsy, multisystem degeneration, chronic epileptic conditions, motor neuron diseases, prion diseases, neurological and psychiatric manifestations associated with peripheral diseases including EPO deficiency, blood loss, renal failure, endstage renal disease, renal transplant, and other diseases associated with anemia including hematological and non-hematological malignancies/tumors, complications associated with chemotherapy and other drugs, hematological disorders, inflammatory and infectious disorders, chronic systemic autoimmune diseases, Hencoh Schonlein Purpura, hemolytic uremic syndrome, chemical, toxic, infectious, and radiation injury of the nervous system, and encephalopathies; plexopathies; neuropathies; Charcot-Marie-Tooth disease; Friedreich's ataxia; metachromatic leukodystrophy; Refsum's disease; adrenomyeloneuropathy; Ataxia-telangiectasia; Djerine-Sottas neuropathy; Lambert Eaton syndrome; and disorders of the cranial nerves. As a further example, peptides in accordance with Structural Motif F may be excluded in methods of the current invention in the indications disclosed in WO/2007/052154 including: immune-mediated inflammation; autoimmune diseases including Hashimoto's thyroiditis, insulin dependent diabetes mellitus, systemic lupus erythmatosus; demylenating disease including multiple sclerosis, traverse myelitis, Guillain-Barre syndrome, and progressive multifocal leukoencephalopathy and demylenation resulting from organophosphate exposure; arthritis; acute cerebrovascular injury; acute spinal cord injury; acute brain injury; acute cardiovascular injury; stroke; traumatic injury; transplant rejection; and graft rejection.

C. Prevention, Treatment, Amelioration, or Management of the Damage, Effects, or Symptoms of Diseases, Disorders or Conditions.

In a further embodiment of the invention, the method of treatment of the current invention is useful for preventing, treating, ameliorating, or managing the damage, effects, or symptoms of the above noted diseases and disorders. In particular, the current method of treatment can be used to address symptoms including, but not limited to, cachexia, carcinogenesis, sterilization, cataract formation, radiodermatitis, beta burns, gamma burns, loss of cells (in particular bone marrow, digestive tract cells), damage to the hematopoietic, gastrointestinal, central nervous, cardiovascular, skin, and/or reproductive systems, acute radiation syndrome (feeling of nausea, vomiting, general illness and fatigue, immune system depression, loss of hair, uncontrollable bleeding (mouth, under the skin, kidneys), massive diarrhea, delirium, coma and death), chronic radiation syndrome, cutaneous radiation syndrome (inflammation, erythema, dry or moist desquamation, hair loss, blistering, reddening, ulceration, damage to sebaceous and sweat glands, atrophy, fibrosis, decreased or increased skin pigmentation, and necrosis), headaches, dizziness, nausea, vomiting, mucosal irritation, dysponea, impaired consciousness, coma, convulsions, tachy- and brady-dysrhythmias, hypotension, cardiovascular collapse, acyanosis, bradycardia, myosis, excessive salivation, diarrhea, involuntary micturition, muscle fasciculation, initial depolarizing flaccid paralysis, spike discharges and convulsions, intermediate syndrome, neurotoxic esterase inhibition, organophosphate-induced delayed neuropathy, erythema, edema, necrosis and vesicles, melanoderma, tracheobronchitis, bronchospasms, bronchial obstruction, hemorrhagic pulmonary edema, respiratory failure, bacterial pneumonia, eye erythema, lachrymation, discomfort of the eyes, severe pain in the eyes, blepharospasm, iritis, blindness, bone marrow suppression, lewisite shock, hepatic necrosis, renal failure secondary to hypoperfusion, burning sensations (eyes, nasopharynx, oropharynx), profuse tearing, rhinorrhoea, coughing hoarseness, dyspnoea, odynophagia, conjunctivitis, corneal injury, naso-orophangyal injury/edema, respiratory distress due to inflammation of the glottic structures, secretions, and/or lyrangospasms, acute respiratory syndromes, disorientation, behavioral modifications, and reactive airway dysfunction syndrome.

As mentioned above, these diseases or disorders associated with tissue damage or damage, effects, or symptoms resulting therefrom are merely illustrative of the range of disorders that can be addressed by the peptides used in the method of the current invention. Accordingly, this invention generally provides preventative, therapeutic, or prophylactic treatment of a disease or disorder associated with tissue damage or damage, effects or symptoms resulting therefrom.

Diseases or disorders associated with tissue damage or damage, effects or symptoms resulting therefrom can be treated or prevented by administration of an effective amount of a peptide of the invention. In certain embodiments, the present invention provides methods of treating or preventing a disease or disorder described herein comprising the step of administering to a subject having the disease or disorder an amount of a peptide of the invention effective to treat or prevent the disease or disorder. In one embodiment, a composition comprising an effective amount of one or more peptides of the invention, or a pharmaceutically acceptable salt thereof, is administered.

D. Treatment in Conjunction with other Therapeutics for a Cumulative or Synergistic Effect.

In certain embodiments, the invention encompasses methods for treating, mediating, ameliorating or preventing a disease or disorder associated with tissue damage or damage, effects or symptoms resulting therefrom, comprising administering to a patient in need thereof an effective amount of a peptide and another suitable therapeutic agent, each being administered according to a regime suitable for the medicament. This may be done to achieve additive, synergistic or offsetting (to counteract side effects of the therapeutic) benefits of the effects of the peptide and therapeutic agents. This includes the concurrent, substantially simultaneous, or non-concurrent administration of the peptide and suitable therapeutic agent. The non-concurrent administration of the peptide and a suitable therapeutic agent includes sequential, alternating, and acute vs. chronic administration of the peptides and suitable therapeutic agents. Also, the peptide and the suitable therapeutic agent may be administered in the same or separate pharmaceutical compositions, and if administered separately they may be administered via the same route of administration or different routes. Suitable therapeutic methods and agents may include, but are not limited to, carbamates (pyridostigmine, physostigmine, aminostigmine, neostigmine, synostigmine, Epastigmine, Mobam, decarbofuran), anticholingerics (trihexyphenidyle, benactyzine, Biperidene, Scopolamine, aprophen, atropine, hyoscin, adiphenine, Caramiphen, pentmethonium, Mecamylamine, Trihexyphenidyle) PANPAL, aminophenols (eseroline), organophosphates (TEPP, Paraxon, Ethyl-4-nitrophenylphosphate), tacrine, 7-MEO- TA, huperzine A, Cholinesterases (BuChE, AChE, triesterase, paraoxonase), oximes/reactivators (HI-6, PAM, Obidoxime, Trimedoxime, Methoxime, Hlo-7, BI-6, K048, K033, pralidoxime chloride (2-PAM Cl), P2S, TMB4, 2-PAMI), Suramine, Benzodiazepines, tubocurine, Memantine, Procyclidine, Nimodipin, Clonidine, pralidoxime, diazepam, enkephalins, phenylmethylsulfonyl fluoride, natrium bicarbonate, vitamin E analogs (α-tocopherol succinate, γ-tocotrienol), superoxide dismutase/catalase mimic (EUK189), selenium, benzyl styryl sulfone, truncated flagellin, statins, genistein, galantamine, hypothermia, 5-androstenediol, CpG-oligodeoxynucleotides, antimicrobials, stem cell transplants, amifostine, Tempol, isoflavones, benzylsulfone analogs, GM-CSF, G-CSF, potassium iodide, aluminum hydroxide, Prussian blue, chelating agents (diethylenetriaminepentaacetate (Ca-DTPA), zinc diethylenetriaminepentaacetate (Zn-DTPA)), keratinocyte growth factor, intestinal peptide hormones, beta glucan, octreotide, pentoxifylline, angiotensin converting enzyme inhibitors, angiotensin II receptor blockers, methemoglobin formers (amyl nitrite, sodium nitrite), sodium thiosulfate, cobalt compounds (hydroxycobalamin (Vitamin B12a), toxoids, antitoxins, vaccines, passive antibodies, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel; Radiation: γ-radiation; Alkylating agents; Nitrogen mustards: cyclophosphamide, Ifosfamide trofosfamide, Chlorambucil; Nitrosoureas: carmustine (BCNU), Lomustine (CCNU), Alkylsulphonates busulfan, Treosulfan; Triazenes: Dacarbazine; Platinum containing compounds: Cisplatin carboplatin, Plant Alkaloids; Vinca alkaloids: vincristine, Vinblastine, Vindesine, Vinorelbine; Taxoids: paclitaxel, Docetaxol; DNA Topoisomerase Inhibitors Epipodophyllins: etoposide, Teniposide, Topotecan, 9-aminocamptothecin irinotecan (Campto®), crisnatol; Mytomycins: Mytomycin C, Mytomycin C; Anti-metabolites, Anti-folates: DHFR inhibitors: methotrexate, Trimetrexate; IMP dehydrogenase Inhibitors: mycophenolic acid, Tiazofurin, Ribavirin EICAR; Ribonuclotide reductase Inhibitors: hydroxyurea; deferoxamine; Pyrimidine analogs: Uracil analogs, 5-Fluorouracil, Floxuridine, Doxifluridine, Ratitrexed; Cytosine analogs: cytarabine (ara C) Cytosine arabinoside fludarabine; Purine analogs: mercaptopurine, Thioguanine; Hormonal therapies; Receptor antagonists: Anti-estrogens, Tamoxifen, Raloxifene megestrol; LHRH agonists: goserelin, Leuprolide acetate; Anti-androgens: flutamide, bicalutamide; Retinoids/Deltoids Vitamin D3 analogs: EB 1089, CB 1093, KH 1060; Photodyamic therapies: vertoporfin (BPD-MA), Phthalocyanine photosensitizer, Pc4 Demethoxy-hypocrellin A (2BA-2-DMHA) Cytokines Interferon-α, Interferon-γ, Tumor necrosis factor; Isoprenylation inhibitors: Lovastatin; Dopaminergic neurotoxins: 1-methyl-4-phenylpyridinium ion; Cell cycle inhibitors: staurosporine; Actinomycins: Actinomycin D, Dactinomycin; Bleomycins: bleomycin A2, Bleomycin B2, Peplomycin; Anthracyclines: daunorubicin, Doxorubicin (adriamycin), Idarubicin, Epirubicin, Pirarubicin, Zorubicin, Mitoxantrone; MDR inhibitors: verapamil; $Ca^{2+}$ ATPase inhibitors: thapsigargin; TNF-α inhibitors/thalidomide angiogenesis inhibitors 3-(3,4-dimethoxy-phenyl)-3-(1-oxo-1,3-dihydro-isoindol-2-yl)-propionamide (SelCIDs™) ImiDs™, Revlimid™, Actimid™. In another aspect of the present invention, a pharmaceutical composition according to the present invention may include a peptide in a formulation with at least one small molecule that exhibits tissue protective functionality. Suitable small molecules include, but are not limited to, steroids (e.g., lazaroids and glucocorticoids), antioxidants (e.g., coenzyme $Q_{10}$, alpha lipoic acid, and NADH), anticatabolic enzymes (e.g., glutathione peroxidase, superoxide dimutase, catalase, synthetic catalytic scavengers, as well as mimetics), indole derivatives (e.g., indoleamines, carbazoles, and carbolines), nitric acid neutralizing agents, adenosine/adenosine agonists, phytochemicals (flavanoids), herbal extracts (ginko biloba and turmeric), vitamins (vitamins A, E, and C), oxidase electron acceptor inhibitors (e.g., xanthine oxidase electron inhibitors), minerals (e.g., copper, zinc, and magnesium), non-steriodal anti-inflammatory drugs (e.g., aspirin, naproxen, and ibuprofen), and combinations thereof. Additionally agents including, but not limited to, anti-inflammatory agents (e.g., corticosteroids, prednisone and hydrocortisone), glucocorticoids, steroids, non-steriodal anti-inflammatory drugs (e.g., aspirin, ibuprofen, diclofenac, and COX-2 inhibitors), beta-agonists, anticholinergic agents and methyl xanthines), immunomodulatory agents (e.g., small organic molecules, T cell receptor modulators, cytokine receptor modulators, T-cell depleting agents, cytokine antagonists, monokine antagonists, lymphocyte inhibitors, or anti-cancer agents), gold injections, sulphasalazine, penicillamine, anti-angiogenic agents (e.g., angiostatin), TNF-α antagonists (e.g., anti-TNFα antibodies), and endostatin), dapsone, psoralens (e.g., methoxalen and trioxsalen), anti-malarial agents (e.g., hydroxychloroquine), anti-viral agents, anti-histamines and antibiotics (e.g., erythromycin and penicillin) may be used in conjunction with the current pharmaceutical compositions.

In other embodiments, the present methods for treating, mediating, ameliorating or preventing a disease or disorder associated with tissue damage or damage, effects or symptoms resulting therefrom further comprise administration of the peptides in conjunction with methods of treatment such as chemotherapy, radiation therapy (x-ray radiation, high-energy megavoltage (radiation of greater that 1 MeV energy), electron beam, orthovoltage x-ray radiation, gamma-ray emitting radioisotopes (radioactive isotopes of radium, cobalt and other elements)), hyperbaric chambers, heart bypass machine, angioplasty, hypothermia, surgery, angioplasty, etc. to achieve additive, synergistic or offsetting (to counteract side effects of the therapeutic method) benefits of the effects of the peptide and therapeutic method. As an example, in a specific embodiment, peptide can be administered to a patient that has undergone surgery as treatment for the cancer concurrently with chemotherapy or radiation therapy. In another specific embodiment, a chemotherapeutic agent or radiation therapy is administered prior or subsequent to administration of a peptide, preferably at least an hour, five hours, 12 hours, a day, a week, a month, more preferably several months (e.g., up to three months). Additionally, the invention provides methods of treatment of cancer or neoplastic disease with a peptide as an alternative to chemotherapy or radiation therapy where the chemotherapy or the radiation therapy has proven or may prove too toxic, e.g., results in unacceptable or unbearable side effects, for the patient being treated. Alternatively, the invention provides methods of treatment wherein the peptide is administered prior to, simultaneously with or following treatment with chemotherapy or radiation in an effort to prevent or ameliorate the toxic side effects of the treatment method. As demonstrated in Example 2, the peptides administered in accordance with the current method are able to ameliorate the side-effects of cis-platinum a known chemotherapeutic. Although, the above examples relate to the treatment of cancers, it is understood that the peptides may be administered in conjunction with other methods of treatment in the art for diseases or disorders associated with tissue damage and damage, effects, or symptoms resulting therefrom including inflammation, and exposure to toxic agents to achieve synergistic, additive or offsetting results.

E. Formulation and Administration of Peptides

In one embodiment, the method of the current invention provides that a pharmaceutical composition comprising a peptide can be administered systemically to protect or treat the targeted cells, tissue or organ. Such administration may be parenterally, via inhalation, or transmucosally, e.g., orally, bucally, nasally, rectally, intravaginally, sublingually, ocularly, submucosally or transdermally. Preferably, administration is parenteral, e.g., via intravenous or intraperitoneal injection, and also including, but is not limited to, intraarterial, intramuscular, intradermal and subcutaneous administration.

For other routes of administration, such as by use of a perfusate, injection into an organ, or other local administration, a pharmaceutical composition will be provided which results in similar levels of a peptide as described above. A level of about 15 pM 30 nM is preferred.

The pharmaceutical compositions of the invention may comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin, hereby incorporated by reference herein in its entirety. Such compositions will contain a therapeutically effective amount of the compound, preferably in purified form, together with a suitable amount of carrier so as to provide the form for proper administration to the patient. The formulation should suit the mode of administration.

Formulations for increasing transmucosal adsorption of peptides such as long acting peptides are also contemplated by the current invention. Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal and pulmonary administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. Alternatively, inhalation of compounds directly into the lungs may be accomplished by inhalation deeply or installation through a mouthpiece into the oropharynx. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered into the nasal cavity directly or into the lungs via the nasal cavity or oropharynx.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of a peptide may be provided for emergency use by ambulances, emergency rooms, and battlefield situations, and even for self-administration in a domestic setting, particularly where the possibility of traumatic amputation may occur, such as by imprudent use of a lawn mower. The likelihood that cells and tissues in a severed foot or toe will survive after reattachment may be increased by administering a peptide to multiple sites in the severed part as soon as practicable, even before the arrival of medical personnel on site, or arrival of the afflicted individual with severed toe in tow at the emergency room.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

Suppositories generally contain active ingredient in the range of 0.5% to 10% by weight; oral formulations preferably contain 10% to 95% active ingredient.

A perfusate composition may be provided for use in situ perfusion. Such pharmaceutical compositions may comprise levels of peptides, or a form of peptides not suitable for acute or chronic, local or systemic administration to an individual, but will serve the functions intended herein in as an organ bath, organ perfusate, or in situ perfusate prior to removing or reducing the levels of the peptide contained therein before exposing or returning the treated organ or tissue to regular circulation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, for example, a peptide can be delivered in a controlled-release system. For example, the peptide may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574, each of which is incorporated by reference herein in its entirety). In another embodiment, the compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327; see generally ibid.). In another embodiment, polymeric materials can be used (see Medical Applications of Controlled Release, Langer and Wise (eds.), CRC Press: Boca Raton, Fla., 1974; Controlled Drug Bioavailability, Drug Product Design and Performance, Smolen and Ball (eds.), Wiley: New York (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105, (each of which is incorporated by reference herein in its entirety).

In yet another embodiment, a controlled release system can be placed in proximity of the therapeutic target, i.e., the target cells, tissue or organ, thus requiring only a fraction of the systemic dose (see, e.g., Goodson, pp. 115-138 in Medical Applications of Controlled Release, vol. 2, supra, 1984, which is incorporated by reference herein in its entirety). Other controlled release systems are discussed in the review by Langer (1990, Science 249:1527-1533, which is incorporated by reference herein in its entirety).

In another embodiment, peptide, as properly formulated, can be administered by nasal, bucal, oral, rectal, vaginal, ocular, transdermal, parenteral, inhalation or sublingual administration.

In a specific embodiment, it may be desirable to administer a peptide of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. A non-limiting example of such an embodiment would be a stent or other scaffolding coated with a peptide of the present invention implanted in a portion of the vasculature, duct, etc.

Selection of the preferred effective dose will be readily determinable by a skilled artisan based upon considering several factors, which will be known to one of ordinary skill in the art. Such factors include the particular form of peptide, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, and according to standard clinical techniques.

In another aspect of the invention, a perfusate or perfusion solution is provided for perfusion and storage of organs for transplant, the perfusion solution includes an amount of a peptide or peptide analog effective to protect responsive cells and associated cells, tissues or organs. Transplant includes but is not limited to allotransplantation, where an organ (including cells, tissue or other bodily part) is harvested from one donor and transplanted into a different recipient, both being of the same species; autotransplantation, where the organ is taken from one part of a body and replaced at another, including bench surgical procedures, in which an organ may be removed, and while ex vivo, resected, repaired, or otherwise manipulated, such as for tumor removal, and then returned to the original location or xenotransplantation, where tissues or organs are transplanted between species. In one embodiment, the perfusion solution is the University of Wisconsin (UW) solution (U.S. Pat. No. 4,798,824, hereby incorporated by reference herein in its entirety) which contains 5% hydroxyethyl starch (having a molecular weight of from about 200,000 to about 300,000 and substantially free of ethylene glycol, ethylene chlorohydrin, sodium chloride and acetone); 25 mM $KH_2PO_4$, 3 mM glutathione; 5 mM adenosine; 10 mM glucose; 10 mM HEPES buffer; 5 mM magnesium gluconate; 1.5 mM $CaCl_2$, 105 mM sodium gluconate; 200,000 units penicillin; 40 units insulin; 16 mg dexamethasone; 12 mg Phenol Red; and has a pH of 7.4-7.5 and an osmolality of about 320 mOsm/l supplemented with an appropriate amount of a peptide of the invention. This particular perfusate is merely illustrative of a number of such solutions that can be adapted for the present use by inclusion of an effective amount of a peptide. In a further embodiment, the perfusate solution contains from about 1 to about 500 ng/ml of a peptide, or from about 40 to about 320 ng/ml peptide. As mentioned above, any form of peptide can be used in this aspect of the invention.

While the preferred recipient of a peptide for the purposes herein throughout is a human, the methods herein apply equally to other mammals, particularly domesticated animals, livestock, companion, and zoo animals. However, the invention is not so limiting and the benefits can be applied to any mammal.

In further aspects of the ex-vivo invention, any peptide such as but not limited to the ones described above may be employed.

In another aspect of the invention, methods and compositions for preventing, treating or managing a disease or disorder associated with tissue damage or damage, effects or symptoms resulting therefrom in cells, tissues or organs which are not isolated from the vasculature by an endothelial cell barrier are provided by exposing the cells, tissue or organs directly to a pharmaceutical composition comprising a peptide, or administering or contacting a pharmaceutical composition containing a peptide to the vasculature of the tissue or organ.

Similar to other tissue protective compounds based on erythropoietin, it is possible that the peptides of the present invention may be transported from the luminal surface to the basement membrane surface of endothelial cells of the capillaries of organs with endothelial cell tight junctions, including, for example, the brain, retina, and testis. Thus, the effects of a disease or disorder associated with tissue damage or damage, effects or symptoms resulting therefrom on cells across the barrier may be treated. While not wishing to be bound by any particular theory, after transcytosis of the peptide may interact with a tissue-protective receptor on a cell, for example, neuronal, eye (e.g., retinal), adipose, connective, hair, tooth, mucosal, pancreatic, endocrine, aural, epithelial, skin, muscle, heart, lung, liver, kidney, small intestine, adrenal (e.g. adrenal cortex, adrenal medulla), capillary, endothelial, testes, ovary, stem or endometrial cell, and receptor binding can initiate a signal transduction cascade resulting in the activation of a gene expression program within the responsive cell or tissue, resulting in the protection of the cell or tissue, or organ, from damage, such as by exposure to a toxic agent, inflammation, hypoxia, etc. In another embodiment, the peptide can be cross-linked to a compound that can cross the barrier, such as CEPO, to be transported across the barrier in accordance with the teaching of PCT Application No. PCT/US01/49479, U.S. patent application Ser. Nos. 10/188,905 and 10/185,841, incorporated herein by reference.

Thus, methods for protecting a tissue from disease or disorder associated with tissue damage or damage, effects or symptoms resulting therefrom are described in detail herein below.

In the practice of one embodiment of the invention, a mammalian patient is undergoing systemic chemotherapy for cancer treatment, including radiation therapy, which commonly has adverse effects such as nerve, lung, heart, ovarian or testicular damage. Administration of a pharmaceutical composition comprising a tissue protective peptide or peptide analog as described above is performed prior to and during chemotherapy and/or radiation therapy, to protect various tissues and organs from damage by the chemotherapeutic agent, such as to protect the testes. Treatment may be continued until circulating levels of the chemotherapeutic agent have fallen below a level of potential danger to the mammalian body.

In the practice of another embodiment of the invention, various organs are planned to be harvested from a victim of an automobile accident for transplant into a number of recipients, some of which required transport for an extended distance and period of time. Prior to organ harvesting, the donor is infused with a pharmaceutical composition comprising tissue protective peptides and peptide analogs as described herein. Harvested organs for shipment are perfused with a perfusate containing tissue protective peptides or peptide analogs as described herein, and stored in a bath comprising tissue protective peptides or peptide analogs. Certain organs are continuously perfused with a pulsatile perfusion device, utilizing a perfusate containing tissue protective peptides and peptide analogs in accordance with the present invention. Minimal deterioration of organ function occurs during the transport and upon implant and reperfusion of the organs in situ.

In another embodiment of the present invention, a participant in a hazardous activity that exposes the individual to toxic agents, one could take a dose of a pharmaceutical composition containing a peptide sufficient to either prevent (i.e. delaying the onset of, inhibiting, or stopping), protect against, or mitigate the effects of exposure to a toxic agent. In particular, this method of treatment may have application in various professions involving contact with toxic agents, such as miners, chemical manufacturers, military personnel (soldiers, paratroopers), emergency personnel (police, fire, EMS, and disaster relief personnel), construction workers, food processors, and employees at power reactors.

In another embodiment of the invention, a surgical procedure to repair a heart valve requires temporary cardioplegia and arterial occlusion. Prior to surgery, the patient is infused with a tissue protective peptide or peptide analog. Such treatment prevents hypoxic ischemic cellular damage, particularly after reperfusion. Additionally, the pharmaceutical compositions of the present invention may be used prophylactically to prepare an individual for surgery in an effort to limit the trauma associated with the surgical procedure or aide in the recovery of the individual from the surgical procedure. Although the present method of treatment using pharmaceutical compositions containing tissue protective peptides and peptide analogs provide a prophylactic use for surgical procedures, it may be particularly useful in procedures that induce temporary ischemic events including, but not limited to, bypass procedures (coronary bypass), angioplasty procedures, amputations, and transplantations, as well as, those performed directly upon responsive cells, tissues, or organs such as brain and spinal cord surgery, and open heart procedures. Such procedures may involve the use of cardiopulmonary (heart lung) bypass.

In another embodiment of the invention, in any surgical procedure, such as in cardiopulmonary bypass surgery, a tissue protective peptide or peptide analog of the invention can be used. In one embodiment, administration of a pharmaceutical composition comprising tissue protective peptides and peptide analogs as described above is performed prior to, during, and/or following the bypass procedure, to protect the function of brain, heart, and other organs.

In the foregoing examples in which a peptide is used for ex-vivo applications, or for in vivo applications to treat a disease or disorder associated with tissue damage or damages, effects or symptoms resulting therefrom, the invention provides a pharmaceutical composition in dosage unit form adapted for prevention, treatment or management of the damages and effects of exposure to a toxic agent or symptoms thereof which comprises an amount within the range from about 0.01 pg to 30 mg, 0.5 pg to 25 mg, 1 pg to 20 mg, 500 pg to 10 mg, 1 ng to 10 mg, 500 ng to 10 mg, 1 μg to 10 mg, 500 μg to 10 mg, or 1 mg to 10 mg of a peptide, and a pharmaceutically acceptable carrier. In a preferred embodiment, the amount of peptide is within the range from about 0.5 pg to 1 mg. In a preferred embodiment, the formulation contains peptides that are non-erythropoietic.

Furthermore, this restorative aspect of the invention is directed to the use of any peptides herein for the preparation of a pharmaceutical composition for the restoration of cellular, tissue or organ dysfunction, wherein treatment is initiated after, and well after, the initial insult responsible for the dysfunction. Moreover, treatment using peptides of the invention can span the course of the disease or condition during the acute phase as well as a chronic phase.

A peptide of the invention may be administered systemically at a dosage between about 1 ng and about 300 μg/kg body weight, preferably about 5-150 μg/kg-body weight, most preferably about 10-100 μg/kg-body weight, per administration. For example, administration may be repeated hourly, daily, as long as clinically necessary, or after an appropriate interval, e.g., every 1-12 hours, preferably every 6 to 12 hours; every 2-6 days, preferably every 2-4 days; every 1 to 12 weeks, preferably, every 1 to 3 weeks. In one embodiment, the effective amount of peptide and a pharmaceutically acceptable carrier may be packaged in a single dose vial or other container. In another embodiment, the peptides, which are capable of exerting the activities described herein but not causing an increase in hemoglobin concentration or hematocrit, are used. Such peptides are preferred in instances wherein the methods of the present invention are intended to be provided chronically.

EXAMPLES

Example 1

Method of Peptide Synthesis

A. Synthesis of Peptide a (SEQ ID NO:2, Corresponding to EPO Amino Acid Sequence 38-57) and Peptide B (SEQ ID NO:3, Corresponding to EPO Amino Acid Sequence 58-82).

Peptide A, SEQ ID NO:2, and Peptide B, SEQ ID NO:3, fragments of EPO, were synthesized using "in situ neutralization" Boc Chemistry stepwise solid-phase peptide synthesis, as described in Band, D., Chopra, N and Kent, S., "Total Synthesis of Crambin," *J. AM. CHEM. SOC.* 2004, 126, 1377-1383 (incorporated by reference herein in its entirety). Briefly, two fragments corresponding to EPO amino acid sequence 38-57 (peptide A, NITVPDTKVN-FYAWKRMEVG, SEQ ID NO:2) and EPO amino acid sequence 58-82 (peptide B, QQAVEVWQGLALLSEAVL-RGQALLV, SEQ ID NO:3) were synthesized on $OCH_2$-Pam-resins (free "carboxyl peptides) or on $HSCH_2CH_2CO$-Leu-$OCH_2$-Pam-Resin ("thioester peptides). During synthesis the side chains of various amino acids were protected as follows: Arg(Tos), Asn(Xan), Asp(OcHex), Cys(4-$CH_3$Bzl) or Cys(ACM), Glu(OcHex), Lys(2-Cl-Z), Ser(Bzl), Thr(Bzl), Tyr(Br-Z). After the peptide chain was assembled, the peptides were deprotected and simultaneously cleaved from the resin support by treatment with anhydrous HF containing p-cresol (90:10, v/v) for 1 hr at 0° C. After evaporation of the HF under reduced pressure, crude products were precipitated and triturated with chilled diethyl ether, and the peptides were dissolved in 50% aqueous acetonitrile containing 0.1% TFA and purified by the preparative HPLC system. Peptide compositions were confirmed using LC-MS.

Peptide ID (UEQLERALNSS, SEQ ID NO: 282) is an 11-amino acid linear peptide with a protected N-terminus (by the 5 membered ring structure of pyroglutamic acid) and a free carboxyl group at the C-terminus. Its molecular weight is 1257 Daltons. It was synthesized using standard Fmoc solid phase peptide synthesis on Wang resin, purified by preparative HPLC and ion-exchange chromatography, and lyophilized. Acetate and ammonium are bound in ionic form to basic and acidic groups of the peptide molecule forming a mixed salt.

Example 2

Tissue Protective Peptides and Peptide Analogs are Non-Erythropoietic

A. In Vitro Assessment

UT-7epo, a human erythropoietin-dependent leukemia cell line, was used for the determination of the erythropoietic potency of the peptides. UT-7epo cells (Deutsche Sammlung von Mikroorganismen and Zellkulturen (DSMZ), Cat. No. ACC 363) are grown in a complete RPMI-1640 medium with 10% FBS and 5 ng/ml erythropoietin. The proliferation/survival (=viability increase) response of the cells exposed to erythropoietin is mediated by the classical erythrocyte-type erythropoietin receptor and is a quantitative measure of the capacity of erythropoietin-variants to stimulate the classical erythropoietin receptor.

UT-7epo cells were transferred to fresh complete RPMI 1640 medium containing 10% donor calf serum, 4 mM L-glutamine, and supplemented with 5 ng/ml of recombinant human erythropoietin. The cells were maintained in 75 cm² flasks with 20 ml of medium/flask in a humidified incubator with 5% $CO_2$ at 37° C. for 48 h. On day two of the assay, i.e., at 48 h, the cells were transferred from the flask into a 50-ml conical tube and centrifuged at 1,000 rpm for 5 minutes at room temperature. The supernatant was discarded and the cells were washed two times with 10 ml of starvation media (3% donor calf serum, 4 mM L-glutamine). The cells were then re-suspended in starvation media, using up and down pipette action to obtain a single cell suspension. The re-suspended cells were diluted with starvation media to obtain a density of $4 \times 10^5$ cells/ml, and plated at a total culture volume of 10 ml per 25 cm² flask. Following a 4 h incubation, the cells were again transferred to a 50-ml conical tube. Control cells were maintained throughout with 5 ng/ml of rhu-erythropoietin.

Figure 1:
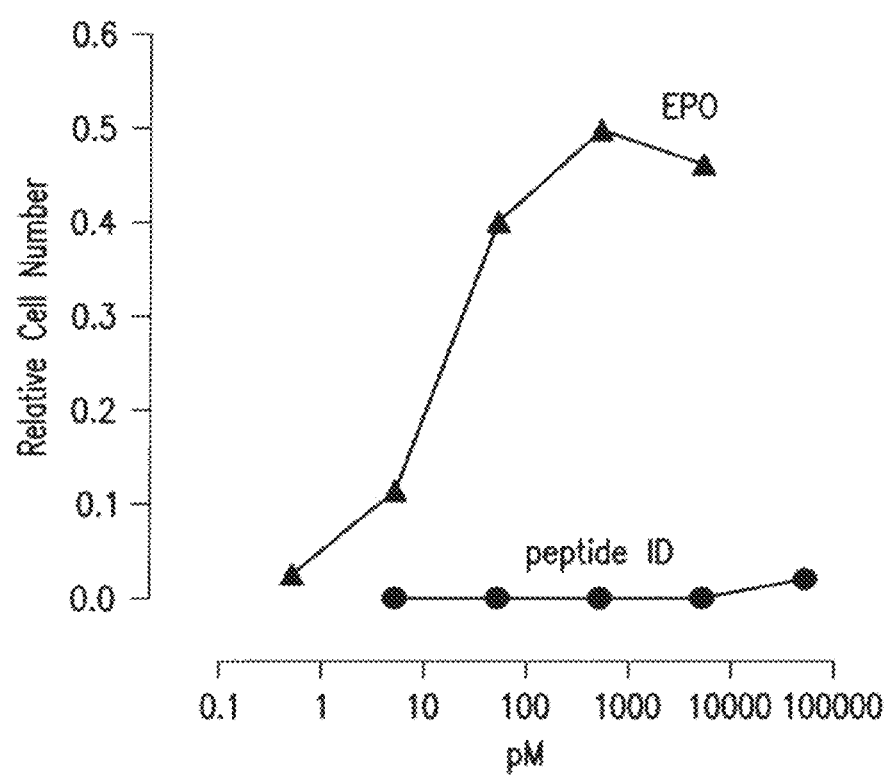
FIG. 1 is a chart regarding the proliferation of UT-7 EPO cells in the presence of EPO or Peptide ID (SEQ ID NO: 282). As shown in the graph, EPO led to a proliferation of the UT-7 EPO cells whereas Peptide ID at all doses did not result in proliferation of the cells, demonstrating that Peptide ID is not erythropoietic.

Cells were diluted to 200,000 cells/ml in starvation medium, plated at 100 µl/well in a 96 well plate and exposed to varying concentrations of erythropoietin, and Peptide ID, SEQ ID NO:282. A series of 10 fold dilutions in RPMI 1640 medium containing 3% serum was used to generate concentrations of test compounds from 5 pM to 50 nM. Following a further for 48 h incubation, a solution of 15 ml WST-I Cell Proliferation Reagent (Roche) was added to each well, and incubated for 1 hour at 37° C. in $CO_2$. After mixing for 1 minute, the plate was read in a plate reader (absorption at 450 nm, subtracted from background absorption at 650 nm). As shown in FIG. 1, Peptide ID had no erythropoeitic activity over the range of doses in comparison to the strong erythropoietic effect of EPO. This was well below the expectation that a non-erythropoietic peptide or peptide analog will have no erythropoietic activity for a dose lower than 1 µg/ml, and more preferably for a dose lower than 10 µg/ml.

B. In Vivo Assessment

Figure 2:
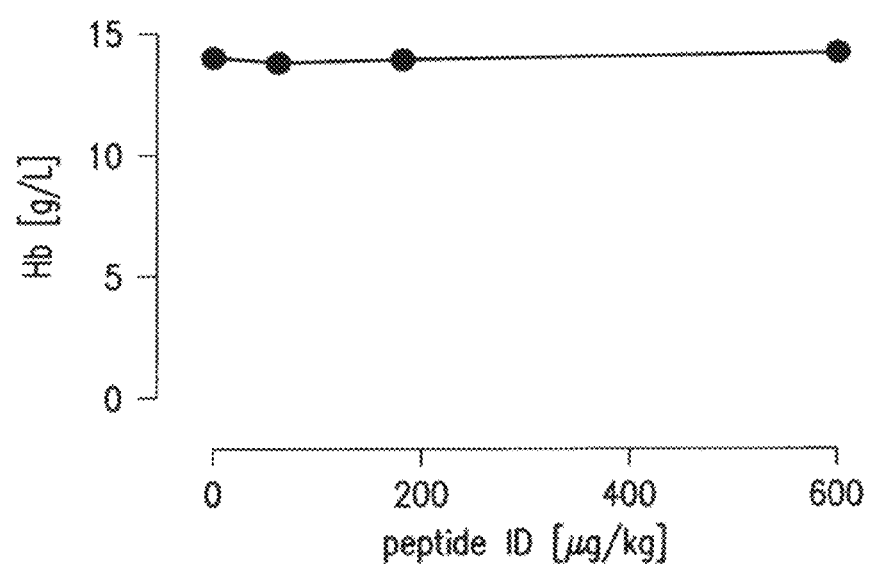
FIG. 2 is a chart indicating the hemoglobin concentration in Sprague Dawley rats administered Peptide ID twice daily i.v. over a 28 day period. As shown in the graph, the hemoglobin concentration of the rats that received no peptide was the same as those that received Peptide ID, thereby demonstrating that Peptide ID is non erythropoietic.

To evaluate the erythropoietic activity of tissue protective peptides and peptide analogs, Peptide ID was administered intravenously twice a day to Sprague Dawley rats for 28 days. Nine male and nine female rats were assigned to groups 1-4 receiving 0, 60, 180, and 600 µg/kg per dose (0, 48, 143, and 477 nmol/kg, respectively) of Peptide ID in PBS by bolus intravenous administration from days 1-28, Blood samples to assay for hematological variables were collected on day 29. Hemoglobin concentration was determined by use of an automated analyzer (Keska Corporation). As shown in FIG. 2, there was no difference in any of the groups in hemoglobin concentrations.

Further the erythropoietic and hematopoietic affects of Peptide ID were evaluated in rabbits. Blood samples were taken of all rabbits prior to the initiation of the study to establish the hematological baseline for the animals. Peptide ID was administered twice daily i.v. to New Zealand White rabbits for 28 days. For this study, six males and females were assigned to groups 1 and 4, and four males and four females were assigned to groups 2 and 3. Group 1 received 0, group 2 received 30 µg (24 nmol/kg bw), group 3 received 90 µg/kg (72 nmol/kg bw); and group 4 received 300 µg/kg (240 nmol/kg bw) per dose Peptide ID in PBS by bolus i.v. administration. Blood samples to assay for hematological variables were collected on day 29. Comparison of baseline vs. day 29 hematological parameters showed no difference in hemoglobin concentration, hematocrit, or platelet count (FIGS. 3A, 3B and 3C).

Example 3

Peptide or Peptide Analog is Tissue Protective in In Vitro Assays

Peptides and peptide analogs can be readily assessed for tissue protection using any number of in vitro assays. For example, protection from excitoxicity can be determined using kainite-induced death of mouse motoneurons. Spinal cords were obtained from 15-day old Sprague-Dawley rat embryos as previously described (Siren et al., 2001, Proc. Natl. Acad. Sci. USA, 98:4044, hereby incorporated by reference in its entirety). The ventral horn was trypsinized and centrifuged through a 4% BSA cushion for 10 min at 300× g. Cells (representing mixed neuron-glia culture) were seeded at a density of 2,000 cells/cm into 24-mm well plates precoated with poly-DL ornithine and laminin. Motoneurons were further purified by immunopanning and the cells were seeded at low density (20,000 cells/cm²) onto 24-mm well plates precoated with poly-DL-ornithine and laminin, and containing complete culture medium [Neurobasal/B27 (2%); 0.5 mM L-glutamine; 2% horse serum; 25 mM 2 mercaptoethanol; 25 mM glutamate; 1% penicillin and streptomycin; 1 ng/ml BDNF]. The medium (without glutamate) was re-added to cultures on days 4 and 6. Cell death was induced on day 6 in culture by incubation for 48 h with kainic acid (5 mM for mixed neuron-glia cultures; 50 mM for purified cultures). Peptide B (5 ng/mL, 1.8 nM), EPO (3.3 nM) or vehicle was added to the cultures 72 h before induction of cell death, and treatment continued for 48 h. The medium was then discarded and the cells were fixed with 4% (vol/vol) paraformaldehyde in PBS for 40 min, permeabilized with 0.2% Triton X-100, were blocked with 10% (vol/vol) FCS in PBS, were incubated with antibodies against non-phosphorylated neurofilaments (SMI-32; 1:9, 000) overnight, and were visualized by using the avidin-biotin method with diaminobenzidine. Viability of motoneurons was assessed morphologically by counting SMI-32 positive cells across four sides of the cover slip and staining for apoptotic bodies was done by using H33258. As shown in FIG. 4, Peptide B protected the cells against the neurotoxic effects of the glutamate receptor agonist kainic acid.

Example 4

Middle Cerebral Artery Occlusion Model

Sprague Dawley rats (8 per group) are subjected to the following MCAO protocol Surgery was performed in accordance with the teachings of Brines et al, 2000, PNAS USA 97:10526-10531 (hereby incorporated by reference in its entirety. Briefly, the rats are anesthetized with chloral hydrate (400 mg/kg-bw, i.p.), the carotid arteries were visualized, and the right carotid was occluded by two sutures and severed. A burr hole adjacent and rostral to the right orbit allowed visualization of the middle cerebral artery ("MCA"), which was cauterized distal to the rhinal artery. To produce a penumbra (border zone) surrounding this fixed MCA lesion, the contralateral carotid artery was occluded for 1 hour by using fraction provided by a fine forceps and then re-opened.

The rats were administered saline, Peptide ID as a single i.v. dose (2 µg/kg bw), or Peptide IX, LSEQARNQSEL, SEQ ID NO: 301), a scrambled version of Peptide IC, SEQ ID NO: 281, as a single I.v. dose (2 µg/kg bw) upon reperfusion, followed by three additional injections at 2-hour intervals. For assessment of injury, rats are subjected to behavioral testing or the volume of the lesion is determined by tetrazolium staining of brain sections performed 24 hours post surgery in accordance with the previously noted protocol.

(a) Volume of Lesion.

The volume of the lesion was then determined by tetrazolium staining of brain sections performed 24 hours post surgery. Peptide ID demonstrated a significant reduction in infarct volume at 24 hours ($225\pm20$ mm$^3$) in comparison to saline treated rats ($291\pm23$ mm$^3$).

(b) Behavioral Testing.

Rats were also tested in a foot fault behavioral protocol. Rats were tested on an elevated stainless steel grid floor 30 cm×30 cm with grid size of 30 mm according to the protocol of Markgraf et al., 1992, *Brain Research* 575:238-246 (hereby incorporated by reference in its entirety). When placed on the grid, a rat would attempt to move around and occasionally place a foot, rather than on the grid, through a grid opening ("foot fault"). The number of foot faults was measured for a 1 minute period.

The number of foot faults is indicative of the cognitive impairment of the rats due to the MCAO, the fewer the number of foot faults the less cognitive impairment. As shown in FIG. 5, Peptide ID significantly improved the rats performance in the foot fault protocol ($11.2\pm1.1$ foot faults) in comparison to the saline treated rats ($20.2\pm0.8$ foot faults) and Peptide IX treated rats ($20.1\pm2.1$ foot faults).

Example 5

Bilateral Renal Ischemia Assay

Sixty male C57/BL6 mice (~25 g; Charles River Laboratories) were anesthetized with ketamine (150 mg/kg) and xylazine (15 mg/kg) i.p. Each animal was placed on a homeothermic blanket set at 37° C., and after a mid-line laparotomy, the renal pedicles were clamped for 30 minutes using nontraumatic vascular clamps. Peptide ID was administered at the indicated dose via i.p. Injection at 1 minute, 6 hours, and 12 hours after reperfusion. In a single dose study, the mice received a control (PBS), 1 µg/kg of Peptide IG at 1 minute, 1 µg/kg of Peptide IG at 30 minutes, 1 µg/kg of Peptide ID at 6 hours, or 10 µg/kg of Peptide ID at 6 hours (12 mice per group). In a multiple dose study, the mice received either multiple doses of a control (PBS), 0.1 µg/kg of Peptide ID, 1 µg/kg of Peptide ID, or 10 µg/kg of Peptide ID at 1 minute, 6 hours and 12 hours into reperfusion.

Twenty-four hours later, mice were reanesthetized and blood was obtained by cardiac puncture. Plasma urea and creatine were used as indicators of renal dysfunction and aspartate aminotransferase was used as an indicator of renal injury. Data were analyzed using ANOVA followed by Dunnett's post hoc test comparison.

As shown in FIGS. 6A, 6B, and 6C and FIGS. 7A, 7B, and 7C, in each graph, 1 µg/kg of Peptide ID or 10 µg/kg of Peptide ID resulted in a reduction in these biochemical markers of renal dysfunction.

Example 6

Wound Healing

A full thickness punch biopsy model of wound healing was used to evaluate Peptide ID. In this experiment, 3.5 mm-diameter full-thickness skin wounds were placed at the corners of a 3 cm-wide square on the shaved and depilated scapular region of Sprauge-Dawley rats. Peptide ID (24 nmol/kg of bw, 9 rats) or PBS (9 rats) was administered subcutaneously daily for 10 days. The area of open wound, measured in a blinded fashion from serial digital photographs, exhibited faster healing in the animals that received Peptide ID as shown in FIG. 8.

Example 7

Enhancement of Cognition

A novel object recognition paradigm in rats was used to evaluate their recall of previously experienced objects. Specifically, adult Wistar rats were exposed to novel test objects and then reexposed to them 24 hours later. Animals were divided into 5 groups receiving either: (1) vehicle, (2) galantamine (3 mg/kg i.p.) 1 hr before testing as a positive control, (3) Peptide ID (24 nmol/kg bw i.p.) 3 hours after the first exposure to the novel objects, (4) Peptide ID (24 nmol/kg bw i.p.) twice daily for 5 days before training and continued through the day immediately after training, and (5) Peptide ID (24 nmol/kg bw i.p.) 1 hour before first exposure to the novel object.

As shown in FIG. 9, the rats from groups 2-4 exhibited improved recognition of the novel objects in the test in comparison to the rats in groups 1 and 5. These results suggest that Peptide ID may influence the consolidation phase of memory acquisition.

Example 8

Cisplatin Induced Nephropathy

Cancer chemotherapeutic agents such as cisplatin (CDDT) are known to induce renal injury among other toxicities. The ability of Peptide IC to protect rats form cisplatin-induced nephropathy was evaluated by administering 2 mg/kg CDDT intraperitoneally, twice a week for 5 weeks. Peptide IC was simultaneously administered at a dose of 0.4 µg/kg, three times a week for 5 weeks. Renal function was evaluated by measuring the volume of urine production. As shown in FIG. 10, concurrent treatment with Peptide IC protected against renal dysfunction due to CDDT.

Also, CDDT is known to induce peripheral neuropathy, among other toxicities. Following the experimental design described above for renal function, the ability of Peptide IC to protect against peripheral neuropathy was also evaluated. 2 mg/kg CDDT was administered intraperitoneally, twice a week for 5 weeks. Peptide IC was simultaneously administered at a dose of 0.4 µg/kg, three times a week for 5 weeks. Neuropathy was evaluated by hotplate latency, the delay period between contact of the rat's foot to a warm surface, and the retraction of the foot. As shown in FIG. 11, concurrent treatment prevented the appearance of peripheral neuropathy.

Example 9

Cortical Tumor Implant

A cortical tumor implant study was conducted in accordance with the protocol of Lampson et al. Cancer Res. 53:176-82:1993 to determine the effect of Peptide ID on the growth of the tumor.

In accordance with the protocol, male CD fisher rats were anesthetized and their right scalp was shaved and washed with disinfectant. A small incision was then made in the scalp overlying the right temporal cerebral cortex. A 1 mm hole was drilled through the calvarium, without puncturing the dura matter. Under aseptic conditions, living 50,000 9 L/LacZ gliosarcoma cells in 5 µl was slowly injected through a 22 gauge needle attached to a precision Hamilton syringe. Bone wax was then applied to the trephanation site, the skin was sutured and a prophylactic dose of antibiotic was administered i.p. Control rats were provided with saline injections i.p. daily. The rats treated with Peptide ID received daily injections of 30 µg/kg i.p. daily for a period of 25 days. At 25 days following implantation, the animal was anesthetized and the brain perfused-fixed with 2% paraformaldehyde. The brain was then removed and cut on a brain matrix device into coronal sections 1 mm thick and the extent of tumor mass was determined by planimetric methodology.

FIG. 12 demonstrates that Peptide ID inhibited the further growth of the cortical tumor in this model. Whereas the relative volume of the tumor in the saline treated rats grew to greater than 0.4 cm$^2$, the tumors in the Peptide ID treated rats experienced no growth in the tumor volume.

Example 10

9 L Gliosarcoma Implantation Model

In accordance with the accordance with the protocol of Lampson et al. Cancer Res. 53:176-82:1993 described above, CD Fisher rats were implanted with 9 L gliosarcoma cells transfected with the LacZ gene by use of a Hamilton syringe. 100,000 cells in 10 microliters were injected into the right caudate.

Two weeks after implantation, animals were divided into three groups for daily intraperitoneal injections: one receiving a Peptide ID with a short plasma half life, another receiving Peptide IW (pegylated form of Peptide IC) and the third group received saline. Peptides were given at a dose of 25 nmole/kg body weight. Three weeks later, the animals were sacrificed and serial 1 mm thick coronal sections cut through the brain and incubated with 5-bromo-4-chloro-3-indolyl-[beta]-D-galactopyranoside (Xgal). Tumor cells (containing the LacZ gene) metabolized Xgal into a dark blue stain, localizing the extent of tumor. High resolution digital images were obtained and the areas stained blue determined using planimetric methodology. Data is expressed as total area of tumor infiltration.

Results, as represented in FIG. 13, show a marked reduction in tumor size in the group treated with the peptide with longer half life (Peptide IW) to a total area equal to that obtained when animals were treated daily with the peptide with shorted half life (Peptide ID) begun on the day of implantation and continued daily until sacrifice. In contrast, while the mean area of the group that received the shorter acting peptide (Peptide ID) at two weeks after implantation was smaller than the saline group, it was not significantly different.

Further, FIG. 14, presents comparative photos of the brains of the saline, Peptide ID, and Peptide IW treated rats. As can be clearly seen the largest tumor (dark area) is present in the saline treated rats. The rats treated with Peptide ID daily had substantially smaller tumors, however the rats treated with Peptide IW after two weeks exhibited the best outcomes.

These findings are consistent with the ability of peptides to cause the regression of the 9 L gliosarcoma cell line.

Example 11: (Prophetic)

Treatment in Cancer Cachexia

The ability of the peptides to address cachexia symptomatic of cancer may be verified by the following protocol.

Rats weighing about 200 g would be inoculated intraperitoneally with 10$^8$ AH-130 Hepatoma cells. Simultaneously, one group of rats would be treated with a peptide of interest such as, Peptide ID or Peptide IW, at a dose that would be in a therapeutically effective range, about 0.10 to 2.0 µg/kd/day. A second group would be treated with a placebo. On day 16, the rats would be sacrificed. The food intake and locomotor activity of the subject rats would be assessed before inoculation and on day 11. The weight and body composition would be evaluated by NMR-scan on day 0 and day 16 after sacrifice.

In comparison to the placebo treated rats, one would expect those treated with a peptide in accordance with the method of the current invention to exhibit less fat and lean mass wasting. In addition, the food intake and locomotor activity of the peptide treated rats would be improved.

Example 12

Histamine Induced Ear Inflammation

The ability of peptides useful in the current therapeutic method to antagonize the pro-inflammatory affects of histamine were evaluated in a mouse model of histamine-induced edema disclosed in Brand et al. "Tea tree oil reduces histamine-induced oedema in murine ears," Inflamm. Res. 51 (2002) 283-289. Briefly, 24 Sprague Dawley rats (male, 250 gm) were used in the study. Prior to the histamine challenge, each rat was anesthetized and the thickness of the rat's ear was measured using a spring loaded micrometer. 20 ul of 60 mg/ml solution of histamine diphosphate was injected intradermally into an ear of the rat and 30 seconds later the rat received either (1) 30 µg/kg Peptide ID IV (12 rats) or (2) Saline IV (12 rats). Then 20 ul of 60 mg/ml solution of histamine diphosphate was injected intradermally to the rat's other ear. The thickness of the rats ears was then measured using a caliper at 15, 30, 45 and sixty minutes following the histamine challenge.

As can be seen in FIG. 15, Peptide ID reduced the amount of edema associated with the histamine challenge in comparison to saline.

Example 13

Histamine Induced Wheal Formation

The ability of Peptide ID to reduce plasma extravasation (wheal) induced by intradermal histamine administration was evaluated in rats. Animals were pre-administered Evans Blue dye (which binds tightly to albumin) to provide a visual marker of vascular leak. To determine the persistence of peptide IG activity, at various time periods after Peptide ID administration (30 µg/kg, administered intravenously), an intradermal dose of 0.12 µg histamine was administered, and the extent of dye leak quantitated by planimetry performed on digital photographs obtained 15 minutes following histamine placement, a time at which wheal surface area is greatest. Each animal was tested at only a single time point to avoid influence of histamine administration on subsequent responses. Single-dose Peptide ID administration was found to suppress wheal formation, and the suppressive effect was detectable up to 24 hours following a single dose, as shown in FIG. 16, showing the difference in area of saline versus Peptide ID-treated animals.

Example 14

Histamine Induced Wheal Formation

Under isoflurane anesthesia, 12 Sprague-Dawley rats' abdomens were shaved and depilated. Each rat was then injected intravenously (via internal jugular) with a dilute solution of Evans Blue (30 mg/ml in saline, 1 ml/kg bw). After 5 minutes, 6 small doses of histamine (Histamine diphosphate, 20 microliters administered intradermally) in a rectangular pattern on each rat's abdomen. After fifteen minutes, when the wheal reaches its maximum size the wheal is photographed and the blister area was determined by digital planimetry. To test the efficacy of various peptides, the peptide of interest was administered to the rats intravenously shortly after the histamine injection. The peptides tested and results are noted below.

A. Erythropoietin.

Rats received either saline or 10 μgm/kg of EPO at time of histamine challenge. FIG. 17 illustrates that the rats that the wheal area (lesion area) of the EPO treated rats (about 0.4 cm$^2$) was half the lesion area of the saline treated animals (about 0.8 cm$^2$).

B. Peptide ID, Peptide IW, and Scrambled Peptide ID (Peptide IY, SEQ ID NO:304, GLpLSEARNQSEL).

Rats received either saline, Peptide IY (30 μg/kg), Peptide ID (30 μg/kg), or Peptide IW (30 μg/kg) at time of histamine challenge. FIG. 18 illustrates that the wheal area (lesion area) of the Peptide ID and Peptide IW treated rats (about 0.35 cm$^2$ and 0.3 cm$^2$ respectively) was half the lesion area of the saline and Peptide IY treated animals (about 0.6 cm$^2$ each). This not only demonstrated the efficacy of Peptides ID and IW in modulating histamine and the inflammatory response associated with histamine but the importance of the above-disclosed motifs to the efficacy of the peptides given that the Peptide IY did not exhibit anti-inflammatory activity.

C. Peptide IW, Retro Inverso Peptide IC (Peptide IZ, SEQ ID No. 300, SSNLARELQEQ, wherein the amino acids of SEQ ID NO. 300 are (D)-amino acids), Peptide ID, and Scrambled Peptide IC (Peptide JA (SEQ ID NO. 301) LSEQARNQSEL).

Rats received either saline, peptide JA (30 μg/kg), peptide IZ (30 μg/kg), peptide IW (30 μg/kg) or peptide ID (30 μg/kg) at time of histamine challenge. FIG. 19 illustrates that the wheal area (lesion area) of the peptide IW, ID and IZ treated rats (about 0.3 cm$^2$, 0.35 cm$^2$ and 0.4 cm$^2$ respectively) was less than the lesion area of the saline and peptide JA treated animals (about 0.6 cm$^2$ each).

Example 15

Decubitus Ulcer Assay

A decubitus ulcer (pressure sore) assay was performed on 24 adult Sprauge-Dawley rats in accordance with the disclosure of Pierce et al., Selective A2A adenosine receptor activation reduces skin pressure ulcer formation and inflammation, *Am J Physiol Heart Circ Physiol* 281:67-74, 2001. Briefly, a ferromagnetic steel plate was implanted under a dorsal region of the rats skin. A rectangular permanent magnet was applied to the area of the skin under which the plate was implanted in order to compress the skin between the plate and the magnet. This compression reduced the flow of blood to the skin causing ischemia. The rats were subjected to a cycle of ischemia-reperfusion (2 hours ischemia with a 0.5 hour reperfusion) for a 72-hour period. The area of the wound on each rat was measured and, subsequently, the rats were treated with either saline, 30 μg/kg Peptide ID administered sc twice: once at the beginning of the first period of ischemia and a second time at 24 hours later, 30 μg/kg Peptide ID administered sc daily, or EPO daily. Daily the area of the wound on each rat was measured for a period of 12 days. FIG. 20 demonstrates that Peptide ID and EPO reduced the size of the wound, and that daily administration of Peptide IG resulted in the smallest wound size.

Example 16 (Prophetic Example)

Skin Prick Test

An initial histamine skin prick test is performed to determine a baseline. The skin prick test is performed on a patient in a semi-recumbent position on the volar aspect of both forearms (more than 5 cm above the distal skin creases of the wrists). The forearm is cleansed with alcohol and allowed to dry. Using a pen, the prospective skin test sites, for histamine and negative control, are marked and label at least 2 cm apart from one another. A drop of histamine dihydrochloride (10 mg/ml) or negative control is placed at the appropriate mark, and then a sterile lancet is introduced through each drop at an 90° angle and withdrawn. The sites are then observed for the presence of erythmea and wheal formation at 15 minutes following administration. A photograph is taken of the wheals and then the size of the wheal is determined using digital planimetry.

The skin prick test is performed again at a time period of at least 3 hours later using the above protocol. One of the above noted peptides may be administered to the patient at a period of 15 minutes to 2 hours prior to administration of the histamine challenge, at the time of administration of the histamine challenge, or 1 to 60 minutes following the histamine challenge to determine the ability of the peptide to prevent, manage/ameliorate or treat histamine induced inflammation, respectively. For example, at the time of the histamine prick the patient may be given a dose of Peptide ID by IV or sc injection. It is expected that the wheal area will be about 50% less after treatment with Peptide ID.

Example 17

Radiomitigating Activity in Hematopoietic Screening Assay

The ability of peptides useful in the current therapeutic method to mitigate the effects of a radioactive agent on the hematopoietic system was evaluated in a murine model of radiation injury. Briefly, 80 C57BL/6 mice (50% female and 50% male, 15-28 gm) were used in the study were divided into two groups.

In both groups the radiation was administered to the mice as a single uniform total body dose of gamma radiation from a $^{137}$Cs radiation source (GammaCell 40; Nordion International, Kanata, Ontario, Canada) at an exposure rate of 65-69 cGy/minute+/−2.5 cGy.

Group A received a LD70/30 dose of radiation (796 cGy) and then 20 of the mice were administered Peptide ID (30 ug/kg subcutaneously) at 24 hrs after irradiation and then once a day for 29 days. The remaining 20 mice (control group) received PBS (subcutaneously) at 24 hrs after irradiation and then once a day for 29 days.

Group B received a LD90/30 dose of radiation (831 cGy) and then 20 of the mice were administered Peptide ID (30 ug/kg subcutaneously) at 24 hrs after irradiation and then once a day for 29 days. The remaining 20 mice (control group) received PBS (subcutaneously) at 24 hrs after irradiation and then once a day for 29 days.

The mice were monitored for survival once a day until signs of early euthanasia appeared, then twice/day until day 30.

As shown in FIG. 21, thirty-day survival and overall survival time of mice receiving Peptide ID administered subcutaneously were significantly increased compared to the mice receiving PBS. In particular, at 796 cGy the treatment mice exhibited a 45% survival rate in comparison to the control group's 10% survival rate, and at 831 cGy the treatment mice exhibited a 20% survival rate in comparison to the control group's 5% survival rate.

Example 18

Radiomitigating Activity in a Gastrointestinal Screening Assay

The ability of peptides useful in the current therapeutic method to mitigate the effects of a radioactive agent on the gastrointestinal system was evaluated in a murine model of radiation injury. Briefly, 30 C57BL/6 mice (male, 20-30 gm) were used in the study.

The radiation was administered to the mice using a Pantak HF320 X-ray (Agfa NDT Ltd., Reading, UK), operated at 300 kV, 10 mA. The X-ray tube has additional filtration to give a radiation quality of 2.3 mm Cu half-value layer (HVL). Mice had their head, thorax, and forelimbs shielded to protect their bone marrow and select for the GI response. The mice were restrained in a jig and positioned at a distance of 700 mm focus from the focus of the X-ray tube. Irradiation was delivered at a dose rate of 75.5 cGy/min (unshielded) and 70.0 cGy/min (shielded) for a period sufficient to expose the mice to 15 Gy of radiation.

At 24 hours following radiation, 15 of the mice were administered Peptide ID (30 ug/kg subcutaneously) and then once a day for the duration of the study and remaining 15 mice (control group) received PBS (subcutaneously) and then once a day for the duration of the study.

The mice were weighed and monitored once a day until signs of diarrhea and early euthanasia appeared, then twice a day.

As shown in FIG. 22, twenty-day survival of mice receiving Peptide ID administered subcutaneously was significantly greater than the mice receiving PBS (6 mice in treatment group vs. 1 in the control group).

This invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed is:

1. A method of treating tissue damage in a subject in need thereof, the method comprising the step of administering to the subject an effective amount of an isolated peptide comprising an amino acid sequence consisting of XEQLER-ALNSS (SEQ ID NO: 282), wherein X is pyroglutamate.

2. The method of claim 1, wherein the subject has cancer, ischemia, trauma or inflammation, or wherein the tissue damage results from exposure to a toxic agent.

3. The method of claim 1, wherein the subject has a cardiovascular disease, cardiopulmonary disease, respiratory disease, kidney disease, disease of the urinary system, disease of the reproductive system, bone disease, skin disease, gastrointestinal disease, endocrine abnormality, metabolic abnormality, cognitive dysfunction, or a disease or disorder of the central or peripheral nervous system.

4. The method of claim 2, wherein the subject has cancer.

5. The method of claim 4, wherein the cancer is infiltrating breast cancer, pre-invasive breast cancer, inflammatory breast cancer, Paget's disease, metastatic breast cancer, recurrent breast cancer, appendix cancer, bile duct cancer, extrahepatic bile duct cancer, colon cancer, esophageal cancer, gallbladder cancer, gastric cancer, intestinal cancer, liver cancer, pancreatic cancer, rectal cancer, stomach cancer, adrenal cancer, bladder cancer, kidney cancer, penile cancer, prostate cancer, testicular cancer, urinary cancer, cervical cancer, endometrial cancer, fallopian tube cancer, ovarian cancer, uterine cancer, vaginal cancer, vulvar cancer, eye cancer, head and neck cancer, jaw cancer, laryngeal cancer, pharyngeal cancer, oral cancer, nasal cavity cancer, salivary gland cancer, sinus cancer, throat cancer, thyroid cancer, tongue cancer, tonsil cancer, Hodgkin's disease, leukemia, acute lymphocytic leukemia, acute granulocytic leukemia, acute myelogenous leukemia, chronic lymphatic leukemia, chronic myelogenous leukemia, multiple myeloma, lymphoma, b-cell lymphoma, lymph node cancer, bone cancer, osteosarcoma, melanoma, skin cancer, basal cell cancer, squamous cell cancer, sarcoma, Ewing's sarcoma, Kaposi's sarcoma, brain cancer, astrocytoma, glioblastoma, glioma, pituitary gland cancer, spinal cord cancer, lung cancer, adenocarcinoma, oat cell cancer, non-small cell lung cancer, small cell lung cancer, squamous cell cancer, or mesothelioma.

6. The method of claim 2, wherein the subject has trauma or inflammation.

7. The method of claim 6, wherein the trauma or inflammation is caused by appendicitis, blepharitis, bronchitis, bursitis, cervicitis, cholangitis, cholecystitis, chorioamnionitis, conjunctivitis, cystitis, dacryoadenitis, dermatitis, endocarditis, endometritis, epicondylitis, epididymitis, fibrositis, gastritis, gingivitis, glossitis, hidradenitis suppurativa, iritis, laryngitis, mastitis, myocarditis, myositis, nephritis, omphalitis, oophoritis, orchitis, osteitis, otitis, parotitis, pericarditis, peritonitis, pharyngitis, pleuritis, phlebitis, pneumonitis (pneumonia), prostatitis, pyelonephritis, rhinitis, salpingitis, sinusitis, stomatitis, synovitis, tonsillitis, uveitis, urethritis, vaginitis, vulvitis, asthma, systemic lupus erythematosus, myasthenia gravis, tendonitis, angiitis, chronic bronchitis, pancreatitis, osteomyelitis, rheumatoid arthritis, psoriatic arthritis, glomeronephritis, optic neuritis, temporal arteritis, encephalitis, meningitis, traverse myelitis, dermatomyositis, polymyositis, necrotizing fasciitis, hepatitis, necrotizing entercolitis, pelvic inflammatory disease, inflammatory bowel disease, ulcerative colitis, Crohn's disease, ileitis, enteritis, proctitis, vasculitis, vascular stenosis, restenosis, hypotension, Type-1 diabetes, Kawasaki disease, Decum's disease, chronic obstructive pulmonary disease, psoriasis, atherosclerosis, scleroderma, Sjogren's syndrome, mixed connective tissue disease, rosacea, gastric ulcers, duodenal ulcers, Alzheimer's disease, adult onset Still's disease, acute retinal pigment epitheliitis, Tietze's syndrome, Bechçet's disease, white dot syndrome, acute posterior multifocal placoid pigment epitheliopathy, serpiginous choroiditis, birdshot chorioretinopathy, multifocal choroiditis with panuveitis, diffuse subretinal fibrosis syndrome, punctuate inner choroidopathy, multiple evanescent white dot syndrome, diffuse unilateral subacute neuroretinitis, granuloma annulare, irritable bowel syndrome, gastroenteritis, Graves' disease, multiple sclerosis, Dupuytren's contracture, graft rejection diseases, allograft rejection, graft-v-host disease, skin graft rejection, solid organ transplant rejection, bone marrow transplant rejection, inflammatory dermatoses, viral cutaneous pathologies such as those derived from human papilloma virus, HIV, RLV infection, bacterial, fungal or other parasital cutaneous pathologies, cutaneous lupus erythematosus, Hyper IgG4 disease, allergies, allergic diseases, inflammation resulting from blunt trauma, inflammation resulting from contusions, inflammation resulting from allergies, rheumatic disease, childhood arthritis, rheumatoid arthritis, Churg-Strauss syndrome, fibromyalgia, giant cell (temporal) arteritis, gout, Henoch-Schoenlin purpura, hypersensitivity vasculitis, ankylosing spondylitis, capsulitis, rheumatic fever, rheumatic heart disease, systemic lupus erythematosus, polymyalgia rheumatica, osteoarthritis, polyarteritis nodosa, Reiter's syndrome, a sports related injury, runner's knee, tennis elbow, frozen shoulder, Achilles tendonitis, plantar fasciitis, bursitis, Osgood-Schlatter disease, a repetitive stress injury, cumulative trauma diseases, focal dystonia, carpal tunnel syndrome, intersection syndrome, reflex sympathetic dystrophy syndrome, stenosing tenosynovitis, De Quervain's syndrome, trigger finger/trigger thumb, thoracic outlet syndrome, tendonitis, tenosynovitis, radial tunnel syndrome, Raynaud's disease, ganglion, gamer's thumb, Wii-itis, sarcoidosis, sciatic nerve injury, peripheral neuropathy, or inflammation resulting from infections.

8. The method of claim 2, wherein the tissue damage results from exposure to a toxic agent.

9. The method of claim 8, wherein the toxic agent is a biological agent, chemical agent or radiation agent.

10. The method of claim 1, wherein the subject is a mammal.

11. The method of claim 10, wherein the mammal is a human.

12. The method of claim 3, wherein the endocrine abnormality or metabolic abnormality is diabetes mellitus type I or diabetes mellitus type II.

13. The method of claim 6, wherein the trauma or inflammation results from ischemic or hypoxic conditions in or around a responsive tissue, cell or organ.

14. The method of claim 1, wherein the method comprises administering to the subject an effective amount of a pharmaceutical composition comprising the isolated peptide and a pharmaceutically acceptable carrier.

15. The method of claim 14, wherein the pharmaceutical composition is substantially free of peptides other than the isolated peptide.

16. The method of claim 14, wherein the isolated peptide is produced by chemical synthesis.

17. The method of claim 16, wherein the pharmaceutical composition has less than about 5% by dry weight of chemical precursors or compounds other than the isolated peptide.

18. A method of treating tissue damage in a subject in need thereof, the method comprising the step of administering to the subject an effective amount of an isolated peptide modified with an addition of polyethylene glycol, wherein the peptide comprises an amino acid sequence consisting of XEQLERALNSS (SEQ ID NO: 282), wherein X is pyroglutamate.

* * * * *